US006653069B2

(12) United States Patent
Gomi et al.

(10) Patent No.: US 6,653,069 B2
(45) Date of Patent: Nov. 25, 2003

(54) METHOD FOR QUALITY CONTROL OF AN ATTENUATED VERICELLA LIVE VACCINE

(75) Inventors: Yasuyuki Gomi, Kanonji (JP); Hiroki Sunamachi, Kanonji (JP); Michiaki Takahashi, Suita (JP); Koichi Yamanishi, Osaka (JP)

(73) Assignee: The Research Foundation for Microbial Diseases of Osaka University, Osaka (JP)

( * ) Notice: Subject to any disclaimer, the term of this patent is extended or adjusted under 35 U.S.C. 154(b) by 37 days.

(21) Appl. No.: 09/913,514

(22) PCT Filed: Jan. 31, 2001

(86) PCT No.: PCT/JP01/00678

§ 371 (c)(1), (2), (4) Date: Aug. 15, 2001

(87) PCT Pub. No.: WO01/56600

PCT Pub. Date: Aug. 9, 2001

(65) Prior Publication Data

US 2003/0082210 A1 May 1, 2003

(30) Foreign Application Priority Data

Jan. 31, 2000 (JP) ....................................... 2000-062734

(51) Int. Cl.[7] ............................ C12Q 1/70; C12Q 1/68; C12N 7/04

(52) U.S. Cl. ................................ 435/5; 435/6; 435/236

(58) Field of Search ............................ 435/5, 6, 235.1, 435/236; 424/230.1

(56) References Cited

U.S. PATENT DOCUMENTS 6,093,535 A * 7/2000 Mori et al. .................... 435/5

FOREIGN PATENT DOCUMENTS

| | | | |
|---|---|---|---|
| EP | 0 540 135 A2 | 5/1993 | |
| EP | 0 839 911 A1 | 5/1998 | |
| EP | 0 839 911 * | 6/1998 | ........... C12N/15/38 |
| EP | 1 074 624 A1 | 2/2001 | |

OTHER PUBLICATIONS

Loparev et al, Improved identification and differentiation of varicella–zoster virus (VZV) wild–type strains and an attenuated varicella vaccine strain using a VZV open reading frame 62–based PCR, Journal of clinical microbiology Sep. 2000, 38.*

Argaw et al. Nucleotide sequences that distinguish Oka vaccine from parental Oka andother varicella–zoster virus isolates. Journal of infectious diseases, Mar. 2000, 181 (3) p1153–7.*

Takada et al. Identification of varicella–zoster virus strains by PCR analysis of three repeat elements and a Pstl–site–less region. Journal of clinical microbiology Mar. 1995, 33 (3) p658–60.*

Faga et al. Identification and mapping of single nucleotide polymorphisms in the varicella–zoster virus genome. Virology 280 (1), 1–6 (2001).*

Santos et al. Varicella–zoster virus gE escape mutant VZV–MSP exhibits an accelerated cell–to–cell spread phenotype in both infected cell cultures and SCID–hu mice. Virology 275 (2), 306–317 (2000).*

Davison et al., J. Gen. Virol. (1986), 67, 1759–1816.

Kinchington et al., Journal of Virology, vol. 59, No. 3, Sep. 1986, pp. 660–668.

LaRussa et al., Journal of Virology, vol. 66, No. 2, Feb. 1992, pp. 1016–1020.

Hondo et al., Japan. J. Exp. Med., vol. 59, 6, pp. 233–237, 1989.

Takada et al., Journal of Clinical Microbiology, vol. 33, No. 3, Mar. 1995, p. 658–660.

* cited by examiner

*Primary Examiner*—Mary E. Mosher
(74) *Attorney, Agent, or Firm*—Birch, Stewart, Kolasch & Birch, LLP

(57) ABSTRACT

Disclosed is a method for quality control of an attenuated varicella live vaccine, which comprises subjecting the genomic DNA of a sample varicella vaccine virus to sequence analysis and confirming that the genomic DNA of the sample varicella vaccine virus conserves the 5,745th G, the 105,356th C, the 105,544th G, the 106,262nd C and the 107,252nd C without suffering mutation, wherein the nucleotide numbers are in accordance with the nucleotide numbering system of the nucleotide sequence of the genomic DNA of the varicella virus Dumas strain of SEQ ID NO: 1.

9 Claims, 2 Drawing Sheets

SEQUENCE LISTING

<160> NUMBER OF SEQ ID NOS: 42

<210> SEQ ID NO 1
<211> LENGTH: 124884
<212> TYPE: DNA
<213> ORGANISM: Varicella virus
<220> FEATURE:
<221> NAME/KEY: misc_feature
<222> LOCATION: (1)..(124884)
<223> OTHER INFORMATION: Dumas Strain

<400> SEQUENCE: 1
aggccagccc tctcgcggcc ccctcgagag agaaaaaaaa aagcgacccc acctccccgc 60

-continued

```
gcgtttgcgg ggcgaccatc ggggggggatg ggattttttg ccgggaaacc cccccccgcc    120
agcctttaac aaaacccgcg ccttttgcgt ccacccctcg tttactgctc ggatggcgac    180
cgtgcactac tcccgccgac ctgggacccc gccggtcacc ctcacgtcgt cccccagcat    240
ggatgacgtt gcgaccccca tcccctacct acccacatac gccgaggccg tggcagacgc    300
gcccccccct tacagaagcc gcgagagtct ggtgttctcc ccgcctcttt ttcctcacgt    360
ggagaatggc accacccaac agtcttacga ttgcctagac tgcgcttatg atggaatcca    420
cagacttcag ctggcttttc taagaattcg caaatgctgt gtaccggctt ttttaattct    480
ttttggtatt ctcaccctta ctgctgtcgt ggtcgccatt gttgccgttt ttcccgagga    540
acctcccaac tcaactacat gaaactactg tccggaaggg gaaggtattt attctcgctt    600
gcagcttgtc gcgcgtgtat gcacaacaaa agctatatat gtcaccaaag ccaacgtcgc    660
catctggagt actacaccca gtacgttgca taacctgtcc atttgcattt tcagttgcgc    720
ggacgccttt ctccgggatc gtggccttgg gacatcaacc agtggaataa gaaccgccgg    780
tggtcttgtt tgaacgacga gtggcgacgc gttgttctgc ataagctctg tatgctgata    840
cataaacaca gagtctgtat cgctatcaga ttcccgaaca ccttccggta ccccatactc    900
cgataccctg gacattgcgg atcccaaaaa tataatatta acaggatttg cttatacttt    960
gctacagctt atataaattt atgtgcgata catcttaagt gcatccgtac gttatttata   1020
cattgcctgt cacgtgaaaa gactgtgtta cccaataaag gttctacaaa aaatgcttta   1080
ttgggtgttt gtttaatagc tattatcgta acccaccccc gtaaaatcat aaaatgcatg   1140
taatttctga gacacttgca tatgggcatg ttcccgcatt tattatgggc tccactctgg   1200
tgcgtcccag tttaaacgcc accgccgagg aaaatcccgc gtcagaaacg cgatgtttat   1260
tacgagtgct tgcggggaga actgtagacc tgccaggcgg aggaacgtta cacattacct   1320
gtaccaaaac ctatgtaatt attggcaaat atagcaaacc cggcgaacgt cttagccttg   1380
cccgtctaat agggcgtgca atgacgcctg gaggtgcaag gacatttatt attttggcga   1440
tgaaggaaaa gcgatccaca acgcttgggt atgaatgtgg tacgggcttg catttactgg   1500
ctccatctat gggtacattt ctccgcacac acggtttaag taacagagat ctctgtttat   1560
ggcggggtaa tatttatgat atgcatatgc aacgtcttat gttttgggag aatatcgcgc   1620
aaaataccac tgaaacacct tgtataacgt cgacgttaac atgcaacttg acagaagact   1680
ctggtgaagc cgcacttacc acgtcagacc gacccactct cccaacccta acagcccaag   1740
gaagaccaac agtttccaac attcgtggaa tattgaaagg atccccccgt caacagccgg   1800
tctgtcaccg ggttagattt gccgaaccta cggagggcgt attgatgtaa tcactaaata   1860
aaatacacct tttttcgatt gtacgtattt ttatttaaat gtgtagttca tagtccgccg   1920
acagccgctc gggcttttcc cccacataca acatgatcgt atgcctcgga tgcaccggtc   1980
caacactccg ccgagaaggg ggatttacaa tgacagtgat acccaatagc cgccagatgt   2040
acacccagct gtccggactc cagcatcatc tgctgagttg cggcgctgaa gggtgcatcg   2100
catagggtgt tataattagc catttccggt aacagtcgtt gggaatttag gaggctgcaa   2160
aacggctgta ggtcaacata cattggggat tcagatggtt tatctcgacg tccaagtcca   2220
atcaaaaaag cgtgtaaatc atcagcccgg ccgcatgttg ctcgaagagc acataacctc   2280
ttaacaccgt acagagggga tggcgtcggt gcatgtgagt tggcagggca tgtccacgtt   2340
gtttccaacg ccagtggcgg tataacttgt gtaaacgacg ccaacgggtc aggtttaaga   2400
ttcactcgga tgggttgact gctttcggaa gctcccgttg tatccattaa ttaaacgttc   2460
```

-continued

```
ggtacacgtc tggtgtgtgt tttacccgaa tcagagacgg aattgcaaag atattggttt   2520
gaaagcaatg taatcccgcc catatatccc caacgtcgcc ttaaaaactc ccacaatatt   2580
acatttttat tagtctttta ttaatataga atcacataaa caattgataa aatcaagggg   2640
tggtgtataa tgattaaaaa tataaattga tatgttttac aagcatgaaa taggtattta   2700
ctattctaac aggtaaatat gcttaatgat taaaaataca aattagtatg ttttgacaag   2760
catgaaaaag gtatttttta ttttagcagt taaaggtact acacttaaaa tatttaccgt   2820
atggacgggc gtcagaaaga tgcccggccc aagttgagag ggtacattca acacgaccac   2880
actcgcgttg gtgggtgatt agggcctcta aaacaccggc cagacatgac ccgggtgtat   2940
attcttgtaa cacttgaacg ttacaactga tatcatcata ttccacaaat ttagagccac   3000
ggacaactat attagcaatg cgggcaatca taacaaacat ataagtagta atacacgtga   3060
tatcactaaa acgttgctgg cgcaacagtt cggggagagt acgagacccc aaatcgttgt   3120
ccctgtttag aagaagacat cttacaaaag gccccagctt taactttaaa ttctccaaaa   3180
gtgacttcga ggttgcaaca atgggattat ttgtgtagat gggcaagttt tttgccgcta   3240
acattttaat ccacgttaac agttcatccg cagactccaa cgcttcaatc aaagattctc   3300
cacgtatgac tctctcacgc aacgcgcggg caatacgtga gtccatttta tatgactcaa   3360
aggtacgata aagttcatgt ccgtacaaca tcaactccgg ccaagatgtg ttttgtttta   3420
tccccggaaa acatccaccg gaagcccatg aatcaccctc ttgtattgtg gcatatcgga   3480
ctaccagttt ttcaattgtt tcatctaaat ggcgtaccga gtcaatggtc acgctggctc   3540
ccgcggtgga gacgacttca atagcacggc ccgtaattcg atcgaccggg atatcatact   3600
cttttcgaat acgctctcgg cgggcgtctc tcttggaaaa tcgcaacctg tacgattcgt   3660
catgtgtctg atcatttctt tctcccgtgg tcattgcagg aggcgttgta ggacgccgtc   3720
ttcgatttga cagggatcga tcacggtgtt ttcttgaact ttgagtgtta taagatctgg   3780
atgatcgtcg atgtccccgt tcgatgcgtg catatccagt ctccacgtct cttcctccat   3840
gatggtttga atcgggtaat acaacaacca aagttttcgg gcgattgtgg tggtagcttt   3900
cacgccttcc gtgccttcgt ttggaatacc gtggattata tgctgtatct gcagtacgct   3960
ccacatacac agttctagac gttgtggagt cctcgcctgg agtggagcca atagcttcat   4020
catttgccca atcggtgact tccaatgcaa agtcatccga aggttcgtct ggtagcaaat   4080
tcataaagtc ttcacaaata gtagacacgt ctgggtcggt tggaattgaa gcagaggcca   4140
tggctgcaaa atatctgaca attgcgtgtt tgcagttgcc tgtatcttcc gccaatgttg   4200
tagaatttat aggctcaccc aaccccgcaa tgggcgtgtt tagtcacatg attaatgctt   4260
ctgggagttt tcactttccc caaacaagct tacctgcacc ctttgttcgt aatgcataaa   4320
aataaccact gctatagcaa atatgacgat ataaaaacat tttatagcaa ggccggacat   4380
tactgtagcg caacatgttg tgcatatacc acgtattccc cccgtattga tatgatttaa   4440
atgattatcc ttggttggtt ttggtctaac ataagatata agctctacta tagcgagcgt   4500
gcatacaaca acccaggcca gaatccgaat gtatgtgggg tataataacg cgcatggtgt   4560
atatgcaacg ccaagcgtta aaagcacaat acatccagat gatatatgag cgataacctc   4620
caaaagcatc aataacgtaa cacctttatg catatataaa aaacttatag ggtcagcatt   4680
aaatacttta ctcataccat cccgtcgcat ggaaacatca cataacaacc ttgccaactt   4740
tgtatatggg taaccaagaa gaatgttcga aataacccgt gttacgtaat tcagtgaata   4800
```

-continued

```
tgatgtgggg gatattaact cacaggatga tcggaatggc ccaaacatac gacgtattcg   4860
tcgaaattgt aaatacatac catatacaaa ccatgcaaaa aaaatcattt ttagctgcac   4920
gcaccaaaaa taagcgtgac aattacgtgt tcccagaaca attcgaattt tgtcatgcaa   4980
aggtgtagaa atagcggttt ttaccatagt atctcctgat aatagatttt cccggcagct   5040
gtaatcgtat ccagataggc catccaaaaa cgttgagtgg tttacaaacg ttacatatat   5100
aagagagttg ttataagacc cccatacaac cggtccacca ttaatcaccg tggttgcata   5160
cacacactca tgttcaaact ttacacgagc ggtataccat agggtaaaaa cagcatgtcc   5220
gctaagtaga cacataatta taaaatgttc tgtcttgatt cctaaagcct gcatgacccg   5280
tggaagatgg caattcaagc acgatgtagt atcacacggt tggtgttaac tcgaagttaa   5340
atttggataa ttaggtactt ctagagtaaa gattgtatgc atgcgattgc tatcgcactt   5400
tgtagcaaaa cattgttgtg caagcgaaat acacaaacgg ttgtgatgat ccactcgcag   5460
agacacaaat gtccggggag ccgttcttcc tccgcgatgg ggatatcgaa gacaagtgaa   5520
ccctttttgtt ccgcatatga gctgaaataa cacccagtcc cttttgatgg cgatacactt   5580
tgatgatgtt aaggtatatt cgcgatcacg cccggggaaa tgaacagcaa tatgctccac   5640
aatagattct aatattgtgc tgtcgacaaa ggcctccagt gtaaatgcgt ccagacaagt   5700
taccccgcgc tcttttagag cctttgttaa agatatttgc ggggagctaa atatttgttt   5760
attacgcgca accttacgtt caaaaaactc tgcgtattcc cccccaaggt tatgtaaaat   5820
aaattgcact ggaacattcg actgcggtct tgaatgaaaa tgaaagtttg ccgggtttct   5880
atgtgatgtc acaaacgcta atatatcaat acactgctca ggtacaacat aaaatgggag   5940
tagttgtcca accgccgtcc ctgtggttgt tactttggag aaaaaaggca gtcttaaact   6000
atgtccgtgg ctataaacac cagtatctat aaacgaaaag tcccgtaaat acggaccaat   6060
atattcaaca aattcccgtt ccagcaacac cgcttgctgt aatatttgtg caaacccctt   6120
taaagtggaa gaccccacta acgcataggg atttgggatt ggtacgcata ccctgaaacc   6180
tattttctct ttacagttac agggtagagt ttcatgcaag ttttcattgt ttgatacatc   6240
ggcgtgtgta tggacttcag acgttgtctg tgtatcaaaa aaccatacat cctctgtata   6300
attctcttct acacacgtgt ataattcgcc attttctatg taaaaatcga tgtcagaatg   6360
gctggttata tccaataaat tatcatcatc caacacctca acggtaggtt caggacatgc   6420
agttttataa aaataacatg ggtctttgtt agggtttacc acggcctttg gaaaaagtaa   6480
ttgcatggcc gttaaaatac catgacgaaa tgctcgcatg ccggcatgta aaatacccaa   6540
tgggatgggt tttcttatat gaaagtctac atcaagtatg aggtttgtga ttataagatt   6600
tgtattaaat agctcattcc tgtttatata aagctgatct ttgggtatgt ttgatgaaat   6660
tttagaaacg tttttaacag acgtagataa tagtaaagtc aactgcatat ctcgtagtga   6720
agcggcaaca aaattacatg gattaatttg tttaaggtcc tccgcaatta atcgagcctc   6780
gtgcggtaaa gtgtaacggt ttgttattga tgaccacgta tcattagcaa taacagcaaa   6840
tgcttgggcg ccgtgaggca aggctacccg atatacaggc attggtccag ttacctcaga   6900
atggccgatg agggcttcta atggagtttt ataactcagg atggatacat catgtgtggc   6960
tatcccagtg gcagcagaga aaaacagtaa tagttttgta atccccgggc tcgtatcaaa   7020
accagtacga ccactttggt taggtgtatc gtttgcaaag ttggctgctc gtaacgcctc   7080
cgcggaaaca cccgaatcct caaaattaga caattcgtca aaaccgggtg gatttgaggg   7140
aatagtggag gaccatccat atggactaaa ttgtttttca atgttttcca cacgacgagt   7200
```

-continued tagcgttgta gctaggtcac atacgcctat aaacttgcta ggttttgcgg catacgtaag 7260
acttaaagta tatgttttag taattgtata tttatgtcca atctcaggtc caagttcagt 7320
gacatcacaa attacgttct tttttatata gtcacgcatg ttgagacgag aacgtacatg 7380
attaaaaaaa ttagcagtag ctctttttcc caggttggat gattttaaga ggaccggttt 7440
attcacaaaa tctgagtatg taaccgcttg taggtggtct gcgatctgtt tccgattgaa 7500
acattcaaaa tgtgccagat aaatataatc aacaaattca cggtctggaa ctttaaggcc 7560
ttttctatcg ttggtaatat actccgatac tgcgtgtatt tccgttgtgt ctgtatgtat 7620
tcgctgtaaa atgtacgata gagcattttt ggctgtcaaa cctcgtgtat atgttgagga 7680
acaacaaaac atggaaagtt tatcaaaaga caacaagtcc gaaatattgt acccactaca 7740
attaggtaat gccgggactt ggtaagttaa aaacaaatct ttaattgcct gtaagtcata 7800
taagggggtt tccaacgtat tgtaacttgt gtccgtttgt aacaagtaat agcgtgtagc 7860
caacactagc gttttttcag agggtccaaa tcgaacaata taccaaaacg gcgagcatcc 7920
ataccccccag tagagtcgtc gatatgcagc caatacttga cgttcgtaat gggcatataa 7980
tgatgttagc tcctgacgac caacggattt tttaactaac ttgcagagtg ttgcctctgt 8040
gatgcatagg ccgttgtccg ataatccctt tcggtttaaa tggtgtgttg ttaccatcag 8100
agtttgtata acttccgagt gaatgtcaaa cgtctccgat atacataggg tatcagatat 8160
tatatgcgga tttaggggtg ctccatacca taacgcctta tataaagctt taaaatcagt 8220
ttgggtttta aaacaacaaa aaaatatagg ccagacccgg gatcgtacat ctccagttga 8280
aaatccacca attaaataaa aaataacgtt gacgtcccta ctacaaaata aatgcattat 8340
ttggttttct tcatcgtttt cagttacttc acgtgggcgt ttagttggga ttacttgcgt 8400
gatctcttcc ctcccatttt tgacaaagac gtcatctaag tcgggagtcc aagtataact 8460
caccacatac agaggttctg tgcttatctg cccggtaagc aacaacagcg agtgggagat 8520
tgcacatccc tttgtggcaa ataataaccg aatcgtcggt ttggaggatt tatccatagt 8580
tcaatacgtt ggaaagccag tcaatcatgc agacggtgtg tgccagctta tgtggatatg 8640
ctcgaatacc aactgaagag ccatcttatg aagaggtgcg tgtaaacacg caccccccaag 8700
gagccgccct gctccgcctc caagaggctt taaccgctgt gaatggatta ttgcctgcac 8760
ctctaacgtt agaagacgta gtcgcttctg cagataatac ccgtcgtttg gtccgcgccc 8820
aggctttggc gcgaacttac gctgcatgtt ctcgtaacat tgaatgttta aaacagcacc 8880
attttactga agataacccc ggtcttaacg ccgtggtccg ttcacacatg gaaaactcaa 8940
aacggcttgc tgatatgtgt ttagctgcaa ttacccattt gtatttatcg gttggcgcgg 9000
tggatgttac tacggatgat attgtcgatc aaaccctgag aatgaccgct gaaagtgaag 9060
tggtcatgtc tgatgttgtt cttttggaga aaactcttgg ggtcgttgct aaacctcagg 9120
catcgtttga tgtttcccac aaccatgaat tatctatagc taaaggggaa aatgtgggtt 9180
taaaaacatc acctattaaa tcggaggcga cacaattatc tgaaattaaa cccccactta 9240
tagaagtatc ggataataac acatctaacc taacaaaaaa aacgtatccg acagaaactc 9300
ttcagcccgt gttgacccca aaacagacgc aagatgtaca acgcacaacc cccgcgatca 9360
agaaatccca tgttatgctt gtataaatat tgaaataaaa actaaaaacg tttctggtgt 9420
atgtttttat tttgtatata aaattaaaac attgctggct ggcgtggtta ttacatttaa 9480
tgttttagta gaaaatcgac atcgtttgtt tctttatcag ttgaaccaaa tccacgcgtt 9540

-continued

```
ccccgttcgc tgggtgtggc tattagatct aacgttttag taaaatacca ttgtacaccc   9600
ggtatgccac atttaccgcg gatagcataa ggaaatgcaa tattacttaa aacgttgtgt   9660
tttaagtgta tttgggtgtt gtgatctatt aacaggacct gtgcaagacg atctcccgtt   9720
tttatacgta tgtcatcacc cgtgagatta tatacgtaga atttacagtg ttctcctgca   9780
ggccatgccg ttggacacac gataatgcct gatcggcttt tcgatgatct tccaaaaata   9840
taagcgttta tactcggatg ttgtaagtcc cagtctctta taatcggtaa gacaattttt   9900
ataaattcat tcctttttaa atataggtta tatggtacac aaatatcata tcccgcgtct   9960
tcttggcgtt ttggattgat gatatgtttg taggttaagg gaacatcgat atggtattct  10020
gcagaatccc tatgtaaagg ttgcccctgc tgtaccgtgg aaatatcagc aaattcaggt  10080
ataacgggtt tttcataatt tgacggcgag tttgataagg gttgaacttg tatcgattta  10140
aaaattggat ccagatgttt aagaacgttt tttgggagaa ggcgactttg tcttaatttt  10200
accgggaaca agtagattgt taaatgtccg ggtaaaataa cggttactcc tggccggtaa  10260
tacaaaaggg ctgaaattac tcctctgtaa cccgcatcaa taactccgtt ggcgacaaaa  10320
aaattgtctt catcagcaag ggcagtatct ttgcattgaa ttaacaacag tgcgtattca  10380
ttgggaggcg ccgacttaac caacagctcc aactgctgca tataaaaacc gccccgtgtt  10440
acagattttt cagatggcag ttcgagtttc ttgtggttcc ggagtaacaa cggttgatgt  10500
cgacttactt tatcgtctaa cacgcattgc agcgtatctg cacattcagg ttgaacttct  10560
attaaaattg tatcttttaa acaccgattc ggaatagttt ggctacaaaa catatcacct  10620
gtatttactg ccgtttccaa gatgggatca attaccgctt cgttcatatt aataacgatg  10680
caaattttat ttttttgtga agacagcagt ggggagccaa actttgcaga acggaatttt  10740
tggcatgcca gctgttcggc tcgtggagtt tatatcgacg gatcaatgat caccaccctt  10800
ttcttctacg catccctttt gggggtgtgt gtagccctta tttcgttagc ttatcatgcg  10860
tgtttccggt tatttactcg ttctgtatta cgcagcacgt ggtaaacccg tttgcctata  10920
aaaggggcag gcgtgtataa gagggcccct gtttaatacg cggtctgccg tgtttggata  10980
tttcacgacc ctatcgttta tttacgtaat ggcatcttcc gacggtgaca gactttgtcg  11040
ctctaatgca gtgcgtcgta aaacaacgcc tagttattcc ggacaatatc gaaccgcgcg  11100
gcgaagtgtg gtcgtaggac cccccgatga ttcagacgac tcgttgggtt acattaccac  11160
agttggggcc gattctcctt ctccagtgta cgcggatctt tattttgaac ataaaaatac  11220
gacccctcgc gtacatcaac caaacgactc cagcggatcg gaagatgact ttgaagacat  11280
cgatgaagta gtggccgcct ttcgggaggc ccgtttgaga catgaactgg ttgaagatgc  11340
tgtatatgaa aacccgctaa gtgtagaaaa accatctaga tcttttacta aaaatgcggc  11400
ggttaaacct aaattagagg attcaccgaa gcgagctccc ccgggagcag gcgcaattgc  11460
cagcgggaga ccaatttcct tcagcactgc accaaaaacc gcaacaagct cgtggtgcgg  11520
tcctacgcca tcatataaca aacgcgtctt ttgtgaagcg gtccggcgcg tagccgccat  11580
gcaggcacaa aaggctgccg aagcggcttg gaatagtaat cccccaagga ataacgccga  11640
attagaccgt ttgttaaccg gagccgttat tcgtattacg gtgcatgagg gtttaaattt  11700
aatacaagcc gctaatgaag cagacctagg tgaaggagca tcggtatcca aacgtggaca  11760
taatcgaaaa actggagatt tacagggggg catgggtaat gaacctatgt acgcacaagt  11820
tcgtaagcca aaaagtcgaa cggatacaca aacgactggg cgtataacta atcgaagtag  11880
ggcccgttct gcatcaagaa ctgatacgcg aaaataggga tataattacg cagtaacggt  11940
```

-continued ttacccggta ttatgtataa taaataaacg tataaaagac agtcgtggtt tgtgtttatt 12000
ataaatgtgt attatatgtc acatattata aactgtttaa atagtaccac gtggtattat 12060
gaacagttta taatcagttg ctaccaaaca aaccccatta gacggcgggt tttgataaag 12120
ggaatcgctt atttaaacta aagattttac tctataagta tggagtgtaa tttaggaacc 12180
gaacatccta gtacagatac gtggaatcgt agtaaaacgg aacaagcggt tgtggacgca 12240
tttgatgaat cgttgtttgg tgatgtagca tcggatattg gatttgaaac gtcgttatat 12300
tcacatgcag ttaaaactgc tccgtctccg ccttgggtag ctagccctaa aattttatat 12360
caacagttaa tacgggatct tgatttttca gaagggccgc gtttactatc atgtcttgaa 12420
acctggaacg aggatttatt ctcatgtttt cctattaatg aggacctata ttccgatatg 12480
atggttttat ccccggatcc agatgacgtt atctcaaccg tttcaaccaa agaccatgtt 12540
gaaatgttta atttaacaac ccggggttcc gttcgattgc ctagtccacc aaagcaaccg 12600
acggggcttc cagcttacgt tcaggaggtc caggattcgt ttaccgtaga actacgcgcc 12660
cgggaagaag catacacaaa actactagtt acttattgta aatcgattat acgttatctc 12720
caaggaacgg cgaaaaggac gacaataggt cttaatatac aaaaccctga ccagaaagct 12780
tacacgcaac tcaggcaaag tattctactt agatattatc gtgaggtggc aagtttggcg 12840
cgtcttctgt acctacattt atatttaacc gtaacgcgtg aattttcctg gcgtttgtac 12900
gccagtcaat ctgcacaccc ggacgtgttt gcggctttaa aattcacctg gaccgaacgt 12960
cgacagttca cgtgtgcgtt tcatcctgta ttatgcaacc acggcattgt gttattagaa 13020
gggaaaccac taacagcgtc tgccttgagg gaaataaatt accgccgccg agaactggga 13080
ctgcctctag ttagatgtgg tcttgttgaa gaaaacaaat ctccgttggt tcaacaaccc 13140
tcattttcgg ttcatttacc acggtcggtg ggttttctta cccaccacat taagcgtaag 13200
ttagacgcat atgcggtcaa acatcctcaa gaaccgagac atgtacgagc ggatcatcct 13260
tacgcaaaag ttgttgaaaa tagaaactac ggtagtagca tcgaagctat gatttagca 13320
cctccgtccc catccgagat cctgccgggg gacccaccac gcccacccac gtgtgggttt 13380
ttaacgcgtt aaacgtcatt ggggtagagg gtgtaaataa attacgaaaa cgtgcatgcg 13440
tttttattt ttacaatgcg ccgtatatgg tatgtctgtc atgtgctcta aagtcccata 13500
tataaaagaa gccccaacga gtgtatgcgt attgcgtacc gcgaccctgg gatgttttac 13560
aggcgcgttt gtttgtctcg gttataagta tgcagtcggg tcattataac cggaggcaat 13620
cccgccgaca gcggatatcg tctaatacca cagactcccc ccgtcacaca cacggaacac 13680
gttatcggtc aaccaattgg tatacacacc caccccagat attgtccaat tcagaaacat 13740
tagttgcggt tcaagaacta ctgaactccg agatggatca ggacagcagt tctgacgcat 13800
cggatgattt tccgggatac gccttacatc attctacata taatggatcc gaacaaaata 13860
catcaacttc cagacatgaa aatcgcatat ttaaattaac ggagagggaa gctaatgagg 13920
aaatcaacat caatacggac gcgatcgacg acgagggaga ggcggaggag ggagaggcgg 13980
aggaggacgc gatcgacgac gagggagagg cggaggaggg agaggcggag gaggacgcga 14040
ttgacgacga gggagaggcg gaggagggag aggcggagga ggacgcgatt gacgacgagg 14100
gagaggcgga ggagggagag gcggaggagg gagaggcgga ggagggagag gcggaggagg 14160
acgcgatcga cgacgaggga gaggcggagg aggacgcggc ggaggaggac gcgatcgacg 14220
acgagggaga ggcggaggag gattattttt ctgtaagtca agtttgcagt cgagacgcgg 14280

-continued

```
atgaggttta ttttacgtta gacccggaaa taagttacag taccgatctt cgcattgcaa  14340
aggttatgga gcctgcggta tcaaaggaac ttaatgtatc aaaacgttgt gttgaacctg  14400
ttaccctaac aggctctatg ttagcgcata atgggtttga tgagtcctgg tttgctatgc  14460
gcgaatgtac ccgtcgcgaa tatattacgg tccaaggatt atacgaccca attcatttac  14520
ggtatcagtt tgatacttcc cggatgacac ccccacagat tttgagaact ataccagccc  14580
ttcctaacat gacacttggt gaacttttat tgatttttcc tattgaattt atggcccagc  14640
caatttctat agaacgtatt ttagttgaag atgtattttt agataggcgg gcttccagta  14700
aaacacataa atacggcccg cgttggaatt ccgtctacgc acttccatat aatgcgggta  14760
aaatgtatgt acaacacatt cctgggtttt atgacgtgtc cttacgtgct gtgggccaag  14820
gaacggccat ttggcatcac atgatattat ccacagcagc atgcgctatt tctaatcgca  14880
tttcacatgg agatggatta ggatttttgt tagacgcggc aattcgtatt agcgcaaact  14940
gtattttttt gggacgtaac gataattttg gcgtgggggga tccatgttgg ttagaagacc  15000
atcttgccgg attaccacga gaagccgtac ccgacgtact ccaagtgaca cagttggttt  15060
tgccaaatcg gggtccaacg gttgccatta tgcgtggttt ttttggggcg ttggcatatt  15120
ggcccgaact aagaattgct ataagtgaac catctacatc tttggtgcga tatgctaccg  15180
gtcacatgga acttgccgaa tggtttttat tttcacgtac acatagttta aagccacaat  15240
ttaccccaac ggaacgggaa atgttagcgt catttttttac gttgtatgtt actcttggtg  15300
gaggaatgtt gaactggatc tgtagagcaa ctgcaatgta tttagctgct ccttaccatt  15360
cccgttcggc ttacatcgcg gtctgtgaat ctctgcccta ttactatatc ccggttaata  15420
gtgacctgtt atgtgattta gaggtattac tgttaggcga ggtcgacctc ccaactgttt  15480
gtgaatccta cgcaactatt gcacacgaat taaccggata tgaggctgtt cgcacagcag  15540
ccacaaattt tatgatagag tttgccgatt gttataagga aagtgagacc gatttaatgg  15600
taagcgcgta cctgggggcc gttttattgt tacaacgggt gttgggtcat gcaaatcttc  15660
ttttgttgct tctctccggt gctgcgttgt acggaggatg ttcaatttac atccccccgag  15720
gtattttaga tgcatataat actttaatgt tggcagcaag tcctctttac gctcaccaaa  15780
ctttaacatc cttttggaaa gaccgcgatg atgcaatgca aactttgggg attcgaccga  15840
caacggacgt tttacccaaa gagcaagaca ggatagttca ggcatcacct atagagatga  15900
acttccgttt tgtgggattg gagaccatct atccccgaga acagcccatt ccctccgtgg  15960
acctagccga aaatcttatg caatacagga atgaaattct gggtttggat tggaaaagcg  16020
tagccatgca tttactacga aaatattaag ggttgtgatt tttttcatta ggatgaaaag  16080
aacgtttcct agccacaccc acaaaggagt ttgtaaaata aaatctctgt ttagacctta  16140
aaatttgttg tgtgtgttgt gtggggggtc cgtgaggatc gacctttaca agatataatt  16200
tgtccatatc gcaatgtttt ctcggtttgc gcgttccttt tccagcgatg atagaacgcg  16260
taaatcttat gatggtagtt accaaagttt taatgccggc gaacgtgatt tgcccacacc  16320
tacccgggac tggtgttcta tttcccaacg cataaccagc gagcgcgtga gggatggatg  16380
tcttattcca acgcccggcg aggctttgga gacggcggta aaggctttat ctgaaaagac  16440
cgacagccta acatcgccgg ttttacaaag taccgaaaga cacagtgttc tgcttggatt  16500
acaccataat aatgttcctg aatcgttggt ggtctcgtgt atgtctaacg atgttcatga  16560
cgggtttatg cagcgttata tggaaacaat tcaaagatgt ttggatgacc tgaaactttc  16620
tggggatgga ctttggtggg tttatgaaaa tacatattgg cagtatctca aatacaccac  16680
```

-continued aggagccgag gtaccggtga cttcagagaa ggtaaataaa aagtctaaat ccacggtttt 16740
gttgttttca tccgtagttg ccaataaacc aatatccaga catcctttta aatctaaagt 16800
tataaattcg gattaccggg gaatatgtca ggagctacgt gaggcgttag gagctgtgca 16860
aaagtatatg tattttatgc gtccagatga tcctacaaac cccagcccgg atacaagaat 16920
acgtgtacaa gaaattgcgg cttacacggc tactggctac gggtggatgt tatggttctt 16980
ggacgttgtg gacgccaggg tatgtcgcca tctcaaactt caatttcgac ggattcgagg 17040
gccgcgcgcg tctgttattc cagatgattt gcttagacga catttaaaaa cgggtcctgc 17100
ggtctcagcg ggcacaggag ttgcgtttat tttagcagca acaactgcca gcgctcttac 17160
tgcgcttttg cgtattagtg tattatggcg aaaggaagag tggcgggatg gtttaaatgg 17220
aaccgcagct gcaattgttg cggcggttga acttattacg cttttgcacc accattttca 17280
atacttaatt aatatgatgc ttattggata tgcatgttgg ggggatgggg gattaaacga 17340
tccttatata ttaaaggcgc tacgtgccca gggacggttt ttatattttg cgggtcagtt 17400
ggtcagaaca atgtcaacac acagttgggt tgtgttagag accagcaccc atatgtggtt 17460
ttcccgggcc gtggcgcaga gtattttagc acatgggggt aaacccacaa agtattatgc 17520
tcaggttctt gccgccagta aacggtatac tccgttacat ttaagacgta tatccgaacc 17580
atcgagtgtg tctgatcagc cgtatattcg ttttaatcga ctgggatctc caatagggac 17640
aggtataggg aatttggaat gtgtctgttt aacgggaaat tatttatctg acgacgtaaa 17700
tgcaagttcg catgtaatta atacagaagc accgttaaac agtatagcac ccgatacaaa 17760
tagacagcgg acttctcgcg ttttagttcg tccagacacg ggtttggatg taactgtccg 17820
aaaaaaccac tgtctggaca taggccatac ggacggtagt ccagttgacc caacgtatcc 17880
tgatcattac acccggataa aggcggaata tgaaggtccg gttcgggatg aatcaaacac 17940
aatgtttgac caaagatcgg atttacgtca catagaaacc caagcatctt taaatgatca 18000
cgtatatgaa aatataccac ccaaggaagt gggttttaac tcatcttcag acctggatgt 18060
ggatagcctt aacgggtaca cctccggaga catgcataca gacgatgact tatcaccaga 18120
ttttataccc aacgacgttc ccgttagatg taaaaccacg gttacgttta ggaaaaatac 18180
gcctaagagt catcattaag tacagcggtt aatagatagt tatggactag gcactttggc 18240
ggtcatttcc acaaccaggt taaaattggg ggatttggga gaaaatagtc tattgcgtat 18300
tttctgttca ataattggac tgcgttattt aaaggtctga ttggttgatt gggttataaa 18360
aggaattact cctttaaatt ttacttaatg tacccacaat atcaagtggt cgtttgtatt 18420
taacgattat taccggtacc atgggagact tgtcatgttg gacaaaggtg ccgggtttta 18480
cgttaaccgg cgaacttcag tacttaaaac aagtggatga tattttaagg tatggagttc 18540
ggaaacgcga tcgaacagga atcggaacgt tatctttatt tggaatgcaa gctcgataca 18600
atttgcgaaa tgaatttcct cttttaacta caaagcgtgt tttttggagg gccgtcgtgg 18660
aagagttgtt atggtttatc cgcgggtcaa ccgattccaa agaactcgcc gctaaagata 18720
tacacatatg ggatatatac ggatcgagca aatttctaaa taggaatggc ttccataaaa 18780
gacacacggg ggaccttggc cccatttacg gcttccagtg gagacatttt ggagcggaat 18840
ataaagactg tcaatcaaac tatttacagc aaggaatcga tcagctgcaa actgttatag 18900
atacaattaa aacaaaccca gaaagccgac gaatgattat atcgtcttgg aatccaaagg 18960
atatcccctt aatggtacta cctccatgtc acacgttatg tcagttttac gttgcaaacg 19020

-continued

```
gtgaattatc ctgccaagta taccagagat cgggggatat gggccttggg gtaccgttca  19080
acattgctgg atatgcactt cttacctaca tagtagcgca tgttacagga cttaaaaccg  19140
gagatttaat tcatacaatg ggggatgcac atatttactt gaatcatata gatgctttaa  19200
aagtgcagct agctcgatcc ccaaaacctt ttccttgcct taaaattatt cgaaatgtaa  19260
cagatataaa cgactttaaa tgggacgatt ttcagcttga tggatataat ccacaccccc  19320
ccctaaaaat ggaaatggct ctttaatgga tttttaaatg ttgtcaagac agtagatgtg  19380
ttgcgaatgt aataaaatga tatacacaga cgcgtttggt tggtttctgt ttatgaacag  19440
caacggatgc atagggttgc gataactgcg ataagaccca atgtcccaag gatagatatc  19500
acaccaatta taactgctac aacggaaaat gtagtggcgt aggtagatgc atcgtaggta  19560
taaacggccg aaaacggagg gaatttttta gggtaaccat ctagatgaca cgaataggtg  19620
ataggtccgt cgagttccga tgttggacaa gaactttgca tgtttacaaa ccgtttgttt  19680
tgatcacaca ccccagtaat ctcactgttt tcgtggttaa tgggagaatc gttaacccac  19740
catacgaaat gtacaacgcc acgtggcaca cattttgccg tacatactat gtgtccatca  19800
ataataccta tagacacgtt gggaaatgga tagacgtcag ggtaacgac agcagaatat  19860
ttcatattag agacgccatc ccgaatccat aaaacattac attggatggc tgggggtggg  19920
taatccattt gtttttgctg tggaattcgt accgccgaaa cataactaaa taatccattg  19980
gcatattctt gtattgcatc ggttataaaa ttttttccga tgttaccaaa ccttgaagtc  20040
caccgaacac gtaccgagtg cggtggataa tactttgata cgttacagta ggctgcgtat  20100
gtctgtccgg ttaagactgg atcgccgaca acggtaatat ttggacgata atacgttgta  20160
actgtaatac tgtgttccga tatgacgttc ttagtttttg tattaacgac tcgccaaata  20220
tacgttccct ccgtggtagc atccatagat aaaattgtta cagaaaaatc agacgttgtt  20280
ttaacatctg gtattacata attttcctta gcgtgtgtaa atatctcagg gttgtttatt  20340
aagtttaaat cggcactgtt gctatataac ataaccggta aatctggcat gcgtattaac  20400
gcattgccca gttgacggtg cggatctata aggtgacgcg taaaccaaac ttcaatatga  20460
agatcggggc gtataagcga cttccacctt gttatatttg aaccttccgg atctaaagaa  20520
tattgttcat atgtttttg ttgctgctta aaggccgcct gttgtccggt cgttagacgc  20580
atgtaacaag gcatgataaa tgtgtgaaaa tagggtatgg attgtattcc gccgtgaacg  20640
cattgtatat tttcatatag aaaaggtggt tgtgaatgtt gggtgttggc tgcgggatcg  20700
ggctttcggg aagcggccga ggtgggcgcg acggcgggat cgggctttcg ggtagcggcc  20760
gaggtgggcg cgacggcggg atcgggcttt cgggaagcgg ccgaggtggg cgcgacggcg  20820
ggatcgggct ttcgggtagc ggccgaggtg ggcgcgacgg cgggatcggg ctttcgggaa  20880
gcggccgagg tgggcgcgac ggcgggatcg ggctttcggg aagcggccga ggtgggcgcg  20940
acggcgggat cgggctttcg ggaagcggcc gaggtgggcg cgacggcggg atcgggcttt  21000
cgggtagcgg ccgaggtata taattcagtt atacttacgg gtgtgggttg agattcagtc  21060
gataattgta tacacgcgat cgttaaaatt aaatttattt gtatccgctt catcctggtt  21120
tttattgaca catccacgct ccccttaaat aaaagattaa aacacccacc gcggaattta  21180
aatgatggaa acgttttttt cgacattggg aataataaaa acggcttttg caactttaaa  21240
aactttattt atctcgatta cgatacatat gtaccacata gatagcatag atttattata  21300
atataaacac acacgtgata tactttagtg atatgagatg ccataaaaca gtcaataggt  21360
ttaacgctta gtctcatcat ctgaatacac gtcaaacccg ccgcaactgt tgatgttaga  21420
```

-continued

```
attataatag ctccccatga aatgccggca aatgttacag ctatacccgt caccgaggtc  21480
gttgtatata atacaattac ccataggttt tttttttctt gatataaaac ggcaaaaccc  21540
tgtaacccaa atgctataat atgacctcct attgaaactg ctaacgttac ttgtgtaagt  21600
ttgataaaat gatttaattt aattatatgt gagattgccc acattaatgg ggtaactata  21660
tataacaccg ggggtataac agacattata cgaattcctt taaacacgcg tttaagggtc  21720
cgggaacttt ctcgatggtc acatactctc ccgcggtcat tttgtgtata tacaacggca  21780
aaacctaaat ctgtataagt gtttaattgc ttatggcgat ttttacgata tatacacgta  21840
tcttgcaaat cggtggcggc atcgacaatt gaaactagtg tgacaataga tatacacaat  21900
ccaataagaa cctcatattt actgacatac atatataaaa taacggttag taaacctccc  21960
aacccagttc ccaacatcat aacataaaaa taaatatgcg gtccattgaa tgtcgtaaca  22020
aagttgtagt aatggatatg cacagcagcc actgttccgg taatcgcgga tatggaaatt  22080
cccagtaatt ctacaaatgg aagatcccgg gatattgggc aaccaaccgc ccataacaca  22140
gcaaaaccca acacgaccac cgtctgcaaa catcgtccca attttgctaa tgtgcgtaga  22200
aatttcacgg atgttggcca taaccccgaa acgacgatca accccataat agttgcattg  22260
acggcagctt cgcagacgtg atattgtaaa attaacccgg acgtgataac gcttgcttgt  22320
agtcccacga gaaacaaccg cgatgctgag gttattgcac acgaattaca ttcttgaggg  22380
tttccgacac atccttggat tgattgagcg cggattaatt ctctgtctaa cacacccagg  22440
ttttcatcat ggacagctct ttcaccattc acggccatgt cttaagttta ataattcaaa  22500
acaaataaaa atgtgttcat ctatggtaca cacaagtttg tatgtaaaat ataagcaaaa  22560
gttgcactta tttaactgta catattacgt cagattcacg tgataattca gaataatcca  22620
gggttcctgc agggtccact ggaggagcca cacaatattc gcgaattccg attccctcct  22680
gccatgtggt ttcggggagt ttcccccca ttttatttcc ggtatttttt tcgtttcttt  22740
ttgttaataa attgcgtctt ttttttaatg gtggttcatc cttcacagat tccatgttcg  22800
caaataattg catcgaggtt aatttttctt taaggtcttt gggacttaag aacgttgcat  22860
aaaaaaaaga atgcacgggt gcggaacgtt ggatatacaa tccaaccatg ggggagttag  22920
ttaaggcgag ataaaaatta atataacacg tctcatcccg tgttaactta agattttgta  22980
cggcagaacg gaatccactg tgtgtttcca ataatactcc aaattcacgc atactcccgc  23040
tgccataaac aacattatta aggatccttt ttgaatttgt gattgagcgt attaaattat  23100
atggtgtagg cttgcttccg tttatatcca aggaaacatt aaatgagata aaaccacccc  23160
cggcggtctg gatgtacata tccgtggctg ttagaatgaa gcatgttgta aacccaaaag  23220
ttttaagtag tcgctgtaaa cgggtgaatt gatcgcgttt taagcaaatg cttatatctg  23280
gagttagatt tggaaacatc attgtataac aagcgagttc acgttttaca acttgtttgt  23340
aacattgtac ttgatcatct ggaccacaat cacccgggcg ttgccatacc atcgtttgga  23400
taatactccg ctcgggggt tgtccggtaa atttaaaata taaccgtgtt ggggtcgacg  23460
gatcttttgt atggcgaaac gcgtcaataa gcgaggaccg tccctccgtt gccgcgagta  23520
caaccattct cggcccagtc caattatact ggtcaaacat atttgccggt ataggaatat  23580
acagttgttc tgtttccaaa ctacagtgaa taattaatcc ttcgtcgctg aatattaaaa  23640
tagaatccct tagtctatta accagaggtg atatagacga aattaaacca gtaagcgttt  23700
tttccgttaa aacagctctg gcgatttctg ggcgtcaaaa acccgcatgc aattccatgt  23760
```

-continued

```
ccaaagcatc gtctgtacgc gacctcaaat ccataattta ctacttaaaa tgtttactat  23820
agaaaaagta atcatatgta aacacacgag tttcgttaat atgtttgttt aacccgatcc  23880
ggtgacttaa gtacataaac aggcatgata tttgaatagt acggcccatg ggagggaaca  23940
tttccacgtg ttccaataca gggggtgttc cttaataggg actgtgcaat aaaatacgta  24000
agaagttacc agatttgatg taatgtttgt cataaaaaat atgtacatca ttatatacgt  24060
ctgtaattaa cacaagatca catcgaagaa ttactgaagc cgctgtgaaa cctttcacaa  24120
gacgatataa acttggttaa gtgtattgat ggggctcttt ggactgacac gctttatcca  24180
tgaacataaa ctggttaaac ccagcatcat ttcaacgcca cccggagttt taacccccgt  24240
ggcggtagac gtatggaacg tcatgtacac attgttggaa cgtttatacc ctgtgggtaa  24300
acgcgagaat ttacacggac catctgtaac gatacattgt cttggagtct tattgcggct  24360
attaacacaa cggtcatact atccgatatt tgtattggaa cgttgtacag acggcccatt  24420
atcacgtgga gccaaggcaa ttatgtcacg ggccatgaac cacgatgaaa ggggaacctc  24480
ggacttaacc cgtgttctac tatcatccaa cacatcatgt tctatcaagt ataacaaaac  24540
atcggaaaca tatgacagtg tgtttcgaaa ctcttccacg agttgtattc ctagcgaaga  24600
aaacaaatcc caggatatgt ttttggacgg ttgtccacga caaactgaca agacgatctg  24660
cctgcgcgac caaaacgtat gcagtcttac ctctacaatg ccatcccgag gacatcctaa  24720
ccatcgatta tatcacaaat tgtgtgcaag tcttattaga tggatggggt atgcatacgt  24780
cgaggcggtt gacattgagg cggacgaggc atgtgcaaac ttatttcata cgcgtacagt  24840
ggctttggtt tatacgacag atactgattt actcttcatg ggctgtgata ttttgttaga  24900
tgcaattcct atgtttgctc cagtagtacg atgtcgcgat ttgcttcaat atttaggaat  24960
tacataccct gaatttttgg ttgcctttgt tcgctgtcag accgatttgc atacaagtga  25020
caacctaaaa tctgttcagc aagttattca ggataccggc ctgaaagttc cacatcaaat  25080
ggacacttca acgcgctccc ccacttacga ctcgtggaga catggcgagg ttttcaaaag  25140
tcttaccgta gccacgtcgg gtaaaacaga aaacggagtg tccgtttcca aatatgcatc  25200
taaccgatcg gaggtgacag tagacgccag ttgggcttta aaccttctgc caccctcatc  25260
ctccccattg gataatttgg aacgcgcatt tgttgaacat ataatcgccg tggtaactcc  25320
attgacccgc ggtcgcctaa agttaatgaa acgtgtaaat attatgcaaa atacggcaga  25380
cccatatatg gttattaaca ccttatatca taacttaaag gggaaaaaa tggctcgcca  25440
atacgcacgt atttttaaac agtttattcc tactccactc ccactaaaca ctgtattaac  25500
aaaatattgg aattaaaaca cacataagag cgacttaatg gttcattgtt ttattttgct  25560
cgtatataca tgttataaat cgtttatcac tgtgcccgca taagatgtac tgtgtctctc  25620
aaaaaaattt gtgtttttat ctgcaatcat aaatgcaagt ggaaagtccg aatcgggagg  25680
tggggtgtta aatagttttg gtacattaat cgctgataaa agcctgtccg cgctgaattt  25740
cacgtattgt gtaattgcat cgacgttcac caaacgggtt ttgggtgcat gggattttaa  25800
aaacgcacac tcgatttcaa cggcttccga aaacagttga tgtattctgg tgatagcggg  25860
tttttcgggt acatagttat tgtatataca acacgatgcg ctggtatgta tggcttcatc  25920
tcggcttata aggtcgttaa attgacaagt tacaacaaat agtccgttat tgcgtaaata  25980
tgcaatagcc gcgaacgatg atacaaaaaa aatgccctct ataagaatca ttagtatata  26040
tttttctgca acggatgggt tgtcccgtac cttttcttcc aaccattgta ctttttgttg  26100
gatcgacgga ttattaatag tgacatttac gtattgtacc cgcaacgatt catcccctct  26160
```

-continued

```
gaacaacatt agttgaattt gactatagac acgcgcgtgg acaacctcga tgcactcttg  26220
ttcaatgtag taatggtgaa tatccttttg ggaaaagagt tgggttagag agcccaaatt  26280
aacatttacc agatcatctg ccgccgataa aaatgtaaaa ataaatctgt agaatattag  26340
ttcatcttcc gttaaacagt ccaagtattg ataatcatct tcaatgataa aatcgctttc  26400
taaccaacga ttcgaaatgc tcagggcacg taaattgttt atatctggac actccggcct  26460
gtaaaaaaaa tgactgcaat ctttctgatc cattttggaa tagtttcccg tgtaaattta  26520
taaagcacaa ctggtacagg ttaattcgcc tcccgcaaac agtccgctgt tcgtagcttt  26580
acgaatttta cagtagtaca tacccgtttt aaggccggct ttataggcac gtataagcaa  26640
attcattatt ttggaggcgg gaattgtccc gtctgggcgt tcctcaataa ataaagtcat  26700
tgattgactt tggtcaataa atggcgccct ttctgcacac atatcaacga gatcctcttg  26760
ctcatattca aacgctgttt tatattttaa gagtgggtga ctattagata aacagccaaa  26820
cgaacgtatt actgaccatt ggtttttctc aagtatgttt ataacttcca gtcgtttttc  26880
ttcacatgaa tacatatctc ttagttcgtc cataaggtct aagttgggtc taagtaactc  26940
acccgaggtg gtgaccttac taaacatatt attataaatt ggagagaaac cctcactgca  27000
ctccgttacc tgtgcagatg aaactgtggg cattaacgct aagaactgcg agttgtataa  27060
cccataagcg caaatatcat ctcgcagggt acaccatggt aaatctaaat aacttatcgt  27120
agaaaaccca tcttggtgta accatccctt agcatattta ctttcggtaa aacccttaaa  27180
cggggctaag ccgccaatct tacacatttc catgcttgtt ttcattgtct catacaacat  27240
taactccgct atttgtacat ttaaccgtct agctggttgg gaagttaaat caaatcctaa  27300
gcggagacaa gttgtatgta acccttgtat gccaatgcca agtgatcggt tgttttttac  27360
acctttacat gatttttttac atggaaagtt cccagccgcc aggacccccgt ttaaaaaaat  27420
aacagtcgtt cttgctgtca attgaaggtc gtttaaatta aatgacactg ggcctttgga  27480
taagcacgtt gtaagattta tgctggcaag attacatacg ccatgttgat gagcgtctgc  27540
cttttgaaca atttccgtac acaaatttga ccccgtgata gcatttcctt gggtattcat  27600
atgataatta cgattacagg catctttgaa cattaaaaag gggcttcctg ttacagcagc  27660
actgcgtatg attgtgaatg cgatatcttg aatgggaaca gaagaaacgc ctaatccttc  27720
tctctctaaa cgtaaatagg ttgaagtgaa tgcctccccg tgtaatgttc gaaggatatc  27780
ggctctgtta tcaaaaagag tccactgaac attactagcc ccttttagat agcttaggta  27840
tctttcaaaa aataaatctg gggtccataa acaacaaaat atgttatcac atcgaaatat  27900
ttcatcacga accaacattc cacgtgtggc caaaacagtt tgtagatcga cgtgccatgg  27960
ttctatgtaa acacaaactc cagttggtcg ttcacaatca ctgttaattg ccataaccat  28020
gcaatctaaa agttttaaaa ctgcaagaag acctttcgtt tgattttccg taggtattaa  28080
attcagactc tgtagagaaa ttcccactcc acctcgactt tgtaataccg ttcccacatc  28140
gcctgtgata gctcgaacag ctctcccaac agtgatggat tccgggtcca ttaaataaca  28200
actggccgtt gccccggtct ctcgacctaa aaacatcata accggtgtag ccgggacaat  28260
tttctgacat gccaacgctg tgaaaaatac ccgacagaca tcagtccatg tataaccatc  28320
atttattccg ggaataagag ttgcgatttt aggcaggttt acgatttctg ttgtcacggt  28380
ggccgccagt cttaaaaaga attggcaaag cgactctaat ttaccttcct ctaacttagt  28440
taaataaaag tcttcgtact ttaaagcaga ctgtagtcca agggtagcta aagcggggta  28500
```

-continued

```
ttgatctttc aaaaacggtt ctaatatagc ccgacgaatt tcgtccctcc gcccttcaat  28560
tgcttggcgg actcggggag ttaaacagag aattggggaa gtcaaccacg tttccatgga  28620
aacggatcgt aggttaatac ggcaatggat aagttctcca caacatcggt acactcgctc  28680
atcttgtcgc gtcaccgcct taagttttga gacgatagtg ctaatatact ccattaattc  28740
caccggtgtg gttgattcgg gcggaatgat gtattccttg tagccatgtt gacataatcg  28800
gtttataatg tcatgaaccg tattaaaaat tcttttgaac tccataacgg ataacgtatt  28860
taggctccgg aataaacctt taaaccctaa actcacagct gagttagttc tacaatattg  28920
tagactccct tatatatggt tacgtacagc ctgcccctcc ccagtatata atatcacgca  28980
aaacccacgc tatgttaaat tcagtttatt ttacatacat gctttaataa taacattcgt  29040
tccatgtatt tgtacccccc cacacaaccc cctctaacca aatagttggc acgttataac  29100
ctccgaaccg ttccatgcgt cttgtataac gcacagactc tgatggaatt gttccaatta  29160
acgtatatgc cgcatacatg caggataatt gtgtgggaag tccccgaaaa tcgccggtcc  29220
attgatacaa tcgctgtcta gccaagttcc aatttactcc tgtaatttcg ccaatactac  29280
atcgagggct tgtcgggtca ttggataact gcacaagcgg caacgccctt gtgttatatg  29340
gctggtgggt atttgcaacc ccttcagtcc cccaggcggc attttcagct cgtatgcgtc  29400
ctaacaggaa gccaatacca cgaccaaaac attgttcgtt tagttggctt aatgcaagat  29460
gcagtcttac accttctcgt tggcgtcgct gtgtatatac aaaaaccaag aacacatgct  29520
tcagtccgtc cgcggaaaga tgtaaatctt tgtcaacgtc ccaaaatacg caggccggga  29580
tgttggctgt gaccctgcga gttgaagttt tgtctgtacg tgcagcttct tggggacctt  29640
tggccacggc ggttatattg cataaattat cctgaatggt atattccagc agggacccaa  29700
aaaaacttat aaatcgatgt ggaaatacat gacattgtac catcgcacgt aaacactccg  29760
aaaaccttat gagccgcgtt tccatacgac tgcatccata ggcagaaaca attgctgttc  29820
tgttggcatc cgctgcctgt ttatccgtat attcttctgc ccggcatgcg gcgatgaaac  29880
ttaatgacgt tacatatgct ctaagccccc caccttctcc aacggtccaa ggagccgtgc  29940
aggcattgaa taggtttcgt aaaccctcta gtagtacatc ggggtcacgt ccagcctgtg  30000
taagtgtatt agcttctcca atcatgtcag atggatgacg aaggattaag acgattgacc  30060
cagcatgctc aatgtccgga cgaaaaaaat cggttaatga cacttgttgg attagctgtg  30120
tcgttgattt aaaattattt aacgggagtc taatggtaac ttgcgggtta ccaattgaag  30180
ttggatttat ttgaatgttg ttcatacgat taataacaat tgaacggggg gttacttgaa  30240
tagacgcggt ttctgtacgt tttggtggta catgtatcgg ttgtttgttc agacctccaa  30300
agcgagggcc aattgttaaa tcgcgactcc aatttccgaa gaagcccgga gcataagtca  30360
tatgaagccc gttccctatt tgaataaaac ggttatttcc taaaagactg atattagttc  30420
cacatagcgt ttgttcgttt aaagtaaaat gcgagttggt tggttgactc cccatagctg  30480
aggggttaaa ttcacacaat gcaatcgtga cgtggtacta tctgaaatgt tgcctggggt  30540
atgtgtacac attatacagt cgtagtaccg tttatataat gttaggtagg aggagcctat  30600
aaaaatattt tgattggcgt taaaaggttc ttcaacttac cgtgacgtcc tttttattaa  30660
catgcgtttt tattgatgtt acatttatgt cttttcattc cggacggatg tagctttttc  30720
atatcacgtt ataaagttaa gtcagcgtag aatataccat ggaagaacca atttgttatg  30780
atacacaaaa acttttggat gatttaagta acttgaaagt acaagaagcg gacaacgaaa  30840
gaccatggtc accagagaaa acagaaatcg ccagagttaa ggtagttaag tttttacgat  30900
```

-continued

```
ctacccagaa aattccagct aaacatttta ttcagatatg ggaacccctg cattctaata  30960
tctgttttgt atattccaat acatttttgg cggaggctgc tttcacggcc gaaaatttac  31020
ccggactgtt gttttggaga ctagatctag actggacgat agaggagcca ggtaatagct  31080
taaaaatttt aacccagcta tcaagtgtag tacaagattc cgagacgtta catcgtttat  31140
cggccaataa attacgaacc tcgtctaaat ttggacccgt ttcgatacac ttcattataa  31200
cggactggat aaatatgtac gaggtcgcct taaaggatgc aacaacagcc attgaatcac  31260
cattcactca cgctcgtatt ggaatgttgg aaagcgccat tgcagcttta acacaacata  31320
aatttgcgat catttacgat atgccatttg ttcaagaggg gattcgtgtt ttaacacaat  31380
atgcaggatg gcttcttccg tttaatgtta tgtggaatca gattcaaaat agctcactca  31440
ctcctctaac acgagccctt tttataatct gtatgattga tgaatatctc acggaaacgc  31500
cagtacatag catatcagaa ttatttgcag atactgtaaa tttaattaaa gatgaggcgt  31560
tcgtatccat cgaagaagcg gtaacgaatc cacgaacggt gcacgagtca cgaatttcct  31620
cagctctggc ttatcgagac ccttatgttt ttgagacatc cccgggaatg cttgctagga  31680
gacttagatt agacaatggt atatgggaaa gcaacctctt atcgttgtcc acccccggaa  31740
ttcatattga ggcgctgtta catttactaa actccgaccc ggaagcggaa accacatctg  31800
gaagtaatgt agcagaacac acccgtggca tttgggaaaa ggttcaggct agtacatcgc  31860
ctagtatgtt aataagcacc cttgccgaat ccgggtttac aagattttca tgcaaattgc  31920
tacgtcggtt tattgctcac cacacactcg ccggttttat tcacggaagc gttgtagcag  31980
acgagcatat tacagatttc caacaaacac taggatgtct cgctttagtg ggtggactgg  32040
cataccaatt agtggaaacg tacgctccta ctaccgagta tgtgttaaca tatacacgga  32100
cagtaaacga gaccgaaaaa cggtatgaaa cgctattacc cgccttagga ttaccaccgg  32160
gaggcctggg acaaattatg cggcgctgtt ttgctccacg accccttatt gaaagtatac  32220
aagcgacacg cgtaatacta cttaatgaaa tttcacatgc agaagctaga gagacaacat  32280
attttaagca aacacataat caatcctcag gtgcgttatt accacaagca ggacaaagtg  32340
ccgtacgcga agccgtacta acctggtttg acctacgtat ggattcaaga tggggtatta  32400
ctcccccggt ggatgtgggt atgacacctc ctatttgtgt tgatccaccg gctacagggt  32460
tggaagctgt catgataaca gaagcactaa agattgcata tcctaccgaa tataatcgct  32520
ctagcgtgtt tgtggaaccg tcgtttgtgc cttatattat tgcaacaagc acgcttgatg  32580
ccctttcggc aacaatagct ttgtcttttg atacacgggg aatacagcaa gccttgtcta  32640
ttcttcagtg ggctcgcgat tatggatccg gaaccgtgcc caatgcagat ggatatcgca  32700
caaaactatc tgctcttata acaatattag aacctttttac ccgtacacac cccccagtac  32760
ttttaccatc tcacgtttct actatagatt cccttatatg cgaacttcat cggactgttg  32820
gcattgccgt tgacctgctt ccccagcacg tccgtccttt ggttcctgac cgtccttcta  32880
ttacaaatag cgttttttta gcaactctct attatgatga actttacggt cgttggaccc  32940
gactggataa aacatcgcag gcgttggttg aaaattttac atccaacgcg ttagtggttt  33000
ctcggtacat gttaatgtta caaaaatttt ttgcgtgtcg tttttatcca acgccagatc  33060
ttcaggctgt tggtatctgt aacccaaagg ttgaacgcga tgaacaattt ggggtatggc  33120
gtttaaacga tcttgctgat gcggttggtc atattgttgg gacaatacaa ggaatccgaa  33180
cgcaaatgag agtgggaata tccagcctgc gcacaattat ggccgatgct tcctcagccc  33240
```

-continued

```
ttagggaatg tgaaaattta atgactaaaa cctccacttc tgctattggg cctctttttt 33300
caacgatggc ttcccggtat gcacggttta cacaggatca aatggacatt ttaatgcgtg 33360
ttgacaaact aacaacagga gaaaatatac ccggtcttgc aaatgtagag attttttttaa 33420
ataggtggga acgaatagca acagcttgta ggcatgccac ggcagtcccg tcggccgaat 33480
ctattgcaac cgtgtgtaat gaattgaggc gcggtttaaa aaatatacaa gaggatcgtg 33540
taaatgcccc aacctcatat atgagtcacg cccgaaatct ggaagatcac aaggcagcag 33600
tttcattcgt tatggactcc aggcaacagt ttattgtgga ttctggacct cagatgggcg 33660
cggttttaac ttcacaatgt aatataggaa catgggagaa tgtaaatgca acgtttttac 33720
atgataatgt taaaataacg acaacggtca gagacgtaat ttcagaggct ccgacgctga 33780
taataggaca aagatggctt cgtccagatg agattttatc taatgtagat ttgcgtcttg 33840
gcgtacccgg gaatacaagt gggagtgacc cttaatataa aacaggcgtg tttatgtaca 33900
ttaaagtatt tgtggttttt attgactggg cgtttcgttt gtataacgct gttgttgcta 33960
gtattttcat aacctcctag gtttttggag ctacacgtgc ttattcaacg ctctttggga 34020
tttgaatcat cgtaaacgta gcgtccctac cagttgagcg cgtaattttc gtaagcaata 34080
aaatggatat aattccgcct atagctgtca ctgttgcggg agtgggaagc cgtaatcaat 34140
ttgacggtgc cctgggaccg gcgtcaggtc tgtcatgttt aagaacatct ttatcgtttt 34200
tgcatatgac atatgcgcat ggaattaatg caaccctgtc atcagacatg attgatggat 34260
gtttacaaga gggtgcagca tggactacgg atctgtctaa tatggggagg ggtgtcccag 34320
atatgtgtgc tcttgttgat ctccccaatc gaatttcata tattaaactg gggacacta 34380
ccagtacgtg ctgcgttttg tctagaatat acggcgatag ccattttttt accgttccag 34440
acgagggttt tatgtgcaca caaattcccg ctagagcgtt tttcgatgat gtgtggatgg 34500
gacgtgaaga gtcgtataca attataactg tagactcaac gggaatggcc atctatcgtc 34560
agggaaacat atcttttatt tttgatccac atggccatgg gactatagga caggctgtag 34620
ttgttcgggt gaataccacg gatgtgtact cttatatcgc atcggagtat acccaccgcc 34680
ccgataacgt agaatcccaa tgggccgctg cattagtttt ttttgtcacc gcaaacgacg 34740
gtcccgtaag cgaagaagcg ctatcttcgg cagtaacgct tatatacgga agctgtgata 34800
catattttac agatgaacaa tattgcgaaa aactggttac agctcaacat ccgttgcttc 34860
tttcacctcc taattccacg acaattgtgc ttaataaatc gtctatagta cctcttcacc 34920
aaaacgttgg tgaaagtgta tccttggaag caaccctaca ttcaacgtta accaacacgg 34980
ttgcactgga ccctagatgt agttacagcg aggttgatcc ttggcatgcg gttctagaaa 35040
caacctcgac tgggtctggc gttttggatt gtcgtcgtag acgccgtcct tcatggactc 35100
ctccttcaag cgaggaaaat ttagcttgta tcgacgatgg cttggtaaat aatacacatt 35160
ccacggataa tttacataaa cccgctaaaa aggttctcaa atttaaacca actgtagacg 35220
tgccggataa aacacaagtg gcacatgtat taccccgcct acgagaagtt gctaacaccc 35280
cagacgttgt gttaaatgta tccaatgtag atacgcctga atccagtccc actttttcac 35340
ggaacatgaa tgtaggaagc agtttgaaag atcggaagcc atttctattt gaacagagtg 35400
gtgatgtcaa catggttgtc gaaaaactac tacaacatgg gcatgaaatt agcaatggat 35460
acgtacaaaa tgcggtgggt acgttggata ctgttattac cggtcataca aatgttccca 35520
tttgggtaac aaggcccttg gttatgccag acgaaaagga tccattggag ctttttatta 35580
acctcaccat tttgcgttta acgggatttg tggtggaaaa tggaacacgt acacatcatg 35640
```

-continued

```
gtgctacaag cgttgtatca gactttatag gtccccttgg ggaaatttta acaggatttc  35700
cctccgccgc ggaacttata cgcgttacaa gtttgatatt aacaaacatg ccgggggcgg  35760
aatatgctat taaaactgtt ctccggaaaa aatgtacaat tggcatgctc attatcgcta  35820
agtttggtct agttgccatg cgggttcagg atacaaccgg cgctttacat gccgaactag  35880
atgtgttaga agcggatcta ggaggttcgt cgcccataga cctctattct agactgtcga  35940
caggtcttat aagtatacta aattcgccta ttatttctca tcccggactt tttgccgagc  36000
ttattccaac ccgtacaggg tccctgtctg aacgaatacg tcttctttgt gaattagtct  36060
cggcccggga gacacgctat atgcgtgaac acaccgcgct tgtttctagt gtaaaggctt  36120
tagagaatgc attacggtct acccgcaata aaattgatgc cattcaaata ccagaagttc  36180
cccaggaacc cccggaagaa accgacattc cacccgaaga gttaattcgg cgtgtatatg  36240
agatacgatc cgaagttaca atgctattga cctcggctgt tacagaatac ttcacccgcg  36300
gagtgttata tagcacacgg gccttgatcg ctgaacaatc ccctaggcgt tttcgggtcg  36360
cgaccgcaag tacggcaccc attcaacggc ttttagattc tcttccggaa ttcgacgcta  36420
aattaacggc aatcatatcg tccctgtcta tacaccctcc tcctgagact atacaaaatc  36480
tccccgtcgt atctctgtta aaagagctta ttaaagaagg ggaagattta aacacagaca  36540
cggctctcgt atcgtggtta tctgtagtcg gggaagctca aaccgcaggt tacttatcca  36600
gacgagagtt cgatgaatta tcacgtacaa ttaaaaccat taatacacgc gcaacgcaac  36660
gggcttccgc ggaagcagag ttgtcttgct ttaatacgct aagcgcggcc gtagaccaag  36720
ccgtaaagga ctatgaaaca tataacaatg gtgaggtcaa gtatcctgaa ataacacggg  36780
atgatttatt agcaacaatt gtacgtgcta cagacgattt ggtgcgacag ataaaaattt  36840
taagtgatcc aatgatccaa tccggtttac aaccttcgat taaaagacga ttggaaacaa  36900
ggcttaaaga ggttcagacg tatgcaaacg aggcccgaac cacacaggac acaataaaga  36960
gtcgaaaaca ggcggcatat aataaactcg gggggttact tcgcccggta accggttttg  37020
tgggacttag ggctgcagta gatttattac cggaacttgc ttctgagtta gatgtccaag  37080
gagccctggt aaatctcagg accaaagtct tagaggcgcc ggtagagatc cgttctcaac  37140
ttacgggtga tttctgggcg ttatttaacc aatatcgaga cattttagaa catcccggaa  37200
acgcacgcac atctgtctta ggaggactgg gagcttgttt tacagctatt atcgaaattg  37260
tgccgatacc tacggagtat agaccatcat tgcttgcgtt ttttggtgac gtggcagatg  37320
tgcttgcatc cgacatcgcg accgtatcta ctaacccgga aagtgagtcc gccataaacg  37380
ctgttgttgc aactcttagt aaagcgacgt tagtttcatc tacagtgcca gccttatcct  37440
ttgtgttgtc gttatataaa aaatatcagg ctttacaaca agaaattacg aatacccata  37500
agttgactga attacaaaaa caacttggag atgacttctc caccctagct gtctcatctg  37560
gacacttgaa gtttatatca tcttcaaatg tagatgatta tgaaataaac gatgcgatat  37620
tatcaataca aacaaatgtg cacgccctaa tggatacggt taaacttgtt gaagttgaac  37680
tgcaaaagct acccccccat tgtattgctg ggacatctac cttatctcga gtagtaaagg  37740
atcttcataa actcgtcaca atggcacatg agaagaagga acaggcaaaa gtgttaatta  37800
ccgattgtga acgtgcacat aaacaacaaa cgactcgggt tttgtatgag cgttggacac  37860
gtgatattat agcatgtctg gaggcaatgg aaacgcgcca tatatttaac gggacagaac  37920
tggcacggtt gcgagatatg gccgctgcgg gagggtttga tatacacgca gtttacccac  37980
```

-continued

```
aagcacgtca ggttgtagcg gcatgtgaaa ctacagccgt tacggcatta gatactgtgt  38040
ttcgccacaa tccatatacc cccgaaaata caaatattcc accacctttg gctttgttaa  38100
gagggttaac atggtttgat gatttttcga ttacggctcc cgtattcacc gttatgtttc  38160
caggtgttag tattgaggga ctccttctgc ttatgcgtat tcgcgcggtt gtgttattat  38220
ccgccgatac gtctattaat ggaataccta actaccgaga tatgatatta cgaacctcgg  38280
gggatctatt acaaataccc gcattggctg ggtatgttga tttttacaca cggtcttatg  38340
atcagtttat aaccgaaagt gtaacgttaa gtgaacttag agcagacatc agacaggctg  38400
ccggggctaa acttacagaa gcaaataagg ctttggagga agtaactcat gttcgggcac  38460
acgaaacggc taaacttgca cttaaagaag gtgtcttcat tacattacca agcgaaggtt  38520
tattgattcg ggctatagag tattttacaa ctttcgatca taaacgattt ataggaacgg  38580
catatgaaag agttttacaa acaatggtag accgcgatct aaaggaggcc aacgcagagc  38640
ttgcacagtt tcgtatggtg tgtcaggcaa caaagaaccg tgcaatacaa attttacaaa  38700
acattgttga tacggccaat gccactgagc aacaagaaga cgtggatttc actaacctga  38760
agacgttatt aaaactaacc ccccctccca aaacaattgc attggccatt gatagatcta  38820
cttccgttca ggacattgtc acgcagtttg cattgctgtt agggcgtctg gaagaagaaa  38880
ctggtacgtt ggacattcag gcggttgact ggatgtacca agctcgcaat attattgact  38940
cccatccact aagtgtgcgt atagacggta ccggcccccct gcatacttat aaagataggg  39000
tggataaact ttatgcgtta cgaactaaat tagatctcct acgacgacga atagaaaccg  39060
gtgaggttac gtgggacgat gcatggacaa catttaaaag agaaacgggg gatatgttgg  39120
catcgggggga cacgtacgct acttccgtag atagtataaa ggcactccag gcatcggcgt  39180
ctgtggttga catgctttgt tccgaacccg aatttttttt attgcctgtg gaaacgaaaa  39240
accgtctcca aaaaaagcaa caggaacgta aaacggcgtt ggatgttgtg ttgcaaaaac  39300
aaagacagtt tgaagagacc gcgtctcgct tacgagcttt aattgaacgt attccaacgg  39360
agagtgacca tgacgttctt cgtatgttat tacgtgattt cgatcaattt acacatttgc  39420
ctatatggat aaaaacacag tatatgacat ttcgaaattt actcatggta cggttaggct  39480
tgtatgcaag ttatgctgag atttttccac ccgcgtctcc aaacggagta tttgctccta  39540
ttcccgccat gtcgggtgta tgtctagaag accaatcccg atgcattcgc gcgcgggtgg  39600
ccgcgtttat gggggaggcg tctgtggtgc aaacgtttag ggaagccaga tcttctatag  39660
acgctttgtt tggaaaaaat ttaacctttt acttggatac tgatggggtt ccacttcgat  39720
atagagtgtg ttataaatca gttggggtta aacttggaac catgctatgc agtcagggtg  39780
gattatcttt acgaccggca cttcccgatg aaggtattgt ggaagaaact acactatcgg  39840
cattacgcgt ggccaatgag gtcaatgagc tacgcattga atacgaatcc gctataaaat  39900
ccgggttttc tgccttttcc acctttgtta ggcatcgcca cgccgaatgg ggtaaaacca  39960
acgcacgcag agccattgca gagatatacg ccggccttat aacaacaaca ttgacacgac  40020
aatacggggt tcattgggac aagcttattt attcttttga aaaacaccac ctaacttctg  40080
taatgggcaa tggactaact aaaccaatcc agagaagggg tgatgtacgc gtattagagt  40140
taaccctatc tgatattgta actattttgg ttgccacaac cccggtacat cttctcaatt  40200
ttgctagatt ggatttaatt aaacagcatg agtatatggc ccgtaccctc agacccgtaa  40260
tcgaggccgc atttagaggt cgtttactcg ttcgctcatt ggatggagac ccgaaaggca  40320
atgcccgggc ctttttttaat gccgccccat ccaaacataa actcccgtta gctcttggat  40380
```

-continued

```
caaaccaaga tcctaccggc gggagaatat ttgcatttcg gatggcagat tggaaacttg  40440
ttaaaatgcc acagaaaata acggatcctt ttgcgccatg gcaactttcc cccccccccg  40500
gggtaaaggc caatgtcgat gcagttaccc gtataatggc aacagatcgt cttgcgacca  40560
ttactgtact tgggcgcatg tgtctcccgc caatttcctt agtgtcaatg tggaatacgc  40620
tgcaaccgga ggaattcgca tacagaacac aagatgatgt ggacattata gttgatgcga  40680
gactggattt gtcatccacg cttaatgcaa gatttgatac cgctcccagc aataccacgt  40740
tagagtggaa tacagaccgt aaagtaatta cagatgctta tattcaaacc ggggcaacga  40800
cagtttttac agtaacgggg gcggcaccaa ctcacgtttc taatgtaaca gcgtttgaca  40860
tagcaactac ggctatttta tttggggctc ctttggttat tgccatggaa cttacatccg  40920
ttttttcaca aaattccgga cttactttgg ggttaaaatt attcgattcc cggcatatgg  40980
ctacagattc gggtatatcc tcagccgtat ctcccgatat tgtttcttgg gggttacgtt  41040
tactgcatat ggatcctcac ccaattgaaa atgcatgttt aattgtccaa ctagaaaaac  41100
tgtccgcgct cattgcaaac aaacctctta caaacaatcc cccgtgttta ctgctattgg  41160
acgaacatat gaatccctct tatgttttat gggaacgaaa agactcgatt ccagctccgg  41220
attatgtggt cttttggggg ccagaatctc ttattgattt gccgtacatc gactccgatg  41280
aggactcttt cccctcgtgt cccgatgatc cattttactc gcaaattatt gccggttatg  41340
cgccccaagg ccccccaaac ctcgacacaa ctgattttta cccaacggag ccactattta  41400
agtctcccgt tcaagttgtt agaagttcca aatgtaaaaa aatgcccgtc cggcccgcgc  41460
agcccgcgca gcccgcgcag cccgcgcagc ccgcgcagac cgtccagccc gcgcagccca  41520
tagaaccggg cacacaaata gtggtacaaa attttaagaa accccaaagc gtaaaaacaa  41580
cccttagcca aaaagatatt cccttgtatg tggaaaccga atcagaaacg gctgtgctta  41640
tacctaagca attaaccacc tccattaaaa caaccgtttg taaaagtatt accccaccaa  41700
ataaccaatt gtcggattgg aaaaataatc cacagcaaaa ccaaacgtta aaccaagcgt  41760
tcagtaaacc aatacttgag attacctcca ttccgacaga tgactcgata tcttaccgga  41820
cttggattga aaaatcaaat caaacacaaa aacggcatca aaatgaccct cgaatgtata  41880
actccaaaac agtattccac cctgtaaata accaattacc ttcttgggtt gacacggcag  41940
ccgatgcccc ccaaacggac ctattgacaa actataaaac aagacagccg tcgccaaact  42000
ttccgcggga cgtacacaca tggggcgtat cttctaaccc gtttaactca ccgaacagag  42060
acctatatca aagtgatttt agtgaacctt ctgacggcta tagcagtgag agtgaaaatt  42120
ctatcgtact aagtctcgac gaacatcggt catgtcgcgt tcctaggcac gtacgcgttg  42180
ttaatgccga tgtagtcacc ggtcgacgtt atgtccgagg gaccgccttg ggagcactgg  42240
cactgttaag ccaggcatgt cggcgtatga tcgacaacgt tagatataca cgtaaacttt  42300
taatggacca cacggaagat atatttcaag gcctggggta tgttaaattg ttattagatg  42360
gaacatatat ataaagtagc gcctattaaa gaaaaaaaaa aaacaacgat tattttctgt  42420
gtatttttat ttacacccta cgacttcttg aagcgtttcc agattgtccc gtgtgtgaca  42480
aggtctgtcc cttacccccc tggggggtat tttgggttgg gggcggggta gactgtggca  42540
cgccttgggc cgcgggcggt gatccggttg ttggctggac agtgcttgac tgtgctccct  42600
gttgcggttg ttgtccagaa gaccccgaca ccacgtgttg ctgttgtcca acggatgccg  42660
acgtcgtttg aggtgggggg tgttgcgggg atgatcccga aaacgccaac gcggcgggct  42720
```

-continued

```
gttgtaaagc agactgatcg gcgctctgtg ttttttgcgg caatatagta ggccccgaga  42780
ttcccaaact catggatgga tttgggggtt gtggtcgtat aatacgcggg ttaaacgtac  42840
gttttaagcc aaccgttggt cttaaccatg tcatagggtc agtctcggca aacatggccg  42900
ttcggcgtat cgtatttgca ttatggttag cgcgtgcacg cgcggcactg gccgcggctc  42960
ccacggtgta aatgcttctg gcatcagcga tgtccacacg gtgaccaggt tgcaaaggtc  43020
cactggcgtt taaaagtcgt attaaagcaa cgggggtgta agccgcaatt gcttccaccg  43080
aaaatgtggt ggggttgctg ggatcaaaga ctacacgaga cgatgcgggt tgtgtcatcg  43140
tttattagtt tacgggacaa tcgataacag catacacgta catctgcgca ggatatgtac  43200
ggaaaggcaa tttatttcca gaaaagcacc gcccctaata caactaccag tacaattaca  43260
atgaacaggg catatgtcac gttagctacg ggtagagcaa gtttccagac acgcgtagtt  43320
tgggtatcgg gtaacgcagg tttaatgtca ctttgcattt gaacagacgt gtttggactt  43380
ccgttctcgg gtggggatct gaatgaaggc cgccagcgta tatattcatc caaattattg  43440
ccagtttcct tatacatgta tgcatccgtg gcgcgggcca taagtttaat ggtgcgagat  43500
ggatcttccg gtcccataaa acgaaaggat aactgaacat atggcattcg cacaaagcag  43560
ttcacccaca ttaaagcctg gagaggtcgg cggtcaatac ccccacctcg tttaattgat  43620
tccaaagcag ataggttgat accggtactt aacgttgaac taagaatcac gttattactg  43680
tcaatggaca cttcagccac tggtgcgtta gtcggacgaa aaaaaaaacc ttgaaatagc  43740
acagacaccc ccgtattttg aatttttatg taagggtcac aatctacttg cgcccaattc  43800
gccattaaac gcataatata ctctaccgga aaggcttcgg atacgttgtc ttcgccgtta  43860
aactgaaaaa cacaacgggc gggggggcgt tgtggatcaa atattggaag atccccatcg  43920
caacattgaa gagcgcttgg taccaccaac cgaatacgtt gtaaaagatt atctccgcaa  43980
cccctcctgc gttcactccg tacatacgtt ctccgtgaca tattgatcta aggttgcaaa  44040
ccaaggcaca cgcgtgaagt atttagacca tttatcgtgg gatataggag gagtttggag  44100
tgatccaccc cctgacgact tattaatgcg tttattttcc ccatgtatta agcatccttc  44160
aatatttcat gcaaatctag aaatttggcc atgactcccg caaagcgttc acggcgacgg  44220
gtcacgctgg cactatgttc acatggaaca acataagcag atttttctga atcgttactt  44280
tctttatgtt ttaaaacgga cgccaggcga ctggtaaatg atatataatt taattgagcg  44340
tcagttgtag gtagaattgc ttctatttcc gggggaatta aattttcaaa ccaaacggaa  44400
agagtaaagg tgctatcagc aggaaaatac tttgactcca gtgcatcgat atttaataga  44460
ttaacatcgg tgtctgtaat taaatcgcgg gccctcatcc cagagatgga tcgggtagaa  44520
tcagaagaac ccatggatgg attcgaatcg cccgtattct ccgaaaatac atcttctaat  44580
tccggatggt gttccgacgc attttccgat tcgtacatcg cttataatcc agcccttctg  44640
ctaaaaaacg atttgttatt ttcagaattg ttatttgcct cccacttaat aaatgttccc  44700
cgtgcaatag aaaacaacgt cacttatgag gcctcttcgg cggtaggtgt ggataatgaa  44760
atgacctcaa gtaccactga atttatagaa gaaattggag acgttttggc gttagacaga  44820
gcctgtttgg tctgcagaac gcttgatttg tataaacgta aatttggact gacaccggaa  44880
tgggttgcgg actacgccat gttatgtatg aaaagtctgg catccccgcc ctgtgcagtt  44940
gtcactttta gcgctgcctt tgaatttgtg tatcttatgg atcgttacta cctgtgccgt  45000
tataacgtta ctttggttgg gtcctttgcc aggcgcacgc tttccctgtt agatatacaa  45060
agacattttt ttttgcatgt atgttttcgt accgatggag ggttaccagg tatacgaccg  45120
```

-continued

```
cccccggta aggaaatggc caacaaagta agatattcca attactcctt ttttgtacag  45180
gcggtagtta gggctgcatt actatcgatc agcacgtctc gtttagacga aaccgaaacg  45240
cgtaagtcat tttactttaa tcaggacgga ctgactggag gccctcaacc tttagcggcc  45300
gccttggcta attggaaaga ttgcgcgcgg atggttgact gttcatcatc ggaacatcgc  45360
acaagtggga tgattacctg cgcggaacgt gcattaaaag aggatataga gtttgaagat  45420
atattaatag acaaacttaa aaaatcgtct tacgtagaag cagcttgggg ttacgcagac  45480
ttggctttat tattactgag tggggttgct acttggaatg tagacgagcg tacaaattgt  45540
gctatagaaa ctcgcgttgg atgtgttaaa tcatactggc aggcgaaccg gattgaaaac  45600
tccagggacg ttccaaaaca attttccaaa tttacgagcg aggatgcctg tcccgaagta  45660
gcatttgggc ctattttgtt aactacctta aaaaacgcaa agtgccgtgg tcgcacgaat  45720
accgaatgca tgttatgttg tttattaacc atagggcact attggatcgc tttgcggcag  45780
tttaaaaggg atatattagc atactcagca aataacacaa gtttatttga ctgtatcgaa  45840
cctgtaatca atgcatggag cctagataac cccattaaac ttaaatttcc atttaatgat  45900
gagggtcgat tcataaccat tgtaaaagca gcaggttccg aggccgtata taaacattta  45960
ttttgcgatc tcctatgcgc tctctcggaa ttacagacaa accctaaaat tttatttgcc  46020
catcctacaa ccgcggataa ggaagtgttg gagttatata aagcccaact ggctgcacaa  46080
aacagatttg aaggtcgtgt atgtgctggc ctgtggacat tggcgtatgc atttaaagcc  46140
taccagattt ttccacgcaa accaaccgcc aatgccgcat tcatacgaga tggaggactt  46200
atgcttcgac gacatgcaat atcgctggtc tccctcgaac acaccctatc gaagtatgtc  46260
taggcgatat aaatccgtat ctcggagcgg gccttcgatg cgtgtacgct ccagaacgcc  46320
atgccgccgt caaaccattc gaggaaaact tatgtcaaag gagcggtctg tgtaccgcca  46380
ttattttaat tacatcgcaa ggtccccccc agaagaacta gctaccgtta gaggcttaat  46440
cgtgccaatt attaagacga cccctgtcac ccttccgttt aacttgggtc agacagtggc  46500
ggataactgc ctgtcgttat ccggaatggg ttatcattta ggtctcggag gttattgtcc  46560
gacatgcact gcatctggag aaccgcgtct atgtcgaacc gatcgggcgg ctctgatact  46620
agcatatgtt cagcagctta acaacatata cgaatatcgt gtgtttcttg catccatttt  46680
ggcgctatca gaccgagcca acatgcaagc agcgtccgct gaacccctat tgtcgagcgt  46740
attggcacaa ccggaattat tttttatgta tcatattatg agggaggggg gcatgcgaga  46800
tatacgcgta cttttttatc gtgatggaga tgccggaggg tttatgatgt atgttatatt  46860
tccgggggaaa tctgttcacc tccattacag actaatcgat catatacagg ccgcgtgtcg  46920
ggggtataaa atagtcgcac acgtttggca gacaacattt ttactgtcgg tatgtcgcaa  46980
cccagaacaa caaacagaga ctgtggtgcc atccattgga acatcggacg tttactgtaa  47040
aatgtgtgac cttaactttg atggagaatt gcttttggaa tacaaaagac tctacgcatt  47100
atttgatgac tttgttcctc ctcggtgatt tcagcttcag tgttcatttt attatcccag  47160
cacggggcgt gtatacaaac aaagcctgcc gcctgcaagc ggtttagcat tttaacgtta  47220
acaactcgtg tctctggaat aaaacgtttt aaaagccgtt ctgtgagttt agtgtcgttt  47280
ccaaataacg ccttaaaagt tacactcgcc gtcccaatga gatgagaaaa ataatagtca  47340
atgtttaaag acagcccgtg tgatgttacg tgaatgggat cttccgctaa gtcagatatt  47400
attaacttac gctttgcttc cccacaccgt ttacctgcgg tattctgtaa aggatctcca  47460
```

-continued

```
cgtagcaaag ctacactttt tgcatcagcc tccacttcgt ctgtgggggc cacaataaca  47520
taagggatgc gttctcgaac gtttgggatt tgaccctgtc tcattactaa tttataatat  47580
actgttaagt gagccaagcg acggtttatg taggcggatg gtggacgact aagctcggcc  47640
gtcataacaa acttattaat atccaatttg ggtgatgtaa tctggcgatg tgcatctgca  47700
attatgcgtc caaacccggc catcccagac ggcatggccc gtctattcca ttcagcaatg  47760
gaaacacacg acgcctccgc cgcagcacgc gagacggtgt cgtcatataa caacagttct  47820
acaagtttgc gggcataatc gttaataaat tgacagttgt tttttctaac caagtcgact  47880
cccttcatta aaacctttcc gccgtaaatt accccaatgt actttttctt tgttataagc  47940
aaaagtttta taaaagtttt ttcacactcc aactttatag gaggacaaaa cagagccgtt  48000
gaaattatat gtgccatttt ctcgccgatt ttagctatcc cctcaacact aacacccttg  48060
aatcggataa acacagaatc cgtatctcca tatataacct ttacctcgta cgctttttgg  48120
gagagaacgc tactttcaat gtctggaaac gctgtaataa aacgttcaaa tgcggcccag  48180
ttattatgaa tataatctct ggtacttaat aacatttgac ggccaattgt agtgacagtg  48240
gccgctacgt ataaacatgg cagaaatccc tgcgcaactc cagtaaaacc gtacacggaa  48300
ttacaaacta cttttatcgc ggcttgttgt ttgtctaata acactgcttc atctgaagaa  48360
cttccgggta tgcgcgctct aatagccttg cgcatagcca accagtcttt taaaagaaca  48420
cccagcagac tttctcgaac gttagagcgc acaaaaaaaa gacgttttcc tccaactgta  48480
aaggtggcat aatcggatgg attcaaacgt ttaaccgtct caaaatttaa cgttagcgtg  48540
gtaaaacata agttatgggc ctgaattata cttggatata aacttgcaaa atccaatacg  48600
accaccggat cgatataaaa tcccgtatca gggtcaaaaa ccctggctcc tttatatcct  48660
acatttcgcc cacttgacgt accagtggga gaaacgctct cgtcttcatc catctcttcc  48720
tcaacatccc cgacatcggg aataacatcc ttatattcaa aagtagctgg gtatccccca  48780
tcgggtaaaa taaatcctcg agacgaagcc agtcctaata aacaggtgta aatcctaacc  48840
tgctgtccgt cgtaaatagc cttggttaaa gtaattctag ctagccttgc aaccgcggat  48900
aactcaaggt gtggtaaata tttaaaaaac agtttcccca caagagccga gtcttgtata  48960
caatattcac caataattcc tcgtgtattc ggtccactag cgtaatatcc cggaatgtct  49020
ttgtagggca aatctctctt ggactcattt agagcttcac gtgcaaccga atctaattta  49080
taactcgaga gttttaattt ttcagttgca attgcataca tatccagaga tatgagaccg  49140
ttgatcttta ccttgcttcg tcgctgaaat ccggatttgc caacatccca tatcttaaac  49200
agacccccac ggtttatact gccataacca tcaagcttga gactgtatat agaattaagt  49260
ttctccataa taaacgccca atcaaaatta acaatgttat aacctgtggc aaactcggga  49320
gcgtactgtt ttacgagggt cataaatgca attaatagct cgaattcact atcaaactcc  49380
agcacagtcg gctccggtaa ccccgcgtcc ttcatttctt gtacatacct ttgtggtaag  49440
tcacaagagc caagggaaaa cagtaaaatg tgttctaaag actgtcgagg gattgaatat  49500
aatagacaag aaatttggat tacaagatcc tccagatgtg ttgcatcggg aaacgccagc  49560
tcattagatc ctcctgattt acattcaata tcgaaacata acaacttgta gtcaggccat  49620
gagtcatcgt ttggtatagc ctgcagatta tccgacatgc agtcaatttc aacgtcgctt  49680
aacgttaatt ggcgacttgc cggtcgaact cgaacacgtt ccccatcaac tccaggtttt  49740
agttgatacc aaccaaaact aacaaagccg ggattatcca ttagaaaacg agtggtagcg  49800
tctacccgac cttcatactt tttcaactcc gggtgaaagt tatcacaaag ataatttgta  49860
```

-continued aatttagatg agggagaata caccctgtaa aacgcacatg gctgtgtatc gtagtaataa 49920
acatctgtgc gctcaataac ctcaacgcga aagctttctg gagatgcgct tttaaacgag 49980
gtaccatgaa aagcgttctt gtctccattt aacgttgcat cattttgtgt tatcatagaa 50040
ctgcgtaaac actcggcaag taatacagat aactcgctac cggaacgtat gccacaagcg 50100
gtatccacct cggctttgtt tatataaaaa tattgacaga tgccgtatac atgaactgcc 50160
acccttttc cacatcggga catgccaagt aaagtaataa cggtaccaag cggtcgtgtt 50220
gcagttgcaa accgggatac atctccatta gacgcggctt ctgttgtttc gacaatatca 50280
tatacatgga atgtgttaaa gcgggggtca aacttatccc cacgaaagtc gatttccccc 50340
caaatattca cgcgtctagg ccaggggctg gaacaacgaa aatccagaat cggaacttct 50400
tttccattac agtaaacttt aggcggtcga ctaagtgtac cgacgtgaac cccctttcgt 50460
tcttccatgg gcacatcttc atctaaacat ttaggggcca aaaattgaaa cgatgacatg 50520
gtagttttgt aactatgaag aaattctctg ttactaccgc gcccggttct tgggttatat 50580
ttaatccctg atgcttgggt taaaaaggga ttacaaaacc ccgttctgat cgccatttta 50640
tgttaacgat tgataatctt gtaaaaagcc agtgttactg agtaacacaa ccccacgccc 50700
ttctaataca taaagtgtaa tcacgtgatt tgttgtggtt tccgcatatg taatacccgt 50760
ttaaaagcct ctcttcttaa tgtatcgaca gactgggttt tgggtggtca tttgaccctg 50820
ccaacaaccc cccattatta cgagtacttc accaaaatgg aaaatactca gaagactgtg 50880
acagtgccca cggggcccct gggttacgtt tatgcgtgcc gggttgaaga tttggatctg 50940
gaggaaattt catttttggc cgctcgtagc acggactctg atttggcttt attacctttg 51000
atgcgtaatt tgaccgtgga aaaaactttt acatccagcc tggcggtggt ttctggagca 51060
cgcactacgg gtcttgccgg agctggtatt accttaaaac tcactaccag tcatttctat 51120
ccatctgtct ttgtctttca cggaggcaaa cacgttttac ccagctccgc ggccccaaat 51180
ctcacacgcg cgtgtaacgc ggctcgagaa cggtttgggt tttcacgctg ccaagggcct 51240
cctgttgacg gtgctgttga gacgaccggc gctgagatat gcacccgcct tggattagag 51300
ccagaaaata caatattata cttggtggtc acggcattgt ttaaggaagc cgtatttatg 51360
tgcaacgtgt ttctgcatta tggaggactc gatattgttc atattaacca tggggatgtt 51420
atacgtatac cgttatttcc ggtacaactt ttcatgcccg atgttaaccg tctggtaccc 51480
gacccattca acactcatca caggtctatc ggagagggtt ttgtataccc aacacccttt 51540
tataacaccg ggttgtgcca tttaatacat gactgtgtta ttgctcccat ggccgttgcc 51600
ttgcgcgtca gaaatgtaac tgccgtcgcc cgaggagcgg cccaccttgc ttttgatgaa 51660
aatcacgagg gggcagtact cccccctgac attacgtaca cgtattttca gtcctcttca 51720
agtggaacca ctaccgcccg tggagcgcgt cgaaacgatg tcaactccac gtctaagcct 51780
agcccatcgg gggggtttga aagacggttg gcgtctatta tggccgctga cacagccttg 51840
cacgcagaag ttatattcaa cactggaatt tacgaagaaa ctccaacaga tatcaaagaa 51900
tggccaatgt ttataggcat ggagggcact ttgccaaggc taaacgctct ggggtcatat 51960
accgctcgtg tggccggggt cattggtgcg atggttttca gcccaaattc tgcgttgtat 52020
ctaactgagg tggaggatag cgggatgacc gaagccaagg atgggggacc gggtccatca 52080
tttaatcgat tttaccagtt tgccggacct catttagctg cgaatcccca aacagatcga 52140
gatggccacg ttctatccag tcagtctacg ggttcatcaa acacagagtt tagcgtggat 52200

-continued

```
tatttggcac tcatttgtgg atttggagca cccctgttgg cgcgactgct tttttatcta  52260
gaacgctgtg acgctggtgc gtttacaggg ggtcacgggg atgcgttaaa atatgttacg  52320
gggacctttg actctgaaat tccatgtagt ttatgtgaaa aacacacgcg gccggtatgc  52380
gctcacacaa cagtacaccg acttagacaa cgcatgccgc gatttggaca agccacccgt  52440
caacctattg ggtgtttgg aacaatgaac agccaatata gcgactgcga tcctctagga  52500
aactatgctc catatttaat ccttcgaaaa cccggggatc aaacggaagc agcaaaggca  52560
accatgcagg acacttatag ggctacacta gaacgcttgt ttatcgatct agaacaagag  52620
cgactactgg atcgcggtgc cccatgttct tccgagggac tatcgtctgt cattgtggat  52680
catccaacgt ttcgtcgcat attagacaca ctgcgtgcgc gtatagaaca gacaacaaca  52740
caatttatga aagtgttggt tgagacccgc gattataaga tccgtgaagg attatccgaa  52800
gccacccatt caatggcgtt aacgtttgat ccatactcag gagcattttg tcccattacc  52860
aattttttag ttaaacgaac acacctagcc gtggtacaag acttagcatt aagccaatgt  52920
cattgtgtat tttacggaca gcaagttgag gggcggaact ttcgtaacca attccaacct  52980
gttttgcggc ggcgttttgt tgacctgttt aatggggggt ttatatcaac acgctctata  53040
accgtaacat tatctgaagg tcctgtatcc gccccaaatc cgacattggg acaagacgcg  53100
cccgcggggc gtacctttga tggggattta gcgcgcgtaa gcgtggaagt tattcgggat  53160
atacgagtta aaaatagggt cgttttttca ggtaactgta caaatctctc tgaggcagcc  53220
cgggcaaggc ttgtaggcct tgcaagtgcg taccaacgcc aagaaaaaag agtggatatg  53280
ttacacgggg ccctagggtt tttgcttaaa cagtttcacg gcctgttatt tcctcggggt  53340
atgccaccaa acagtaaatc cccaacccg cagtggtttt ggaccctgtt acaacgcaac  53400
cagatgccgg cagataaact tacacacgaa gagattacca ctattgcagc tgttaaacgg  53460
tttaccgagg aatatgcagc aataaacttt attaatctac ccccaacctg cataggagaa  53520
ttagcccagt tttatatggc aaatcttatt cttaaatact gcgatcattc acagtacctt  53580
ataaatacct taacttctat aattacgggt gccaggcgcc cgcgtgaccc atcatccgtt  53640
ttgcattgga ttcgtaaaga tgtcacgtcc gccgcggaca tagaaaccca agcaaaggcg  53700
cttcttgaaa aaacggaaaa cttaccggaa ttatggacta cggcttttac ttcaactcat  53760
ttagtccgcg cggccatgaa tcaacgtccc atggtcgttt taggaataag cattagtaaa  53820
tatcacggag cggcaggaaa caaccgcgtc tttcaggcag ggaattggag cggtttaaac  53880
gggggtaaaa atgtatgccc gctatttaca tttgatcgca ctcgccgttt tataatagca  53940
tgtcctagag gaggttttat ctgccccgta acaggtccct cgtcgggaaa tcgagaaacc  54000
accctatccg accaagttcg cggtataatt gtcagtggcg gggccatggt tcaattagcc  54060
atatacgcca cggttgtgcg tgcagtgggc gctcgagcac aacatatggc atttgacgac  54120
tggttaagtc ttacagacga tgagttttta gccagagact tggaggagtt acacgaccag  54180
attatccaaa ccctggaaac gccctggacc gtagaaggcg ctctagaagc agtaaagatt  54240
ctagatgaaa aaacgacagc gggagatggg gaaacccccca caaacctagc atttaatttt  54300
gattcttgtg aaccaagcca tgacaccaca tctaacgtat taaacatttc agggtcaaac  54360
atttcagggt caactgtccc tggtcttaaa cgaccccccg aagatgacga actctttgat  54420
cttagtggta ttcccataaa acatgggaac attacaatgg aaatgattta acctccctct  54480
ttatccaatt aaagcccaca cgcgggtgag tgtacgtaat aaacaagtca atattacata  54540
ttctgttgtg ttttcttttt ttgtgtgtag tccttaccca tatgacctgt aatatagtgt  54600
```

-continued

```
gtctccaacc attcagctta cagtccagtg gacagtaaca gcccgataac atggaattgg  54660
atattaatcg aacattgttg gttctactgg gtcaagttta tacgtacatc tttcaggttg  54720
aactgctacg tcgatgtgat ccaagggtgg cgtgtcgctt tttatatcgg ttagcggcta  54780
actgtttgac agttcgttat ttattaaagc tgtttctccg ggatttaat acccagctaa  54840
aatttggaaa cactcccacg gtttgtgcac tgcattgggc attatgttat gtaaagggag  54900
aaggtgagcg tttgtttgag ttgctacaac attttaaaac gcgttttgtt tatggtgaga  54960
ctaaagactc aaactgtatc aaagattact ttgtctcagc gtttaactta aaaacctgcc  55020
aatatcacca tgagctgtcg ttaacaacat acggaggtta cgtatcgagt gaaattcagt  55080
ttttacacga cattgagaat tttttaaaac agcttaatta ctgctatatt atcacgtctt  55140
ctcgtgaggc gctaaacaca ttggaaaccg tgacgcggtt tatgacagat actataggaa  55200
gcggtctaat accacccgtg gagttgtttg atccggcgca tccatgtgct atatgttttg  55260
aagaattatg tataacagct aaccaaggtg agaccttaca tcgtagatta ttaggatgta  55320
tctgcgatca cgttactaag caagttcggg ttaacgtgga tgttgacgat attattcggt  55380
gtttaccata tatccctgat gtaccggata tcaaacgtca atccgccgtt gaagcgttac  55440
gaacacttca aaccaagacg gtagtcaatc ccatgggagc aaagaacgat acgtttgacc  55500
aaacatacga aattgcgagc accatgcttg attcttataa tgtttttaaa cctgcccctc  55560
ggtgtatgta cgccatcagc gagcttaaat tctggttaac gtctaattcc actgaaggac  55620
cccaacgtac tttagacgtg tttgttgata atttggatgt attaaacgaa catgaaaaac  55680
acgcagaact tacagccgta acggttgagt tggcgttatt tggaaaaact cccatacact  55740
ttgatagggc gttttctgaa gaactcggat ctctggatgc aattgatagt attttggttg  55800
gcaatcgctc atcctcacca gacagtcaga tagaagcatt aattaaagcc tgttatgccc  55860
atcatctatc gtcgcctctc atgcgtcaca tttctaaccc gagtcatgat aacgaagccg  55920
ccttacgcca acttttagaa agagttgggt gtgaggatga tttaaccaaa gaggcgagtg  55980
acagcgctac agcatccgaa tgtgatctga acgatgatag tagcataact tttgctgttc  56040
atggatggga aaacctgtta tccaaagcaa aaattgacgc tgcggaaaga aaacgagtat  56100
atcttgaaca tctgtctaag cgctctctaa ccagcctcgg tagatgtatc cgcgaacagc  56160
gccaagagct agaaaaaaca ctcagggtaa acgtttatgg agaggcctta ttgcagacat  56220
ttgtttcgat gcaaaatggg tttggggcac gaaacgtgtt tttagctaag gtttcccagg  56280
cagggtgtat tatcgacaat cgcattcagg aagcggcctt tgatgcacat agatttataa  56340
ggaatacctt agttcgacat acagtagatg cggctatgtt acctgcactt acacataaat  56400
tttttgagtt ggtcaacggc ccattgttta atcacgatga acaccgtttt gcacaacccc  56460
ctaacaccgc cttatttttt accgtggaaa acgttggcct atttccgcac ttaaaagagg  56520
aattggcaaa gtttatgggc ggtgtcgttg gttccaactg gcttctcagt ccatttaggg  56580
gcttttattg cttttctggg gtagaaggcg ttacttttgc acagagactt gcctggaaat  56640
atattaggga gcttgtgttt gcaaccacac tattcacctc tgttttccat tgtggggagg  56700
tgcggttatg tcgcgttgac cgtctaggta aggatccacg cgggtgcacg tctcaaccta  56760
aaggtatagg cagttcccac ggacccttag acggcattta tttaacgtac gaagaaacat  56820
gtccccttgt ggctattatt caaagtggag aaacagggat cgaccagaat accgtcgtaa  56880
tctacgattc agacgttttt tctcttctat acaccctaat gcagcggctg gctccggatt  56940
```

-continued

```
caacggaccc ggcgttttca taacctccgt tacgggggtg tggttatgct ttttatgcat  57000
attttctatg tttgttacgg cggttgtgtc ggtctctcca agctcgtttt atgagagttt  57060
acaagtagag cccacacaat cagaagatat aacccggtct gctcatctgg gcgatggtga  57120
tgaaatcaga gaagctatac acaagtccca ggacgccgaa acaaaaccca cgttttacgt  57180
ctgcccaccg ccaacaggct ccacaatcgt acgattagaa ccaactcgga catgtccgga  57240
ttatcacctt ggtaaaaact ttacagaggg tattgctgtt gtttataaag aaaacattgc  57300
agcgtacaag tttaaggcga cggtatatta caaagatgtt atcgttagca cggcgtgggc  57360
cggaagttct tatacgcaaa ttactaatag atatgcggat agggtaccaa ttcccgtttc  57420
agagatcacg gacaccattg ataagtttgg caagtgttct tctaaagcaa cgtacgtacg  57480
aaataaccac aaagttgaag cctttaatga ggataaaaat ccacaggata tgcctctaat  57540
cgcatcaaaa tataattctg tgggatccaa agcatggcat actaccaatg acacgtacat  57600
ggttgccgga acccccggaa catataggac gggcacgtcg gtgaattgca tcattgagga  57660
agttgaagcc agatcaatat tcccttatga tagttttgga ctttccacgg gagatataat  57720
atacatgtcc ccgtttttg gcctacggga tggtgcatac agagaacatt ccaattatgc  57780
aatggatcgt tttcaccagt ttgagggtta tagacaaagg gatcttgaca ctagagcatt  57840
actggaacct gcagcgcgga actttttagt cacgcctcat ttaacggttg gttggaactg  57900
gaagccaaaa cgaacggaag tttgttcgct tgtcaagtgg cgtgaggttg aagacgtagt  57960
tcgcgatgag tatgcacaca attttcgctt tacaatgaaa acactttcta ccacgtttat  58020
aagtgaaaca aacgagttta atcttaacca aatccatctc agtcaatgtg taaaggagga  58080
agcccgggct attattaacc ggatctatac aaccagatac aactcatctc atgttagaac  58140
cggggatatc cagacctacc ttgccagagg ggggtttgtt gtggtgtttc aacccctgct  58200
gagcaattcc ctcgcccgtc tctatctcca agaattggtc cgtgaaaaca ctaatcattc  58260
accacaaaaa cacccgactc gaaataccag atcccgacga agcgtgccag ttgagttgcg  58320
tgccaataga acaataacaa ccacctcatc ggtggaattt gctatgctcc agtttacata  58380
tgaccacatt caagagcatg ttaatgaaat gttggcacgt atctcctcgt cgtggtgcca  58440
gctacaaaat cgcgaacgcg ccctttggag cggactattt ccaattaacc caagtgcttt  58500
agcgagcacc attttggatc aacgtgttaa agctcgtatt ctcggcgacg ttatctccgt  58560
ttctaattgt ccagaactgg gatcagatac acgcattata cttcaaaact ctatgagggt  58620
atctggtagt actacgcgtt gttatagccg tcctttaatt tcaatagtta gtttaaatgg  58680
gtccgggacg gtggagggcc agcttggaac agataacgag ttaattatgt ccagagatct  58740
gttagaacca tgcgtggcta atcacaagcg atattttcta tttgggcatc actacgtata  58800
ttatgaggat tatcgttacg tccgtgaaat cgcagtccat gatgtgggaa tgattagcac  58860
ttacgtagat ttaaacttaa cacttcttaa agatagagag tttatgccgc tgcaagtata  58920
tacaagagac gagctgcggg atacaggatt actagactac agtgaaattc aacgccgaaa  58980
tcaaatgcat tcgctgcgtt tttatgacat agacaaggtt gtgcaatatg atagcggaac  59040
ggccattatg cagggcatgg ctcagttttt ccagggactt gggaccgcgg gccaggccgt  59100
tggacatgtg gttcttgggg ccacgggagc gctgctttcc accgtacacg gatttaccac  59160
gtttttatct aacccatttg gggcattggc cgtgggatta ttggttttgg cgggactggt  59220
agcggccttt tttgcgtacc ggtacgtgct taaacttaaa acaagcccga tgaaggcatt  59280
atatccactc acaaccaagg ggttaaaaca gttaccggaa ggaatggatc cctttgccga  59340
```

-continued gaaacccaac gctactgata ccccaataga agaaattggc gactcacaaa acactgaacc 59400
gtcggtaaat agcgggtttg atcccgataa atttcgagaa gcccaggaaa tgattaaata 59460
tatgacgtta gtatctgcgg ctgagcgcca agaatctaaa gcccgcaaaa aaaataagac 59520
tagcgccctt ttaacttcac gtcttaccgg ccttgcttta cgaaatcgcc gaggatactc 59580
ccgtgttcgc accgagaatg taacgggggt gtaaatagcc aggggggtttg ttttaattta 59640
ttaataaaaa tgtgtattac gttactcatg tgtctccatt acgcatcaca gggggtattt 59700
atacccgata atatacaaaa cgcgttttgt acctctaccg cacccgatat cttaacgggg 59760
ttattatgga atcgtctaac attaacgcgc tacaacaacc gtcgtctatc gcacatcatc 59820
cgtccaaaca gtgcgcttca agtctcaatg aaacagtaaa agattctccc cccgcgattt 59880
atgaagatag gttagaacac acgccggtac aattaccccg cgacggtaca ccccgagacg 59940
tatgttctgt gggacagcta acctgtcgag catgtgcaac gaaacctttt cgccttaacc 60000
gcgacagcca atacgactac ttaaacacat gtccaggggg ccgtcatatt tcactggcac 60060
tggagattat aacgggtcga tgggtttgca tcccgcgtgt gtttccggat accccagagg 60120
aaaaatggat ggcgccatat attattccag accgagaaca accatcatca ggggatgaag 60180
attctgacac cgattaaatt taacttaaat aaaaccttac cacccataaa aacgccttct 60240
gtttgtttaa cacgacaccg cttaacaaaa aaaaaaaaac caaacacgcc ttttatgaat 60300
gtaatacttt tatttgttgg ttaacaccgc cccaccatca tctgatttgc aaacatatcg 60360
gcgtcgtctg ccgtggaccc ctgtattaaa ggggccttgg aactcgcctc cactgcattt 60420
acatcttgtc caactgtatc tgtatgtggg gtgcttgttg tattttggga tgagcataga 60480
cccgaaacgc tttgaagctg ttttaataaa atcgatattc gaggatcccg tgtcccctct 60540
ggtatatttg tatggtgcga caaaggcatt tgtgtcccat tttgtgattt tagctctgta 60600
acctcctgtt gcagttttgc cacaacccca gcaagctctt cgtgctgacc attagaaact 60660
ctgtgtctcc tctgccaata tgatggagaa actcgacgtc tccgatgcgt tatatacgtt 60720
ggttcaccgg gaaaatatat atttgaggga aactctccgt ccatttgaga ctccccacta 60780
taaaaagaat ccaattccct ttgatccatg ctcttgaaat cccgttttcc tggacgacgg 60840
acatcggttt tgtctggaaa atttacacac ggggtctgca agtcaatacc ccgttcggcg 60900
gccaatgcgt tcataaatgc ggacatttgc atttccaaac gattgggtgg tggatatccc 60960
ggaaacccgt acggtccccc gaagtgtccc ggagggcaac cataaccccc tgtattaggt 61020
gggaaggcag gcgggtgtgg agatccatat ggcccgacga tatactgtcc gttatttgga 61080
gctccaattg atacctgcgg atttttagtc tgcccggtta acagctgtga ataatacgcg 61140
gtaggtatca gtacaaattc ccctccggtt ggaacgcccg acgggggctg tggtgagata 61200
ttactagcgt tacctgctac agaagccata tcgctgtcgt tcctacacaa ctgcgtaacc 61260
tttaaatgcg gaacagtctt ttcacaatct tcatttgatt ccccaacacc caacgcgaga 61320
tcgtatatgg gcccgccggg gtggaatgtg gcgtttataa cacccgcgtt gggtaattta 61380
gactccaccc cattaacgtt ggttatccga gcaagtccat atccggtgct agcctgaaga 61440
taaacgtgac ccataattcc ggcttcgcgt ctacgttttg caaccacgtc ccatctatct 61500
cttaaaagca tattgttcac ggctgtggat aataacacct tggcgagttt atcttcgcta 61560
accttccata ctttatttaa acccgcgtag tctttaacca gcgacaataa ccgcgcttta 61620
ctttccatcg ataaaacccg gaatggttca attgaagatt ccggggtaca gtcataattg 61680

-continued

```
accactgttc caacgcgtct tccaacaaca cataacgcaa catgggtaaa aaaattaccg  61740
tctggtatct cattcgggga caatcgtttt gaagacaggg atacggaggg taagtaattt  61800
gtgaccaagt ataacgcacg ttctagcgga gataatacag aatctctatt tccaaaaaaa  61860
ttcgaatggg ccgcttcaaa cagcaccgca tgtagttgag ggcatctaac gatacccaaa  61920
aaaaaaggtc cgcgtatgtc ctcaatgatt gcgattactt cacccacgac acagtctttt  61980
cgatgatcga tgtttattgg tattttacta gtaggcggca aagcggaccg cacaatctct  62040
ggggtaatat ttaattcccc ttcgtccttt gaatataagg ctaaataccc agccacgtat  62100
aacgcttcac agttctcttc gtcagcttca gcagccatta taaacacccc acggaccgga  62160
tagtgaatac tcacggtgtg gaggcaaact gaggaatgac acccaaacag acaaaatata  62220
gaagatcata gtcactgtta acgttgaact gcgcaaggcg gcgactttct tccaatgccg  62280
cccttacacg cggttggtgc attaacattc caagtccccg ttcatattgc aacataacac  62340
tgtcatgtat tgataccacg gcggctatgg gtagggatgt aacattttgt cggcggtgtt  62400
ctaattccaa tgcaattaag cttatgagcc gatcttggta ctgtccagaa gaaatatcta  62460
ttacggttct tcctaaactt ccacgactaa gctgggtatg cgcgtctaaa caaagagcaa  62520
ctaatccagg aaacatttca gtcagctctg tggtccgatt taacgtatac agtggtgcta  62580
tatatcgttc acataaaaat tgaaagttat tattaccgct tttaaacttc ccatcaaacc  62640
ccgtcgctcc gcgcaagatt acattgttgg taggggttcc tgttgcttct gacacaatca  62700
aacccagttg aaaattattt tttagtttat ctccgtatac gttcccgttc cataataagc  62760
gccttaataa taataacgcc gtaatcgtgt caattgttaa ccttaataga gtttggtctt  62820
ccataagaaa cacgttttgg gcccgttcta aatacgccgc ggccgcctgt tgaatcttgt  62880
ccacatatgc ggtatgattg cgatcaataa tgtcattaac cccaggatta aactgtccag  62940
gtgcaggcgg taggacctgc aaccgtataa gcgcatccat aacagaatgt gacgttaagg  63000
cgccttgatc ataccgcccc ccacgagcat gaaactggtc gcgtggtaga cgatcatagc  63060
aaaattgata actgttttta ttttcgtgtg ttgtcatata attcacaaat gtctcagtat  63120
attccggtag gtgctctata aggttcccga aggacgaaac ttgaggttcg tggacactat  63180
tagatgtcct atacattaaa tataaacata ataccgcaca ctcgaacgcg gagtacgctc  63240
tatctccaac atacattctc ccggcggact gtagacatgt taccgttgtg ttcataaacg  63300
tacgggaaat gcgcccgtct ttacaatcaa ctccgcgtgc agctacgggc ctatctaaca  63360
caagccgttc ctgcagagta cgataccatg gcccgaaaac aatccctgga gagttattgc  63420
cccttgccct tcccaagtac accagggtga taaaatccac ttgaaagttt gtatcgtact  63480
gcaacggtgc atcattttg gcaatctgta cctcggggtg tatagactca ttgcgtatta  63540
tttctgtacg tgtacattcc tcagattgtg catctgcttc ttccgcctcg gcagcagccg  63600
tctccaggga atccaaaacc ttggccatgc gcgttagttg ttcttcgagg ggctttaaac  63660
gacgatctat ttccgttggt aacgtaatcg tttccccgcg aaggttgtct aatgcggcaa  63720
cggccgccgc attttttaac gttaacgtat ttttttccaa atcgggattc atacgccctc  63780
ttaactcaaa cgcgggagcc gtccagtagt gtatggggaa gttgggggct ataaagttct  63840
tagtggtaga caaaaatatc ccacatttat tcggaaacga gatagatccg aacccatatc  63900
tcgccgtcat ggtgtctgca gcaaacaaag tcaactggcg tgaatataaa ccggtactgc  63960
tttaaaagct gttttcttac ccatgggaaa acatcccggt tatactttgt aaaattccac  64020
cacaagcacc taaagaaggc cttctaaggg gtaaatccac cccacaagct gcattttctt  64080
```

-continued

```
caaactttgt taaagcggaa cgatggcatg atttcgcacg ctttttcgca agagaacata  64140
cgtgaatttt ctttttgcat agacgtcttc gctctctaac ggaccttatc ggggggggtat  64200
attccgctac attctccaaa tgcgacgcta gcataacaag gtttccatga atcacctttg  64260
ggggtaaccg agttacctgt aacaggttca gaccccgttg agatacaaac acaaggaggg  64320
gggtcaccat tatttcatca gatcccgtgg gtgtggtttc ctttattaaa gccatggtat  64380
ccctcagctg gcgcataccc tcgcaaaact ggtgatactt agtaggggta tgtatattag  64440
cgctaaaacg gcaagatttt aattccacta taaaacaaac ggtctttccg gcaccactgg  64500
attccgtttg tataatacaa acacaatcgg ggcgtcggcg tcccaaattt acttcaaacg  64560
acattgatat gcgtacagcc ctttgaacat ccacgtggga taacggcgac aggagttttg  64620
ccagcctcgg gttgaacgcg tccgcgaaac ctcgacgtac gttatcaata tcctttttga  64680
gtacatcgta aaaacgagtg tggcaacgtt gtcccaaacg aaaacacttg gcccgaattc  64740
gactagcgga catatttgaa gttccgtccc agaagataac ctaagacgcg tttgtctaca  64800
ataaacatgt caacggataa aaccgatgta aaaatgggcg ttttgcgtat ttatttggac  64860
ggggcgtatg gaattggaaa aacaaccgcc gccgaagaat ttttacacca ctttgcaata  64920
acaccaaacc ggatcttact cattggggag cccctgtcgt attggcgtaa ccttgcaggg  64980
gaggacgcca tttgcggaat ttacggaaca caaactcgcc gtcttaatgg agacgtttcg  65040
cctgaagacg cacaacgcct cacggctcat tttcagagcc tgttctgttc tccgcatgca  65100
attatgcatg cgaaaatctc ggcattgatg gacacaagta catcggatct cgtacaagta  65160
aataaggagc cgtataaaat tatgttatcc gaccgacacc caatcgcctc aactatatgt  65220
tttcccttgt ccagatactt agtgggagat atgtccccag cggcgcttcc tgggttattg  65280
tttacgcttc ccgctgaacc ccccgggacc aacttggtag tttgtaccgt ttcactcccc  65340
agtcatttat ccagagtaag caaacgggcc agaccgggag aaacggttaa tctgccgttt  65400
gttatggttc tgagaaatgt atatataatg cttattaata caattatatt tcttaaaact  65460
aacaactggc acgcgggctg gaacacactg tcattttgta atgatgtatt taaacagaaa  65520
ttacaaaaat ccgagtgtat aaaactacgc gaagtacctg ggattgaaga cacgttattc  65580
gccgtgctta aacttccgga gctttgcgga gagtttggaa atattctgcc gttatgggca  65640
tggggaatgg agaccctttc aaactgctca cgaagcatgt ctccgttcgt attatcgtta  65700
gaacagacac cccagcatgc ggcacaagaa ctaaaaactc tgctacccca gatgaccccg  65760
gcaaacatgt cctccggtgc atggaatata ttgaaagagc ttgttaatgc cgttcaggac  65820
aacacttcct aaatatacct agtatttacg tatgtaccag taaaaagatg atacacattg  65880
tcatactcgc gtgtacgtgt ttttcttttt tatatatgcg tcatttatta ccacatcctt  65940
taatcccgcc tttatctccc taaaacggag tggtaatatt aaaagccgcc aagcctgttg  66000
gtgggtgagg aggggtaaag gcacgctgtg tgcataacgt tgcggtgata ttgtagcgca  66060
agtaacagcg actatgtttg cgctagtttt agcggtggta attcttcctc tttggaccac  66120
ggctaataaa tcttacgtaa caccaacccc tgcgactcgc tctatcggac atatgtctgc  66180
tcttctacga gaatattccg accgtaatat gtctctgaaa ttagaagcct tttatcctac  66240
tggtttcgat gaagaactca ttaaatcact tcactgggga aatgatagaa aacacgtttt  66300
cttggttatt gttaaggtta accctacaac acacgaagga gacgtcgggc tggttatatt  66360
tccaaaatac ttgttatcgc cataccattt caaagcagaa catcgagcac cgtttcctgc  66420
```

-continued

```
tggacgtttt ggatttctta gtcaccctgt gacacccgac gtgagcttct ttgacagttc  66480
gtttgcgccg tatttaacta cgcaacatct tgttgcgttt actacgttcc caccaaaccc  66540
ccttgtatgg catttggaaa gagctgagac cgcagcaact gcagaaaggc cgtttggggt  66600
aagtctttta cccgctcgcc caacagtccc caagaatact attctggaac ataaagcgca  66660
ttttgctaca tgggatgccc ttgcccgaca tacttttttt tctgccgaag caattatcac  66720
caactcaacg ttgagaatac acgttcccct ttttgggtcg gtatggccaa ttcgatactg  66780
ggccaccggt tcggtgcttc tcacaagcga ctcgggtcgt gtggaagtaa atattggtgt  66840
aggatttatg agctcgctca tttctttatc ctctggacca ccgatagaat taattgttgt  66900
accacataca gtaaaactga acgcggttac aagcgacacc acatggttcc agctaaatcc  66960
accgggtccg gatccggggc catcttatcg agtttattta cttggacgtg ggttggatat  67020
gaatttttca aagcatgcta cggtcgatat atgcgcatat cccgaagaga gtttggatta  67080
ccgctatcat ttatccatgg cccacacgga ggctctgcgg atgacaacga aggcggatca  67140
acatgacata aacgaggaaa gctattacca tatcgccgca agaatagcca catcaatttt  67200
tgcgttgtcg gaaatgggcc gtaccacaga atattttctg ttagatgaga tcgtagatgt  67260
tcagtatcaa ttaaaattcc ttaattacat tttaatgcgg ataggagcag gagctcatcc  67320
caacactata tccggaacct cggatctgat ctttgccgat ccatcgcagc ttcatgacga  67380
actttcactt ctttttggtc aggtaaaacc cgcaaatgtc gattatttta tttcatatga  67440
tgaagcccgt gatcaactaa agaccgcata cgcgctttcc cgtggtcaag accatgtgaa  67500
tgcactttct ctcgccaggc gtgttataat gagcatatac aaggggctgc ttgtgaagca  67560
aaatttaaat gctacagaga ggcaggcttt attttttgcc tcaatgattt tattaaattt  67620
ccgcgaagga ctagaaaatt catctcgggt attagacggt cgcacaactt tgcttttaat  67680
gacatccatg tgtacggcag ctcacgccac gcaagcagca cttaacatac aagaaggcct  67740
ggcatactta aatccttcaa aacacatgtt tacaatacca aacgtataca gtccttgtat  67800
gggttccctt cgtacagacc tcacggaaga gattcatgtt atgaatctcc tgtcggcaat  67860
accaacacgc ccaggactta acgaggtatt gcatacccaa ctagacgaat ctgaaatatt  67920
cgacgcggca tttaaaacca tgatgatttt taccacatgg actgccaaag atttgcatat  67980
actccacacc catgtaccag aagtatttac gtgtcaagat gcagccgcgc gtaacggaga  68040
atatgtgctc attcttccag ctgtccaggg acacagttat gtgattacac gaaacaaacc  68100
tcaaaggggt ttggtatatt ccctggcaga tgtggatgta tataacccca tatccgttgt  68160
ttatttaagc agggatactt gcgtgtctga acatggtgtc atagagacgg tcgcactgcc  68220
ccatccggac aatttaaaag aatgtttgta ttgcggaagt gtttttctta ggtatctaac  68280
cacgggggcg attatggata taattattat tgacagcaaa gatacagaac gacaactagc  68340
cgctatggga aactccacaa ttccaccctt caatccagac atgcacgggg atgactctaa  68400
ggctgtgttg ttgtttccaa acggaactgt ggtaacgctt ctaggattcg aacgacgaca  68460
agccatacga atgtcgggac aataccttgg ggcctcttta ggaggggcgt ttctggcggt  68520
agtggggttt ggtattatcg gatggatgtt atgtggaaat tcccgccttc gagaatataa  68580
taaaatacct ctgacataaa aacatgtat aataaaaagt cactataaac gtattctcta  68640
caatacttta ttcgcgaata atacacacta cctttgggtt tttttcccgt ccccaaatgg  68700
tgtttggtgc actctaccaa aaaatagagc gcctaaatat gctatataac gcctcccagc  68760
aaaatacggt tcaaaggcat tacccgatat tgtattgtag tacagggcaa tgggaattga  68820
```

-continued

```
tgatcccaat aaacggcata gacgcacagc gccgttatag caggggtctc cagagtacag  68880
ggtatctaag taccgggata tctcatactc atgcctttcc gtgacagaaa catcaaccgg  68940
aacagtatcc gataaaccaa ctcctgtttt tgcaaggcgt aaaattcgca caccttcctt  69000
ttttgcaaga tgtgacgttt ccttgtaaca gggaagctgg gggagtggta agaacaacaa  69060
agtttcagcc aacgtgccaa taaagcccac ttccctcaag aggctgtttg ctgtatccac  69120
aatggtccgt attaaatctt gagcaacttg atccgtgtca tcatcactgg gtaacgcgtt  69180
aacataacta cgcgttaaat cttcaataac ggcataacaa ttaaacgctt cccaccgaga  69240
cagtatatat tgaacaatca cgaaccgttg acaggacgtc agatcacgtc cgtaagcatg  69300
cccgaaaaat ggaagttccc cccgttcgcc atataccgca acaactgcag tatatatcgt  69360
ctcacgggct tcattaagtt catcttcaag tccaggccat tttctggctt taaatataac  69420
ctcgtccgca aaaaaaaccg cacatgataa cgcgcggata caatgagtag tggctttatg  69480
gcgaggatcc caaatgtcca ttacccgggg gatggtccta atctgtacaa agttacttag  69540
tgtaatatga tcggacttct tacgccgtct aggctgtttc tcagaatacg gttcacccga  69600
aatcggcaca tcatctgctt ttacgtcttc cgtaaccaca tcagcagcgc gccgactaac  69660
aattatactt gttttttcat cgtcgttact tccgttaagc gcgtctcgta tctcgggcgt  69720
cccgtcgaat aatccactca ctagctcctg caaactttct ggtaactcca acatacgcat  69780
atacaccaat gaaaaactgg cttcgtttgg tacgtacata aagccatttg tggtattaat  69840
ggcggtgggt gttggaaaca attttagctt attctcgcgc gtaacatcta cccccgccac  69900
caatgttaaa tgcgtcacgg ggagggacac gagataatct gcgagcgtag ggtcctccac  69960
ttcaacatca aatgttccgc aaaggtcgcg atccaccgcc cccgatcccg ctgcaagtaa  70020
ggccactcga tccaaaaaca cgcagttatt attggatgat accgcccatg tcttcccggt  70080
gcgattgagc tcacttcgaa cgtaactggc aacagatctg tcaccgggtc cgaccccgcg  70140
aacaacatgt ccaaattttg cgatctcgcc tccatgtttg cggggtatgg aaattaagca  70200
tcccccgcat ataaaatacg ccctggtagc acgctcgtta aaataaaacg ttacgccgtt  70260
ataagatacg gttgaatgat atggaaattc catattaaag cgtttatcgg aacattaacc  70320
tcgaacttgc cgtcccgtga tcgtgtgatc gccaacctta ggtccacacc gaatatgaga  70380
aatatataac tacacgcaaa cattcaaaac accgtggtat cattaacgtc atatgaaaag  70440
atccaatcaa tccaatcaac cacacctcct accgtttagc acgtcagcta tgtgacatgc  70500
tccaaacata cgtaaacatt tagagagggt gttataacag tctgtcaggc ggggtatatt  70560
ctacataata caaggatcgg ctttaacttt gtcaacattt ttactttgga ctataaactg  70620
cgactgaacg ttatgaaccc accccaagcc cgcgtctcgg aacagacaaa ggacttgctt  70680
agcgttatgg ttaaccagca ccccgaagag gacgcaaaag tgtgtaaatc cagtgataat  70740
tcaccgcttt ataacaccat ggttatgtta tcgtatgggg gtgatacgga cttactatta  70800
agctctgcat gtacccgcac atctaccgta aacaggtcgg cgtttacgca acactccgtg  70860
ttttatatta tatccacggt gttgattcaa ccaatatgtt gtatcttctt tttttttac  70920
tataaagcga cacgctgtat gctcttattc acagccgggt tacttctgac gattctacat  70980
cactttcgac ttattattat gttattgtgt gtctacagaa atatacgatc agacctgcta  71040
cccttatcta catcccagca actgctgctt ggaattattg ttgtgactcg aacaatgcta  71100
ttttgtatta cggcgtatta tactcttttt atagacaccc gggtgttctt tttgattacc  71160
```

-continued

```
ggacacttgc aaagtgaggt tatttttcca gatagcgttt caaaaatact tcctgtgtcg  71220
tggggtccaa gtccagccgt gttactggta atggcggcag ttatttacgc tatggactgt  71280
ttggtggaca cggtatcctt tattgggcca agggtgtggg tccgtgttat gttaaaaaca  71340
tctatttcgt tttagtccat ttcaataaat gtactataat tgttcagtct aaaaataatg  71400
ttgggtattt ataattaccg cccccgtgtt acttggaaac acccatacat atgttccact  71460
ctacatcaaa cttctcgcag ttttcttgtt cccgcacacg tttacacgtc cggattcaag  71520
tcgcaacgct gctgacaaaa tgacaacggt ttcatgtccc gctaacgtga ttactacaac  71580
ggaatctgat cgtattgctg ggttatttaa catcccagcg gggatcattc caactggaaa  71640
tgtgctgtca accatagagg tgtgtgcaca ccgttgcatt tttgattttt ttaaacaaat  71700
acgatcagat gataacagcc tttactcggc tcaattcgat attcttttgg ggacatactg  71760
caatacatta aactttgtgc gttttctaga acttggactg tctgtcgctt gcatctgtac  71820
taaatttccg gagctggctt acgtgcgaga tggcgttatt caatttgagg tacaacaacc  71880
catgatagca cgtgatggcc cacatcccgt cgatcagcct gttcataatt atatggttaa  71940
gcggatacac aagcgttcgt taagcgctgc gtttgcaatt gcatcggaag cgttgagttt  72000
gttaagtaac acatatgtcg atgggacaga gattgactca tcgttacgta taagagctat  72060
ccaacagatg gctcgtaatt tacgcaccgt tttggactca tttgaacgag gcactgccga  72120
tcaacttctt ggtgttctat tggagaaagc cccaccgcta tcgctgcttt caccaattaa  72180
taaattccaa cccgagggac atctaaatcg tgttgcacgc gcggccctac tttcggacct  72240
caaacgtaga gtctgtgcgg atatgttttt tatgacccga cacgccaggg aacctaggct  72300
gatctctgcg tatctgtcgg atatggtttc gtgcacccaa ccatcggtga tggtatcacg  72360
aataactcat acaaacactc gcggacggca ggttgacggt gtgttggtaa caacagcaac  72420
cttaaaacgg caactattac agggaatttt acaaattgac gacaccgccg ctgacgtacc  72480
agtaacatat ggcgaaatgg ttctacaggg gacaaacttg gtaaccgccc ttgtgatggg  72540
aaaggccgtc cgcggaatgg atgatgtagc ccgccatctc cttgatataa ccgaccctaa  72600
cacgttaaac ataccgtcta tacccccaca atccaactcc gattcaacga cagctgggct  72660
tccggttaac gcccgtgttc ctgcggattt agtgattgtt ggggataaac ttgtattctt  72720
agaagcatta gaacggcggg tctaccaagc tacgcgcgtt gcctaccctc ttattggaaa  72780
tatagatatt acgtttatca tgccaatggg agtgtttcag gcaaactcca tggacagata  72840
tacacgacac gccggcgatt tttcaactgt atccgaacag gatccacgtc aatttccacc  72900
ccaagggatt ttttttata ataaagatgg gatattaaca cagttgactc ttcgtgatgc  72960
aatgggtacc atctgccaca gttcattgct tgatgtcgag gccacacttg ttgccctccg  73020
ccaacaacat ttagatcgtc agtgttattt tggtgtatac gtggccgagg gtacagagga  73080
cacattggat gttcaaatgg ggaggtttat ggaaacgtgg gcagatatga tgcctcatca  73140
ccctcattgg gtaaacgaac atttaacaat tctacagttt atagctccga gcaacccgcg  73200
tctaaggttt gaattaaacc ccgcctttga tttttttgtt gcaccggggg acgtagacct  73260
tcccggaccg cagcgtcccc cggaagccat gccaaccgtt aacgcaacat tacggattat  73320
caacggaaac attcccgtgc ctctatgtcc catttcattt cgagactgtc gcggaaccca  73380
actcggtttg ggaagacata caatgacccc ggcaaccatt aaagccgtaa aggatacatt  73440
tgaagaccgc gcatacccaa ctattttcta catgctagag gctgttattc atggaaacga  73500
aagaaacttc tgtgcgttac tgcgactgtt aacacagtgt attcgcgggt attgggagca  73560
```

-continued

```
atcccacagg gtggcatttg taaataactt tcacatgtta atgtacataa ctacatatct  73620
cggaaacggt gagcttcccg aagtctgtat taatatatat cgggatttac tgcagcatgt  73680
aagagcatta cgccaaacta taaccgattt tacaatacaa ggagagggcc ataacggcga  73740
gacctcggaa gcgctaaata acatccttac ggatgacacg tttattgcac ctattctatg  73800
ggattgtgat gcgttaatat accgtgatga agccgcccga gaccgactcc ccgcaattcg  73860
tgtaagcggg cgaaacggat accaagccct tcactttgtg gatatggccg ggcataactt  73920
ccaacgacgc gataatgtgt taatccacgg gagacccgtt cggggagaca cgggtcaggg  73980
tattcccatt actccacacc atgaccgtga atggggtatt ctctccaaga tttactacta  74040
tattgtcatt cctgcatttt cccgcggttc ctgttgtaca atgggcgtgc gttatgatcg  74100
cctataccct gcgttacagg cagttatcgt tccggaaatt cccgctgatg aagaagcccc  74160
aactacccca gaagatccaa gacaccctct tcacgcacac caactcgttc cgaactctct  74220
taacgtttac ttccataatg cacacctaac cgttgatggt gatgcattgc tcacactaca  74280
agagttaatg ggagatatgg ctgaacgaac gacggccatt ttagtatcaa gcgcccccga  74340
tgcgggagcc gccacggcaa caaccagaaa tatgagaata tatgacggag cgctttacca  74400
tggccttatt atgatggcat atcaggcgta cgatgaaacc attgcaacgg gtactttttt  74460
ttatcccgtt ccggtcaacc ctctgtttgc atgtccggaa catttggcat cattgcgtgg  74520
aatgacaaat gctaggcggg ttttggcaaa aatggtacca ccaatccctc cttttctggg  74580
agccaaccac cacgcaacta tacgccaacc cgttgcctac catgtaacgc atagtaagtc  74640
ggattttaat actcttacat attctcttct tggagggtat tttaagttta caccaatatc  74700
tcttacacat caactacgaa cggatttca ccccgggatt gcctttaccg tagtgcgcca  74760
ggatcgcttt gccacagagc aacttttata tgccgagcgt gcttctgaat cgtactttgt  74820
cggacaaatc caagtacacc atcatgatgc tattgggggg gtaaacttta ccctaaccca  74880
acccagagct cacgtggacc tgggagtcgg gtatacagct gtatgtgcca cagcagccct  74940
gcgatgccct ctcacggata tgggcaatac tgcccaaaat cttttttttt cacgaggagg  75000
agtgccaatg ttacatgata acgttaccga atcgttgcgt cgtataacag catcgggggg  75060
tcgcttaaat cccaccgaac ccctacccat cttcggcgga ctacgtcctg ctacatcggc  75120
aggaattgca cgagggcaag cctctgtgtg tgagtttgtg gccatgccgg tgtccactga  75180
cctacaatat tttagaactg catgcaatcc tagaggtcga gcatctggaa tgttatatat  75240
gggtgaccgt gacgccgaca tagaggctat aatgtttgat cacacacaat cggatgttgc  75300
ttatacagat cgagcaactc ttaacccatg ggcatcacaa aaacattcat acggtgacag  75360
gctatacaac ggaacataca accttacagg cgcttctcct atctacagcc catgctttaa  75420
gtttttttaca ccagcggagg ttaacactaa ttgtaataca ctggatcggc ttctaatgga  75480
ggcaaaggct gtggcgtcgc aaagctccac cgacactgaa tatcaattta aacgccctcc  75540
cggttctacc gaaatgacac aggatccgtg tggccttttt caagaagcat atccaccact  75600
atgctcaagc gatgcggcca tgttacgaac ggctcacgcg ggagaaaccg gggcagatga  75660
agttcactta gcccaatatc tgattcgaga cgcgtcgccc cttaggggat gtcttcctct  75720
tccgcgataa tttcaccacg cccacatacc cactcccaat aaaagccctg tagagcgcat  75780
tggcatctta cttgagattt ggatacgctc ggccgacttg gtctgtttca cgcttcctta  75840
aacaacatgg ctatgccatt tgagatagag gtattgttac caggagaact atccccggcg  75900
```

-continued

```
gaaacatctg cattacagaa atgtgaggga aaaattatta ccttctcaac cctgcgtcat  75960
cgagcttcac tggtggatat agcgctgtcg tcatattaca ttaacggtgc tccaccagac  76020
acgctctcgc tgttagaggc ataccgaatg cgattcgcgg cagttataac acgggtcatc  76080
ccgggaaagt tgttggcgca tgccattggc gtgggtactc ctacacccgg gttgtttatt  76140
caaaatacat cccccgttga tctttgtaat ggcgattaca tctgcttact tcctccggtt  76200
ttcgggtccg cagactcaat tcgcttggac tctgtaggac tggaaattgt tttcccttta  76260
accatccccc agaccttaat gcgagaaatc atcgccaaag tggttgcacg ggccgttgag  76320
cgcacggccg cgggtgctca aattttaccc cacgaagttc tacgaggcgc ggatgtcatt  76380
tgttacaatg gaaggcgtta tgaactcgaa acaaatttac aacatcggga cggatcggat  76440
gcggctattc gcacattggt tttaaatcta atgttttcca taaacgaggg atgtctgctt  76500
ttattggcgc tgattccaac tttgttagtc caaggagcac acgacggtta tgtaaattta  76560
ttgatacaaa cggccaattg cgttagagaa accggccagt taattaatat accgccaatg  76620
ccgcggattc aagacggcca tcgccgattt cccatatatg aaactatttc atcttggata  76680
tcaacatcat ctagactggg ggataccttg ggaactcgcg caattttacg cgtctgtgtg  76740
tttgatggac cctctactgt tcatccggga gaccgcacgg ccgtgattca agtgtaaaca  76800
ggtgttaata aaaacacaac cagtctagtt acatttcacg cgtcttgttt ttatttaata  76860
ggcataaaca cggaatccgg tatacatgaa ctgccaatat acacggacat aattaatgca  76920
accatcagat catctgacat tgttcccgtg gtacctttac ccgtgtaagt ttttgtgtct  76980
agattaccca taccgccttt aattacctct gtcaggttat ccaactgttt acatagatac  77040
tccacggggt ctacacctaa ctttactgtt agggatacaa gctcctgtga ggctattata  77100
tttccggagt taaatcgttt aacaaaatag tctacggccg gcgttttttg tttttgtaat  77160
aaaaaaaaag ggtacgccac gctacatccg ggaggtatgg aatgataaaa cagtaacact  77220
ggagcggaag atagcacgtt tcccttttcg aggacagcaa actgttgtgc tatagccaac  77280
gatatggcaa ctgcagaatc ctggctgctg tttccctcta tagaaacgtg tacgtttgta  77340
aatgtattgg ggtgtaaagc gagtatgtgg cctaagcatt gagtaacgca acgccctatc  77400
tcactggaag acgtgccagt taaagctcta agaaaaaagt gctccaatcc aaatataatc  77460
caatccgact tataacgacc aacaatcgct acaccagtac cagacgctcg tgtatttgag  77520
gtaaatgcag ggtctacgta aacgtacaac actgacgata atatagcaca attcgcaacg  77580
gttgacggcc gatataaaat aaacctctca cgggcagttt ttgtaaataa tggccggtca  77640
aaccccacac ccccagaatt ctgtttacgc ccacctacaa tttcctgcac gaaggagtcg  77700
gccataaata aatctgcagt gcgccgcatg gctccatcca ttgtgatgaa aaccggctta  77760
tttaatacat aacacgaaca agctgtgaca tcgctatgtg ctaaaacacg cggcatgtga  77820
tcgtcgcata catatgtaac aacgtttaac aactgatccg acgatccacg taagttatac  77880
aaaaaacttg tacttgcttt tccggtattt gttgatgaaa caaaaaataat tttacaattg  77940
gtttgattta aaaatccgac tatagtttgt acagcatcag gtcgaataaa attagcttca  78000
tccacaaaca gaagattaaa atcttgacct cggataccct ggaacgatag aaagatatat  78060
agttacccca ccaaagttta aatgtatcct taaataccac gtacgtaaaa aatgtttgaa  78120
tacgtacata tttctttttt ttttccagta caaccatatc cggtgtataa tggaagccca  78180
tttggcaaat gaaaccaaac atgcactttg gcataatgat cacacaaaag gattactaca  78240
cgttgtgata cctaacgcgg ggcttattgc ggccggaata gatcccgcat tactgatttt  78300
```

-continued

```
aaagaaaccc ggacaacgct tcaaggttga agtacaaaca agatatcatg ctacaggtca  78360
atgcgaaccg tggtgtcaag ttttcgccgc gtacattccc gataacgcct taacaaatct  78420
cttaatacca aaaacggaac catttgtttc acacgttttt tcggccacgc ataattcagg  78480
gggattgatt ttatcattgc ctgtttatct tagccccggt ttattctttg atgcatttaa  78540
cgttgtagcg atacgaataa atactggaaa ccgcaagcac cgtgatattt gtattatgta  78600
tgcagaacta atcccaaacg gaacgcgtta ttttgctgat ggacaacggg tacttttatt  78660
atgcaaacag ctgattgcgt atatccgatg cacccctcgt cttgcatcgt ctataaaaat  78720
atacgcagag catatggtgg cagccatggg tgaatcacac acgtcaaatg gggacaatat  78780
tggacccgtt tcatccataa tcgatcttga tcgacagtta acttctggag gtattgatga  78840
ctcccctgct gaaacacgca tacaggaaaa taatcgggac gtccttgagc taataaaacg  78900
ggccgtaaac attgttaact ccaggcaccc cgtccgacct tctagttccc gcgttgcatc  78960
tgggttgctt caaagtgcaa agggccacgg agcgcaaact tccaacacag atccgatcaa  79020
taacggttcc tttgatggcg tccttgagcc gcctggacaa gggcgattta cgggaaagaa  79080
aaacaattcg tccgccagca tcccaccttt acaagacgtt ctattgttta ccccagcttc  79140
gacagaaccc caaagtctta tggaatggtt cgacatctgt tatgcccaat tagttagcgg  79200
ggacactcca gcagatttct ggaaacggcg tcccctatca attgtaccgc gacattacgc  79260
agaatccccc agtccgttga ttgtagtatc ttacaacgga tcctctgcct ggggaggacg  79320
tattaccgga agtccaattt tatatcactc tgcacaggct attattgatg ctgcgtgtat  79380
aaatgcccgg gttgacaatc cccaaagcct acatgtgaca gctcgccaag agctagtcgc  79440
gcgtttaccg tttttggcta acgtcctaaa taatcaaacc cccttacccg cctttaaacc  79500
aggcgccgaa atgtttttaa accaggtatt taaacaagcg tgtgtgacat cgctaaccca  79560
aggtcttata acggagttac aaacgaaccc gactctacaa caactcatgg aatatgatat  79620
tgcagattct tcccaaacgg ttattgatga aattgtagcc cgcacaccag acctgattca  79680
gactatagtt tcggtgttaa cggaaatgtc aatggatgcg ttttataaca gctccttgat  79740
gtatgcggtt ttggcgtatc tgtcatctgt atatacacga ccacaaggtg gggggtatat  79800
accctacctt cacgcttcct tcccatgctg gttaggtaat cgttctatat atttatttga  79860
ctattataat tcaggagggg aaatacttaa gctttccaag gtccccgttc ccgtagcctt  79920
agaaaaggtt ggtattggta attccacaca actgaggggt aaatttatac gcagcgcgga  79980
tattgttgat attggaattt gttctaagta tttacccggt caatgttacg cgtacatttg  80040
tctaggattt aaccagcaat tacaatccat tttagtttta ccgggggat ttgcggcatg  80100
tttttgtatt accgataccc tacaggcagc actacctgca tcgttaatcg gacctattct  80160
agacagattc tgcttctcta ttcccaaccc ccataaataa attagtgtca ctataaaaac  80220
ataacaccag aatctcttca tatgtaattt tacgtcattt ctcccgtttc cacccccctct  80280
taaaatataa aataaccggg tgggtggcat taaacccaca agtacccggg cggcaatccg  80340
ctagactgtt tttctgctca tggaattaca acgcatattt ccgctgtaca ccgctacggg  80400
tgcagcgcgc aaattaaccc ccgaggcagt tcagagactc tgcgatgcat taacgctgga  80460
tatgggatta tggaagtcca tcctgaccga tccccgggtg aaaataatgc gatcaactgc  80520
ttttataact ttaaggatcg ctccgtttat ccccccttcaa acggatacta ctaatattgc  80580
cgttgttgta gccacaattt acatcacgcg cccacgtcag atgaacttac ctccgaagac  80640
```

-continued

```
ttttcatgta attgtaaatt ttaattacga ggtctcgtac gcaatgacgg cgactttaag  80700
aatttatccg gttgaaaaca tagaccatgt ttttggagca acgtttaaga acccgatcgc  80760
gtacccctt ccaacatcta ttccggatcc tcgagcagat cccacccccg cagatcttac  80820
accaacgcca aacttaagca actacttaca accccgcgg cttccgaaaa atccatacgc  80880
atgtaaagtt atttctccgg gagtgtggtg gtcagacgaa cgaaggcgtt tatatgtact  80940
ggctatggaa cctaatttaa tagggctatg tcccgccgga tggcatgctc ggatacttgg  81000
ctctgtatta aatcgactcc tcagccatgc ggacggatgt gatgaatgta atcatagagt  81060
tcacgtgggg gcactgtatg cgttacccca tgtcacaaat catgcggaag gttgtgtgtg  81120
ttgggctccg tgtatgtgga gaaaggccgg tcagcgggaa ttaaaagtgg aggtagacat  81180
tggcgccacg caggttcttt ttgtagatgt caccacctgc attcgaatta cgagtactaa  81240
aaatcctcgc attaccgcaa atcttggcga cgttatagcg ggaaccaacg ccagtggtct  81300
ctctgtacca gtaaattcat ctgggtggca gctttatatg tttggagaaa cattaagccg  81360
ggctattatt aacggctgtg gtctgcttca gcgaatttgc ttccccgaga cacaaagatt  81420
atcgggtgaa ccggaaccta caaccaccta gtataccta actcaaccgc cgttgtggaa  81480
aggtatatgt caacatttac agtaatatat taaaggttaa atttataaaa cactcacgtt  81540
tgtgttgtga cttgacgcga acaccgctgt gctgtaagac ccgtcggtaa atgaaaacgt  81600
aatagattcg ccttttacat gatccacgta atttgcccca aaccactgtt ccaggcgaga  81660
cttgataccc tcaaacacgg gttccgttgc tttgcgtata tgagccgtat aacccacttt  81720
aattcctcta aacgtggcca ttactaaagc tattaatggt acaagaaacc atgttttccc  81780
atgtctacgt ggtaccaaaa acacagttga tttttgtttg aagtgttcta aaacactgtc  81840
agaaacactt ggcgtgttaa acactgtacg cagaaagcag tcaactctgt cggcatgatc  81900
gcccaatagc accgatgaaa taaaatgcgt ggtgtgcatg aggatcattt tttgaaacag  81960
ttccaacgtc cccttatatc tgccatagat tggaacgtca acctttgcgc gtttgccatg  82020
acttccacac tcttcaatac tctcaaaaga tgtttccaca aggtacgaaa accgttgtgt  82080
aaaggtagac aactgacaga aactatccga cagagaaaac gcgcgaaatg tgttcataac  82140
accgctatac gcatttcgat gaggtgctgc ttcttccggt gaatattcat aaaactgtac  82200
actactgaca gcctttttta attcagggct tacgtttgca tttaccgaat atcgccatgg  82260
tttcaaaact acattggggg tacagttgta ccctgttgac gatagaaacg cgccaaacat  82320
tgcccgtcga gcagtagccg agaacagtgg aatatattca caacagttgt gaagcgttcc  82380
aattccggga ataacggcct gatgacgtcg ggttacatct atagcaaaat tcagaaacgg  82440
gatttgggtt gcgtttccca gagacccttg ccgcgtggaa cacggggtag gggactccaa  82500
cgtcccaaag cgttcatccc tacgacgctt tagacgttca aaatatctta cagattcttc  82560
accaagcgta cgaccaaaca ttatcaatga catttaacat caattcacgg aatccgcctc  82620
atctcttgta agcagtaaaa caggaagccg cgtcatctta cgtactcgtt acgtatatat  82680
cataaacatt ttcagggccg cattcattca ctttggtcat gtcaggccac actccaacct  82740
acgcttctca taggcgtaac cgtgtcaaac tagttgaggc gcataaccgc gcggggttat  82800
ttaaagaacg gaccctcgat ctaatccgtg gggtgcgag tgtacaagat ccagcatttg  82860
tgtatgcctt tactgctgca aaagaggcct gcgccgattt aaataaccag ctccgctctg  82920
cagctcgcat agcttcagtt gaacagaaga ttcgtgatat acaatccaag gttgaggaac  82980
aaacaagtat tcaacagatt ttaaatacaa acagacgcta tatagcaccc gatttattc  83040
```

-continued gcggtttgga taaaacagaa gacgataata ccgataatat agacagactg gaagacgcgg 83100
taggaccgaa catcgaacac gaaaatcata cttggtttgg agaagacgac gaagcgttac 83160
ttacacaatg gatgctgacg acacaccccc caacctccaa atatctccaa ctgcaggacc 83220
tttgcgttcc caccacaata ccgacggaca tgaaccaaat gcaaccgcag ccgatcagca 83280
agaacgagaa tccaccaacc ccacacacgg atgtgtaaat catccatggg ccaatccgtc 83340
aactgcaaca tgcatggaat caccagaacg atcacaacag acaagcttat ttttattaaa 83400
gcacggctta acgagagatc caatacatca acgcgaaagg gtggacgttt ttccacaatt 83460
taacaaaccc ccatgggttt ttagaatttc caaattatcc cgtttaattg tacccatctt 83520
cacgctcaat gaacagttat gtttttctaa attacagatt cgagatagac ccaggtttgc 83580
gggacgggga acgtatgggc gtgttcatat atacccatcg tcaaaaatag ctgtaaaaac 83640
catggacagt cgtgttttta atagagagtt aattaacgcg attttagcga gtgagggttc 83700
tatacgagca ggggaaaggc taggtatttc tagcatagtt tgccttttag gtttttcgtt 83760
acaaaccaaa cagctactgt ttccggcata cgacatggat atggatgaat acattgttcg 83820
cctgtccaga cggttgacaa tacctgatca catagacaga aaaattgccc atgtattttt 83880
agatttggct caagcgttga cgtttttaaa tcgaacgtgc ggcctgaccc acctagatgt 83940
gaaatgtggc aatatttttc ttaacgtcga caactttgcc tcgttggaaa taaccacagc 84000
agtaatcgga gactatagcc tagtaacatt aaatacgtat tccctttgta ctcgagcgat 84060
atttgaagtt ggaaatccat cccacccgga gcacgtacta cgcgtacccc gggatgcatc 84120
gcagatgtca tttcgtttgg tgttgagtca tggaacaaac caaccccctg aaatcttgct 84180
tgattatatt aatggaacgg gccttactaa atatactgga accttgcccc aaagagttgg 84240
acttgcgatt gatctttatg cattgggcca agcactctta gaagttatcc tgctaggacg 84300
tcttcccgga caactgccca tttcagtaca tcggaccccg cattatcact actacggtca 84360
taagttatca ccagatttgg cgcttgatac gctggcatat cgatgtgtcc tggcgccata 84420
tatactccca tctgacatcc ccggggactt aaattataat ccctttatac acgccggaga 84480
gctgaacacc cgtatttccc ggaattcttt acgccggata ttccagtgtc acgcagtgcg 84540
ttacggcgta acgcactcaa agcttttcga aggcatacgc attccggcct cattataccc 84600
agccactgtt gttacatcgt tgttgtgtca cgataattca gaaatacgct cggatcaccc 84660
tttattatgg cacgatcggg attggatagg atcgacataa gcccccagcc agccaaaaaa 84720
attgcccgtg tgggaggtct acagcaccct tttgtaaaaa cggatattaa cacgattaac 84780
gttgaacacc attttataga cacgctacag aagacatcac cgaacatgga ctgtcgcggg 84840
atgacagcgg gtatttttat tcgtttatcc cacatgtata aaattctaac aactctggag 84900
tctccaaatg atgtaaccta cacaacaccc ggttctacca acgcactgtt ctttaagacg 84960
tccacacagc ctcaggagcc gcgtccggaa gagttagcat ccaaattaac ccaagacgac 85020
attaaacgta ttctattaac aatagaatcg gagactcgtg gtcagggcga caatgccatt 85080
tggacactac tcagacgaaa tttaatcacc gcatcaactc ttaaatggag tgtatctgga 85140
cccgtcattc cacctcagtg gttttaccac cataacacta cagacacata cggtgatgcg 85200
gcggcaatgg cgtttggaaa aaccaacgaa ccggcggcac gagcgatagt tgaagcattg 85260
tttatagatc cggctgatat ccgtactcct gatcatttaa cgccagaagc tacaactaag 85320
ttttttaatt ttgacatgct caataccaaa tctccaagtc tccttgtggg tacaccaaga 85380

-continued

```
atcggaacgt atgaatgtgg acttttaatc gacgttcgaa cgggacttat aggcgcgtcg  85440
ttggacgttc ttgtatgtga cagggaccct ttaactggca ccctaaatcc ccaccctgca  85500
gaaaccgaca tttcattttt tgaaattaaa tgtcgtgcta aatacctctt tgatccagat  85560
gacaaaaata acccgctcgg tcggacgtac accacgttaa taaatagacc tacaatggca  85620
aatctacggg actttttata tactataaaa aacccatgtg taagcttctt tggaccctca  85680
gcaaacccaa gtacacgcga ggccttaata acggatcacg ttgaatggaa acgtttagga  85740
tttaaaggtg ggagggccct tacagaactc gacgcccatc atttgggcct caatcggaca  85800
atctcatccc gagtgtgggt atttaatgat ccggacatac aaaaggggac aattacaacc  85860
attgcatggg ccactggaga tacggctctt caaattcctg tatttgccaa tccgcggcac  85920
gctaacttta aacaaattgc cgtacaaacc tatgtattat ccggttactt tccagcgcta  85980
aaactacggc ccttccttgt cacctttata ggacgtgtgc gccgaccaca cgaggtggga  86040
gtcccattgc gcgtcgatac acaagcggct gccatttacg aatataactg gccgactatc  86100
ccaccccact gtgcggttcc ggttatagcc gttctaacgc ctatcgaagt tgatgtgcct  86160
agagtgacac aaatacttaa agacacagga aacaacgcga ttacatcagc attgcggtca  86220
ttgcgatggg acaatcttca tccagcggtc gaggaggaat ctgtggattg tgcaaacggt  86280
acaacgagct tgttacgtgc aacggagaaa ccgttgcttt gaactcagag ttctttgaag  86340
actttgactt tgatgagaat gtaacagagg acgccgataa atccacacaa cgccgcccac  86400
gagtgatcga tgtaacacca aaacgaaaac cttcgggaaa gagctcccat tccaaatgcg  86460
caaaatgtta aaccctgata aaccctgata aacgttctaa taaaaacatc aaatcatggt  86520
tggttactgt gaatgtttgt tttattgctt ggggggtttac aagtacaacc cacgctactc  86580
ccacccactg tttgatcgct cgtataacag ctcatcctcg cggtccgttt catatgttga  86640
gtcattttca tagacgtagc cgtagccttg tgatgggtaa tttgtgcggc gagaatttct  86700
atgtgcaggt tttacttttc gtatgtatcc ccgtacccgc tcgggtactc ttcttacggc  86760
accgtagaac cgactgcgtt tctgtcgatg atacacatat gcacgcatca atctgagaag  86820
caacatgaca acggaaaaca cggccaggca agccaaggtt ccccgagttg tgggaattaa  86880
ccgtggagat tgaaccgata tagggtcata taatcggtcc atatacgagt gcgcggcggt  86940
tcccaacgta gcacaggcca cgagcgttcc cagggacggt cctattaaca cgtgtatata  87000
atgcgccaaa attaattctg atactataag atatacaact gacaatgtac taaatgtaga  87060
catggccacg gacaccgatg accacagtcc cgtatgtaga tgattcgcca ccacaagttc  87120
cagcattaat gatacaaata ggatacatat cgccatcaac gcagccatca aattcacgaa  87180
cactgcgcgc gtaggccccg caaggcgata taaaaagacg ctctgctgtc gtaaatttgc  87240
gaccgctttt atgttcgttt cgtccaattt tccgcgtcca caaaaatacg ttgtaaatat  87300
tacacttgtc gcaaaatgtc caagatataa tgtagcagcc acgccgattt gcttgtaagc  87360
taataataac acaacggcgt ttaataacca caatgacaaa agaccccaaa aaagtgttgt  87420
gggatctaca actaaccatg caacaccgga gctttgccgg acacgttgat ttttcgtttc  87480
tcggtgtata atcgcggccg tgatcagtgt atataccgcc atggccattg ccgttaaagc  87540
cgtgtagtaa gtaaatgcca caacgctatg tggttccaaa aacaaaaccg gggcgctgta  87600
tccacctcta tttccggacc atacccccc atctagggtg gcgttaaata actcataatc  87660
aactacggca gcataaaaac aagggatccc ggtatattca gaagaggcgg caattaacgt  87720
agccaggagc attaccgcac ccaaagtgaa catcatcacc tgaattatcc aaattcgcca  87780
```

-continued

```
attaagcgta tccatttgat gatctaacgc ttccacctcg ggtgtcgtgg tgtcgtacgg  87840
cgagactttt tcagaacgcg gccccttctt ttgagttccc atgtctccca acaccgggga  87900
gagcaacgcc gccgtctatg cgtccagtac acagctcgcg cgggcgttat atggagggga  87960
tctggtttcg tggattaaac acacccaccc gggaattagc ctggaactgc aattggatgt  88020
tccagtaaaa ctaataaaac ctggtatgtc acaaactcgc ccggtaaccg tcgtacgtgc  88080
ccctatgggc tctggtaaaa caacagcctt gcttgagtgg cttcaacacg cgttaaaggc  88140
agatattagc gtactggttg tctcatgtcg ccgtagcttt acccagacgt tgattcaacg  88200
gtttaacgat gcaggcctct ccggattcgt aacatatttg acatccgaga catatattat  88260
gggttttaaa cgtttgattg tgcaacttga aagcctacac cgcgtatcca gcgaagctat  88320
cgacagctac gacgtattaa tactggatga ggtaatgtca gtgattggac aattatactc  88380
ccccacaatg agacgtcttt ccgcggttga tagcctatta tatcgtcttt taaatcgctg  88440
ttctcaaatt atcgcgatgg atgctacagt aaactcgcag tttattgatt taatctccgg  88500
attgcgtgga gatgaaaaca tacacacaat tgtgtgtaca tacgcgggag ttgggttctc  88560
cggaagaact tgcacgatcc tgcgtgatat gggcatcgac acgcttgtgc gagtcattaa  88620
acgatctcct gaacacgagg atgtacgtac catacaccaa ctacgtggaa catttttga  88680
cgaactagca ctacgattac aatgtgggca taacatctgt atattttcat caactttatc  88740
gttttcggag ctagttgctc agttttgtgc aatatttaca gactctattc ttattttaaa  88800
ctcaactcgg cccctatgta atgtaaacga atggaaacat tttcgcgtgt tggtgtacac  88860
taccgtcgtg accgttggat tgagttttga catggctcat tttcatagca tgtttgctta  88920
cataaagcca atgtcatatg ggccggatat ggtatcggtc taccagtcat tagggcgtgt  88980
acgtttattg ctacttaatg aagttttgat gtacgtcgat ggctcaagga ccagatgcgg  89040
acccctgttc tcgccaatgt tactaaactt taccatcgca aataaatttc aatggtttcc  89100
tacacacacc caaataacta acaaactgtg ctgtgcattt aggcaacgat gtgcaaatgc  89160
atttacacgc tcgaacaccc atctcttctc aagatttaaa tacaaacacc ttttcgagag  89220
atgctctctt tggagtttag ccgatagcat taatatctta caaactcttt tggcctctaa  89280
ccaaattttg gttgtattgg atggcatggg tccaataacg gacgtttccc cagttcaatt  89340
ttgtgcattt atacacgatc tcagacatag cgctaacgcc gtagcttcct gtatgcgttc  89400
tcttagacag gacaatgaca gctgcttgac cgattttggc ccttccggat ttatggccga  89460
taacattacc gcgtttatgg aaaagtatct tatggagtca attaataccg aagaacaaat  89520
taaagtattt aaagcccttg catgtccaat agaacagcct agactagtca atacggcaat  89580
attgggggcg tgtatacgaa tacctgaagc gttggaagca tttgacgtat ttcaaaaaat  89640
atacacgcac tacgcttccg gttggtttcc cgtcctggac aaaaccgggg aatttagcat  89700
cgcgactata actaccgccc caaatttaac cacacattgg gagctgtttc gccgttgtgc  89760
ctatattgca aaaacactca agtggaatcc gtccaccgaa ggctgtgtaa cacaagtttt  89820
ggatacggac attaatacac ttttcaatca acacggggat tcgctggctc aactaatatt  89880
tgaggttatg cgctgtaacg ttactgacgc taagattata ttaaaccgcc cggtttggcg  89940
aacaaccgga ttcttagatg gatgccataa tcaatgcttc cgtccaatcc ctacaaaaca  90000
cgaatataac attgctctat ttcgtttaat ttgggaacaa ttatttggcg cccgcgtaac  90060
taaaagtacc cagacctttc cgggaagtac tcgtgtgaaa aacctaaaaa aaaaagatct  90120
```

-continued agaaacttta cttgattcaa ttaacgtgga tcgttctgca tgtcgtacct accgccagtt 90180
gtataacctg cttatgagcc agcgccattc gttctctcaa cagcgttaca aaattactgc 90240
ccccgcttgg gcacgccacg tgtattttca agcacatcaa atgcacttgg ccccgcatgc 90300
cgaagccatg ctacaattag cgctatcgga actgtccccg ggatcgtggc cgcggataaa 90360
cggggcggta aattttgaaa gtttataacc cgttaatacc atatatggac atccataggg 90420
ggggttacat aaatactaag cctctgtaca acacaaaggg cctctaacaa tgcactgaac 90480
cacaaccaag ctatggacgc aacgcagatt accttggtta gagaaagcgg acacatttgt 90540
gccgcaagca tatacacatc ctggacacag tccggacaat taacacagaa cggtctttcc 90600
gtgttatact acttattatg caaaaactca tgtgggaaat acgtccctaa gtttgccgaa 90660
attaccgtac aacaagagga tttatgtcgc tactccaggc atggggggag tgtttctgcg 90720
gcaacgtttg cgtctatctg cagggcggcg tcctcggctg cgttagacgc ctggcccctt 90780
gaaccactgg gtaacgcaga cacctggcgt tgtctccatg gcactgccct ggccacttta 90840
cggcgcgtat tagggtttaa atcgttttat tcgccagtaa cattcgagac tgatacgaat 90900
acaggtcttc tgttaaaaac aatccccgat gaacacgcgt tgaataatga caacacgcca 90960
tctaccggag tattgagggc taattttccc gtggccattg atgtttcagc agtcagcgca 91020
tgtaacgccc acacgcaagg tacgtcgcta gcctacgccc gcctgaccgc acttaaatct 91080
aacggtgaca cccagcaaca aacaccttta gacgtggagg taattacacc aaaggcctac 91140
atacgtcgga aatataagtc tacgttttcc ccccctatag agcgggaagg ccaaacctcc 91200
gatttgttta accttgaaga acgccgcttg gttcttagtg gcaatcgcgc aattgtggta 91260
agggtactct taccgtgtta ttttgactgt ttaacaacgg attccaccgt tacatcttcc 91320
ctttcaatat tagcaacata tagactgtgg tacgcggcgg cgtttggaaa acccggggtt 91380
gtccgtccaa tctttgcgta tttaggcccg gaactcaatc cgaagggtga agacagagac 91440
tacttttgta ctgtcggatt tcccggatgg accactcttc ggacacaaac tccagccgtc 91500
gaatctattc gcacggctac ggagatgtac atggaaacgg atgggttgtg gccagtaacc 91560
ggtattcagg cctttcatta tctagccccc tggggacagc atcccccctt acctccgcgg 91620
gtgcaggatc ttattgggca aatccctcaa gatactggac atgcagatgc aactgtcaat 91680
tgggacgcgg gccggatatc taccgtcttc aaacagcctg tacaactaca agatcgttgg 91740
atggcaaagt ttgatttcag cgccttttt cccacgatat actgcgctat gttccccatg 91800
cattttagat taggcaaaat cgtcctggct agaatgcgtc gaggaatggg gtgcctaaaa 91860
cccgcgttgg tgtcttttt tgggggtta cggcacatac tcccgagtat atacaaagct 91920
attattttta tagccaatga aattagcctt tgcgtcgaac aaacggcctt ggaacagggc 91980
tttgctatat gtacttatat aaaagatgga ttttggggaa tcttcaccga tttacatacg 92040
cgcaatgtat gttcagatca ggcacgttgt tcggccttaa atttagcggc cacctgcgaa 92100
agagcagtca cgggcttatt acgaattcaa ctaggtctta actttacacc cgccatggaa 92160
ccggtactcc gggtcgaggg tgtgtacact cacgcattta cctggtgtac cacgggaagc 92220
tggctgtgga atttacaaac aaacacgcct ccggatttag ttggcgtgcc atggcgaagt 92280
caggcggcgc gagatttaaa ggagcgtctt tcaggactcc tatgtaccgc aacaaaaatt 92340
cgagaacgga tacaggaaaa ttgcatatgg gaccatgtcc tatacgacat atgggccgga 92400
caagttgtgg aggctgccag aaaaacatac gtcgattttt ttgaacatgt tttgatcgc 92460
cgttatactc cggtatactg gagtcttcag gagcaaaatt cggaaacaaa agcaataccg 92520

-continued gcatcttatc tgacatacgg acacatgcaa gataaggatt ataaaccaag acagataatt 92580
atggttcgta atcccaaccc acatggacct cctactgttg tttactggga attgctacca 92640
tcgtgtgcct gtattccccc catagactgc gctgctcatc tcaagcccct tatacacacg 92700
tttgtcacta ttattaacca tcttctagat gctcataatg atttttcaag tccatcattg 92760
aaatttactg acgatcccct tgcttcatat aacttcttgt ttttatgaca aaaaaacacg 92820
ccgcaacaac ccatccttaa aataaaaggt ttatttactt tacaacccgt ggtgaatttt 92880
tatacgtttc aaataactga acatttttcg gtgttaccat ggtgcgattt aaccaccaaa 92940
aatatacgct cttctgatat tccgaatctc gtaaaggtcc atttaacaat cccgggggta 93000
cttgcaccac accatctgga caggggggggg ttccgtgggg caggtcaaaa cgctgaccca 93060
ccccacatga atatatagcc tttataatat tgggggccgt tccaggctga gggttcagta 93120
acttaacaaa catataatgc ggcaatacgc gggtttttgt aaaggggttg ttatcaacga 93180
catacattag agtgtttaac aaccataaaa ctccctcata taaaaaccga cgcatttttt 93240
ccaaaggtcc tatttgacac tcaacgcgtc taagatatac agacaattgt acaaacagcg 93300
atggagatgc cccggagggc ccaatgcctt ccagatacat taaaataaca cataaggtaa 93360
aatctaggac attatccggg cggaatagag tcatccgata gattaacagg cgcggaggca 93420
cccccaccgt atacacccta tcttcaaccg cagttaatac ggaaaaaata aatccgcgga 93480
acgctggttg agtaacacac tccatgtagt aacgatcaca ggacacctca cttgaatcac 93540
cattcaacac tactaaaacg gtctcttggt gttccggttt tacgcgcagt gatacaacag 93600
agtttgccaa aaagcgtggc ttcaaaccgg ttacctcccg cgcctcgcat acgaatcttg 93660
gtattgcttg tattctaaga tcttcgatca cgtcgctcac atccaacccc tcttcggctc 93720
gtgttagtaa gttgtcgatc gttacgctgc aacctaaaat gctgggtata tttattccgg 93780
acatcccatc ggccatcccc gcgcctccgg tttgctcgaa ttttatccag taaggtcgaa 93840
tccgctgcat ttaccttgtg tacccgtaac ctctcagggg ggtgtccttt cataaaatgg 93900
gataggtttt tatatccaac atgcatgtat tggttattta ttttattggg ttccgggatt 93960
ctttcgtcat cttctgtagg gtcaggcaaa ccccaggaag gacttggtgt tctccgtggg 94020
ccccgtttta ttacctctgc gcgaacctgc atttcatata atattcggat ttgggataaa 94080
taggactctg ttctcgcctt tttaaaaata gcctggcata actcttcctc tgacctatgt 94140
acctcgcttt gagttaccaa gaatcctaat cgggtggccc gtaatatgaa tgaaaaatac 94200
ggcgcaacta gtaatgagat tgacgcattt gaatatgata cagaaatttc ctggccttga 94260
ttattgttta cccggtgaag cttaaaacag cgaacaagtt cctgtttcca tagctcagac 94320
aaacgtttta tatcatctcc ataagggggg atataacgag attgaaaact attggcaata 94380
tatgcatcat cccctattat gccggtaaga tctataacct cgtgatttaa atcggcaata 94440
cgtgtttctt ctgccattgt aatatgtgac cctttagatg gctttatttt taccctctct 94500
tcccgtaacc gtttcagctc tccttctttg aactggagcc tttcggtcag atcgctgttc 94560
acatccttga gaccctcaat ggttttgaat aaattattca cataaccctc gagcatgccg 94620
ttgatactgt taaccaccga agttttaaac gcactttgaa cgtttgttgt tccggacatt 94680
gcccccccgt taaaggattg gttggccttg ccaaaccccg gttgtgatgt gtccaccgat 94740
ccacttcctt ccagaatgtg attgcccgtt tcttctagat aggaacgtac ggtttcggta 94800
atatctccaa catgtctcat gttttttaag ttaactatta gctttacaag tctagacgcg 94860

-continued

```
gccgatccag cccgtgttgt atcgttctcg cccattatac gatcaaccgc acgtgtgctg  94920
tgagatctat catcttcatt ccggcgacct attaacacgc gcaaaggggc tgtatttaaa  94980
acttggcaga cgcgagcatg ttcacgtaat gcataacagg ccaacacctc cccagaaagc  95040
cgctgtaagg gtgagtcaaa tactacaccc tccccacata caacgggcgg ccacacgacc  95100
aaacactctc ccttcatgcc cgttacatca tcctttgcca taattaatct tcggttataa  95160
ttataataaa gacgcgtcct atcataatcc ataatagcaa cattttgcat acactcaact  95220
aggcttgtga caaccgccgc tcctctggcc aacgttgcat cggcaacttt taacatctgg  95280
gacagttctg ccgcttgacc catatacgta tttaatggtg caggggttcc attctgttct  95340
gatcgtacct ttcttacaac gggcacaata cctacacagg ctatccagtc cacgtatttg  95400
gcaaaaccga cccttccatt taaaccactg gtatagagac aaccggttat tccacgcaga  95460
aactcaagta acgatgactg taatgtttga cgccaggttt caaaaacctg atgtgcaagc  95520
cgtacggctt ctgattctcc acatagccca taacgttccg ctagagcccc ggcatgcagg  95580
ttacattgtt ggatgtggtg ttcccaatct gctgctaggt cctcataccg agttgcatcc  95640
aacgcgttca tcaaaacggt tgcctgaact tggcgaatta cagtttccgt agaccgtaca  95700
gcgctatata tgccttgtcc atcggtatat ccaaagtcac cggctaggat ttttcgaaac  95760
aacatacttt gcgtggttgg gtgtattaac atccagccat cttcctccgg aaatgtacaa  95820
aaccctatat ccggggcgta ctcattccag tatatatcga acatgttctt gtattggtca  95880
tttgggttac ttccattcaa gccctggtca atagaaacag aacttgctat ccttttttct  95940
tcactaccgg aactgttatt aaaaagagac gttatttcgg ccattgaaaa ccacgatgaa  96000
aagatcaatt tctgtagaca gttcttcacc caaaaacgtt tttaatccag agacgcccaa  96060
tggatttgat gacagtgtat atttaaactt cacctctatg catagcattc aacctatcct  96120
ctcacggatt cgagaacttg ccgcaattac gattccaaaa gaacgtgttc cgcggttgtg  96180
ttggtttaaa cagttactcg aactgcaagc gcctcctgaa atgcagagga atgagctccc  96240
cttctccgtt tatttaatta gcggaaatgc cggctccgga aaaagcacgt gtatccaaac  96300
gcttaacgaa gctatcgatt gcattattac cggatccacc agggttgctg cccaaaatgt  96360
tcatgctaag ttatcaacgg cttatgcgag tcgtccgata aacacaatct ttcatgaatt  96420
tggttttcgc ggaaatcaca ttcaggctca gctgggccgt tacgcatata actggactac  96480
gacccccct tctattgagg acctgcaaaa aagagatatt gtatactact gggaagtttt  96540
aattgatata acaaaacgag tgtttcaaat gggggacgac ggtcgcggag gaacatcgac  96600
atttaaaacc ctgtgggcaa ttgaacgttt gcttaataaa cctacaggct caatgtccgg  96660
aaccgcgttt atcgcatgcg gttcccttcc ggcttttacc cggagcaacg ttattgttat  96720
tgatgaagca ggattgctag ggcgtcatat tctcacggcc gttgtttact gttggtggct  96780
tttgaatgct atatatcaaa gccctcagta cataaacggt cgaaaaccgg tcatagtatg  96840
cgtcggttcg cccacccaaa ctgactcgtt agaatctcat tttcaacatg acatgcagcg  96900
ttcacacgta actcctagtg aaaatatact cacgtatata atctgcaatc aaactctgcg  96960
tcaatatact aacatctcac ataactgggc aatctttatt aataacaaac gatgtcaaga  97020
ggacgatttt ggaaatcttt taaaaacgct tgagtacggg ctacctatta ccgaagcaca  97080
tgcgcgtctg gtcgatacat ttgttgtacc tgcatcctat attaacaatc ctgctaatct  97140
tcccggatgg acgcgtctgt attcgtcgca taaggaggtg agcgcgtata tgagtaagtt  97200
acacgcgcat ttaaaactat cgaaaaatga ccatttttct gtgtttgcct taccgactta  97260
```

-continued

```
tacattcatc cggctaacgg catttgatga ataccgcaaa ttaacgggac aacccggact  97320
ttctgttgaa cattggatac gggcaaactc cggtcgtttg cacaattatt cccaaagccg  97380
agatcatgac atgggaacag ttaaatacga aacacattca aatcgcgact taattgtagc  97440
ccgtacagac atcacttacg tgctaaatag tctcgtagtt gtaaccacaa gactacgtaa  97500
gttagttatt ggattcagtg gtacatttca atcgtttgca aaggttttac gtgacgactc  97560
ctttgtgaag gctcgaggag agacatccat cgaatatgct taccggtttc tgtcaaacct  97620
aatctttgga ggcttgatta acttttacaa ttttttgtta aataaaaacc tacatcccga  97680
taaggtatcg ttagcataca aacggttagc tgccttaacc ctggagttat tgtctggaac  97740
aaacaaagcc cccttacacg aagcagcggt taatggggcg ggtgccggga ttgactgtga  97800
tggtgcagct acttctgccg ataaagcctt ctgctttacc aaagccccccg agtccaaagt  97860
aacggcctcc atacccgaag acccggatga tgtaattttt acggcactta acgacgaggt  97920
tattgacttg gtatactgcc agtacgaatt ttcctatccc aaatcatcca atgaggtcca  97980
tgctcagttt ctgttaatga aagctattta cgatggtcga tatgccatat tagcagagct  98040
tttcgaaagc agctttacaa ccgccccctt tagcgcgtat gtcgataatg ttaatttcaa  98100
cggaagcgag cttttgatcg gcaatgtgcg gggggggctg ttatctttgg cattacaaac  98160
agatacgtat acccttttgg ggtatacttt tgcacccgtg ccagtctttg tagaggaact  98220
gacccgaaaa aagctgtacc gcgaaactac cgaaatgtta tatgctctac acgtacctct  98280
tatggtctta caggatcaac atgggtttgt gtccatcgta aacgctaacg tatgtgaatt  98340
taccgagtct atagaggatg cagaattggc aatggccacc acggtggact atggccttag  98400
ttctaaacta gccatgacaa ttgcacgctc acagggtctg agtttagaga aggtagctat  98460
ctgttttacg gcggataaac tgcgcctaaa tagtgtgtat gttgccatgt cgcgtacggt  98520
ctcctctagg ttcttaaaaa tgaatctaaa ccctctacgg gaacgatatg aaaaatccgc  98580
agaaattagc gatcacattc ttgccgctct acgtgatccc aacgtacacg ttgtgtatta  98640
aagcattgta taaaaacacg catgcgggct tgctgttctc atttctaggt tttgtcttaa  98700
atacacccgc catgagcatc tctggacccc caacgacgtt tattttatat aggttacatg  98760
gggttaggcg ggttcttcac tggactttac cggatcatga acaaacactc tacgcattta  98820
cgggtgggtc aagatcaatg gcggtgaaga cggacgctcg atgtgataca atgagcggtg  98880
gtatgatcgt ccttcaacac acccatacag tgaccctgct aaccatagac tgttctactg  98940
acttttcatc atacgcattt acgcaccggg atttccactt acaggacaaa ccccacgcaa  99000
catttgcgat gccgtttatg tcctgggtcg gttctgaccc aacatctcag ctgtacagta  99060
atgtgggggg ggtactatcc gtaataacgg aagatgacct atccatgtgt atctcaattg  99120
ttatatacgg tttacgggta aacagacctg acgatcagac cacaccaaca ccaaccccgc  99180
accagtatac atcgcaaagg cggcagcctg aaaccaactg tccttcttca ccacaaccgg  99240
ccttttcac atcagacgac gacgttcttt cgttaatatt acgggacgcc gcaaacgcgt  99300
aaagacagat tcaagactaa catttatccc aactgattac atttcatacg cgaataaacg  99360
acacaaaaaa tttatattta acggctttta atttgaagac acctatcctc ttaacgttga  99420
tgagccttgc aggttgggtg ccgcgcttca ccggtattat acataaccga tttaccgtgt  99480
ttacggcagt ctgaccattt accagtgtat gtctgtaata cgacgttgtt gtgtcccgac  99540
aaaattaact cgcgtacaaa tttctgatgt tcccccggcg tggcaacgct ggcatttcca  99600
```

-continued

```
aacacattac gttctcgtac gtccatgacc gctattttca gtattaattg gttggtcggt  99660
caaagtattt tccttatgta aaaggacacg atctaaagcc gtaaactcat acacaaacac  99720
tggtaccaac ggacgcgatt ttccgtccgt tgagcgggtg taatatcggc gaggtcttct  99780
tgcacgaata ctctcgtaca gtaggtttct gacacggggt gcatgggttt tttgacacaa  99840
cacaaacatt tgcaggctct tatgactgga tggattgaat ttatttttag atagggtcac  99900
gtgtttttgt cgtgacacgc ctcgaccaga aaaggctgcg gttttcgtac acgcgaccgt  99960
tatttcacag gcgttcataa ccaagctgcg gcggatggtg tcggttaatt gtctccgccc 100020
aagttcgtca atagatgata ccatgaacaa cgtatcaaat ggtacatagt cgtctttggt 100080
tttctcaata cagcccgcgt gcccaatcgg aaatttttca tttgcatcaa cgctattttc 100140
tgtaaaatcg ttctgaacac tgtgttggct ggctacctgt ttaaaatttg ggatcgaaca 100200
cggtccacga tgcaatcccc aaccccattg aagcaatgcc gtcggtacgg aaggaggcaa 100260
ctccgaaaac attatggtac gcaagagggt cgattggagt gttatataac actccaatcg 100320
atctcgggtt cgcctttacg cgtaaaatac tcattggctt gaacgaaatg tcgacaattc 100380
cgaaatggaa cacgggacaa tggcgacgga tgcgcgtgtg ttagcaccag atgacatctt 100440
gaattcggtt gggttgtctt ctgtgcatgc gcaccccaca gcataaaaac taaccctgta 100500
cggttctcgc ataacctctg tagcacgcgt tgcaccagcc gcccccagcc taagtataca 100560
tgcgaccccg gagtcccgcg acgaaccgta agcgtggtat tcagcaataa cacccccctgc 100620
cttgcccaac tctccaggca tccgtgagtg ggcggagtca tatttgggta tgattccatg 100680
agggccgcaa aaatattttt aagactagac ggtggtgtta tgccacgttt tacactaaac 100740
gctagcccat gtgcatgtcc cgcggtaggg tatggatctt gaccaataat tacaacgcga 100800
atgctctggg gtccgcaaaa tcgcgtccat gcaaaaatat cgcctgtaga tggaagtatt 100860
tcttcccctg aatttaaaag acgattgtat tctaaaaaaa tacctttcgc gtacggctct 100920
ttaagttcgt ccgacaacag gtcataccac tcaggggaaa tgttaaactt gctgaaaact 100980
tcaaccgaat ccagttgcga agagacgggg gtgaacgttt ccgtgtcgta atgatgtgac 101040
atgttattta acttgaaggt tggggggtct agcttaaccc ccaaaggcag cccgcggggt 101100
cgcttgcggg ttttttttggt aaccggatgg gccaaaacat aaatgtcctt tgaatccgat 101160
agtttcattt cattggcata cgcgttggaa caaacggtcg gctccccaga cacatccatt 101220
ttccgggata tttgtggaag atggagtaga gtctacccat acaccggaaa gggcatccaa 101280
caaagcatcg cgtatgtccc cgcttttatg ttcttcacca acagattgtg ccagcccctt 101340
taaggtgacg tatggatttg tccagtacgc catttgtttg tctttaaacc aaagtataac 101400
ttccggtact ggacattttg tcttaaccac gattcccgat agcgcctcgc tgaggtttga 101460
taccggggt gccgcatagt cccacgcctc atataccgat gacacgcacg gttccgttat 101520
aatcaaactc acatccgata gcggtttggc tccaaaaaac aacggagtgt cgtcttggag 101580
atgaagacaa tacgcgattg tgatagtttt taaaaaaact atctgcagta accatttatg 101640
tgatgccatg acgcttgtgt tttcccttca ctacgacgtt gtcgtatcct ttgaaaaact 101700
tgaccactct aatggaagca tggacaagta tgagttttat atatacagtt ggcctttagt 101760
taaactcttg gtgtcatatc tcattttcct aaaaagggcg atcttaatat gtcaaacgtc 101820
acggcgtgcc gacaaagcga atttccatgc aagatttgga tgtagtattt atacacccaa 101880
tcacatgtca cgtattaagc tttacagtcc cccgttatct gatataatca cttttcttaa 101940
cacgtcatcg ggaaaacaga tgtttatatt atacctctcg cggtcattta cggcaaatac 102000
```

-continued ttagaccgtt ttcaagcgga ctgaaaacgc tcaaattgcc ttttggaggc ctgcccaacg 102060
gccattatcc cttggatcta agattgattt gcggtaacgt ttgccaatca agctttaaaa 102120
acgtacccca aacttaaaac gctcaaattg ccttttggag gcctgcccaa cggccattat 102180
cccttggatc tgagattgat ttacggtaac gtttgccaaa cccacgcatt tcagtttaaa 102240
tatttctaag cattcttagt gcgtacttgg cagcgtgctt aaaatatcaa ccaatatcca 102300
ttatgctaca cgtttccttc tatccgtttc aatccattaa aagtccatta acaaaaatga 102360
tgcatcatac ctaattcacc taaaaacctg actcattgca gcagcgtttc ctccttgcag 102420
actatccagt tggcatttta aacgggtccg gctgcctaaa ccgaaaacac cgttgccttt 102480
actgtaagta caaaactaaa atttatattt gcgtgcgtat tttgtaacat atatgccttt 102540
tatccccccg caagtttgct ttaccctcgc cttcaccacc cccgccacct tccggccatt 102600
ttaataactt taattgctat aagacatacc caaaccggat gatttttgcc gctggaaaaa 102660
cagcttctaa ttttcccgtc tcaactcggc cttggttgca tctccaagta tacctttagt 102720
ttgctcccgt agaggtgtat aaatacaaac ggtgacaagt attgagcgta atctcaaatt 102780
tttgtaattt agggcggagc gcttacgaca gcacatgcgt actgttagac tgttatgttt 102840
attgtatttg cagagcagga tgccccggtt actccgagac cggattgcgg gcattccgaa 102900
tcgtgtacgg acttaccagg gggcagtatt tacaccttgg gttccagata taccaaccct 102960
tacgaccaat agcaacactc aggtattttt aaaatgcacg tttaatgatc ataatttaca 103020
tacagttggt aataaagcag actgtggatg tttaaggcat ttccttcccc ctcccaacaa 103080
actaggactt cttcatcttg tttggaatac ctttacccgc tttaccggca gagctttttt 103140
tggtaaggtg tttcagtgaa cctgatgttg atccggaggt ggagggggta ttggactccc 103200
cctgtggaga ggcaactttg cgggttttac ttcccttaca tgccgaatca gactcagatg 103260
tcaggtctat tgttaagcat cgtttaacgt ctctgccggt atgaaataaa cggcgcttag 103320
caccccttgc gcttcccggt ttaatccccg gtaacacaga aaaaagcctg actttttggg 103380
gtgtatttac caatcgggta tccctttcat cgccacgaga ggtctccccg gttgaggtgg 103440
tttctggtct tacaattgga cctgtaatta gttggatggc tgtatctttc caggtccagg 103500
tttgcatggt taggcgggtt ggatcggtac atcgatccaa caagaataac atgtttgtta 103560
caaacggtcc tgttgaatca tgcaaaagac aacgcaggga tgtttttaat cccgcctcat 103620
cacgcccgta aatacctata tagtttaata tcaacatttt tgtaggctct acaatttcgg 103680
gttgatacag ttccgcaagt tgatcatcaa gccatccgag taaaggttgc atgtaacacg 103740
ggaatctcgc gtttccctct gttcctctat ccgtggctcg aaaaggcagt ctgtccatgg 103800
ttcgtgggtc ttgattaatt cccacagata ctggacgatc acggtagtcc tgccccccgg 103860
tccggggttg ctgtgcagat tcaatcgagc catacaccac cggggtcgcc gatcgaacag 103920
caggttggtc tttaaaaaat accttccgta aaaatgatgc ggtagagcat gttttggtta 103980
caccagggct cgagtctcgg gtcggtggtt gtatagaatc ctgttgagag tcacttggtg 104040
actctgctgt gggctctcta gccgacgatt gaaggggccc agggtttggt gattgaatgg 104100
gctcccgact cgatcttgat gttggctgtt ggatggactc ccgactcggt cctgggcttg 104160
gtggcagaag atctatgaca tctcccggta ggatgtcgat ggaatcttca aatgacggct 104220
cagaaaaacc atcgtcgtcg gatgggtgca cttcatattc cttgtaactt gtatcactta 104280
cgatcttatg caggatggat tgcactggac accggcagag aggacactgg acgctggtgg 104340

-continued aggtccatgc ccgaatacaa acaaagcaga agtcgtgcaa acacggcatg gtttttccga 104400
gatcggaaac ggtgctcatg catatggtgc aggtattatc cgaagcgtcg gaggtgccgc 104460
taccgcccgc taatatggta tccatggtaa caactggctg tattctaatg tccgggcatc 104520
caaacacgta gcagaactgc catgcgttct aaattgtgag ttgtggcgag tacattttta 104580
taattggtac caacgaagac acacccctat atccctccac ccatttcttt taagtcccac 104640
ccactaaaac gtgggtataa aatgtgtatt ggggtaggcg gacagtccca acaaacaggg 104700
aagttgattg gtataacctt gggccgggta tacagctaag tgacatttta gattctgtct 104760
ttatttagat aaagagcgat acgaagacat ttctccaccc ccctgtaata cccgtaaata 104820
aaggtaagtc cacaaacaaa agcactgtat ataggaagtc gggtgtattg ggacagttac 104880
tccattagag gcgtacaaac aatactggga tagggtaatg caagtccccc ccgatggtcg 104940
ccccgcaaac gcgcggggag gtggggtcgc tttttttttt ctctctcgag ggggccgcga 105000
gagggctggc ctcctctccc ggggtccgcc gggcgcccag aaaccggggg ggggttattt 105060
tcgggggggg gtccgaccag cccgcccgtc gcccgcccgc acagacagac agacactttt 105120
ttcataaaaa ccgttccgct tttattaaca acaaacagtc cgcgcgccag tggcgctcac 105180
gagaaaagga ggggactccg tcacccccga ctctgcgggg ggctcctccc cccgcgccct 105240
ccccacacat cgtcctcgtc ctcggaggac gaggacgagg acaacagctc caccttgacc 105300
gccgggcgca aacccacccg gcggtctcgc agcacacccg gggccaccga cacgatgctc 105360
accccaaagg atgaccccgg tgcgtccccg tcgtccccgc ccccctcctc gctgtcccac 105420
gcgtcttcac accccacctc ccaatcgtcc agctccaaag cgtgttctct gtcgtctgcg 105480
gtgcgccgct gtcgccccgc ctgggtttct gacggccgtt ccgagccccc gtggtgtccg 105540
aacacgaacc gtgttccgtc gctcccctcc aacaccgtct ccgcggcccc aaaaccgggc 105600
ggccacatta ctctgggaat cggggggagg gcattccgag cctcgtccgc cgacgcatac 105660
agcgccaccg accgaccggc cacgggtgga agcacgagtg gttctgcggc agggtcgggt 105720
tccagcaggg cgtggcggca aaacaccctc gcccaggtgg gtacgtcgcc ggcctccggc 105780
ccggcggccc ccggtctccg tccctcggga aggaagacgg gtcgaagcgc ggcacccagg 105840
ccccatcggt ttgctgcgcg gtggctatgt gccgcctcgt ccacaaagtc ggctgccccg 105900
agccccagac cccgagactg tcgcgcgagg tccttgcaac cgtcaaaacc cggcagcacg 105960
tactgccggt attcacgggg cgacaggggg acgcgggtct tggggcccgc gcgggtacac 106020
acggtgtatg cgacgttccc accgcggcac aaacacaggg gttgttcgcc cgggtacagg 106080
ttggcaaacg cagtctcgat acgagcaaaa ctcgctggcc caaaggtgcg cgacgatgca 106140
aacacggccc gggcgagtcc ttctgtgacc gccgagtctg gccatcggac gacggcctgg 106200
gcgtccggtc gcgccggggc ccggacgtac acgtgatact gagacaaagc gggtccatcc 106260
ctgggccacc tctcgagggc caccgcgtcc aacaccagca accggcgccg ggcagaggcc 106320
aaccgcgagc ctagatactc gacggccccg gcaaaggcca ggtctcgggt cgacagtaat 106380
aaaacgcccc gggcgttcaa agcggacacg tccggcgggc cggtccagtt cccggcccag 106440
gcatgagtgc tcggcaggca caaccggtta ctcagggctg ccaggaccac agacagtccc 106500
cctcgggatg gactccatga cggtcccgga tctgtcgcga gggtgctctc gaggggggccg 106560
ttgatgtcct ctccgggcaa cggatcgtag atgatcagaa gcctcacatc ctccgggtct 106620
gggatctgcc gcatccaggc gcacctccgt cgcagcgcct ccactccgct gggtggacca 106680
aaccgtcggt ctcctccgcc cggacgccga gcggcgattt ccgccaaggc gccgggatca 106740

-continued aagcttagcg cagggcgcca ggccgtggga aacaatgggt cgtcgaccag acgggcgatg 106800
gtttcggggg tacagtacgc cttgcgagcc tggtccgacg ggaccggggt atgcagggcc 106860
ccccggggaa tacgccgaaa tcccccgttt ggggccggtc cgtcaagtgg catcgttatt 106920
acggcggggg gatccaccac agggcccgag gtgatggtca cgggctcgga tacccgcctc 106980
ttggccttgg aaaccacatg atcgtctgca acccgggcgt ccgcgacggg tgtctcccta 107040
atcttgtcga ggaggcttct gctctcgact ggctgggact tgcgcttgcg cggagttcgt 107100
aaacgatcat ccggtggaca cacagaaaga gagcgtgcgg cggccgacgg ctgagggtcg 107160
ggagcctgtg tggccggggt tgttggagaa gggtgaccgc gggagatccg cgccgccgga 107220
ctggagcccg ttgcctcggg gtatgccatg ctggcaaagg ctctgcggag actctgtagg 107280
ataaagtgtt tttgggcccg gtcgtatcga cggctcatag ccacggccgc ggccgcgtgg 107340
gggagagccc agagggcctc ccccgtggcc atggcttcgc ctacatgcgg aacgggagac 107400
gctacgctcc ccgtaacggc ggtacccgcc cgtcccggtg gcaacagctt ttggtagaac 107460
tggttcaggg ccgagttgac accggtcagc ttggggttct ggagccatgc tatagggtct 107520
ctgtctggac agtagatcag gttaatcagc gcgcggtact gtctagccgg atctcccaac 107580
tccggcacgt aaagcggcac gggttccgtt gaggcctcgt aacgagcccg cgccgctctc 107640
acagcctcat cctcccagtg accctctctg gtctccccgg acggtccaaa ccgcaccctg 107700
ttggatggga ggggtgccga tccgggccaa gggcttccgt cgggcatcat gagcggcccc 107760
gacaccgggg gaattatcgg ggttctggat cgcggcaggg aaaatgattt ctgtctctgg 107820
cgccccggtt cccccgcaag acgtttggtc ttacgaatcc tcggatcggg accgctgatg 107880
gatcgatatc ccggttggat attttgtttc gtcgacccac catcatttga gtccgaatca 107940
tccgaatttg acggggaagg ggcgtgttcg cgtccggacc tgctgcctgt agtttcactt 108000
cccaccgaaa cgcgccgggg ttcatcgtct tcatcctccg atgacgatcc ccacgacgag 108060
gaagaggatg aagacgaaac aaactcacga ctctttggct ttttctccac tgggctgtca 108120
tcctcaatcg ggtctggtgc gtgggatctt cccggcaggg ccaaaaaacgc tctaggtttg 108180
ccccccgacg aacgtccagg gacgcgaggt gttataccccc gggcatcatg tttccttggg 108240
cgggtatcat cggtctcaaa cggcaggtcc gcctttgccc ccttagcggg aacgctgtcc 108300
gaaaggacgt ggtacaattg ctcaaccggg ccgggtacag gtccaccggg tttccgcgcc 108360
gggagtggga ccttaacctt caaagtcttt ttcttcgggc tctttccctg agcgggccgt 108420
tgagttttct ggagaactac tccgtccccc gatgcatgcg catgacccgc ttgctcatcg 108480
cccggctttt tacccgagat ggactgagtt tgtctgtctc gatggaccac cgacggcaaa 108540
cctggtgaat ttcctctcgt cgtttgtcgg ggtatagacc gctggtcttc ccgttgatcg 108600
ttcccggcgg cgtctccaac aggagacgcg ggggatacag gggagaaggc ctgcgggaac 108660
ggaggggtcg tacctctgcc cgtttcccca tcgttcatcg gtggttttgg agacctagca 108720
agcttcgttc cgagagagac tgtctcaagg gagcgatcgg ctcctgttgg ttctcgcgcg 108780
ccggcctccg agaatcgggt gtggaagacc tcggccagcg ggattacagg cgagcccatt 108840
agatcctgac cgtcctcgca tacgtagtcg tcttgtgtta gctcttcgcc aacatcttcc 108900
gttctgggtt ctggttgaag tcccgatacg gagggaattg aaacgatctc gtgttcccgt 108960
cccaccatga ccccgttctc tccaaatagt agatcgtcag gctgactcga ggtgaccacc 109020
cgggccctgt gttcggcggc cgccgcggcc gcgtccaaca ggtccattaa ctccaaagta 109080

-continued

```
tcaggcgacc ccgcgcgttg gggtgtagag cgctgcatcg gcggcgtatc catcgcactg 109140
gggtgaattt agacgtaccc gagttttcca aacgctctcg cagccttcaa aggattgcga 109200
ttgcggttgg tgagggagtt ccaacagtac ttaaaacgtg ttgtgccccc ccctcgaccg 109260
catatttcct ccccgtgtcg tcaccgtgta aatattctta atgataagac gatgtagtga 109320
ttggacgaga ctcgaggcgg gaagttcatg gaccatagta tgcgtttaag gagagaccgc 109380
tggttggcga tgtacgcccg gtgtctattt ccgcatacct tacaacatca taacaaggga 109440
taccagacat gtgaatttca tttacatatg tttaaataac aaccaatcat cgtgtgtcta 109500
cagacgatat ataatataca taaacacaat tggggttgtc tcacatgcaa aacatcttat 109560
ataacacggg ttgtttccac ccatccggca tctagttaat caaatgcacg tcgacggtgt 109620
gtttgggtcc ctctccgtcg tcattacgtt cgcgcaatca acaagcgtat acaccaccac 109680
ccctcccaac gattatgtca ggcggcacga agcccgcgat aacccataaa atacacacgg 109740
ggttgtggtg ttcacgtaac cccccgccga tggggagggg gcgcggtacc ccgccgatgg 109800
ggaggggggcg cggtaccccg ccgatgggga gggggcgcgg taccccgccg atggggaggg 109860
ggcgcggtac cccgccgatg gggagggggc gcggtacccc gccgatgttt ataaccataa 109920
ttctctaaac cgttgtagaa aatcacaaaa aaatttattc aaaaacaagt cgaagaactt 109980
catatctgag gcatgtaaac ccgttcgcac ttcctggggt ggaatggggt ggggtggggg 110040
ggtgaaaaag ggggggggtt aaattgggcg tccgcatgtc tgtggtgtac gccaatcgga 110100
tacactcttt tgatctgcat tcgcacttcc cgttttttca ctgtatgggt tttcatgttt 110160
tggcatgtgt ccaaccaccg ttcgcacttt ctttctatat atatatatat atatatatat 110220
atatatagag aaagagagag agtttcttgt tcgcgcgtgt tcccgcgatg tcgcggtttt 110280
atggggtgtg ggcgggcttt tcacagaata tatatattcc aaatggagcg gcaggctttt 110340
taaaatcgat ttgacgtgat aaaaaaaaac acacggggcc ccccccttt tttggtgtta 110400
taaaggcaac ccaatcgaag gtctcccgcc ccggaatccc ccattgccat tttacccaag 110460
tagccttatt catagatgta aacgtttggg tgtgtgtttt gttgtgcagg gttcgtccga 110520
ttcataacgc gacagcgtcg agtcggtttt aagggaaaag gttactacgg ccccaaggac 110580
atgttttgca cctcaccggc tacgcggggc gactcgtccg agtcaaaacc cggggcatcg 110640
gttgatgtta acggaaagat ggaatatgga tctgcaccag gacccctgaa cggccgggat 110700
acgtcgcggg gccccggcgc gttttgtact ccgggttggg agatccaccc ggccaggctc 110760
gttgaggaca tcaaccgtgt ttttttatgt attgcacagt cgtcgggacg cgtcacgcga 110820
gattcacgaa gattgcggcg catatgcctc gacttttatc taatgggtcg caccagacag 110880
cgtcccacgt tagcgtgctg ggaggaattg ttacagcttc aacccaccca gacgcagtgc 110940
ttacgcgcta ctttaatgga agtgtcccat cgaccccctc gggggggaaga cgggttcatt 111000
gaggcgccga atgttccttt gcataggagc gcactggaat gtgacgtatc tgatgatggt 111060
ggtgaagacg atagcgacga tgatgggtct acgccatcgg atgtaattga atttcgggat 111120
tccgacgcgg aatcatcgga cggggaagac tttatagtgg aagaagaatc agaggagagc 111180
accgattctt gtgaaccaga cggggtaccc ggcgattgtt atcgagacgg ggatgggtgc 111240
aacaccccgt ccccaaagag accccagcgt gccatcgagc gatacgcggg tgcagaaacc 111300
gcggaatata cagccgcgaa agcgctcacc gcgttgggcg aggggggtgt agattggaag 111360
cgacgtcgac acgaagcccc gcgccggcat gatataccgc ccccccatgg cgtgtagtct 111420
ttataaataa atacaatggt ttggctcgtg tctttttttg atgtctgtct gtgggggagt 111480
```

-continued ggggtgttgt ggatattaga gggtagaggg tgctggtttg aacgtctcca ttaacccacg 111540
gggtccccac acgggccgtg tggtatgaat ctctgcggat cccgcggtga gcacccgggc 111600
ggtgaatatg ccggacttta ctgcacacga cacgataccc ccgcgcacca ggctctcatg 111660
aacgacgccg aacggtactt cgccgccgcg ctatgcgcca tatctaccga ggcctacgag 111720
gcttttatac acagcccctc cgagagaccg tgcgcgagtt tgtgggggag ggcaaaggac 111780
gccttcggac ggatgtgcgg ggagctcgca gcggatagac aacgtccacc ctcggttccg 111840
ccgatccgca gagcggtgtt atcgttatta cgcgagcaat gcatgccgga tccacaatcg 111900
catctggagc tcagcgagcg gctgatattg atggcatatt ggtgctgttt gggacacgcc 111960
ggacttccga ctattggatt gtcgcccgat aataaatgca tccgcgccga attatatgac 112020
cgccccgggg gaatttgtca caggcttttt gacgcgtacc tgggctgcgg gtcccttgga 112080
gtcccaagaa cctacgagag atcctgacac cccatccctt tatatagaaa aaaaaaataa 112140
atttaaaaca tacaccggat aaaagcgtac tgtttttat ttaaatttac acgctcggcg 112200
ttgccccggt tcggtgatca ccgggtctta tctatataca ccgtgtaact cgaacccccg 112260
tgactccctc caatcgcgtt accaaactct tcttccgtat ccgtagattc cgagtcctcg 112320
aaatcgtcca cttatccaac aaattgtgac gttatatatc ccaaggcaaa ggccgctccc 112380
gtcatagcaa atacaaagac aattattagc gtaatataac agaatttttt acgatgatat 112440
attttatgtt gatattttcc aattcgacgc aaaaattcat ctgccgtttc attttcgcta 112500
tcactataat aacacttttc agccgaacgg ctcggttgta tggctgttat cgttgtatta 112560
tttggttgcg ctcgcggggt taccaccgct tccatcagta aggccacggc ctcaccctcc 112620
atggtgtttt gtccggccat agaaatccag attgtaaggc cagcaggcta gtttaaaagt 112680
gtttaatacc acacctttg atatttatat acatgcaaga ttctagatta ttcatcaata 112740
ggtcgtttaa agcgcgtttt cataaacgtt gtcagctata ccgacattct cacaaagagg 112800
taaagttacc ttacgttatt attaaataaa acatgtagac attattaata atcctaggaa 112860
caatcaaatc catatttgta agttatgttt aacccctccc ctttttgtca ttatctccgc 112920
cctcttataa tcggatcact ttataagtgt gtcggtgagt atattttgta cagttgttgg 112980
acaacaggtt tttggttcat taacactatc aacataagtc ggggtataca agtataatga 113040
acgacgttga tgcaacagac acctttgttg gacaaggaaa gttccgtggc gccatctcaa 113100
catcaccgtc acatattatg caaacatgtg ggtttataca acagatgttt ccagttgaaa 113160
tgtcgcccgg catagaatct gaggatgatc ccaattatga cgttaacatg gatatacagt 113220
cttttaatat atttgatggt gtacacgaaa ctgaagccga agcctctgtg gcattgtgcg 113280
cagaagcacg cgttggaatt aataaagcgg gatttgtaat attaaaaacg tttacaccag 113340
gggcggaagg ttttgcgttt gcgtgtatgg acagtaaaac atgtgaacat gtggtcatta 113400
aagcgggtca acgtcaagga acggccaccg aggcaaccgt gttaagagcg ttaacccacc 113460
catccgttgt acagcttaaa ggaacgttta cgtataacaa aatgacatgt cttatattac 113520
cacgttaccg aacagattta tactgctatc tagctgcaaa gcgcaacctc cccatatgtg 113580
acattttagc aattcagcga tctgtattac gcgcgttaca gtatcttcat aataacagta 113640
ttattcaccg tgatataaaa tctgaaaata tatttattaa ccacccaggt gatgtttgtg 113700
tgggagactt tggagcagcg tgtttccccg tggatattaa tgccaacagg tattatggct 113760
gggctggaac aatcgccaca aactctcctg agttattggc tagagatcca tatggacctg 113820

-continued ccgtggacat atggagtgcc gggattgtat tatttgaaat ggctacagga cagaactcgt 113880
tatttgaacg agacggttta gatggcaatt gtgacagtga gcgtcaaatt aaacttatta 113940
tacgacgatc tggaactcat cccaatgaat ttcccattaa ccctacatca aatcttcgtc 114000
gacaatacat tggtttggca aaacggtctt ctcgaaaacc cggatccagg ccattgtgga 114060
caaatctata tgagttgcca attgatttgg agtatttgat atgtaagatg ttatcgtttg 114120
acgcacgtca tcgaccatca gcagaggtgt tgcttaacca ctctgttttc caaactcttc 114180
ccgatccata tccaaatcca atggaagttg gagattaaaa ttcattaagc ctgttaataa 114240
aatattgtat aaattgtgtt tataacgtat aacccgttaa ggcaaatagg gtacaaacgc 114300
gcaatgtttt gaaatactaa tataaataac ataaccaata gaaacttaat acagagtcac 114360
gccccattac aacaaggata aaacacggga tcattttctt aacattgtag tagcgctgaa 114420
aagcgtcccc tcccccggct cacagagctg ctcttcggtg tagttgggta tactggtgcg 114480
cctcatttaa tcgcgatgtt tttaatccaa tgtttgatat cggccgttat attttacata 114540
caagtgacca acgctttgat cttcaagggc gaccacgtga gcttgcaagt taacagcagt 114600
ctcacgtcta tccttattcc catgcaaaat gataattata cagagataaa aggacagctt 114660
gtctttattg gagagcaact acctaccggg acaaactata gcggaacact ggaactgtta 114720
tacgcggata cggtggcgtt ttgtttccgg tcagtacaag taataagata cgacggatgt 114780
ccccggatta gaacgagcgc ttttatttcg tgtaggtaca aacattcgtg gcattatggt 114840
aactcaacgg atcggatatc aacagagccg gatgctggtg taatgttgaa aattaccaaa 114900
ccgggaataa atgatgctgg tgtgtatgta cttcttgttc ggttagacca tagcagatcc 114960
accgatggtt tcattcttgg tgtaaatgta tatacagcgg gctcgcatca caacattcac 115020
ggggttatct acacttctcc gtctctacag aatggatatt ctacaagagc ccttttttcaa 115080
caagctcgtt tgtgtgattt acccgcgaca cccaaagggt ccggtacctc cctgtttcaa 115140
catatgcttg atcttcgtgc cggtaaatcg ttagaggata accettggtt acatgaggac 115200
gttgttacga cagaaactaa gtccgttgtt aaggagggga tagaaaatca cgtatatcca 115260
acggatatgt ccacgttacc cgaaaagtcc cttaatgatc ctccagaaaa tctacttata 115320
attattccta tagtagcgtc tgtcatgatc ctcaccgcca tggttattgt tattgtaata 115380
agcgttaagc gacgtagaat taaaaaacat ccaatttatc gcccaaatac aaaaacaaga 115440
aggggcatac aaaatgcgac accagaatcc gatgtgatgt tggaggccgc cattgcacaa 115500
ctagcaacga ttcgcgaaga atcccccccca cattccgttg taaacccgtt tgttaaatag 115560
aactaattat cccggatttt atattaaata aactatatgc gttttattta gcgttttgat 115620
tacgcgttgt gatatgaggg gaaggattaa gaatctccta actataagtt aacacgccca 115680
catttgggcg gggatgtttt atgaagcctt aaaggccgag ctggtataca cgagagcagt 115740
ccatggtttt agacctcggg cgaattgcgt ggttttaagt gactatattc cgagggtcgc 115800
ctgtaatatg gggacagtta ataaacctgt ggtgggggta ttgatggggt tcggaattat 115860
cacgggaacg ttgcgtataa cgaatccggt cagagcatcc gtcttgcgat acgatgattt 115920
tcacaccgat gaagacaaac tggatacaaa ctccgtatat gagccttact accattcaga 115980
tcatgcggag tcttcatggg taaatcgggg agagtcttcg cgaaaagcgt acgatcataa 116040
ctcaccttat atatggccac gtaatgatta tgatggattt ttagagaacg cacacgaaca 116100
ccatggggtg tataatcagg gccgtggtat cgatagcggg gaacggttaa tgcaacccac 116160
acaaatgtct gcacaggagg atcttgggga cgatacgggc atccacgtta tccctacgtt 116220

-continued aaacggcgat gacagacata aaattgtaaa tgtggaccaa cgtcaatacg gtgacgtgtt 116280
taaaggagat cttaatccaa aaccccaagg ccaaagactc attgaggtgt cagtggaaga 116340
aaatcacccg tttactttac gcgcaccgat tcagcggatt tatggagtcc ggtacaccga 116400
gacttggagc tttttgccgt cattaacctg tacgggagac gcagcgcccg ccatccagca 116460
tatatgttta aaacatacaa catgctttca agacgtggtg gtggatgtgg attgcgcgga 116520
aaatactaaa gaggatcagt tggccgaaat cagttaccgt tttcaaggta agaaggaagc 116580
ggaccaaccg tggattgttg taaacacgag cacactgttt gatgaactcg aattagaccc 116640
ccccgagatt gaaccgggtg tcttgaaagt acttcggaca gaaaaacaat acttgggtgt 116700
gtacatttgg aacatgcgcg gctccgatgg tacgtctacc tacgccacgt ttttggtcac 116760
ctggaaaggg gatgaaaaaa caagaaaccc tacgcccgca gtaactcctc aaccaagagg 116820
ggctgagttt catatgtgga attaccactc gcatgtattt tcagttggtg atacgtttag 116880
cttggcaatg catcttcagt ataagataca tgaagcgcca tttgatttgc tgttagagtg 116940
gttgtatgtc cccatcgatc ctacatgtca accaatgcgg ttatattcta cgtgtttgta 117000
tcatcccaac gcaccccaat gcctctctca tatgaattcc ggttgtacat ttacctcgcc 117060
acatttagcc cagcgtgttg caagcacagt gtatcaaaat tgtgaacatg cagataacta 117120
caccgcatat tgtctgggaa tatctcatat ggagcctagc tttggtctaa tcttacacga 117180 cggggggcacc acgttaaagt ttgtagatac acccgagagt ttgtcgggat tatacgtttt 117240
tgtggtgtat tttaacgggc atgttgaagc cgtagcatac actgttgtat ccacagtaga 117300
tcattttgta aacgcaattg aagagcgtgg atttccgcca acggccggtc agccaccggc 117360
gactactaaa cccaaggaaa ttacccccgt aaaccccgga acgtcaccac ttctacgata 117420
tgccgcatgg accggagggc ttgcagcagt agtactttta tgtctcgtaa tatttttaat 117480
ctgtacggct aaacgaatga gggttaaagc ctatagggta gacaagtccc cgtataacca 117540
aagcatgtat tacgctggcc ttccagtgga cgatttcgag gactcggaat ctacggatac 117600
ggaagaagag tttggtaacg cgattggagg gagtcacggg ggttcgagtt acacggtgta 117660
tatagataag acccggtgat caccgaaccg gggcaacgcc gagcgtgtaa atttaaataa 117720
aaaacagtac gcttttatcc ggtgtatgtt ttaaatttat tttttttttc tatataaagg 117780
gatggggtgt caggatctct cgtaggttct tgggactcca agggacccgc agcccaggta 117840
cgcgtcaaaa agcctgtgac aaattccccc ggggcggtca tataattcgg cgcggatgca 117900
tttattatcg ggcgacaatc caatagtcgg aagtccggcg tgtcccaaac agcaccaata 117960
tgccatcaat atcagccgct cgctgagctc cagatgcgat tgtggatccg gcatgcattg 118020
ctcgcgtaat aacgataaca ccgctctgcg gatcggcgga accgagggtg gacgttgtct 118080
atccgctgcg agctccccgc acatccgtcc gaaggcgtcc tttgccctcc cccacaaact 118140
cgcgcacggt ctctcggagg ggctgtgtat aaaagcctcg taggcctcgg tagatatggc 118200
gcatagcgcg gcggcgaagt accgttcggc gtcgttcatg agagcctggt gcgcgggggt 118260
atcgtgtcgt gtgcagtaaa gtccggcata ttcaccgccc gggtgctcac cgcgggatcc 118320
gcagagattc ataccacacg gcccgtgtgg ggaccccgtg ggttaatgga gacgttcaaa 118380
ccagcaccct ctaccctcta atatccacaa caccccactc ccccacagac agacatcaaa 118440
aaaagacacg agccaaacca ttgtatttat ttataaagac tacacgccat gggggggcgg 118500
tatatcatgc cggcgcgggg cttcgtgtcg acgtcgcttc caatctacac ccccctcgcc 118560

-continued caacgcggtg agcgctttcg cggctgtata ttccgcggtt tctgcacccg cgtatcgctc 118620
gatggcacgc tggggtctct ttggggacgg ggtgttgcac ccatccccgt ctcgataaca 118680
atcgccgggt accccgtctg gttcacaaga atcggtgctc tcctctgatt cttcttccac 118740
tataaagtct tccccgtccg atgattccgc gtcggaatcc cgaaattcaa ttacatccga 118800
tggcgtagac ccatcatcgt cgctatcgtc ttcaccacca tcatcagata cgtcacattc 118860
cagtgcgctc ctatgcaaag gaacattcgg cgcctcaatg aacccgtctt ccccccgagg 118920
gggtcgatgg gacacttcca ttaaagtagc gcgtaagcac tgcgtctggg tgggttgaag 118980
ctgtaacaat tcctcccagc acgctaacgt gggacgctgt ctggtgcgac ccattagata 119040
aaagtcgagg catatgcgcc gcaatcttcg tgaatctcgc gtgacgcgtc ccgacgactg 119100
tgcaatacat aaaaaaacac ggttgatgtc ctcaacgagc ctggccgggt ggatctccca 119160
acccggagta caaaacgcgc cggggccccg cgacgtatcc cggccgttca ggggtcctgg 119220
tgcagatcca tattccatct ttccgttaac atcaaccgat gccccgggtt ttgactcgga 119280
cgagtcgccc cgcgtagccg gtgaggtgca aaacatgtcc ttggggccgt agtaaccttt 119340
tcccttaaaa ccgactcgac gctgtcgcgt tatgaatcgg acgaaccctg cacaacaaaa 119400
cacacaccca aacgtttaca tctatgaata aggctacttg ggtaaaatgg caatggggga 119460
ttccggggcg ggagaccttc gattgggttg cctttataac accaaaaaaa gggggggggcc 119520
ccgtgtgttt ttttttatca cgtcaaatcg attttaaaaa gcctgccgct ccatttggaa 119580
tatatatatt ctgtgaaaag cccgcccaca ccccataaaa ccgcgacatc gcgggaacac 119640
gcgcgaacaa gaaactctct ctctttctct atatatatat atatatatat atatatatat 119700
agaaagaaag tgcgaacggt ggttggacac atgccaaaac atgaaaaccc atacagtgaa 119760
aaaacgggaa gtgcgaatgc agatcaaaag agtgtatccg attggcgtac accacagaca 119820
tgcggacgcc caatttaacc cccccccttt ttcacccccc caccccaccc cattccaccc 119880
caggaagtgc gaacgggttt acatgcctca gatatgaagt tcttcgactt gtttttgaat 119940
aaattttttt gtgattttct acaacggttt agagaattat ggttataaac atcggcgggg 120000
taccgcgccc cctccccatc ggcggggtac cgcgcccccct ccccatcggc ggggtaccgc 120060
gcccccctccc catcggcggg gtaccgcgcc ccctccccat cggcggggta ccgcgccccc 120120
tccccatcgg cgggggggtta cgtgaacacc acaaccccgt gtgtatttta tgggttatcg 120180
cgggcttcgt gccgcctgac ataatcgttg ggaggggtgg tggtgtatac gcttgttgat 120240
tgcgcgaacg taatgacgac ggagagggac ccaaacacac cgtcgacgtg catttgatta 120300
actagatgcc ggatgggtgg aaacaacccg tgttatataa gatgttttgc atgtgagaca 120360
accccaattg tgtttatgta tattatatat cgtctgtaga cacacgatga ttggttgtta 120420
tttaaacata tgtaaatgaa attcacatgt ctggtatccc ttgttatgat gttgtaaggt 120480
atgcggaaat agacaccggg cgtacatcgc caaccagcgg tctctcctta aacgcatact 120540
atggtccatg aacttcccgc ctcgagtctc gtccaatcac tacatcgtct tatcattaag 120600
aatatttaca cggtgacgac acggggagga aatatgcggt cgaggggggg gcacaacacg 120660
ttttaagtac tgttggaact ccctcaccaa ccgcaatcgc aatcctttga aggctgcgag 120720
agcgtttgga aaactcgggt acgtctaaat tcaccccagt gcgatggata cgccgccgat 120780
gcagcgctct acaccccaac gcgcggggtc gcctgatact ttggagttaa tggacctgtt 120840
ggacgcggcc gcggcggccg ccgaacacag ggcccgggtg gtcacctcga gtcagcctga 120900
cgatctacta tttggagaga acggggtcat ggtgggacgg gaacacgaga tcgtttcaat 120960

-continued tccctccgta tcgggacttc aaccagaacc cagaacggaa gatgttggcg aagagctaac 121020
acaagacgac tacgtatgcg aggacggtca ggatctaatg ggctcgcctg taatcccgct 121080
ggccgaggtc ttccacaccc gattctcgga ggccggcgcg cgagaaccaa caggagccga 121140
tcgctccctt gagacagtct ctctcggaac gaagcttgct aggtctccaa aaccaccgat 121200
gaacgatggg gaaacgggca gaggtacgac ccctccgttc ccgcaggcct tctcccctgt 121260
atcccccgcg tctcctgttg gagacgccgc cgggaacgat caacgggaag accagcggtc 121320
tataccccga caaacgacga gaggaaattc accaggtttg ccgtcggtgg tccatcgaga 121380
cagacaaact cagtccatct cgggtaaaaa gccgggcgat gagcaagcgg gtcatgcgca 121440
tgcatcgggg gacggagtag ttctccagaa aactcaacgg cccgctcagg gaaagagccc 121500
gaagaaaaag actttgaagg ttaaggtccc actcccggcg cggaaacccg gtggacctgt 121560
acccggcccg gttgagcaat tgtaccacgt cctttcggac agcgttcccg ctaagggggc 121620
aaaggcggac ctgccgtttg agaccgatga tacccgccca aggaaacatg atgcccgggg 121680
tataacacct cgcgtccctg gacgttcgtc gggggcaaa cctagagcgt ttttggccct 121740
gccgggaaga tcccacgcac cagacccgat tgaggatgac agcccagtgg agaaaaagcc 121800
aaagagtcgt gagtttgttt cgtcttcatc ctcttcctcg tcgtggggat cgtcatcgga 121860
ggatgaagac gatgaacccc ggcgcgtttc ggtgggaagt gaaactacag gcagcaggtc 121920
cggacgcgaa cacgcccctt ccccgtcaaa ttcggatgat tcggactcaa atgatggtgg 121980
gtcgacgaaa caaaatatcc aaccgggata tcgatccatc agcggtcccg atccgaggat 122040
tcgtaagacc aaacgtcttg cgggggaacc ggggcgccag agacagaaat cattttccct 122100
gccgcgatcc agaaccccga taattccccc ggtgtcgggg ccgctcatga tgcccgacgg 122160
aagcccttgg cccggatcgg caccctccc atccaacagg gtgcggtttg gaccgtccgg 122220
ggagaccaga gagggtcact gggaggatga ggctgtgaga gcggcgcggg ctcgttacga 122280
ggcctcaacg gaacccgtgc cgctttacgt gccggagttg ggagatccgg ctagacagta 122340
ccgcgcgctg attaacctga tctactgtcc agacagagac cctatagcat ggctccagaa 122400
ccccaagctg accggtgtca actcggccct gaaccagttc taccaaaagc tgttgccacc 122460
gggacgggcg ggtaccgccg ttacggggag cgtagcgtct cccgttccgc atgtaggcga 122520
agccatggcc acgggggagg ccctctgggc tctcccccac gcggccgcgg ccgtggctat 122580
gagccgtcga tacgaccggg cccaaaaaca ctttatccta cagagtctcc gcagagcctt 122640
tgccagcatg gcataccccg aggcaacggg ctccagtccg gcggcgcgga tctcccgcgg 122700
tcacccttct ccaacaaccc cggccacaca ggctcccgac cctcagccgt cggccgccgc 122760
acgctctctt tctgtgtgtc caccggatga tcgtttacga actccgcgca agcgcaagtc 122820
ccagccagtc gagagcagaa gcctcctcga caagattagg gagacacccg tcgcggacgc 122880
ccgggttgca gacgatcatg tggtttccaa ggccaagagg cgggtatccg agcccgtgac 122940
catcacctcg ggccctgtgg tggatccccc cgccgtaata acgatgccac ttgacggacc 123000
ggccccaaac gggggatttc ggcgtattcc ccgggggggcc ctgcataccc cggtcccgtc 123060
ggaccaggct cgcaaggcgt actgtacccc cgaaaccatc gcccgtctgg tcgacgaccc 123120
attgtttccc acggcctggc gccctgcgct aagctttgat cccggcgcct tggcggaaat 123180
cgccgctcgg cgtccgggcg gaggagaccg acggtttggt ccacccagcg gagtggaggc 123240
gctgcgacgg aggtgcgcct ggatgcggca gatcccagac ccggaggatg tgaggcttct 123300

-continued gatcatctac gatccgttgc ccggagagga catcaacggc cccctcgaga gcaccctcgc 123360
gacagatccg ggaccgtcat ggagtccatc ccgaggggga ctgtctgtgg tcctggcagc 123420
cctgagtaac cggttgtgcc tgccgagcac tcatgcctgg gccgggaact ggaccggccc 123480
gccggacgtg tccgctttga acgcccgggg cgttttatta ctgtcgaccc gagacctggc 123540
ctttgccggg gccgtcgagt atctaggctc gcggttggcc tctgcccggc gccggttgct 123600
ggtgttggac gcggtggccc tcgagaggtg gcccagggat ggacccgctt tgtctcagta 123660
tcacgtgtac gtccgggccc cggcgcgacc ggacgcccag gccgtcgtcc gatggccaga 123720
ctcggcggtc acagaaggac tcgcccgggc cgtgtttgca tcgtcgcgca cctttgggcc 123780
agcgagtttt gctcgtatcg agactgcgtt tgccaacctg tacccgggcg aacaacccct 123840
gtgtttgtgc cgcggtggga acgtcgcata caccgtgtgt acccgcgcgg gccccaagac 123900
ccgcgtcccc ctgtcgcccc gtgaataccg gcagtacgtg ctgccgggtt ttgacggttg 123960
caaggacctc gcgcgacagt ctcggggtct ggggctcggg gcagccgact ttgtggacga 124020
ggcggcacat agccaccgcg cagcaaaccg atggggcctg ggtgccgcgc ttcgacccgt 124080
cttccttccc gagggacgga gaccgggggc cgccgggccg gaggccggcg acgtacccac 124140
ctgggcgagg gtgttttgcc gccacgccct gctggaaccc gaccctgccg cagaaccact 124200
cgtgcttcca cccgtggccg gtcggtcggt ggcgctgtat gcgtcggcgg acgaggctcg 124260
gaatgccctc cccccgattc ccagagtaat gtggccgccc ggttttgggg ccgcggagac 124320
ggtgttggag gggagcgacg gaacacggtt cgtgttcgga caccacgggg gctcggaacg 124380
gccgtcagaa acccaggcgg ggcgacagcg gcgcaccgca gacgacagag aacacgcttt 124440
ggagctggac gattgggagg tggggtgtga agacgcgtgg gacagcgagg agggggggcgg 124500 ggacgacggg gacgcaccgg ggtcatcctt tggggtgagc atcgtgtcgg tggccccggg 124560
tgtgctgcga gaccgccggg tgggtttgcg cccggcggtc aaggtggagc tgttgtcctc 124620
gtcctcgtcc tccgaggacg aggacgatgt gtggggaggg cgcgggggga ggagcccccc 124680
gcagagtcgg gggtgacgga gtcccctcct tttctcgtga gcgccactgg cgcgcggact 124740
gtttgttgtt aataaaagcg gaacggtttt tatgaaaaaa gtgtctgtct gtctgtgcgg 124800
gcgggcgacg ggcgggctgg tcggaccccc ccccgaaaat aacccccccc cggtttctgg 124860
gcgcccggcg gaccccggga gagg 124884

<210> SEQ ID NO 2
<211> LENGTH: 125157
<212> TYPE: DNA
<213> ORGANISM: Varicella virus
<220> FEATURE:
<221> NAME/KEY: misc_feature
<222> LOCATION: (1)..(125157)
<223> OTHER INFORMATION: Attenuated Oka strain

<400> SEQUENCE: 2
ggcccagccc tctcgcggcc ccctcgagag agaaaaaaaa aagcgacccc acctccccgc 60
gcgtttgcgg ggcgaccatc gggggggatg ggattttttg ccgggaaacc ccccccgcca 120
gcctttaaca aaacccgcgc cttttgcgtc cacccctcgt ttactgctcg gatggcgacc 180
gtgcactact cccgccgacc tggaccccg ccggtcaccc tcacgtcgtc ccccggcatg 240
gatgacgttg cgaccccat tccctaccta cccacatacg ccgaggccgt ggcagacgcg 300 ccccccctt acagaagccg cgagagtctg gtgttctccc cgcctctttt tcctcacgtg 360
gagaatggca ccacccaaca gtcttacgat tgcctagact gcgcttatga tggaatccac 420

-continued

```
agacttcagc tggcttttct aagaattcgc aaatgctgtg taccggcttt tttaattctt    480
tttggtattc tcacccttac tgctgtcgtg gtcgccattg ttgccgtttt tcccgaggaa    540
cctcccaact caactacacg aaactactgt ccggaagggg aaggtattta ttctcgcttg    600
cagcttgtcg cgcgtgtatg cacaacaaaa gctatatatg tcaccaaagc caacgtcgcc    660
atctggagta ctacacccag tacattgcat aacctgtcca tytgcatttt cagttgcgcg    720
gacgcctttc tccgggatcg tggccttggg acatcaacca gyggaataag aaccgccggt    780
ggtcttgccc gaacgacgag tggcgacgcg ttgttctgca taagctctgt atgctgatac    840
ataaacacag agtctgtatc gctatcagat tcccgaacac cttccggtac cccatactcc    900
gataccctgg acattgcgga tcccaaaaat ataatattaa caggatttgc ttatactttg    960
ctacagctta tataaattta tgtgcgatac atcttaagtg catccgtacg ttatttatac   1020
attgcctgtc acgtgaaaag actgtgttac ccaataaagg ttctacaaaa aatgctttat   1080
tgggtgtttg tttaatagct attatcgtaa cccacccccg taaaatcata aaatgcatgt   1140
aatttctgag acacttgcat atgggcatgt tcccgcattt attatgggct ccactctggt   1200
gcgtcccagt ttaaacgcca ccgccgagga aaatcccgcg tcagaaacgc gatgtttatt   1260
acgagtgctt gcggggagaa ctgtagacct gccaggcgga ggaacgttac acattacctg   1320
taccaaaacc tatgtaatta ttggcaaata tagcaaaccc ggcgaacgtc ttagccttgc   1380
ccgtctaata gggcgtgcaa tgacgcctgg aggtgcaagg acatttatta ttttggcgat   1440
gaaggaaaag cgatccacaa cgcttgggta tgaatgtggt acgggcttgc atttactggc   1500
tccatctatg ggtacatttc tccgcacaca cggtttaagt aacagagatc tctgtttatg   1560
gcggggtaat atttatgata tgcatatgca acgtcttatg ttttgggaga atatcgcgca   1620
aaataccact gaaacacctt gtataacgtc gacgttaaca tgcaacttga cagaagactc   1680
tggtgaagcc gcacttacca cgtcagaccg acccactctc ccaaccctaa cagcccaagg   1740
aagaccaaca gtttccaaca ttcgtggaat attgaaagga tccccccgtc aacagccggt   1800
ctgtcaccgg gttagatttg ccgaacctac ggagggcgta ttgatgtaat cactaaataa   1860
aatacacctt ttttcgattg tacgtatttt tatttaaatg tgtagttcat agtccgccga   1920
cagccgctcg ggcttttccc ccacatacaa catgatcgta tgcctcggat gcaccggtcc   1980
aacactccgc cgagaagggg gatttacaat gacagtgata cccaatagcc gccagatgta   2040
cacccagctg tccggactcc agcatcatct gctgagttgc ggcgctgaag ggtgcatcgc   2100
atagggtgtt ataattagcc atttccggta acagtcgttg ggaatttagg aggctgcaaa   2160
acggctgtag gtcaacatac attggggatt cagatggttt atctcgacgt ccaagtccaa   2220
tcaaaaaagc gtgtaaatca tcagcccggc cgcatgttgc tcgaagagca cataacctct   2280
taacaccgta cagaggggat ggcgtcggtg catgtgagtt ggcagggcat gtccacgttg   2340
tttccaacgc cagtggcggt ataacttgtg taaacgacgc caacgggtca ggtttaagat   2400
tcactcggat gggttgactg ctttcggaag ctcccgttgt atccattaat taaacgttcg   2460
gtacacgtct ggtgtgtgtt ttacccgaat cagagacgga attgcaaaga tatyggtttg   2520
aaagcaatgt aatcccgccc atatatcccc aacgtcgcct taaaaactcc cacaatatta   2580
catttttatt agtcttttat taatatagaa tcacataaac aattgataaa atcaaggggt   2640
ggtgtataat gattaaaaat ataaattgat atgttttaca agcatgaaat aggtatttac   2700
tattctaaca ggtaaatatg cttaatgatt aaaaatacaa attagtatgt tttgacaagc   2760
```

-continued atgaaaaagg tattttttat tttagcagtt aaaggtacta cacttaaaat atttaccgta 2820
tggacgggcg tcagaaagat gcccggccca agttgagagg gtacattcaa cacgaccaca 2880
ctcgcgttgg tgggtgatta gggcctctaa aacaccggcc agacatgacc cgggtgtata 2940
ttcttgtaac acttgaacgt tacaactgat atcatcatat tccacaaatt tagagccacg 3000
gacaactata ttagcaatgc gggcaatcat aacaaacata taagtagtaa tacacgtgat 3060
atcactaaaa cgttgctggc gcaacagttc ggggagagta cgagacccca aatcgttgtc 3120
cctgtttaga agaagacatc ttacaaaagg ccccagcttt aactttaaat tctccaaaag 3180
tgacttcgag gttgcaacaa tgggattatt tgtgtagatg ggcaagtttt ttgccgctaa 3240
cattttaatc cacgttaaca gttcatccgc agactccaac gcttcaatca aagattctcc 3300
acgtatgact ctctcacgca acgcgcgggc aatacgtgag tccattttat atgactcaaa 3360
ggtacgataa agttcatgtc cgtacaacat caactccggc caagatgtgt tttgttttat 3420
ccccggaaaa catccaccgg aagcccatga atcaccctct tgtattgtgg catatcggac 3480
taccagtttt tcaattgttt catctaaatg gcgtaccgag tcaatggtca cgctggctcc 3540
cgcggtggag acgacttcaa tagcacggcc cgtaattcga tcgaccggga tatcatactc 3600
ttttcgaata cgctctcggc gggcgtctct cttggaaaat cgcaacctgt acgattcgtc 3660
atgtgtctga tcatttcttt ctcccgtggt cattgcagga ggcgttgtag gacgccgtct 3720
tcgatttgac agggatcgat cacggtgttt tcttgaactt tgggtgttat aagatctgga 3780
tgatcgtcga tgtccccgtt cgatgcgtgc atatccagtc tccacgtctc ttcctccatg 3840
atggtttgaa tcgggtaata caacaaccaa agttttcggg cgattgtggt ggtagctttc 3900
acgccttccg tgccttcgtt tggaataccg tggattatat gctgtatctg cagtacgctc 3960
cacatacaca gttctagacg ttgtggagtc ctcgcctgga gtggagccaa tagcttcatc 4020
atttgcccaa tcggtgactt ccaatgcaaa gtcatccgaa ggttcgtctg gtagcaaatt 4080
cataaagtct tcacaaatag tagacacgtc tgggtcggtt ggaattgaag cagaggccat 4140
ggctgcaaaa tatctgacaa ttgcgtgttt gcagttgcct gtatcttccg ccaatgttgt 4200
agaatttata ggctcaccca accccgcaat gggcgtgttt agtcacatga ttaatgtttc 4260
tgggagtttt cactttcccc aaacaagctt acctgcaccc tttgttcgta atgcataaaa 4320
ataaccactg ctatagcaaa tatgacgata taaaaacatt ttatagcaag gccggacatt 4380
actgtagcgc aacatgttgt gcatatacca cgtattcccc ccgtattgat atgatttaaa 4440
tgattatcct tggttggttt tggtctaaca taagatataa gctctactat agcgagcgtg 4500
catacaacaa cccaggccag aatccgaatg tatgtggggt ataataacgc gcatggtgta 4560
tatgcaacgc caagcgttaa aagcacaata catccagatg atatatgagc gataacctcc 4620
aaaagcatca ataacgtaac acctttatgc atatataaaa aacttatagg gtcagcatta 4680
aatactttac tcataccatc ccgtcgcatg gaaacatcac ataacaacct tgccaacttt 4740
gtatatgggt aaccaagaag aatgttcgaa ataacccgtg ttacgtaatt cagtgaatat 4800
gatgtggggg atattaactc acaggatgat cggaatggcc caaacatacg acgtattcgt 4860
cgaaattgta aatacatacc atatacaaac catgcaaaaa aaatcatttt tagctgcacg 4920
caccaaaaat aagcgtgaca attacgtgtt cccagaacaa ttcgaatttt gtcatgcaaa 4980
ggtgtagaaa tagcggtttt taccatagta tctcctgata atagattttc ccggcagctg 5040
taatcgtatc cagataggcc atccaaaaac gttgagtggt ttacaaacgt tacatatata 5100
agagagttgt tataagaccc ccatacaacc ggtccaccat taatcaccgt ggttgcatac 5160

-continued acacactcat gttcaaactt tacacgagcg gtataccata gggtaaaaac agcatgtccg 5220
ctaagtagac acataattat aaaatgttct gtcttgattc ctaaagcctg catgacccgt 5280
ggaagatggc aattcaagca cgatgtagta tcacacggtt ggtgttaact cgaagttaaa 5340
tttggataat taggtacttc tagagtaaag attgtatgca tgcgattgct atcgcacttt 5400
gtagcaaaac attgttgtgc aagcgaaata cacaaacggt tgtgatgatc cactcgcaga 5460
gacacaaatg tccggggagc cgttcttcct ccgcgatggg gatatcgaag acaagtgaac 5520
ccttttgttc cgcatatgag ctgaaataac acccagtccc ttttgatggc gatacacttt 5580
gatgatgtta aggtatattc gcgatcacgc ccggggaaat gaacagcaat atgctccaca 5640
atagattcta atattgtgct gtcgacaaag gcctccagtg taaatgcgtc cagacaagtt 5700
accccgcgct cttttagagc ctttgttaaa gatatttgcg gggggctaaa tatttgttta 5760
ttacgcgcaa ccttacgttc aaaaaactct gcgtattccc ccccaaggtt atgtaaaata 5820
aattgcactg gaacattcga ctgcggtctt gaatgaaaat gaaagtttgc cgggtttcta 5880
tgtgatgtca caaacgctaa tatatcaata cactgctcag gtacaacata aaatgggagt 5940
agttgtccaa ccgccgtccc tgtggttgtt actttggaga aaaaaggcag tcttaaacta 6000
tgtccgtggc tataaacacc agtatctata aacgaaaagt cccgtaaata cggaccaata 6060
tattcaacaa attcccgttc cagcaacacc gcttgctgta atatttgtgc aaaccccttt 6120
aaagtggaag accccactaa cgcataggga tttgggattg gtacgcatac cctgaaacct 6180
attttctctt tacagttaca gggtagagtt tcatgcaagt tttcattgtt tgatacatcg 6240
gcgtgtgtat ggacttcaga cgttgtctgt gtatcaaaaa accatacatc ctctgtataa 6300
ttctcttcta cacacgtgta taattcgcca ttttctatgt aaaaatcgat gtcagaatgg 6360
ctggttatat ccaataaatt atcatcatcc aacacctcaa cggtaggttc aggacatgca 6420
gttttataaa aataacatgg gtctttgtta gggtttacca cggcctttgg aaaaagtaat 6480
tgcatggccg ttaaaatacc atgacgaaat gctcgcatgc cggcatgtaa aatacccaat 6540
gggatgggtt ttcttatatg aaagtctaca tcaagtatga ggtttgtgat tataagattt 6600
gtattaaata gctcattcct gtttatataa agctgatctt tgggtatgtt tgatgaaatt 6660
ttagaaacgt ttttaacaga cgtagataat agtaaagtca actgcatatc tcgtagtgaa 6720
gcggcaacaa aattacatgg attaatttgt ttaaggtcct ccgcaattaa tcgagcctcg 6780
tgcggtaaag tgtaacggtt tgttattgat gaccacgtat cattagcaat aacagcaaat 6840
gcttgggcgc cttgaggcaa ggctacccga tatacaggca ttggtccagt tacctcagaa 6900
tggccgatga gggcttctaa tggagtttta taactcagga tggatacatc atgtgtggct 6960
atcccagtgg cagcagagaa aaacagtaat agttttgtaa tccccgggct cgtatcaaaa 7020
ccagtacgac cactttggtt aggtgtatcg tttgcaaagt tggctgctcg taacgcctcc 7080
gcggaaacaa ccgaatcctc aaaattagac aattcgtcaa aaccgggtgg atttgaggga 7140
atagtggagg accatccata tggactaaat tgtttttcaa tgttttccac acgacgagtt 7200
agcgttgtag ctaggtcaca tacgcctata aacttgctag gttttgcggc atacgtaaga 7260
cttaaagtat atgttttagt aattgtatat ttatgtccaa tctcaggtcc aagttcagtg 7320
acatcacaaa ttacgttctt ttttatatag tcacgcatgt tgagacgaga acgtacatga 7380
ttaaaaaaat tagcagtagc tctttttccc aggttggatg attttaagag gaccggttta 7440
ttcacaaaat ctgagtatgt aaccgcttgt aggtggtctg cgatctgttt ccgattgaaa 7500

-continued

```
cattcaaaat gtgccagata aatataatca acaaattcac ggtctggaac tttaaggcct   7560
tttctatcgt tggtaatata ctccgatact gcgtgtattt ccgttgtgtc tgtatgtatt   7620
cgctgtaaaa tgtacgatag agcatttttg gctgtcaaac ctcgtgtata tgttgaggaa   7680
caacaaaaca tggaaagttt atcaaaagac aacaagtccg aaatattgta cccactacaa   7740
ttaggtaatg ctgggacttg gtaagttaaa aacaaatctt taattgcctg taagtcatat   7800
aagggggttt ccaacgtatt gtaacttgtg tccgtttgta acaagtaata gcgtgtagcc   7860
aacactagcg ttttttcaga gggtccaaat cgaacaatat accaaaacgg cgagcatcca   7920
tacccccagt agagtcgtcg atatgcagcc aatacttgac gttcgtaatg ggcatataat   7980
gatgttagct cctgacgacc aacggatttt ttaactaact tgcagagtgt tgcctctgtg   8040
atgcataggc cgttgtccga taatcccttt cggtttaaat ggtgtgttgt taccatcaga   8100
gtttgtataa cttccgagtg aatgtcaaac gtctccgata tacatagggt atcagatatt   8160
atatgcggat ttaggggtgc tccataccat aacgccttat ataaagcttt aaaatcagtt   8220
tgggttttaa aacaacaaaa aaatataggc cagacccggg atcgtacatc tccagttgaa   8280
aatccaccaa ttaaataaaa aataacgttg acgtccctac tacaaaataa atgcattatt   8340
tggttttctt catcgttttc agttacttca cgtgggcgtt tagttgggat tacttgcgtg   8400
atctcttccc tcccattttt gacaaagacg tcatctaagt cgggagtcca agtataactc   8460
accacataca gaggttctgt gcttatctgc ccggtaagca acaacagcga gtgggagatt   8520
gcacatccct ttgtggcaaa taataaccga atcgtcggtt tggaggattt atccatagtt   8580
caatacgttg gaaagccagt caatcatgca gacggtgtgt gccagcttat gtggatatgc   8640
tcgaatacca actgaagagc catcttatga agaggtgcgt gtaaacacgc acccccaagg   8700
agccgccctg ctccgcctcc aagaggcttt aaccgctgtg aatggattat tgcctgcacc   8760
tctaacgtta gaagacgtag tcgcttctgc agataatacc cgtcgtttgg tccgcgccca   8820
ggctttggcg cgaacttacg ctgcatgttc tcgtaacatt gaatgtttaa aacagcacca   8880
ttttactgaa gataaccccg gtcttaacgc cgtggtccgt tcacacatgg aaaactcaaa   8940
acggcttgct gatatgtgtt tagctgcaat tacccatttg tatttatcgg ttggcgcggt   9000
ggatgttact acggatgata ttgtcgatca aaccctgaga atgaccgctg aaagtgaagt   9060
ggtcatgtct gatgttgttc ttttggagaa aactcttggg gtcgttgcta aacctcaggc   9120
atcgtttgat gtttcccaca accatgaatt atctatagct aaaggggaaa atgtgggttt   9180
aaaaacatca cctattaaat cggaggcgac acaattatct gaaattaaac ccccacttat   9240
agaagtatcg gataataaca catctaacct aacaaaaaaa acgtatccga cagaaactct   9300
tcagcccgtg ttgaccccaa aacagacgca agatgtacaa cgcacaaccc ccgcgatcaa   9360
gaaatcccat gttatgcttg tataaatatt gaaataaaaa ctaaaaacgt ttctggtgta   9420
tgtttttatt ttgtatataa aattaaaaca ttgctggccg gcgtggttat tacatttaat   9480
gttttagtag aaaatcgaca tcgtttgttt ctttatcagt tgaaccaaat ccacgcgttc   9540
cccgttcgct gggtgtggct attagatcta acgttttagt aaaataccat tgtacacccg   9600
gtatgccaca tttaccgcgg atagcataag gaaatgcaat attacttaaa acgttgtgtt   9660
ttaagtgtat ttgggtgttg tgatctatta acaggacctg tgcaagacga tctcccgttt   9720
ttatacgtat gtcatcaccc gtgagattat atacgtagaa tttacagtgt tctcctgcag   9780
gccatgccgt tggacacacg ataatgcctg atcggctttt cgatgatctt ccaaaaatat   9840
aagcgtttat actcggatgt tgtaagtccc agtctcttat aatcggtaag acaattttta   9900
```

-continued

```
taaattcatt ccttttttaaa tataggttat atggtacaca aatatcatat cccgcgtctt   9960
cttggcgttt tggattgatg atatgtttgt aggttaaggg aacatcgata tggtattctg  10020
cagaatccct atgtaaaggt tgcccctgct gtaccgtgga aatatcagca aattcagata  10080
taacgggttt ttcataattt gacggcgagt ttgataaggg ttgaacttgt atcgatttaa  10140
aaattggatc cagatgttta agaacgtttt ttgggagaag gcgactttgt cttaatttta  10200
ccgggaacaa gtagattgtt aaatgtccgg gtaaaataac ggttactcct ggccggtaat  10260
acaaaagggc tgaaattact cctctgtaac ccgcatcaat aactccgttg gcgacaaaaa  10320
aattgtcttc atcagcaagg gcagtatctt tgcattgaat taacaacagt gcgtattcat  10380
tgggaggcgc cgacttaacc aacagctcca actgctgcat ataaaaaccg ccccgtgtta  10440
cagatttttc agatggcagt tcgagtttct tgtggttccg gagtaacaac ggttgatgtc  10500
gacttacttt atcgtctaac acgcattgca gcgtatctgc acattcaggt tgaacttcta  10560
ttaaaattgt atcttttaaa caccgattcg gaatagtttg gctacaaaac atatcacctg  10620
tatttactgc cgtttccaag atgggatcaa ttaccgcttc gttcatatta ataacgatgc  10680
aaattttatt tttttgtgaa gacagcagtg gggagccaaa ctttgcagaa cggaattttt  10740
ggcatgccag ctgttcggct cgtggagttt atatcgacgg atcaatgatc accacccttt  10800
tcttctacgc atccctttttg ggggtgtgtg tagcccttat ttcgttagct tatcatgcgt  10860
gtttccggtt atttactcgt tctgtattac gcagcacgyg gtaaacccgt ttgcctataa  10920
aaggggcagg cgtgtataag agggcccctg tttaatacgc ggtctgccgt gtttggatat  10980
ttcacgaccc tatcgtttat ttacgtaatg gcatcttccg acggtgacag actttgtcgc  11040
tctaatgcag tgcgtcgtaa aacaacgcct agttattccg gacaatatcg aaccgcgcgg  11100
cgaagtgtgg tcgtaggacc ccccgatgat tcagacgact cgttgggtta cattaccaca  11160
gttggggccg attctccttc tccagtgtac gcggatcttt attttgaaca taaaaatacg  11220
acccctcgcg tacatcaacc aaacgactcc agcggatcgg aagatgactt tgaagacatc  11280
gatgaagtag tggccgcctt tcgggaggcc cgtttgagac atgaactggt tgaagatgct  11340
gtatatgaaa acccgctaag tgtagaaaaa ccatctagat cttttactaa aaatgcggcg  11400
gttaaaccta aattagagga ttcaccgaag cgagctcccc cgggagcagg cgcaattgcc  11460
agcgggagac caatttcctt cagcactgca ccaaaaaccg caacaagctc gtggtgcggt  11520
cctacgccat catataacaa acgcgtcttt tgtgaagcgg tccggcgcgt agccgccatg  11580
caggcacaaa aggctgccga agcggcttgg aatagtaatc cccaaggaa taacgccgaa  11640
ttagaccgtt tgttaaccgg agccgttatt cgtattacgg tgcatgaggg tttaaattta  11700
atacaagccg ctaatgaagc agacctaggt gaaggagcat cggtatccaa acgtggacat  11760
aatcgaaaaa ctggagattt acagggggc atgggtaatg aacctatgta cgcacaagtt  11820
cgtaagccaa aaagtcgaac ggatacacaa acgactgggc gtataactaa tcgaagtagg  11880
gcccgttcgg catcaagaac tgatgcgcga aaatagggat ataattacgc agtaacggtt  11940
tacccggtat tatgtataat aaataaacgt ataaaagaca gtcgtggttt gtgtttatta  12000
taaatgtgta ttatatgtca catattataa actgtttaaa tagtaccacg tggtattatg  12060
aacagtttat aatcagttgc taccaaacaa accccattag acggcgggtt ttgataaagg  12120
gaatcgctta tttaaactaa agattttact ctataagtat ggagtgtaat ttaggaaccg  12180
aacatcatag tacagatacg tggaatcgta gtaaaacgga acaagcggtt gtggacgcat  12240
```

-continued

```
ttgatgaatc gttgtttggt gatgtagcat cggatattgg atccgaaacg tcgttatatt  12300
cacatgcagt taaaactgct ccgtctccgc cttgggtagc tagccctaaa attttatatc  12360
aacagttaat acgggatctt gatttttcag aagggccgcg tttactatca tgtcttgaaa  12420
cctggaacga ggatttattc tcatgttttc ctattaatga ggacctatat tccgatatga  12480
tggttttatc cccggatcca gatgacgtta tctcaaccgt ttcaaccaaa gaccatgttg  12540
aaatgtttaa tttaacaacc cggggttccg ttcgattgcc tagtccacca aagcaaccga  12600
cggggcttcc agcttacgtt caggaggtcc aggattcgtt taccgtagaa ctacgcgccc  12660
gggaagaagc atacacaaaa ctactagtta cttattgtaa atcgattata cgttatctcc  12720
aaggaacggc gaaaaggacg acaataggtc ttaatataca aaaccctgac cagaaagytt  12780
acacgcaact caggcaaagt attctactta gatattatcg tgaggtggca agtttggcgc  12840
gtcttctgta cctacattta tatttaaccg taacgcgtga attttcctgg cgtttgtacg  12900
ccagtcaatc tgcacacccg gacgtgtttg cggctttaaa attcacctgg accgaacgtc  12960
gacagttcac gtgtgcgttt catcctgtat tatgcaacca cggcattgtg ttattagaag  13020
ggaaaccact aacagcgtct gccttgaggg aaataaatta ccgccgccga gaactgggac  13080
tgcctctagt tagatgtggt cttgttgaag aaaacaaatc tccgttggtt caacaaccct  13140
cattttcggt tcatttacca cggtcggtgg ggtttcttac ccaccacatt aagcgtaagt  13200
tagacgcata tgcggtcaaa catcctcaag aaccgagaca tgtacgagcg gatcatcctt  13260
acgcaaaagt tgttgaaaat agaaactacg gtagtagcat cgaagctatg attttagcac  13320
ctccgtcccc atccgagatc ctgccggggg acccaccacg cccacccacg tgtgggtttt  13380
taacgcgtta aacgtcattg gggtaaaggg tgtaaataaa ttacgaaaac gtgcatgcgt  13440
tttttatttt tacaatgcgc cgtatatggt atgtctgtca tgtgctctaa agtcccatat  13500
ataaaagaag ccccaacgag tgtatgcgta ttgcgtaccg cgaccctggg atgttttaca  13560
ggcgcgtttg tttgtctcgg ttataagtat gcagtcgggt cattataacc ggaggcaatc  13620
ccgccgacag cggatatcgt ctaataccac agactccccc cgtcacacac acggaacacg  13680
ttatcggtca accaattggt atacacaccc accccagata ttgtccaatt cagaaacatt  13740
agttgcggtt caagaactac tgaactccga gatggatcag gacagcagtt ctgacgcatc  13800
ggatgatttt ccgggatacg ccttacatca ttctacatat aatggatccg aacaaaatac  13860
atcaacttcc agacatgaaa atcgcatatt taaattaacg gagagggaag ctaatgagga  13920
aatcaacatc aatacggacg cgatcgacga cgagggagag gcggaggagg gagaggcgga  13980
ggaggacgcg atcgacgacg agggagaggc ggaggaggga gaggcggagg aggacgcgat  14040
tgacgacgag ggagaggcgg aggagggaga ggcggaggag gacgcggcgg aggaggacgc  14100
gatcgacgac gagggagagg cggaggagga cgcgatcgac gacgagggag aggcggagga  14160
ggacgcgatc gacgacgagg gagaggcgga ggaggattat ttttctgtaa gtcaagtttg  14220
cagtcgagac gcggatgagg tttattttac gttagacccg gaaataagtt acagtaccga  14280
tcttcgcatt gcaaaggtta tggagcctgc ggtatcaaag gaacttaatg tatcaaaacg  14340
ttgcgttgaa cctgttaccc taacaggctc tatgttagcg cataatgggt ttgatgagtc  14400
ctggtttgct atgcgcgaat gtacccgtcg cgaatatatt acggtccaag gattatacga  14460
cccaattcat ttacggtatc agtttgatac ttcccggatg acaccccccac agattttgag  14520
aactatacca gcccttccta acatgacact tggtgaactt ttattgattt ttcctattga  14580
atttatggcc cagccaattt ctatagaacg tattttagtt gaagatgtat ttttagatag  14640
```

-continued

```
gcgggcttcc agtaaaacac ataaatacgg cccgcgttgg aattccgtct acgcacttcc  14700
atataatgcg ggtaaaatgt atgtacaaca cattcctggg ttttatgacg tgtccttacg  14760
tgctgtgggc caaggaacgg ccatttggca tcacatgata ttatccacag cagcatgcgc  14820
tatttctaat cgcatttcac atggagatgg attaggattt ttgttagacg cggcaattcg  14880
tattagcgca aactgtattt ttttgggacg taacgataat tttggcgtgg gggatccatg  14940
ttggttagaa gaccatcttg ccggattacc acgagaagcc gtacccgacg tactccaagt  15000
gacacagttg gttttgccaa atcggggtcc aacggttgcc attatgcgtg gtttttttgg  15060
ggcgttggca tattggcccg aactaagaat tgctataagt gaaccatcta catctttggt  15120
gcgatatgct accggtcaca tggaacttgc cgaatggttt ttattttcac gtacacatag  15180
tttaaagcca caatttaccc caacggaacg ggaaatgtta gcgtcatttt ttacgttgta  15240
tgttactctt ggtggaggaa tgttgaactg gatctgtaga gcaactgcaa tgtatttagc  15300
tgctccttac cattcccgtt cggcttacat cgcggtctgt gaatctctgc cctattacta  15360
tatcccggtt aatagtgacc tgttatgtga tttagaggta ttactgttag gcgaggtcga  15420
cctcccaact gtttgtgaat cctacgcaac tattgcacac gaattaaccg gatatgaggc  15480
tgttcgcaca gcagccacaa attttatgat agagtttgcc gattgttata aggaaagtga  15540
gaccgattta atggtaagcg cgtacctggg ggccgtttta ttgttacaac gggtgttggg  15600
tcatgcaaat cttcttttgt tgcttctctc cggtgctgcg ttgtacggag gatgttcaat  15660
ttacatcccc cgaggtattt tagatgcata taatacttta atgttggcag caagtcctct  15720
ttacgctcac caaactttaa catccttttg gaaagaccgc gatgatgcaa tgcaaacttt  15780
ggggattcga ccgacaacgg acgttttacc caaagagcaa gacaggatag ttcaggcatc  15840
acctatagag atgaacttcc gttttgtggg attggagacc atctatcccc gagaacagcc  15900
cattccctcc gtggacctag ccgaaaatct tatgcaatac aggaatgaaa ttctgggttt  15960
ggattggaaa agcgtagcca tgcatttact acgaaaatat taagggttgt gatttttttc  16020
attaggatga aaagaacgtt tcctagccac acccacaaag gagtttgtaa aataaaatct  16080
ctgtttagac cttaaaattt gttgtgtgtg ttgtgtgggg ggtccgtgag gatcgacctt  16140
tacaagatat aatttgtcca tatcgcaatg ttttctcggt ttgcgcgttc cttttccagc  16200
gatgatagaa cgcgtaaatc ttatgatggt agttaccaaa gttttaatgc cggcgaacgt  16260
gatttgccca cacctacccg ggactggtgt tctatttccc aacgcataac cagcgagcgc  16320
gtgagggatg gatgtcttat tccaacgccc ggcgaggctt tggagacggc ggtaaaggct  16380
ttatctgaaa agaccgacag cctaacatcg ccggttttac aaagtaccga aagacacagt  16440
gttctgcttg gattacacca taataatgtt cctgaatcgt tggtggtctc gtgtatgtct  16500
aacgatgttc atgacgggtt tatgcagcgt tatatggaaa caattcaaag atgtttggat  16560
gacctgaaac tttctgggga tggactttgg tgggtttatg aaaatacata ttggcagtat  16620
ctcaaataca ccacaggagc cgaggtaccg gtgacttcag agaaggtaaa taaaaagtct  16680
aaatccacgg ttttgttgtt ttcatccgta gttgccaata aaccaatatc cagacatcct  16740
tttaaatcta aagttataaa ttcggattac cggggaatat gtcaggagct acgtgaggcg  16800
ttaggagctg tgcaaaagta tatgtatttt atgcgtccag atgatcctac aaaccccagc  16860
ccggatacaa gaatacgtgt acaagaaatt gcggcttaca cggctactgg ctacgggtgg  16920
atgttatggt tcttggacgt tgtggacgcc agggtatgtc gccatctcaa acttcaattt  16980
```

-continued

```
cgacggattc gagggccgcg cgcgtctgtt attccagatg atttgcttag acgacattta  17040
aaaacgggtc ctgcggtctc agcgggcaca ggagttgcgt ttattttagc agcaacaact  17100
gccagcgctc ttactgcgct tttgcgtatt agtgtattat ggcgaaagga agagtggcgg  17160
gatggtttaa atggaaccgc agctgcaatt gttgcggcgg ttgaacttat tacgcttttg  17220
caccaccatt ttcaatactt aattaatatg atgcttattg gatatgcatg ttggggggat  17280
gggggattaa acgatcctta tatattaaag gcgctacgtg cccagggacg gtttttatat  17340
tttgcgggtc agttggttag aacaatgtca acacacagtt gggttgtgtt agagaccagc  17400
acccatatgt ggttttcccg ggccgtggcg cagagtattt tagcacatgg gggtaaaccc  17460
acaaagtatt atgctcaggt tcttgccgcc agtaaacggt atactccgtt acatttaaga  17520
cgtatatccg aaccatcgag tgtgtctgat cagccgtata ttcgttttaa tcgactggga  17580
tctccaatag ggacaggtat agggaatttg gaatgtgtct gtttaacggg aaattattta  17640
tctgacgacg taaatgcaag ttcgcatgta attaatacag aagcaccgtt aaacagtata  17700
gcacccgata caaatagaca gcggacttct cgcgttttag ttcgtccaga cacgggtttg  17760
gatgtaactg tccgaaaaaa ccactgtttg gacataggcc atacggacgg tagtccagtt  17820
gacccaacgt atcctgatca ttacacccgg ataaaggcgg aatatgaagg tccggttcgg  17880
gatgaatcaa acacaatgtt tgaccaaaga tcggatttac gtcacataga aacccaagca  17940
tctttaaatg atcacgtata tgaaaatata ccacccaagg aagtgggttt taactcatct  18000
tcagacctgg atgtggatag ccttaacggg tacacttccg gagacatgca tacagacgat  18060
gacttatcac cagattttat acccaacgac gttcccgtta gatgtaaaac cacggttacg  18120
tttaggaaaa atacgcctaa gagtcatcat taagtacagc ggttaataga tagttatgga  18180
ctaggcactt tggcggtcat ttccacaacc aggttaaaat tgggggattt gggagaaaat  18240
agtctattgc gtattttctg ttcaataatt ggactgcgtt atttaaaggt ctgattggtt  18300
gattgggtta taaaaggaat tactccttta aattttactt aatgtaccca caatatcaag  18360
tggtcgtttg tatttaacga ttattaccgg taccatggga gacttgtcat gttggacaaa  18420
agtgccgggt tttacgttaa ccggcgaact tcagtactta aaacaagtgg atgatatttt  18480
aaggtatgga gttcggaaac gcgatcgaac aggaatcgga acgttatctt tatttggaat  18540
gcaagctcga tacaatttgc gaaatgaatt tcctctttta actacaaagc gtgttttttg  18600
gagggccgtc gtggaagagt tgttatggtt tatccgcggg tcaaccgatt ccaaagaact  18660
cgccgctaaa gatatacaca tatgggatat atacggatcg agcaaatttc taaataggaa  18720
tggcttccat aaaagacaca cgggggacct tggccccatt tacggcttcc agtggagaca  18780
ttttggagcg gaatataaag actgtcaatc aaactattta cagcaaggaa tcgatcagct  18840
gcaaactgtt atagatacaa ttaaaacaaa cccagaaagc cgacgaatga ttatatcgtc  18900
ttggaatcca aaggatatcc ccttaatggt actacctcca tgtcacacgt tatgtcagtt  18960
ttacgttgca aacggtgaat tatcctgcca agtataccag agatcggggg atatgggcct  19020
tggggtaccg ttcaacattg ctggatatgc acttcttacc tacatagtag cgcatgttac  19080
aggacttaaa accggagatt taattcatac aatgggggat gcacatattt acttgaatca  19140
tatagatgct ttaaaagtgc agctagctcg atccccaaaa ccttttcctt gccttaaaat  19200
tattcgaaat gtaacagata taaacgactt taaatgggac gattttcagc ttgatggata  19260
taatccacac ccccccctaa aaatggaaat ggctctttaa tggattttta aatgttgtca  19320
agacagtaga tgtgttgcga atgtaataaa atgatataca cagacgcgtt tggttggttt  19380
```

-continued

```
ctgtytatga acagcaacgg atgcataggg ttgcgataac tgcgataaga cccaatgtcc  19440
caaggataga tatcacacca attataactg ctacaacgga aaatgtagtg gcgtaggtag  19500
atgcatcgta ggtataaacg gccgaaaacg gagggaattt tttagggtaa ccatctagat  19560
gacacgaata ggtgataggt ccgtcgagtt ccgatgttgg acaagaactt tgcatgttta  19620
caaaccgttt gttttgatca cacaccccag taatctcact gttttcgtgg ttgatgggag  19680
aatcgttaac ccaccatacg aaatgtacaa cgccacgtgg cacacatttt gccgtacata  19740
ctatgtgtcc atcaataata cctatagaca cgttgggaaa tggatagacg tcaggggtaa  19800
cgacagcaga atatttcata ttagagacgc catcccgaat ccataaaaca ttacattgga  19860
tggctggggg tgggtaatcc atttgttttt gctgtggaat tcgtaccgcc gaaacataac  19920
taaataatcc attggcatat tcttgtattg catcggttat aaaatttttt ccgatgttac  19980
caaaccttga agtccaccga acacgtaccg agtgcggtgg ataatacttt gatacgttac  20040
agtaggctgc gtatgtctgt ccggttaaga ctggatcgcc gacaacggta atatttggac  20100
gataatacgt tgtaactgta atactgtgtt ccgatatgac gttcttagtt tttgtattaa  20160
cgactcgcca aatatacgtt ccctccgtgg tagcatccat agataaaatt gttacagaaa  20220
aatcagacgt tgttttaaca tctggtatta cataattttc cttagcgtgt gtaaatatct  20280
cagggttgtt tattaagttt aaatcggcac tgttgctata taacataacc ggtaaatctg  20340
gcatgcgtat taacgcattg cccagttgac ggtgcggatc tataaggtga cgcgtaaacc  20400
aaacttcaat atgaagatcg gggcgtataa gcgacttcca ccttgttata tttgaacctt  20460
ccggatctaa agaatattgt tcatatgttt tttgttgctg cttaaaggcc gcctgttgtc  20520
cggtcgttag acgcatgtaa caaggcatga taaatgtgtg aaaatagggt atggattgta  20580
ttccgccgtg aacgcattgt atattttcaa atagaaaagg tggttgtgaa tgttgggcgt  20640
tggctgcggg atcgggcttt cgggtagcgg ccgaggtggg cgcgacggcg ggatcgggat  20700
ttcgggaagc ggccgaggtg ggcgcgacgg cgggatcggg atttcgggaa gcggccgagg  20760
tgggcgcgac ggcgggatcg ggatttcggg tagcggccga ggtgggcgcg acggcgggat  20820
cgggctttcg ggaagcggcc gaggtgggcg cgacggcggg atcgggcttt cgggaagcgg  20880
ccgaggtggg cgcgacggcg ggatcgggct ttcgggaagc ggccgaggtg ggcgcgacgg  20940
cgggatcggg ctttcgggaa gcggccgagg tatataattc agttatactt acgggtgtgg  21000
gttgagattc agtcgataat tgtatacacg cgatcgttaa aattaaattt atttgtatcc  21060
gcttcatcct ggtttttatt gacacatcca cgctcccctt aaataaaaga ttaaaacacc  21120
caccgcggaa tttaaatgat ggaaacgttt ttttcgacat tgggaataat aaaaacggct  21180
tttgcaactt taaaaacttt atttatctcg attacgatac atatgtacca catagatagc  21240
atagatttat tataatataa acacacacgt gatatacttt agtgatatga gatgccataa  21300
aacagtcaat aggtttaacg cttaatctca tcatctgaat acacgtcaaa cccgccgcaa  21360
ctgttgatgt tagaattata atagctcccc atgaaatgcc ggcaaatgtt acagctatac  21420
ccgtcaccga ggtcgttgta tataatacaa ttacccatag gttttttttt tcttgatata  21480
aaacggcaaa accctgtaac ccaaatgcta taatatgacc tcctattgaa actgctaacg  21540
ttacttgtgt aagtttgata aaatgattta atttaattat atgtgagatt gcccacatta  21600
atggggtaac tatatataac accgggggta taacagacat tatacgaatt cctttaaaca  21660
cgcgtttaag ggtccgggaa ctttctctat ggtcacatac tctcccgcgg tcattttgtg  21720
```

-continued

```
tatatacaac ggcaaaacct aaatctgtat aagtgtttaa ttgcttatgg cgatttttac  21780
gatatataca cgtatcttgc aaatcggtgg cggcatcgac aattgaaact agtgtgacaa  21840
tagatataca caatccaata agaacctcat atttactgac atacatatat aaaataacgg  21900
ttagtaaacc tcccaaccca gttcccaaca tcataacata aaaataaata tgcggtccat  21960
tgaatgtcgt aacaaagttg tagtaatgga tatgcacagc agccactgtt ccggtaatcg  22020
cggatatgga aattcccagt aattctacaa atggaagatc ccgggatatt gggcaaccaa  22080
ccgcccataa cacagcaaaa cccaacacga ccaccgtctg caaacatcgt cccaattttg  22140
ctaatgtgcg tagaaatttc acggatgttg gccataaccc cgaaacgacg atcaacccca  22200
taatagttgc attgacggca gcttcgcaga cgtgatattg taaaattaac ccggacgtga  22260
taacacttgc ttgtagtccc acgagaaaca accgcgatgc tgaggttatt gcacacgaat  22320
tacattcttg agggtttccg acacatcctt ggattgattg agcgcggatt aattctctgt  22380
ctaacacacc caggttttca tcatggacag ctctttcacc attcacggcc atgtcttaag  22440
tttaataatt caaaacagat aaaaatgtgt tcatctatgg tacacacaag tttgtatgta  22500
aaatataagc aaaagttgca cttatttaac tgtacatatt acgtcagatt cacgtgataa  22560
ttcagaataa tccagggttc ctgcagggtc cactggagga gccacacaat attcgcgaat  22620
tccgattccc tcctgccatg tggtttcggg gagtttcccc cccattttat ttccggtatt  22680
tttttcgttt ctttttgtta ataaattgcg tctttttttt aatggtggtt catccttcac  22740
agattccgtg ttcgcaaata attgcatcga ggttaatttt tctttaaggt ctttgggact  22800
taagaacgtt gcataaaaaa aagaatgcac gggtgcggaa cgttggatat acaatccaac  22860
catgggggag ttagttaagg cgagataaaa attaatataa cacgtctcat cccgtgttaa  22920
cttaagattt tgtacggcag aacggaatcc actgtgtgtt tccaataata ctccaaattc  22980
acgcatactc ccgctgccat aaacaacatt attaaggatc ctttttgaat ttgtgattga  23040
gcgtattaaa ttatatggtg taggcttgct tccgtttata tccaaggaaa cattaaatga  23100
gataaaacca cccccggcgg tctggatgta catatccgtg gctgttagaa tgaagcatgt  23160
tgtaaaccca aaagttttaa gtagtcgctg taaacgggtg aattgatcgc gttttaagca  23220
aatgcttata tctggagtta gatttgggaa catcattgta taacaagcga gttcacgttt  23280
tacaacttgt ttgtaacatt gtacttgatc atctggacca caatcacccg ggcgttgcca  23340
taccatcgtt tggataatac tccgctcggg gggttgtccg gtaaatttaa aatataaccg  23400
tgttggggtc gacggatctt ttgtatggcg aaacgcgtca ataagcgagg accgtccctc  23460
cgttgccgcg agtacaacca ttctcggccc agtccaatta tactggtcaa acatatttgc  23520
cggtatagga atatacagtt gttctgtttc caaactacag tgaataatta atccttcgtc  23580
gctgaatatt aaaatagaat cccttagtct attaaccaga ggtgatatag acgaaattaa  23640
accagtaagc gttttttccg ttaaaacagc tctggcgatt tctggggcgt caaaacccgc  23700
atgcaattcc atgtccaaag catcgtctgt acgcgacctc aaatccataa tttactactt  23760
aaaatgttta ctatagaaaa agtaatcata tgtaaacaca cgagtttcgt taatatgttt  23820
gtttaacccg atccggtgac ttaagtacat aaacaggcat gatatttgaa tagtacggcc  23880
catgggaggg aacatttcca cgtgttccaa tacagggggt gttccttaat agggactgtg  23940
caataaaata cgtaagaagt taccagattt gatgtaatgt ttgtcataaa aaatatgtac  24000
atcattatat acgtctgtaa ttaacacaag atcacatcga agaattactg aagccgctgt  24060
gaaacctttc acaagacgat ataaacttgg ttaagtgtat tgatggggct ctttggactg  24120
```

-continued acacgcttta tccatgaaca taaactggtt aaacccagca tcatttcaac gccacccgga 24180
gttttaaccc ccgtggcggt agacgtatgg aacgtcatgt acacattgtt ggaacgttta 24240
taccctgtgg gtaaacgcga gaatttacac ggaccatctg taacgataca ttgtcttgga 24300
gtcttattgc ggctattaac acaacggtca tactatccga tatttgtatt ggaacgttgt 24360
acagacggcc cattatcacg tggagccaag gcaattatgt cacgggccat gaaccacgat 24420
gaaaggggaa cctcggactt aacccgtgtt ctactatcat ccaacacatg ttctatcaag 24480
tataacaaaa catcggaaac atatgacagt gtgtttcgaa actcttccgc gagttgtatt 24540
cctagcgaag aaaacaaatc ccaggatatg tttttggacg gttgtccacg acaaactgac 24600
aagatgatct gcctgcgcga ccaaaacgta tgcagtctta cctctacaat gccatcccga 24660
ggacatccta accatcgatt atatcacaaa ttgtgtgcaa gtcttattag atggatgggg 24720
tatgcatacg tcgaggcggt tgacattgag gcggacgagg catgtgcaaa cttatttcat 24780
acgcgtacag tggctttggt ttatacgaca gatactgatt tactcttcat gggctgtgat 24840
attttgttag atgcaattcc tatgtttgct ccagtagtac gatgtcgcga tttgcttcaa 24900
tatttaggaa ttacataccc tgaatttttg gttgcctttg ttcgctgtca gaccgatttg 24960
catacaagtg acaacctaaa atctgttcag caagttattc aggataccgg cctgaaaatt 25020
ccacatcaaa tggacacttc aacgcgctcc cccacttacg actcgtggag acatggcgag 25080
gttttcaaaa gtcttaccgt agccacgtcg ggtaaaacag aaaacggagt gtccgtttcc 25140
aaatatgcat ctaaccgatc ggaggtgaca gtagacgcca gttgggcttt aaaccttctg 25200
ccaccctcat cctccccatt ggataatttg gaacgcgcat ttgttgaaca tataatcgcc 25260
gtggtaactc cattgacccg cggtcgccta aagttaatga aacgtgtaaa tattatgcaa 25320
aatacggcag acccatatat ggttattaac accttatatc ataacttaaa gggggaaaaa 25380
atggctcgcc aatacgcacg tatttttaaa cagtttattc ctactccact cccactaaac 25440
actgtattaa caaaatattg gaattaaaac acacataaga gcgacttaat ggttcattgt 25500
tttattttgc tcgtatatac atgttataaa tcgtttatca ctgtgcccgc ataagatgta 25560
ctgtgtctct caaaaaaatt tgtgttttta tctgcaatca taaatgcaag tggaaagtcc 25620
gaatcgggag gtggggtgtt aaatagtttt ggtacattaa tcgctgataa aagcctgtcc 25680
gcgctgaatt tcacgtattg tgtaattgca tcgacgttca ccaaacgggt tttgggtgca 25740
tgggatttta aaaacgcaca ctcgatttca acggcttccg aaaacagttg atgtattctg 25800
gtgatagcgg gtttttcggg tacatagtta ttgtatatac aacacgatgc gctggtatgt 25860
atggcttcat ctcggcttat aaggtcgtta aattgacaag ttacaacaaa tagtccgtta 25920
ttgcgtaaat atgcaatagc cgcgaacgat gatacaaaaa aaatgccctc tataagaatc 25980
attagtatat atttttctgc aacggatggg ttgtcccgta ccttttcttc caaccattgt 26040
actttttgtt ggatcgacgg attattaata gtgacgttta cgtattgtac ccgcaacgat 26100
tcatcccctc tgaacaacat tagttgaatt tgactataga cacgcgcgtg gacaacctcg 26160
atgcactctt gttcaatgta gtaatggtga atatcctttt gggaaaagag ttgggttaga 26220
gagcccaaat taacatttac cagatcatct gccgccgata aaaatgtaaa aataaatctg 26280
tagaatatta gttcatcttc cgttaaacag tccaagtatt gataatcatc ttcaatgata 26340
aaatcgcttt ctaaccaacg attcgaaatg ctcagggcac gtaaattgtt tatatctgga 26400
cactccggcc tgtaaaaaaa atgactgcaa tctttctgat ccattttgga atagtttccc 26460

-continued

```
gtgtaaattt ataaagcaca actggtacag gttaattcgc ctcccgcaaa cagtccgctg  26520
ttcgtagctt tacgaatttt acagtagtac atacccgttt taaggccggc tttataggca  26580
cgtataagca aattcattat tttggaggcg ggaattgtcc cgtctgggcg ttcctcaata  26640
aataaagtca ttgattgact ttggtcaata aatggcgccc tttctgcaca catatcaacg  26700
agatcctctt gctcatattc aaacgctgtt ttatatttta agagtgggtg actattagat  26760
aaacagccaa acgaacgtat tactgaccat tggtttttct caagtatgtt tataacttcc  26820
agtcgttttt cttcacatga atacatatct cttagttcgt ccataaggtc taagttgggt  26880
ctaagtaact cacccgaggt ggtgacctta ctaaacatat tattataaat tggagagaaa  26940
ccctcactgc actccgttac ctgtgcagat gaaactgtgg gcattaacgc taagaactgc  27000
gagttgtata acccataagc gcaaatatca tctcgcaggg tacaccatgg taaatctaaa  27060
taacttatcg tagaaaaccc atcttggtgt aaccatccct tagcatattt actttcggta  27120
aaacccttaa acggggctaa gccgccaatc ttacacattt ccatgcttgt tttcattgtc  27180
tcatacaaca ttaactccgc tatttgtaca tttaaccgtc tagctggttg ggaagttaaa  27240
tcaaatccta agcggagaca agttgtatgt aacccttgta tgccaatgcc aagtgatcgg  27300
ttgtttttta cacctttaca tgattttttta catggaaagt tcccagccgc caggaccccg  27360
tttaaaaaaa taacagtcgt tcttgctgtc aattgaaggt cgtttaaatt aaatgacact  27420
gggcctttgg ataagcacgt tgtaagattt atgctggcaa gattacatac gccgtgttga  27480
tgagcgtctg ccttttgaac aatttccgta cacaaatttg accccgtgat agcatttcct  27540
tgggtattca tatgataatt acgattacag gcatctttga acattaaaaa ggggcttcct  27600
gttacagcag cactgcgtat gattgtgaat gcgatatctt gaatgggaac agaagaaacg  27660
cctaatcctt ctctctctaa acgtaaatag gttgaagtga atgcctcccc gtgtaatgtt  27720
cgaaggatat cggctctgtt atcaaaaaga gtccactgaa cattactagc cccttttaga  27780
tagcttaggt atctttcaaa aaataaatct ggggtccata aacaacaaaa tatgttatca  27840
catcgaaata tttcatcacg aaccaacatt ccacgtgtgg ccaaaacagt ttgtagatcg  27900
acgtgccatg gttctatgta aacacaaact ccagttggtc gttcacaatc actgttaatt  27960
gccataacca tgcaatctaa aagttttaaa actgcaagaa gacctttcgt ttgattttcc  28020
gtaggtatta aattcagact ctgtagagaa attcccactc cacctcgact ttgtaatacc  28080
gttcccacat cgcctgtgat agctcgaaca gctctcccaa cagtgatgga ttccgggtcc  28140
attaaataac aactggccgt tgccccggtc tctcgaccta aaaacatcat aaccggtgta  28200
gccgggacaa ttttctgaca tgccaacgct gtgaaaaata cccgacagac atcagtccat  28260
gtataaccat catttattcc gggaataaga gttgcgattt taggcaggtt tacgatttct  28320
gttgtcacgg tggccgccag tcttaaaaag aattggcaaa gcgactctaa tttaccttcc  28380
tctaacttag ttaaataaaa gtcttcgtac tttaaagcag actgtagtcc aagggtagct  28440
aaagcggggt attgatcttt caaaaacggt tctaatatag cccgacgaat ttcgtccctc  28500
cgcccttcaa ttgcttggcg gactcgggga gttaaacaga gaattgggga agtcaaccac  28560
gtttccatgg aaacggatcg taggttaata cggcaatgga taagttctcc acaacatcgg  28620
tacactcgct catcttgtcg cgtcaccgcc ttaagttttg agacgatagt gctaatatac  28680
tccattaatt ccaccggtgt ggttgattcg ggcggaatga tgtattcctt gtagccatgt  28740
tgacataatc ggtttataat gtcatgaacc gtattaaaaa ttcttttgaa ctccataacg  28800
gataacgtat ttaggctccg gaataaacct ttaaacccta aactcacagc tgagttagtt  28860
```

-continued

```
ctacaatatt gtagactccc ttatatatgg ttacgtacag cctgcccctc cccagtatat  28920
aatatcacgc aaaacccacg ctatgttaaa ttcagtttat tttacataca tgctttaata  28980
ataacattcg ttccatgtat ttgtaccccc ccacacaacc ccctctaacc aaatagttgg  29040
cacgttataa cctccgaacc gttccatgcg tcttgtataa cgcacagact ctgatggaat  29100
tgttccaatt aacgtatatg ccgcatacat gcaggataat tgtgtgggaa ggccccgaaa  29160
atcgccggtc cattgataca atcgctgtct agccaagttc caatttactc ctgtaatttc  29220
gccaatacta catcgagggc ttgtcgggtc attggataac tgcacaagcg gcaacgccct  29280
tgtgttatat ggctggtggg tatttgcaac cccttcagtc ccccaggcgg cattttcagc  29340
tcgtatgcgt cctaacagga agccaatacc acgaccaaaa cattgttcgt ttagttggct  29400
taatgcaaga tgcagtctta caccttctcg ttggcgtcgc tgtgtatata caaaaaccaa  29460
gaacacatgc ttcagtccgt ccgcggaaag atgtaaatct ttgtcaacgt cccaaaatac  29520
gcaggccggg atgttggctg tgaccctgcg agttgaagtt ttgtctgtac gtgcagcttc  29580
ttggggacct ttggccacgg cggttatatt gcataaatta tcctgaatgg tatattccag  29640
cagggaccca aaaaaactta taaatcgatg tggaaataca tgacattgta ccatcgcacg  29700
taaacactcc gaaaacctta tgagccgcgt ttccatacga ctgcatccat aggcagaaac  29760
aattgctgtt ctgttggcat ccgctgcctg tttatccgta tattcttctg cccggcatgc  29820
ggcgatgaaa cttaatgacg ttacatatgc tctaagcccc ccaccttctc caacggtcca  29880
aggagccgtg caggcattga ataggtttcg taaaccctct agtagtacat cggggtcacg  29940
tccagcctgt gtaagtgtat tagcttctcc aatcatgtca gatggatgac gaaggattaa  30000
gacgattgac ccagcatgct caatgtccgg acgaaaaaaa tcggttaatg acacttgttg  30060
gattagctgt gtcgttgatt taaaattatt taacgggagt ctaatggtaa cttgcgggtt  30120
accaattgaa gttggattta tttgaatgtt gttcatacga ttaataacaa ttgaacgggg  30180
ggttacttga atagacgcgg tttctgtacg ttttggtggt acatgtatcg gttgtttgtt  30240
cagacctcca aagcgagggc caattgttaa atcgcgactc caatttccga agaagcccgg  30300
agcataagtc atatgaagcc cgttccctat ttgaataaaa cggttatttc ctaaaagact  30360
gatattagtt ccacatagcg tttgttcgtt taaagtaaaa tgcgagttgg ttggttgact  30420
ccccatagct gaggggttaa attcacacaa tgcaatcgtg acgtggtact atctgaaatg  30480
ttgcctgggg tatgtgtaca cattatacag tcgtagtacc gtttatataa tgttaggtag  30540
gaggagccta taaaaatatt ttgattggcg ttaaaaggtt cttcaactta ccgtgacgtc  30600
ctttttatta acatgcgttt ttattgatgt tacatttatg tcttttcatt ccggacggat  30660
gtagcttttt catatcacgt tataaagtta agtcagcgta gaatatacca tggaagaacc  30720
aatttgttat gatacacaaa aacttttgga tgatttaagt aacttgaaag tacaagaagc  30780
ggacaacgaa agaccatggt caccagagaa aacagaaatc gccagagtta aggtagttaa  30840
gtttttacga tctacccaga aaattccagc taaacatttt attcagatat gggaacccct  30900
gcattctaat atctgttttg tatattccaa tacatttttg gcggaggctg ctttcacggc  30960
cgaaaattta cccggactgt tgttttggag actagatcta gactggacga tagaggagcc  31020
aggtaatagc ttaaaaattt taacccagct atcaagtgta gtacaagatt ccgagacgtt  31080
acatcgttta tcggccaata aattacgaac ctcgtctaaa tttggacccg tttcgataca  31140
cttcattata acggactgga taaatatgta cgaggtcgcc ttaaaggatg caacaacagc  31200
```

-continued

```
cattgaatca ccattcactc acgctcgtat tggaatgttg gaaagcgcca ttgcagcttt  31260
aacacaacat aaatttgcga tcatttacga tatgccattt gttcaagagg ggattcgtgt  31320
tttaacacaa tatgcaggat ggcttcttcc gtttaatgtt atgtggaatc agattcaaaa  31380
tagctcactc actcctctaa cacgagccct ttttataatc tgtatgattg atgaatatct  31440
cacggaaacg ccagtacata gcatatcaga attatttgca gatactgtaa atttaattaa  31500
agatgaggcg ttcgtatcca tcgaagaagc ggtaacgaat ccacgaacgg tgcacgagtc  31560
acgaatttcc tcagctctgg cttatcgaga cccttatgtt tttgagacat ccccgggaat  31620
gcttgctagg agacttagat tagacaatgg tatatgggaa agcaacctct tatcgttgtc  31680
cayccccgga attcatattg aggcgctgtt acatttacta aactccgacc cggaagcgga  31740
aaccacatct ggaagtaatg tagcagaaca cacccgtggc atttgggaaa aggttcaggc  31800
tagtacatcg cctagtatgt taataagcac ccttgccgaa tccgggttta caagattttc  31860
atgcaaattg ctacgtcggt ttattgctca ccacacactc gccggtttta ttcacggaag  31920
cgttgtagca gacgagcata ttacagattt ccaacaaaca ctaggatgtc tcgctttagt  31980
gggtggactg gcataccaat tagtggaaac gtacgctcct actaccgagt atgtgttaac  32040
atatacacgg acagtaaacg agaccgaaaa acggtatgaa acgctattac ccgccttagg  32100
attaccaccg ggaggcctgg gacaaattat gcggcgctgt tttgctccac gaccccttat  32160
tgaaagtata caagcgacac gcgtaatact acttaatgaa atttcacatg cagaagctag  32220
agaggcaaca tattttaagc aaacacataa tcaatcctca ggtgcgttat taccacaagc  32280
aggacaaagt gccgtacgcg aagccgtact aacctggttt gacctacgta tggattcaag  32340
atggggtatt actcccccgg tggatgtggg tatgacacct cctatttgtg ttgatccacc  32400
ggctacaggg ttggaagctg tcatgataac agaagcacta aagattgcat atcctaccga  32460
atataatcgc tctagcgtgt ttgtggaacc gtcgtttgtg ccttatatta ttgcaacaag  32520
cacgcttgat gccctttcgg caacaatagc tttgtctttt gatacacggg gaatacagca  32580
agccttgtct attcttcagt gggctcgcga ttatggatcc ggaaccgtgc ccaatgcaga  32640
tggatatcgc acaaaactat ctgctcttat aacaatatta gaacctttta cccgtacaca  32700
ccccccagta cttttaccat ctcacgtttc tactatagat tcccttatat gcgaacttca  32760
tcggactgtt ggcattgccg ttgacctgct tccccagcac gtccgtcctt tggttcctga  32820
ccgtccttct attacaaata gcgttttttt agcaactctc tattatgatg aactttacgg  32880
tcgttggacc cgactggata aaacatcgca ggcgttggtt gaaaatttta catccaacgc  32940
gttagtggtt tctcggtaca tgttaatgtt acaaaaattt tttgcgtgtc gtttttatcc  33000
aacgccagat cttcaggctg ttggtatctg taacccaaag gttgaacgcg atgaacaatt  33060
tggggtatgg cgtttaaacg atcttgctga tgcggttggt catattgttg ggacaataca  33120
aggaatccga acgcaaatga gagtgggaat atccagcctg cgcacaatta tggccgatgc  33180
ttcctcagcc cttagggaat gtgaaaattt aatgactaaa acctccactt ctgctattgg  33240
gcctcttttt tcaacgatgg cttcccggta tgcacggttt acacaggatc aaatggacat  33300
tttaatgcgt gttgacaaac taacaacagg agaaaatata cccggtcttg caaatgtaga  33360
gatttttttta aataggtggg aacgaatagc aacagcttgt aggcatgcca cggcagtccc  33420
gtcggccgaa tctattgcaa ccgtgtgtaa tgaattgagg cgcggtttaa aaaatataca  33480
agaggatcgt gtaaatgccc caacctcata tatgagtcac gcccgaaatc tggaagatca  33540
caaggcagca gtttcattcg ttatggactc caggcaacag tttattgtgg attctggacc  33600
```

-continued tcagatgggc gcggttttaa cttcacaatg taatatagga acatgggaga atgtaaatgc 33660
aacgttttta cacgacaacg ttaaaataac gacaacggtc agagacgtaa tttcagaggc 33720
tccgacgctg ataataggac aaagatggct tcgtccagat gagattttat ctaatgtaga 33780
tttgcgtctt ggcgtacccg ggaatacaag tgggagtgac ccttaatata aaacaggcgt 33840
gtttatgtac attaaagtat ttgtggtttt tattgactgg gcgtttcgtt tgtataacgc 33900
tgttgttgct agtattttca taacctccta ggtttttgga gctacacgtg cttattcaac 33960
gctctttggg atttgaatca tcgtaaacgt agcgtcccta ccagttgagc gcgtaatttt 34020
cgtaagcaat aaaatggata taattccgcc tatagctgtc actgttgcgg gagtgggaag 34080
ccgtaatcaa tttgacggtg ccctgggacc ggcgtcaggt ctgtcatgtt taagaacatc 34140
tttatcgttt ttgcatatga catatgcgca tggaattaat gcaaccctgt catcagacat 34200
gattgatgga tgtttacaag agggtgcagc atggactacg gatctgtcta atatggggag 34260
gggtgtccca gatatgtgtg ctcttgttga tctccccaat cgaatttcat atattaaact 34320
gggggacact accagtacgt gctgcgtttt gtctagaata tacggcgata gccatttttt 34380
taccgttcca gacgagggtt ttatgtgcac acaaattccc gctagagcgt ttttcgatga 34440
tgtgtggatg ggacgtgaag agtcgtatac aattataact gtagactcaa cgggaatggc 34500
catctatcgt cagggaaaca tatcttttat ttttgatcca catggccatg ggactatagg 34560
acaggctgta gttgttcggg tgaataccac ggatgtgtac tcttatatcg catcggagta 34620
tacccaccgc cccgataacg tagaatccca atgggccgct gcattagttt tttttgtcac 34680
cgcaaacgac ggtcccgtaa gcgaagaagc gctatcttcg gcagtaacgc ttatatacgg 34740
aagctgtgat acatatttta cagatgaaca atattgcgaa aaactggtta cagctcaaca 34800
tccgttgctt ctttcacctc ctaattccac gacaattgtg cttaataaat cgtctatagt 34860
acctcttcac caaaacgttg gtgaaagtgt atccttggaa gcaaccctac attcaacgtt 34920
aaccaacacg gttgcactgg accctagatg tagttacagc gaggttgatc cttggcatgc 34980
ggttctagaa acaacctcga ctgggtctgg cgttttggat tgtcgtcgta gacgccgtcc 35040
ttcatggact cctccttcaa gcgaggaaaa tttagcttgt atcgacgatg gcttggtaaa 35100
taatacacat tccacggata atttacataa acccgctaaa aaggttctca aatttaaacc 35160
aactgtagac gtgccggata aaacacaagt ggcacatgta ttaccccgcc tacgagaagt 35220
tgctaacacc ccagacgttg tgttaaatgt atccaatgta gatacgcctg aatccagtcc 35280
cactttttca cggaacatga atgtaggaag cagtttgaaa gatcggaagc catttctatt 35340
tgaacagagt ggtgatgtca acatggttgt cgaaaaacta ctacaacatg ggcatgaaat 35400
tagcaatgga tacgtacaaa atgcggtggg tacgttggat actgttatta ccggtcatac 35460
aaatgttccc atttgggtaa caaggccctt ggtcatgcca gacgaaaagg atccattgga 35520
gctttttatt aacctcacca ttttgcgttt aacgggattt gtggtggaaa atggaacacg 35580
tacacatcat ggtgctacaa gcgttgtatc agactttata ggtccccttg ggaaattttt 35640
aacaggattt ccctccgccg cggaacttat acgcgttaca agtttgatat taacaaacat 35700
gccgggggcg gaatatgcta ttaaaactgt tctccggaaa aaatgtacaa ttggcatgct 35760
cattatcgct aagtttggtc tagttgccat gcgggttcag gatacaaccg gcgctttaca 35820
tgccgaacta gatgtgttag aagcggatct aggaggttcg tcgcccatag acctctattc 35880
tagactgtcg acaggtctta taagtatact aaattcgcct attatttctc atcccggact 35940

-continued

```
ttttgccgag cttattccaa cccgtacagg gtccctgtct gaacgaatac gtcttctttg  36000
tgaattagtc tcggcccggg agacacgcta tatgcgtgaa cacaccgcgc ttgtttctag  36060
tgtaaaggct ttagagaatg cattacggtc tacccgcaat aaaattgatg ccattcaaat  36120
accagaagtt ccccaggaac ccccggaaga aaccgacatt ccacccgaag agttaattcg  36180
gcgtgtatat gagatacgat ccgaagttac aatgctattg acctcggctg ttacagaata  36240
cttcacccgc ggagtgttat atagcacacg ggccttgatc gctgaacaat cccctaggcg  36300
ttttcgggtc gcgaccgcaa gtacggcacc cattcaacgg cttttagatt ctcttccgga  36360
attcgacgct aaattaacgg caatcatatc gtccctgtct atacaccctc ctcctgagac  36420
tatacaaaat ctccccgtcg tatctctgtt aaaagagctt attaaagaag gggaagattt  36480
aaacacagac acggctctcg tatcgtggtt atctgtagtc ggggaagctc aaaccgcagg  36540
ttacttatcc agacgagagt tcgatgaatt atcacgtaca attaaaacca ttaatacacg  36600
cgcaacgcaa cgggcttccg cggaagcaga gttgtcttgc tttaatacgc taagcgcggc  36660
cgtagaccaa gccgtaaagg actatgaaac atataacaat ggtgaggtca agtatcctga  36720
aataacacgg gatgatttat tagcaacaat tgtacgtgct acagacgatt tggtgcgaca  36780
gataaaaatt ttaagtgatc caatgatcca atccggttta caaccttcga ttaaaagacg  36840
attggaaaca aggcttaaag aggttcagac gtatgcaaac gaggcccgaa ccacacagga  36900
cacaataaag agtcgaaaac aggcggcata taataaactc ggggggttac ttcgcccggt  36960
aaccggtttt gtgggactta gggctgcagt agatttatta ccggaacttg cttctgagtt  37020
agatgtccaa ggagccctgg taaatctcag gaccaaagtc ttagaggcgc cggtagagat  37080
ccgttctcaa cttacgggtg atttctgggc gttatttaac caatatcgag acattttaga  37140
acatcccgga aacgcacgca catctgtctt aggaggactg ggagcttgtt ttacagctat  37200
tatcgaaatt gtgccgatac ctacggagta tagaccatca ttgcttgcgt tttttggtga  37260
cgtggcagat gtgcttgcat ccgacatcgc gaccgtatct actaacccgg aaagtgagtc  37320
cgccataaac gctgttgttg caactcttag taaagcgacg ttagtttcat ctacagtgcc  37380
agccttatcc tttgtgttgt cgttatataa aaaatatcag gctttacaac aagaaattac  37440
gaatacccat aagttgactg aattacaaaa acaacttgga gatgacttct ccaccctagc  37500
tgtctcatct ggacacttga agtttatatc atcttcaaat gtagatgatt atgaaataaa  37560
cgatgcgata ttatcaatac aaacaaatgt gcacgccctg atggatacgg ttaaacttgt  37620
tgaagttgaa ctgcaaaagc tacccccccca ttgtattgct gggacatcta ccttatctcg  37680
agtagtaaag gatcttcata aactcgtcac aatggcacat gagaagaagg aacaggcaaa  37740
agtgttaatt accgattgtg aacgtgcaca taaacaacaa acgactcggg ttttgtatga  37800
gcgttggaca cgtgatatta tagcatgtct ggaggcaatg gaaacgcgcc atgtatttaa  37860
cgggacagaa ctggcacggt tgcgagatat ggccgctgcg ggagggtttg atatacacgc  37920
agtttaccca caagcacgtc aggttgtagc ggcatgtgaa actacagccg ttacggcatt  37980
agatacygtg tttcgccaca atccacatac ccccgaaaat acaaatattc ccccaccttt  38040
ggctttgtta agagggttaa catggtttga tgatttttcg attacggctc ccgtattcac  38100
cgttatgttt ccaggtgtta gtattgaagg actccttctg cttatgcgta ttcgcgcggt  38160
tgtgttatta tccgccgata cgtctattaa tggaatacct aactaccgag atatgatatt  38220
acgaacctcg gggatctat tacaaatacc cgcattggct gggtatgttg atttttacac  38280
acggtcttat gatcagttta taaccgaaag tgtaacgtta agtgaactta gagcagacat  38340
```

-continued

```
cagacaggct gccggggcta aacttacaga agcaaataag gctttggagg aagtaactca  38400
tgttcgggca cacgaaacgg ctaaacttgc acttaaagaa ggtgtcttca ttacattacc  38460
aagcgaaggt ttattgattc gggctataga gtattttaca actttcgatc ataaacgatt  38520
tataggaacg gcatatgaaa gagttttaca aacaatggta gaccgcgatc taaaggaggc  38580
caacgcagag cttgcacagt ttcgtatggt gtgtcaggca acaaagaacc gtgcaataca  38640
aattttacaa aacattgttg atactgctaa tgccactgag caacaagaag acgtggattt  38700
cactaacctg aagacgttat taaaactaac ccccctccc aaaacaattg cattggccat  38760
tgatagatct acttccgttc aggacattgt cacgcagttt gcattgctgt tagggcgtct  38820
ggaagaagaa actggtacgt tggacattca ggcggttgac tggatgtacc aagctcgcaa  38880
tattattgac tcccatccac taagtgtgcg tatagacggt accggccccc tgcatactta  38940
taaagatagg gtggataaac tttatgcgtt acggactaaa ttagatctcc tacgacgacg  39000
aatagaaacc ggtgaggtta cgtgggacga tgcatggaca acatttaaaa gagaaacggg  39060
ggatatgttg gcatcggggg acacgtacgc tacttccgta gatagtataa aggcactcca  39120
ggcatcggcg tctgtggttg acatgctttg ttccgaaccc gaattttttt tattgcckgt  39180
ggaaacgaaa aaccgtctcc aaaaaaagca acaagaacgt aaaacggcgt tggatgttgt  39240
gttgcaaaaa caaagacagt ttgaagagac cgcgtctcgc ttacgagctt taattgaacg  39300
tattccaacg gagagtgacc atgacgttct tcgtatgtta ttacatgatt tcgatcaatt  39360
tacacatttg cctatatgga taaaaacaca gtatatgaca tttcgaaatt tactcatggt  39420
acggttaggc ttgtatgcaa gttatgctga gatttttcca cccgcgtctc caaacggagt  39480
gtttgctcct attcccgcca tgtcgggtgt atgtctagaa gaccaatccc gatgcattcg  39540
cgcgcgggtg gccgcgttta tgggggaggc gtctgtggtg caaacgttta gggaagccag  39600
atcttctata gacgctttgt ttggaaaaaa tttaaccttt tacttggata ctgatggggt  39660
tccacttcga tatagagtgt gttataaatc agttggggtt aaacttggaa ccatgctatg  39720
cagtcagggt ggattatctt tacgaccggc acttcccgat gaaggtattg tggaagaaac  39780
tacactatcg gcattacgcg tggccaatga ggtcaatgag ctacgcattg aatacgaatc  39840
cgctataaaa tccgggtttt ctgccttttc cacctttgtt aggcatcgcc acgccgaatg  39900
gggtaaaacc aacgcacgca gagccattgc agagatatac gccggcctta taacaacaac  39960
attgacacga caatacgggg ttcattggga caagcttatt tattcttttg aaaaacacca  40020
cctaacttct gtaatgggca atggactaac taaaccaatc cagagaaggg gtgatgtacg  40080
cgtattagag ttaaccctat ctgatattgt aactattttg gttgccacaa ccccggtaca  40140
tcttctcaat tttgctagat tggatttaat taaacagcat gagtatatgg cccgtaccct  40200
cagacccgta atcgaggccg catttagagg tcgtttactc gttcgctcat tggatggaga  40260
cccgaaaggc aatgcccggg ccttttttaa tgccgcccca tccaaacata aactcccgtt  40320
agctcttgga tcaaaccagg atcctaccgg cgggagaata tttgcatttc ggatggcaga  40380
ttggaaactt gttaaaatgc cacagaaaat aacggatcct tttgcgccat ggcaactttc  40440
cccccccccc ggggtaaagg ccaatgtcga tgcagttacc cgtataatgg caacagatcg  40500
tcttgcgacc attactgtac ttgggcgcat gtgtctcccg ccaatttcct tagtgtcaat  40560
gtggaatacg ctgcaaccgg aggaattcgc atacagaaca caagatgatg tggacattat  40620
agttgatgcg agactggatt tgtcatccac gcttaatgca agatttgata ccgctcccag  40680
```

-continued

```
caataccacg ttagagtgga atacagaccg taaagtaatt acagatgctt atattcaaac  40740
cggggcaacg acagttttta cagtaacggg ggcggcacca actcacgttt ctaatgtaac  40800
agcgtttgac atagcaacta cggctatttt atttggggct cctttggtta ttgccatgga  40860
acttacatcc gtttttcac aaaattccgg acttactttg ggttaaaat tattcgattc  40920
ccggcatatg gctacagatt cgggtatatc ctcagccgta tctcccgata ttgtttcttg  40980
ggggttacgt ttactgcata tggatcccca cccaattgaa aatgcatgtt taattgtcca  41040
actagaaaaa ctgtccgcgc tcattgcaaa caaacctctt acaaacaatc ccccgtgttt  41100
actgctattg gacgaacata tgaatccctc ttatgtttta tgggaacgaa aagactcgat  41160
tccagctccg gattatgtgg tcttttgggg gccagaatct cttattgatt tgccgtacat  41220
cgactccgat gaggactctt tcccctcgtg tcccgatgat ccattttact cgcaaattat  41280
tgccggttat gcgccccaag gccccccaaa cctcgacaca actgattttt acccaacgga  41340
gccactattt aagtctcccg ttcaagttgt tagaagttcc aaatgtaaaa aaatgcccgt  41400
ccagcccgtc cagcccgtcc agcccgcgca gcccgtccag cccgcgcagc ccgcgcagcc  41460
cgtccagccc gcgcagcccg tccagcccgc gcagcccata gaaccgggca cacaaatagt  41520
ggtacaaaat tttaagaaac cccaaagcgt aaaaacaacc cttagccaaa aagatattcc  41580
cttgtatgtg gaaactgaat cagaaacggc tgtgcttata cctaagcaat taaccacctc  41640
cattaaaaca accgtttgta aaagtattac cccaccaaat aaccaattgt cggattggaa  41700
aaataatcca cagcaaaacc aaacgttaaa ccaagcgttc aataaaccaa tacttgagat  41760
tacctccatt ccgacagatg actcgatatc ttaccggact tggattgaaa aatcaaatca  41820
aacacaaaaa cggcatcaaa atgaccctcg aatgtataac tccaaaacag tattccaccc  41880
tgtaaataac caattacctt cttgggttga cacggcagcc gatgcccccc aaacggacct  41940
attgacaaac tataaaacaa gacagccgtc gccaaacttt ccgcgggacg tacacacatg  42000
gggcgtatct tctaacccgt ttaactcacc gaacagagac ctatatgaaa gtgattttag  42060
tgaaccttct gacggctata gcagtgagag tgaaaattct atcgtactaa gtctcgacga  42120
acatcggtca tgtcgcgttc ctaggcacgt acgtgttgtt aatgccgatg tagtcaccgg  42180
tcgacgttat gtccgaggga ccgccttggg agcactggcc ctgttaagcc aggcatgtcg  42240
gcgtatgatc gacaacgtta gatatacacg taaactttta atggaccaca cggaagatat  42300
atttcaaggc ctggggtatg ttaaattgtt attagatgga acatatatat aaagtagcgc  42360
ctattaaaga aaaaaaaaca acgattattt tctgtgtatt tttatttaca ccctacgact  42420
tcttgaagcg tttccagatt gtcccgtgtg ggacaaggtc tgtcccttac ccccctgggg  42480
ggtattttgg gttgggggcg gggtagactg tggcacgcct tgggccgcgg gcggtgatcc  42540
ggttgttggc tggacagtgc ttgactgtgc tccctgttgc ggttgttgtc cagaagaccc  42600
cgacaccacg tgttgctgtt gtccaacgga tgccgacgtc gtttgaggtg gggggtgttg  42660
cggggatgat cccgaaaacg ccaacgcggc gggctgttgt aaagcagact gatcggcgct  42720
ctgtgttttt tgcggcaata tagtaggccc cgagattccc aaactcatgg atggatttgg  42780
gggttgtggt cgtataatac gcgggttaaa cgtacgtttt aagccaaccg ttggtcttaa  42840
ccatgtcata gggtcagtct cggcaaacat ggccgttcgg cgtatcgtat ttgcattatg  42900
gttagcgcgt gcacgcgcgg cactggccgc ggctcccacg gtgtaaatgc ttctggcatc  42960
agcgatgtcc acacggtgac caggttgcaa aggtccactg gcgtttaaaa gtcgtattaa  43020
agcaacgggg gtgtaagccg caattgcttc caccgaaaat gtggtggggt tgctgggatc  43080
```

-continued

```
aaagactaca cgagacgatg cgggttgtgt catcgtttat tagtttacgg gacaatcgat  43140
aacagcatac acgtacatct gcgcaggata tgtacggaaa ggcaatttat ttccagaaaa  43200
gcaccgcccc taatacaact accagtacaa ttacaacgaa cagggcatat gtcacgttag  43260
ctacgggtag agcaagtttc cagacacgcg tagtttgggt atcgggtaac gcaggtttaa  43320
tgtcactttg catttgaaca gacgtgtttg gacttccgtt ctcgggtggg gatctgaatg  43380
aaggccgcca gcgtatatat tcatccaaat tattgccagt ttccttatac atgtatgcat  43440
ccgtggcgcg ggccataagt ttaatggtgc gagatggatc ttccggtccc ataaaacgaa  43500
aggataactg aacatatggc attcgcacaa agcagttcac ccacattaaa gcctggagag  43560
gtcggcggtc aatacccca cctcgtttaa ttgattccaa agcagatagg ttgataccgg  43620
tacttaacgt tgaactaaga atcacgttat tactgtcaat ggacacttca gccactggtg  43680
cgttagtcgg acgaaaaaaa aaaccttgaa atagcacaga cacccccgta ttttgaattt  43740
ttatgtaagg gtcacaatct acttgcgccc aattcgccat taaacgcata atatactcta  43800
ccggaaaggc ttcggatacg ttgtcttcgc cgttaaactg aaaaacacaa cgggcggggg  43860
ggcgttgtgg atcaaatatt ggaagatccc catcgcaaca ttgaagagcg cttggtacca  43920
ccaaccgaat acgttgtaaa agattatctc cgcaacccct cctgcgttca ctccgtacat  43980
acgttctccg tgacatattg atctaaggtt gcaaaccaag gcacacgcgt gaagtattta  44040
gaccatttat cgtgggatat aggaggagtt tggagtgatc cacccccctga cgacttatta  44100
atgcgtttat tttccccatg tattaagcat ccttcaatat ttcatgcaaa tctagaaatt  44160
tggccatgac tcccgcaaag cgttcacggc gacgggtcac gctggcacta tgttcacatg  44220
gaacaacata agcagatttt tctgaatcgt tactttcttt atgttttaaa acggacgcca  44280
ggcgactggt aaatgatata taatttaatt gagcgtcagt tgtaggtaga attgcttcta  44340
tttccggggg aattaaattt tcaaaccaaa cggaaagagt aaaggtgcta tcagcaggaa  44400
aatactttga ctccagtgca tcgatattta atagattaac atcggtgtct gtaattaaat  44460
cgcgggccct catcccagag atggatcggg tagaatcaga agaacccatg gatggattcg  44520
aatcgcccgt attctccgaa aatacatctt ctaattccgg atggtgttcc gacgcatttt  44580
ccgattcgta catcgcttat aatccagccc ttctgctaaa aaacgatttg ttattttcag  44640
aattgttatt tgcctcccac ttaataaatg ttccccgtgc aatagaaaac aacgtcactt  44700
atgaggcctc ttcggcggta ggtgtggata atgaaatgac ctcaagtacc actgaattta  44760
tagaagaaat tggagacgtt ttggcgttag acagagcctg tttggtctgt agaacgcttg  44820
atttgtataa acgtaaattt ggactgacac cggaatgggt tgcggactac gccatgttat  44880
gtatgaaaag tctggcatcc ccgccctgtg cagttgtcac ttttagcgct gcctttgaat  44940
ttgtgtatct tatggatcgt tactacctgt gccgttataa cgttactttg gttgggtcct  45000
ttgccaggcg cacgctttcc ctgttagata tacaaagaca tttttttttg catgtatgtt  45060
ttcgtaccga tggagggtta ccaggtatac gaccgccccc cggtaaggaa atggccaaca  45120
aagtaagata ttccaattac tcctttttttg tacaggcggt agttagggct gcattactat  45180
cgatcagcac gtctcgttta gacgaaaccg aaacgcgtaa gtcattttac tttaatcagg  45240
acggactgac tggaggccct caacctttag cggccgcctt ggctaattgg aaagattgcg  45300
cgcggatggt tgactgttca tcatcggaac atcgcacaag tgggatgatt acctgcgcgg  45360
aacgtgcatt aaaagaggat atagagtttg aagatatatt aatagacaaa cttaaaaaat  45420
```

-continued

| | | | | | | |
|---|---|---|---|---|---|---|
| cgtcttacgt | agaagcagct | tggggttacg | cagacttggc | tttattatta | ctgagtgggg | 45480 |
| ttgctacttg | gaatgtagac | gagcgtacaa | attgtgctat | agaaactcgc | gttggatgtg | 45540 |
| ttaaatcata | ctggcaggcg | aaccggattg | aaaactccag | ggacgttcca | aaacaatttt | 45600 |
| ccaaatttac | gagcgaggat | gcctgtcccg | aagtagcatt | tgggcctatt | ttgttaacta | 45660 |
| ccttaaaaaa | cgcaaagtgc | cgtggtcgca | cgaataccga | atgcatgtta | tgttgtttat | 45720 |
| taaccatagg | gcactattgg | atcgctttgc | ggcagtttaa | aagggatata | ttagcatact | 45780 |
| cagcaaataa | cacaagttta | tttgactgta | tcgaacctgt | aatcaatgca | tggagcctag | 45840 |
| ataaccccat | taaacttaaa | tttccattta | atgatgaggg | tcgattcata | accattgtaa | 45900 |
| aagcagcagg | ttccgaggcc | gtatataaac | atttattttg | cgatctccta | tgcgctctct | 45960 |
| cggaattaca | gacaaaccct | aaaattttat | ttgcccatcc | tacaaccgcg | gataaggaag | 46020 |
| tgttggagtt | atataaagcc | caactggctg | cacaaaacag | atttgaaggt | cgtgtatgtg | 46080 |
| ctggcctgtg | gacattggcg | tatgcattta | aagcctacca | gatttttcca | cgcaaaccaa | 46140 |
| ccgccaatgc | cgcattcata | cgagatggag | gacttatgct | tcgacgacat | gcaatatcgc | 46200 |
| tggtctccct | cgaacacacc | ctatcgaagt | atgtctaggc | gatataaatc | cgtatctcgg | 46260 |
| agcgggcctt | cgatgcgtgt | acgctccaga | acgccatgcc | gccgtcaaac | cattcgagga | 46320 |
| aaacttatgt | caaaggagcg | gtctgtgtac | cgccattatt | ttaattacat | cgcaaggtcc | 46380 |
| cccccagaag | aactagctac | cgttagaggc | ttaatcgtgc | caattattaa | gacgacccct | 46440 |
| gtcacccttc | cgtttaactt | gggtcagaca | gtggcggata | actgcctgtc | gttatccgga | 46500 |
| atgggttatc | atttaggtct | cggaggttat | tgtccgacat | gcactgcatc | tggagaaccg | 46560 |
| cgtctatgtc | gaaccgatcg | ggcggctctg | atactagcat | atgttcagca | gcttaacaac | 46620 |
| atatacgaat | atcgtgtgtt | tcttgcatcc | attttggcgc | tatcagaccg | agccaacatg | 46680 |
| caagcagcgt | ccgctgaacc | cctattgtcg | agcgtattgg | cacaaccgga | attatttttt | 46740 |
| atgtatcata | ttatgaggga | ggggggcatg | cgagatatac | gcgtactttt | ttatcgtgat | 46800 |
| ggagatgccg | gagggtttat | gatgtatgtt | atatttccgg | ggaaatctgt | tcacctccat | 46860 |
| tacagactaa | tcgatcatat | acaggccgcg | tgtcgggggt | ataaaatagt | cgcacacgtt | 46920 |
| tggcagacaa | catttttact | gtcggtatgt | cgcaacccag | aacaacaaac | agagactgtg | 46980 |
| gtgccatcca | ttggaacatc | ggacgtttac | tgtaaaatgt | gtgaccttaa | ctttgatgga | 47040 |
| gaattgcttt | tggaatacaa | aagactctac | gcattatttg | atgactttgt | tcctcctcgg | 47100 |
| tgatttcagc | ttcagtgttc | attttattat | cccagcgcgg | ggcgtgtata | caaacaaagc | 47160 |
| ctgccgcctg | caagcggttt | agcattttaa | cgttaacaac | tcgtgtctct | ggaataaaac | 47220 |
| gttttaaaag | ccgttctgtg | agtttagtgt | cgtttccaaa | taacgcctta | aaagttacac | 47280 |
| tcgccgtccc | aatgagatga | gaaaaataat | agtcaatgtt | taaagacagc | ccgtgtgatg | 47340 |
| ttacgtgaat | gggatcttcc | gctaagtcag | atattattaa | cttacgcttt | gcttccccac | 47400 |
| accgtttacc | tgcggtattc | tgtaaaggat | ctccacgtag | caaagctaca | ctttttgcat | 47460 |
| cagcctccac | ttcgtctgtg | ggggccacaa | taacataagg | gatgcgttct | cgaacgtttg | 47520 |
| ggatttgacc | ctgtctcatt | actaatttat | aatatactgt | taagtgagcc | aagcgacggt | 47580 |
| ttatgtaggc | ggatggtgga | cgactaagct | cggccgtcat | aacaaactta | ttaatatcca | 47640 |
| atttgggtga | tgtaatctgg | cgatgtgcat | ctgcaattat | gcgtccaaac | ccggccatcc | 47700 |
| cagacggcat | ggcccgtcta | ttccattcag | caatggaaac | acacgacgcc | tccgccgcag | 47760 |
| cacgcgagac | ggtgtcgtca | tataacaaca | gttctacaag | tttgcgggca | taatcgttaa | 47820 |

-continued taaattgaca gttgtttttt ctaaccaagt cgactccctt cattaaaacc tttccgccgt 47880
aaattacccc aatgtacttt ttctttgtta taagtaaaag ttttataaaa gttttttcac 47940
actccaactt tataggagga caaaacagag ccgttgaaat tatatgtgcc attttctcgc 48000
cgattttagc tatcccctca acaccaacac ccttgaatcg gataaacaca gaatccgtat 48060
ctccatatat aacctttacc tcgtacgctt tttgggagag aacgctactt tcaatgtctg 48120
gaaacgctgt aataaaacgt tcaaatgcgg cccagttatt atgaatataa tctctggtac 48180
ttaataacat ttgacggcca attgtagtga cagtggccgc tacgtataaa catggcagaa 48240
atccctgcgc aactccagta aaaccgtaca cggaattaca aactactttt atcgcggctt 48300
gttgtttgtc taataacact gcttcatctg aagaacttcc gggtatgcgc gctctaatag 48360
ccttgcgcat agccaaccag tcttttaaaa gaacacccag cagactttct cgaacgttag 48420
agcgcacaaa aaaaagacgt tttcctccaa ctgtaaaggt ggcataatcg gatggattca 48480
aacgtttaac cgtctcaaaa tttaacgtta gcgtggtaaa acataagtta tgggcctgaa 48540
ttatacttgg atataaactt gcaaaatcca atacgaccac cggatcgata taaaatcccg 48600
tatcagggtc aaaaaccctg gctcctttat atcctacatt tcgcccactt gacgtaccag 48660
tgggagaaac gctctcgtct tcatccatct cttcctcaac atccccgaca tcgggaataa 48720
catccttata ttcaaaagta gctgggtatc ccccatcggg taaaataaat cctcgagacg 48780
aagccagtcc taataaacaa gtgtaaatcc taacctgctg tccgtcgtaa atagccttgg 48840
ttaaagtaat tctagctagc cttgcaaccg cggataactc aaggtgtggt aaatatttaa 48900
aaaacagttt ccccacaaga gccgagtctt gtatacaata ttcaccaata attcctcgtg 48960
tattcggtcc actagcgtaa tatcccggaa tgtctttgta gggcaaatct ctcttggact 49020
catttagagc ttcacgtgca accgaatcta atttataact cgagagtttt aatttttcag 49080
ttgcaattgc atacatatcc agagatatga gaccgttgat ctttaccttg cttcgtcgct 49140
gaaatccgga tttgccaaca tcccatatct taaacagacc cccacggttt atactgccat 49200
aaccatcaag cttgagactg tatatagaat taagtttctc cataataaac gcccaatcaa 49260
aattaacaat gttataacct gtggcaaact cgggagcgta ctgttttacg agggtcataa 49320
atgcaattaa tagctcgaat tcactatcaa actccagcac agtcggctcc ggtaaccccg 49380
cgtccttcat ttcttgtaca tacctttgtg gtaagtcaca agagccaagg gaaaacagta 49440
aaatgtgttc taaagactgt cgagggattg aatataatag acaagaaatt tggattacaa 49500
gatcctccaa atgtgttgca tcgggaaacg ccagctcatt agatcctcct gatttacatt 49560
caatatcgaa acataacaac ttgtagtcag gccatgagtc atcgtttggt atagcctgca 49620
gattatccga catgcagtca atttcaacgt cgcttaacgt taattggcga cttgccggtc 49680
gaactcgaac acgttcccca tcaactccag gttttagttg ataccaacca aaactaacaa 49740
agccgggatt atccattaga aaacgagtgg tagcgtctac ccgaccttca tactttttca 49800
actccgggtg aaagttatca caaagataat ttgtaaattt agatgaggga gaatacaccc 49860
tgtaaaacgc acatggctgt gtatcgtagt aataaacatc tgtgcgctca ataacctcaa 49920
cgcgaaagct ttctggagat gcgcttttaa acgaggtacc atgaaaagcg ttcttgtctc 49980
catttaacgt tgcatcattt tgtgttatca tagaactgcg taaacactcg gcaagtaata 50040
cagataactc gctacaggaa cgtatgccac aagcggtatc cacctcggct ttgtttatat 50100
aaaaatattg acagatgccg tatacatgaa ctgccaccct ttttccacat cgggacatgc 50160

-continued

```
caagtaaagt aataacggta ccaagcggtc gtgttgcagt tgcaaaccgg gatacatctc  50220
cattagacgc ggcttctgtt gtttcgacaa tatcatatac atggaatgtg ttaaagcggg  50280
ggtcaaactt atccccacga aagtcgattt ccccccaaat attcacgcgt ctaggccagg  50340
ggctggaaca acgaaaatcc agaatcggaa cttcttttcc attacagtaa actttaggcg  50400
gtcgactaag tgtaccgacg tgaacccccct ttcgttcttc catgggcaca tcttcatcta  50460
aacatttagg ggccaaaaat tgaaacgatg acatggtagt tttgtaacta tgaagaaatt  50520
ctctgttact accgcgcccg gttcttgggt tatatttaat ccctgatgct tgggttaaaa  50580
agggattaca aaaccccgtt ctgatcgcca ttttatgtta acgattgata atcttgtaaa  50640
aagccagtgt tactgagtaa cacaacccca cgcccttcta atacataaag tgtaatcacg  50700
tgatttgttg tggtttccgc atatgtaata cccgtttaaa agcctctctt cttaatgtat  50760
cgacagactg ggttttgggt ggtcatttga ccctgccaac aaccccccat tattacgagt  50820
acttcaccaa aatggaaaat actcagaaga ctgtgacagt gcccacgggg cccctgggtt  50880
acgtttatgc gtgccgggtt gaagatttgg atctggagga aatttcattt ttggccgctc  50940
gtagcacgga ctctgatttg gctttattac ctttgatgcg taatttgacc gtggaaaaaa  51000
cttttacatc cagcctggcg gtggtttctg gagcacgcac tacgggtctt gccggagctg  51060
gtattacctt aaaactcact accagtcatt tctatccatc tgtctttgtc tttcacggag  51120
gcaaacacgt tttacccagc tctgcggccc caaatctcac acgcgcgtgt aacgcggctc  51180
gagaacggtt tgggttttca cgctgccaag ggcctcctgt tgacggtgct gttgagacga  51240
ccggcgctga gatatgcacc cgccttggat tagagccaga aaatacaata ttatacttgg  51300
tggtcacggc attgtttaag gaagccgtat ttatgtgcaa cgtgtttctg cattatggag  51360
gactcgatat tgttcatatt aaccatgggg atgttatacg tataccgtta tttccggtac  51420
aacttttcat gcccgatgtt aaccgtctgg tacccgaccc attcaacact catcacaggt  51480
ctatcggaga gggttttgta tacccaacac ccttttataa caccgggttg tgccatttaa  51540
tacatgactg tgttattgct cccatggccg ttgccttgcg cgtcagaaat gtaactgccg  51600
tcgcccgagg agcggcccac cttgcttttg atgaaaatca cgaggggggca gtactccccc  51660
ctgacattac gtacacgtat tttcagtcct cttcaagtgg aaccactacc gcccgtggag  51720
cgcgtcgaaa cgatgtcaac tccacgtcta agcctagccc atcggggggg tttgaaagac  51780
ggttggcgtc tattatggcc gctgacacag ccttgcacgc agaagttata ttcaacactg  51840
gaatttacga agaaactcca acagatatca aagaatggcc aatgtttata ggcatggagg  51900
gcactttgcc aaggctaaac gctctggggt catataccgc tcgtgtggcc ggggtcattg  51960
gtgcgatggt tttcagccca aattctgcgt tgtatctaac tgaggtggag gatagcggga  52020
tgaccgaagc caaggatggg ggaccgggtc catcatttaa tcgattttac cagtttgccg  52080
gacctcattt agctgcgaat ccccaaacag atcgagatgg ccacgttcta tccagtcagt  52140
ctacgggttc atcaaacaca gagtttagcg tggattattt ggcactcatt tgtggatttg  52200
gagcacccct gttggcgcga ctgctttttt atctagaacg ctgtgacgct ggtgcgttta  52260
cagggggtca cggggatgcg ttaaaatatg ttacggggac ctttgactct gaaattccat  52320
gtagtttatg tgaaaaacac acgcggccgg tatgcgctca cacaacagta caccgactta  52380
gacaacgcat gccgcgattt ggacaagcca cccgtcaacc tattggggtg tttggaacaa  52440
tgaacagcca atatagcgac tgcgatcctc taggaaacta tgctccatat ttaatccttc  52500
gaaaacccgg ggatcaaacg gaagcagcaa aggcaaccat gcaggacact tatagggcta  52560
```

-continued

```
cactagaacg cttgtttatc gatctagaac aagagcgact actggatcgc ggtgccccat  52620
gttcttccga gggactatcg tctgtcattg tggatcatcc aacgtttcgt cgcatattag  52680
acacactgcg tgcgcgtata gaacagacaa caacacaatt tatgaaagtg ttggttgaga  52740
cccgcgatta taagatccgt gaaggattat ccgaagccac ccattcaatg gcgttaacgt  52800
ttgatccata ctcaggagca ttttgtccca ttaccaattt tttagttaaa cgaacacacc  52860
tagccgtggt acaagactta gcattaagcc agtgtcattg tgtattttac ggacagcaag  52920
ttgaggggcg gaactttcgt aaccaattcc aacctgtttt gcggcggcgt tttgttgacc  52980
tgtttaatgg ggggtttata tcaacacgct ctataaccgt aacattatct gaaggtcctg  53040
tatccgcccc aaatccgaca ttgggacaag acgcgcccgc ggggcgtacc tttgatgggg  53100
atttagcgcg cgtaagcgtg gaagttattc gggatatacg agttaaaaat agggtcgttt  53160
tttcaggtaa ctgtacaaat ctctctgagg cagcccgggc aaggcttgta ggccttgcaa  53220
gtgcgtacca acgccaagaa aaaagagtgg atatgttaca cggggcccta gggtttttgc  53280
ttaaacagtt tcacggcctg ttatttcctc ggggtatgcc accaaacagt aaatccccca  53340
acccgcagtg gttttggacc ctgttacaac gcaaccagat gccggcagat aaacttacac  53400
acgaagagat taccactatt gcagctgtta aacggtttac cgaggaatat gcagcactaa  53460
actttattaa tctacccccca acctgcatag gagaattagc ccagttttat atggcaaatc  53520
ttattcttaa atactgcgat cattcacagt accttataaa taccttaact tctataatta  53580
cgggtgccag gcgcccgcgt gacccatcat ccgttttgca ttggattcgt aaagatgtca  53640
cgtccgccgc ggacatagaa acccaagcaa aggcgcttct tgaaaaaacg gaaaacttac  53700
cggaattatg gactacggct tttacttcaa ctcatttagt ccgcgcggcc atgaatcaac  53760
gtcccatggt cgttttagga ataagcatta gtaaatatca cggagcggca ggaaacaacc  53820
gcgtctttca ggcagggaat tggagcggtt taaacggggg taaaaatgta tgcccgctat  53880
ttacatttga tcgcactcgc cgttttataa taacatgtcc tagaggaggt tttatctgcc  53940
ccgtaacagg tccctcgtcg ggaaatcgag aaaccaccct atccgaccaa gttcgcggta  54000
taattgtcag tggcggggcc atggttcaat tagccatata cgccacggtt gtgcgtgcag  54060
tgggcgctcg agcacaacat atggcatttg acgactggtt aagtcttaca gacgatgagt  54120
ttttagccag agacttggag gagttacacg accagattat ccaaaccctg gaaacgccct  54180
ggaccgtaga aggcgctcta gaagcagtaa agattctaga tgaaaaaacg acagcgggag  54240
atggggaaac ccccacaaac ctagcattta attttgattc ttgtgaacca agccatgaca  54300
ccacatctaa cgtattaaac atttcagggt caactgtccc tggtcttaaa cgacccccccg  54360
aagatgacga actctttgat cttagtggta ttcccataaa acatgggaac attacaatgg  54420
aaatgattta acctccctct ttatccaatt aaagcccaca cgcgggtgag tgtacgtaat  54480
aaacaagtca atattacata ttctgttgtg ttttcttttt tgcgtgtagt ccttacccat  54540
atgacctgta atatagtgtg tctccaacca ttcagcttac agtccagtgg acagtaacag  54600
cccgataaca tggaattgga tattaatcga acattgttgg ttctactggg tcaagtttat  54660
acgtacatct ttcaggttga actgctacgt cgatgtgatc caagggtggc gtgtcgcttt  54720
ttatatcggt tagcggctaa ctgtttgaca gttcgttatt tattaaagct gtttctccgg  54780
ggatttaata cccagctaaa atttggaaac actcccacgg tttgtgcact gcattgggca  54840
ttatgttatg taaagggaga aggtgagcgt ttgtttgagt tgctacaaca ttttaaaacg  54900
```

-continued

```
cgttttgttt atggtgagac taaagactca aactgtatca aagattactt tgtctcagcg  54960
tttaacttaa aaacctgcca atatcaccat gagctgtcgt taacaacata cggaggttac  55020
gtatcgagtg aaattcagtt tttacacgac attgagaatt ttttaaaaca gcttaattac  55080
tgctatatta tcacgtcttc tcgtgaggcg ctaaacacat tggaaaccgt gacgcggttt  55140
atgacagata ctataggaag cggtctaata ccacccgtgg agttgtttga tccggcgcat  55200
ccatgtgcta tatgttttga agaattatgt ataacagcta accaaggtga gaccttacat  55260
cgtagattat taggatgtat ctgcgatcac gttactaagc aagttcgggt taacgtggat  55320
gttgacgata ttattcggtg tttaccatat atccctgatg taccggatat caaacgtcaa  55380
tccgccgttg aagcgttacg aacacttcaa accaagacgg tagtcaatcc catgggagca  55440
aagaacgata cgtttgacca aacatacgaa attgcgagca ccatgcttga ttcttataat  55500
gtttttaaac ctgcccctcg gtgtatgtac gccatcagcg agcttaaatt ctggttaacg  55560
tctaattcca ctgaaggacc ccaacgtact ttagacgtgt ttgttgataa tttggatgta  55620
ttaaacgaac atgaaaaaca cgcagaactt acagccgtaa cggttgagtt ggcgttattt  55680
ggaaaaactc ccatacactt tgatagggcg ttttctgaag aactcggatc tctggatgca  55740
attgatagta ttttggttgg caatcgctca tcctcaccgg acagtcagat agaagcatta  55800
attaaagcct gttatgccca tcatctatcg tcgcctctca tgcgtcacat ttctaacccg  55860
agtcatgata acgaagccgc cttacgccaa cttttagaaa gagttgggtg tgaggatgat  55920
ttaaccaaag aggcgagtga cagcgctaca gcatccgaat gtgatctgaa cgatgatagt  55980
agcataactt ttgctgttca tggatgggaa aacctgttat ccaaagcaaa aattgacgct  56040
gcggaaagaa aacgagtata tcttgaacat ctgtctaagc gctctctaac cagcctcggt  56100
agatgtatcc gcgaacagcg ccaagagcta gaaaaaacac tcagggtaaa cgtttatgga  56160
gaggccttat tgcagacatt tgtttcgatg caaaatgggt ttggggcacg aaacgtgttt  56220
ttagctaagg tttcccaggc agggtgtatt atcgacaatc gcattcagga agcggccttt  56280
gatgcacata gatttataag gaataccta gttcgacata cagtagatgc ggctatgtta  56340
cctgcactta cacataaatt ttttgagttg gtcaacggcc cattgtttaa tcacgatgaa  56400
caccgttttg cacaaccccc taacaccgcc ttattttta ccgtggaaaa cgttggccta  56460
tttccgcact taaaagagga attggcaaag tttatgggcg gtgtcgttgg ttccaactgg  56520
cttctcagtc catttagggg cttttattgc ttttctgggg tagaaggcgt tacttttgca  56580
cagagacttg cctggaaata tattagggag cttgtgtttg caaccacact attcacctct  56640
gttttccatt gtggggaggt gcggttatgt cgcgttgacc gtctaggtaa ggatccacgc  56700
gggtgcacgt ctcaacctaa aggtataggc agttcccacg gacccttaga cggcatttat  56760
ttaacgtacg aagaaacatg tccccttgtg gctattattc aaagtggaga aacagggatc  56820
gaccagaata ccgtcgtaat ctacgattca gacgtttttt ctcttctata caccctaatg  56880
cagcggctgg ctccggattc aacggacccg gcgttttcat aacctccgtt acgggggtgt  56940
ggttatgctt tttatgcata ttttctatgt ttgttacggc ggttgtgtcg gtctctccaa  57000
gctcgtttta tgagagttta caagtagagc ccacacaatc agaagatata acccggtctg  57060
ctcatctggg cgatggtgat gaaatcagag aagctataca caagtcccag gacgccgaaa  57120
caaaacccac gttttacgtc tgcccaccgc caacaggctc cacaatcgta cgattagaac  57180
cacctcggac atgtccggat tatcaccttg gtaaaaactt tacagagggt attgctgttg  57240
tttataaaga aaacattgcc gcgtacaagt ttaaggcgac ggtatattac aaagatgtta  57300
```

-continued tcgttagcac ggcgtgggcc ggaagttctt atacgcaaat tactaataga tatgctgata 57360
gggtaccaat tcccgtttca gagatcacgg acaccattga taagtttggc aagtgttctt 57420
ctaaagcaac gtacgtacga aataaccaca aagttgaagc ctttaatgag gataaaaatc 57480
cacaggatat gcctctaatc gcatcaaaat ataattctgt gggatccaaa gcatggcata 57540
ctaccaatga cacgtacatg gttgccggaa cccccggaac atataggacg ggcacgtcgg 57600
tgaattgcat cattgaggaa gttgaagcca gatcaatatt cccttatgat agttttggac 57660
tttccacggg agatataata tacatgtccc cgttttttgg cctacgggat ggtgcataca 57720
gagaacattc caattatgca atggatcgtt ttcaccagtt tgagggttat agacaaaggg 57780
atcttgacac tagagcatta ctggaacctg cagcgcggaa ctttttagtc acgcctcatt 57840
taacggttgg ttggaactgg aagccaaaac gaacggaagt ttgttcgctt gtcaagtggc 57900
gtgaggttga agacgtagtt cgcgatgagt atgcacacaa ttttcgcttt acaatgaaaa 57960
cactttctac cacgtttata agtgaaacaa acgagtttaa tcttaaccaa atccatctca 58020
gtcaatgtgt aaaggaggaa gcccgggcta ttattaaccg gatctataca accagataca 58080
actcatctca tgttagaacc ggggatatcc agacctacct tgccagaggg gggtttgttg 58140
tggtgtttca accccctgctg agcaattccc tcgcccgtct ctatctccaa gaattggtcc 58200
gtgaaaacac taatcattca ccacaaaaac acccgactcg aaataccaga tcccgacgaa 58260
gcgtgccagt tgagttgcgt gccaatagaa caataacaac cacctcatcg gtggaatttg 58320
ctatgctcca gtttacatat gaccacattc aagagcatgt taatgaaatg ttggcacgta 58380
tctcctcgtc gtggtgccag ctacaaaatc gcgaacgcgc cctttggagc ggactatttc 58440
caattaaccc aagtgcttta gcgagcacca ttttggatca acgtgttaaa gctcgtattc 58500
tcggcgacgt tatctccgtt tctaattgtc cagaactggg atcagataca cgcrttatac 58560
ttcaaaactc tatgagggta tctggtagta ctacgcgttg ttatagccgt cctttaattt 58620
caatagttag tttaaatggg tccgggacgg tggagggcca gcttggaaca gataacgagt 58680
taattatgtc cagagatctg ttagaaccat gcgtggctaa tcacaagcga tattttctat 58740
ttgggcatca ctacgtatat tatgaggatt atcgttacgt ccgtgaaatc gcagtccatg 58800
atgtgggaat gattagcact tacgtagatt taaacttaac acttcttaaa gatagagagt 58860
ttatgccgct gcaagtatat acaagagacg agctgcggga tacaggatta ctagactaca 58920
gtgaaattca acgccgaaat caaatgcatt cgctgcgttt ttatgacata gacaaggttg 58980
tgcaatatga tagcggaacg gccattatgc agggcatggc tcagtttttc cagggacttg 59040
ggaccgcggg ccaggccgtt ggacatgtgg ttcttggggc cacgggagcg ctgctttcca 59100
ccgtacacgg atttaccacg tttttatcta acccatttgg ggcattggcc gtgggattat 59160
tggttttggc gggactggta gcggcctttt ttgcgtaccg gtacgtgctt aaacttaaaa 59220
caagcccgat gaaggcatta tatccrctca caaccaaggg gttaaaacag ttaccggaag 59280
gaatggatcc ctttgccgag aaacccaacg ctactgatac cccaatagaa gaaattggcg 59340
actcacaaaa cactgaaccg tcggtaaata gcgggtttga tcccgataaa tttcgagaag 59400
cccaggaaat gattaaatat atgacgttag tatctgcggc tgagcgccaa gaatctaaag 59460
cccgcaaaaa aaataagact agcgcccttt taacttcacg tcttaccggc cttgctttac 59520
gaaatcgccg aggatactcc cgtgttcgca ccgagaatgt aacgggggtg taaatagcca 59580
gggggtttgt tttaatttat taataaaaat gtgtattacg ttactcatgt gtctccatta 59640

-continued

```
cgcatcacag ggggtattta tacccgataa tatacaaaac gcgttttgta cctctaccgc  59700
acccgatatc ttaacggggg ttattatgga atcgtctaac attaacgcgc tacaacaacc  59760
gtcgtctatc gcacatcatc cgtccaaaca gtgcgcttca agtctcaatg aaacagtaaa  59820
agattctccc cccgcgattt atgaagatag gttagaacac acgccggtac aattaccccg  59880
cgacggtaca ccccgagacg tatgttctgt gggacagcta acctgtcgag catgtgcaac  59940
gaaacctttt cgccttaacc gcgacagcca atacgactac ttaaacacat gtccaggggg  60000
ccgtcatatt tcactggcac tggagattat aacgggtcga tgggtttgca tcccgcgtgt  60060
gtttccggat accccagagg aaaaatggat ggcgccatat attattccag accgagaaca  60120
accatcatca ggggatgaag attctgacac cgattaaatt taacttaaat aaaaccttac  60180
cacccataaa aacgccttct gtttgtttaa cacgacaccg cttaacaaaa aaaaacccaa  60240
acacgccttt tatgaatgta atacttttat ttgttggtta acaccgcccc accatcatct  60300
gatttgcaaa catatcggcg tcgtctgccg tggacccctg tattaaaggg gccttggaac  60360
tagcctccac tgcatttaca tcttgtccaa ctgtatctgt atgtggggtg cttgttgtat  60420
tttgggatga gcatagaccc gaaacgcttt gaagctgttt taataaaatc gatattcgag  60480
gatcccgtgt cccctctggt atatttgtat ggtgcgacaa aggcatttgt gtcccatttt  60540
gtgattttag ctctgtaacc tcctgttgca gttttgccac aaccccagca agctcttcgt  60600
gctgaccatt agaaactctg tgtctcctct gccaatatga tggagaaact cgacgtctcc  60660
gatgcgttat atacgttggt tcaccgggaa aatatatatt tgagggaaac tctccgtcca  60720
tttgagactc cccactagaa aaagaatcca attccctttg atccatgctc ttgaaatccc  60780
gttttcctgg acgacggaca tcggttttgt ctggaaaatt tacacacggg gtctgcaagt  60840
caataccccg ttcggcggcc aatgcgttca taaatgcgga catttgcatt tccaaacgat  60900
tgggtggtgg atatcccgga aacccgtacg gtcccccgaa gtgtcccgga gggcaaccat  60960
aaccccctgt attaaatggg aaggcaggcg ggtgtggaga tccatatggc ccgacgatat  61020
actgtccgtt atttggagct ccaattgata cctgcggatt tttagtctgc ccggttaaca  61080
gctgtgaata atacgcggta ggtatcagta caaattcccc tccggttgga acgcccgacg  61140
ggggctgtgg tgagatacca ctagcgttac ctgctacaga agccatatcg ctgtcgttcc  61200
tacacaactg cgtaaccttt aaatgcggaa cagtcttttc acaatcttca tttgattccc  61260
caacacccaa cgcgagatcg tatatgggcc cgccggggtg gaatgtggcg tttataacac  61320
ccgcgttggg taatttagac tccaccccat taacgttggt tatccgagca agtccatatc  61380
cggtgctagc ctgaagataa acgtgaccca taattccggc ttcgcgtcta cgttttgcaa  61440
ccacgtccca tctatctctt aaaagcatat tgttcacggc tgtggataat aacaccttgg  61500
cgagtttatc ttcgctaacc ttccatactt tatttaaacc cgcgtagtct ttaaccagcg  61560
acaataaccg cgctttactt tccatcgata aaacccggaa tggttcaatt gaagattccg  61620
gggtacagtc ataattgacc actgttccaa cgcgtcttcc aacaacacat aacgcaacat  61680
gggtaaaaaa attaccgtct ggtatctcat tcggggacaa tcgttttgaa gacagggata  61740
cggagggtaa gtaatttgtg accaagtata acgcacgttc tagcggagat aatacagaat  61800
ctctatttcc aaaaaaattc gaatgggccg cttcaaacag caccgcatgt agttgagggc  61860
atctaacgat acccaaaaaa aaaggtccgc gtatgtcctc aatgattgcg attacttcac  61920
ccacgacaca gtcttttcga tgatcgatgt ttattggtat tttactagta ggcggcaaag  61980
cggaccgcac aatctctggg gtaatattta attccccttc gtcctttgaa tataaggcta  62040
```

-continued

```
aatacccagc cacgtataac gcttcacagt tctcttcgtc agcttcagca gccattataa  62100
acaccccacg gaccggatag tgaatactca cggtgtggag gcaaactgag gaatgacacc  62160
caaacagaca aaatatagaa gatcatagtc actgttaacg ttgaactgcg caaggcggcg  62220
actttcttcc aatgccgccc ttacacgcgg ttggtgcatt aacattccaa gtccccgttc  62280
atattgcaac ataacactgt catgtattga taccacggcg gctatgggta gggatgtaac  62340
attttgtcgg cggtgttcta attccaatgc aattaagctt atgagccgat cttggtactg  62400
tccagaagaa atatctatta cggttcttcc taaacttcca cgactaagct gggtatgcgc  62460
gtctaaacaa agagcaacta atccaggaaa catttcagtc agctctgtgg tccgatttaa  62520
cgtatacagt ggtgctatat atcgttcaca taaaaattga aagttattat taccgctttt  62580
aaacttccca tcaaaccccg tcgctccgcg caagattaca ttgttggtag gggttcctgt  62640
tgcttctgac acaatcaaac ccagttgaaa attatttttt agtttatctc cgtatacgtt  62700
cccgttccat aataagcgcc ttaataataa taacgccgta atcgtgtcaa ttgttaacct  62760
taatagagtt tggtcttcca taagaaacac gttttgggcc cgttctaaat acgccgcggc  62820
cgcctgttga atcttgtcca catatgcggt atgattgcga tcaataatgt cattaacccc  62880
aggattaaac tgtccaggtg caggcggtag gacctgcaac cgtataagcg catccataac  62940
agaatgtgac gttaaggcgc cttgatcata ccgcccccca cgagcatgaa actggtcgcg  63000
tggtagacga tcatagcaaa attgataact gtttttattt tcgtgtgttg tcatataatt  63060
cacaaatgtc tcagtatatt ccggtaggtg ctctataagg ttcccgaagg acgaaacttg  63120
aggttcgtgg acactattag atgtcctata cattaaatat aaacataata ccgcacactc  63180
gaacgcggag tacgctctat ctccaacata cattctcccg gcggactgta gacatgttac  63240
cgttgtgttc ataaacgtac gggaaatgcg cccgtcttta caatcaactc cgcgtgcagc  63300
tacgggccta tctaacacaa gccgttcctg cagagtacga taccatggcc cgaaaacaat  63360
ccctggagag ttattgcccc ttgcccttcc caagtacacc agggtgataa aatccacttg  63420
aaagtttgta tcgtactgca acggtgcatc atttttggca atctgtacct cggggtgtat  63480
agactcattg cgtattattt ctgtacgtgt acattcctca gattgtgcat ctgcttcttc  63540
cgcctcggca gcagccgtct ccagggaatc caaaaccttg gccatgcgcg ttagttgttc  63600
ttcgaggggc tttaaacgac gatctatttc cgttggtaac gtaatcgttt ccccgcgaag  63660
gttgtctaat gcggcaacgg ccgccgcatt ttttaacgtt aacgtatttt tttccaaatc  63720
gggattcata cgccctctta actcaaacgc gggagccgtc cagtagtgta tggggaagtt  63780
gggggctata aagttcttag tggtagacaa aaatatccca catttattcg gaaacgagat  63840
agatccgaac ccatatctcg ccgtcatggt gtctgcagca aacaaagtca actggcgtga  63900
atataaaccg gtactgcttt aaaagctgtt ttcttaccca tgggaaaaca tcccggttat  63960
actttgtaaa attccaccac aagcacctaa agaaggcctt ctaaggggta aatccacccc  64020
acargctgca ttttcttcaa actttgttaa agcggaacga tggcatgatt tcgcacgctt  64080
tttcgcaaga gagcatacgt gaattttctt tttgcataga cgtcttcgct ctctaacgga  64140
ccttatcggg ggggtatatt ccgctacatt ctccaaatgc gacgctagca taacaaggtt  64200
tccatgaatc accttcgggg gtaaccgagt tacctgtaac aggttcagac cccgttgaga  64260
tacaaacaca aggagggggg tcaccattat ttcatcagat cccgtgggtg tggtttcctt  64320
tattaaagcc acggtatccc tcagctggcg cataccctcg caaaactggt gatacttagt  64380
```

-continued

```
aggggtatgt atattagcgc taaaacggca agattttaat tccactataa aacaaacggt  64440
ctttccggca ccactggatt ccgtttgtat aatacaaaca caatcggggc gtcggcgtcc  64500
caaatttact tcaaacgaca ttgatatgcg tacagccctt tgaacatcca cgtgggataa  64560
cggcgacagg agttttgcca gcctcgggtt gaacgcgtcc gcgaaacctc gacgtacgtt  64620
atcaatatcc tttttgagta catcgtaaaa acgagtgtgg caacgttgtc ccaaacgaaa  64680
acacttggcc cgaattcgac tagcggacat atttgaagtt ccgtcccaga agataaccta  64740
agacgcgttt gtctacaata aacatgtcaa cggataaaac cgatgtaaaa atgggcgttt  64800
tgcgtattta tttggacggg gcgtatggaa ttggaaaaac aaccgccgcc gaagaatttt  64860
tacaccactt tgcaataaca ccaaaccgga tcttactcat tggggagccc ctgtcgtatt  64920
ggcgtaacct tgcaggggag gacgctattt gcggaattta cggaacacaa actcgccgtc  64980
ttaatggaga cgtttcgcct gaagacgcac aacgcctcac ggctcatttt cagagcctgt  65040
tctgttctcc gcatgcaatt atgcatgcga aaatctcggc attgatggac acaagtacat  65100
cggatctcgt acaagtaaat aaggagccgt ataaaattat gttatccgac cgacacccaa  65160
tcgcctcaac tatatgtttt cccttgtcca gatacttagt gggagatatg tccccagcgg  65220
cgcttcctgg gttattgttt acgcttcccg ctgaaccccc cgggaccaac ttggtagttt  65280
gtaccgtttc actccccagt catttatcca gagtaagcaa acgggccaga ccgggagaaa  65340
cggttaatct gccgtttgtt atggttctga gaaatgtata tataatgctt attaatacaa  65400
ttatatttct taaaactaac aactggcacg cgggctggaa cacactgtca ttttgtaatg  65460
atgtatttaa acagaaatta caaaaatccg agtgtataaa actacgcgaa gtacctggga  65520
ttgaagacac gttattcgcc gtgcttaaac ttccggagct ttgcggagag tttggaaata  65580
ttctgccgtt atgggcatgg ggaatggaga ccctttcaaa ctgcttacga agcatgtctc  65640
cgttcgtatt atcgttagaa cagacacccc agcatgcggc acaagaacta aaaactctgc  65700
taccccagat gaccccggca aacatgtcct ccggtgcatg gaatatattg aaagagcttg  65760
ttaatgccgt tcaggacaac acttcctaaa tatacctagt atttacgtat gtaccagtaa  65820
aaagatgata cacattgtca tactcgcgtg tacgtgtttt tctttttttat atatgcgtca  65880
tttattacca catcctttaa tcccgccttt atctccctaa aacggagtgg taatattaaa  65940
agccgccaag cctgttggtg ggtgaggagg ggtaaaggca cgctgtgtgc ataacgttgc  66000
ggtgatattg tagcgcaagt aacagcgact atgtttgcgc tagttttagc ggtggtaatt  66060
cttcctcttt ggaccacggc taataaatct tacgtaacac caacccctgc gactcgctct  66120
atcggacata tgtctgctct tctacgagaa tattccgacc gtaatatgtc tctgaaatta  66180
gaagcctttt atcctactgg tttcgatgaa gaactcatta aatcacttca ctggggaaat  66240
gatagaaaac acgttttctt ggttattgtt aaggttaacc ctacaacaca cgaaggagac  66300
gtcgggctgg ttatatttcc aaaatacttg ttatcgccat accatttcaa agcagaacat  66360
cgagcaccgt ttcctgctgg acgttttgga tttcttagtc accctgtgac acccgacgtg  66420
agcttctttg acagttcgtt tgcgccgtat ttaactacgc aacatcttgt tgcgtttact  66480
acgttcccac caaacccccct tgtatggcat ttggaaagag ctgagaccgc agcaactgca  66540
gaaaggccgt ttggggtaag tcttttaccc gctcgcccaa cagtccccaa gaatactatt  66600
cttgaacata aagcgcattt tgctacatgg gatgcccttg cccgacatac tttttttttct  66660
gccgaagcaa ttatcaccaa ctcaacgttg agaatacacg ttccccctttt tgggtcggta  66720
tggccaattc gatactgggc caccggttcg gtgcttctca caagcgactc gggtcgtgtg  66780
```

-continued

```
gaagtaaata ttggtgtagg atttatgagc tcgctcattt ctttatcctc tggactaccg  66840
atagaattaa ttgttgtacc acatacagta aaactgaacg cggttacaag cgacaccaca  66900
tggttccagc taaatccacc gggtccggat ccggggccat cttatcgagt ttatttactt  66960
ggacgtgggt tggatatgaa tttttcaaag catgctacgg tcgatatatg cgcatatccc  67020
gaagagagtt tggattaccg ctatcattta tccatggccc acacggaggc tctgcggatg  67080
acaacgaagg cggatcaaca tgacataaac gaggaaagct attaccatat cgccgcaaga  67140
atagccacat caatttttgc gttgtcggaa atgggccgta ccacagaata ttttctgtta  67200
gatgagatcg tagatgttca gtatcaatta aaattcctta attacatttt aatgcggata  67260
ggagcaggag ctcatcccaa cactatatcc ggaacctcgg atctgatctt tgccgatcca  67320
tcgcagcttc atgacgaact ttcacttctt tttggtcagg taaaacccgc aaatgtcgat  67380
tattttattt catatgatga agcccgtgat caactaaaga ccgcatacgc gctttcccgt  67440
ggtcaagacc atgtgaatgc actttctctc gccaggcgtg ttataatgag catatacaag  67500
gggctgcttg tgaagcaaaa tttaaatgct acagagaggc aggctttatt ttttgcctca  67560
atgattttat taaatttccg cgaaggacta gaaaattcat ctcgggtatt agacggtcgc  67620
acaactttgc ttttaatgac atccatgtgt acggcagctc acgccacgca agcagcactt  67680
aacatacaag aaggcctggc atacttaaat ccttcaaaac acatgtttac aataccaaac  67740
gtatacagtc cttgtatggg ttcccttcgt acagacctca cggaagagat tcatgttatg  67800
aatctcctgt cggcaatacc aacacgccca ggacttaacg aggtattgca tacccaacta  67860
gacgaatctg aaatattcga cgcggcattt aaaaccatga tgatttttac cacatggact  67920
gccaaagatt tgcatatact ccacacccat gtaccagaag tatttacgtg tcaagatgca  67980
gccgcgcgta acggagaata tgtgctcatt cttccagctg tccagggaca cagttatgtg  68040
attacacgaa acaaacctca aaggggtttg gtatattccc tggcagatgt ggatgtatat  68100
aaccccatat ccgttgttta tttaagcaag gatacttgcg tgtctgaaca tggtgtcata  68160
gagacggtcg cactgcccca tccggacaat ttaaaagaat gtttgtattg cggaagtgtt  68220
tttcttaggt atctaaccac gggggcgatt atggatataa ttattattga cagcaaagat  68280
acagaacgac aactagccgc tatgggaaac tccacaattc caccccttcaa tccagacatg  68340
cacggggatg actctaaggc tgtgttgttg tttccaaacg gaactgtggt aacgcttcta  68400
ggattcgaac gacgacaagc catacgaatg tcgggacaat accttggggc ctctttagga  68460
ggggcgtttc tggcggtagt ggggtttggt attatcggat ggatgttatg tggaaattcc  68520
cgccttcgag aatataataa aatacctctg acataaaaaa catgtataat aaaaagtcac  68580
tataaacgta ttctctacaa tactttattc gcgaataata cacactacct ttgggttttt  68640
ttcccgtccc caaatggtgt ttggtgcact ctaccaaaaa atagagcgcc taaatatgct  68700
atataacgcc tcccagcaaa atacggttca aaggcattac ccgatattgt attgtagtac  68760
agggcaatgg gaattgatga tcccaataaa cggcatagac gcacagcgcc gttatagcag  68820
gggtctccag agtacagggt atctaagtac cgggatatct catactcatg cctttccgtg  68880
acagaaacat caaccggaac agtatccgat aaaccaactc ctgtttttgc aaggcgtaaa  68940
attcgcacac cttccttttt tgcaagatgt gacgtttcct tgtaacaggg aagctggggg  69000
agtggtaaga acaacaaagt ttcagccaac gtgccaataa agcccacttc cctcaagagg  69060
ctgtttgctg tatccacaat ggtccgtatt aaatcttgag caacttgatc cgtgtcatca  69120
```

-continued

```
tcactgggta acgcgttaac ataactacgc gttaaatctt caataacggc ataacaatta  69180
aacgcttccc accgagacag tatatattga acaatcacga accgttgaca ggacgtcaga  69240
tcacgtccgt aagcatgccc gaaaaatgga agttcccccc gttcgccata taccgcaaca  69300
actgcggtat atatcgtctc acgggcttca ttaagttcat cttcaagtcc aggccatttt  69360
ctggctttaa atataacctc gtccgcaaaa aaaaccgcac atgataacgc gcggatacaa  69420
tgagtagtgg ctttatggcg aggatcccaa atgtccatta cccgggggat ggtcctaatc  69480
tgtacaaagt tacttagtgt aatatgatcg gacttcttac gccgtctagg ctgtttctca  69540
gaatacggtt cacccgaaat cggcacatca tctgctttta cgtcttccgt aaccacatca  69600
gcagcgcgcc gactaacaat tatacttgtt ttttcatcgt cgttacttcc gttaagcgcg  69660
tctcgtatct cgggcgtccc gtcgaataat ccactcacta gctcctgcaa accttctggt  69720
aactccaaca tacgcatata caccaatgaa aaactggctt cgtttggtac gtacataaag  69780
ccatttgtgg tattaatggc ggtgggtgtt ggaaacaatt ttagcttatt ctcgcgcgta  69840
acatctaccc ccgccaccaa tgttaaatgc gtcacgggga gggacacgag ataatctgcg  69900
agcgtagggt cctccacttc aacatcaaat gttccgcaaa ggtcgcgatc caccgccccc  69960
gatcccgctg caagtaaggc cactcgatcc aaaaacacgc agttattatt ggatgatacc  70020
gcccatgtct tcccggtgcg attgagctca cttcgaacgt aactggcaac agatctgtca  70080
ccgggtccga ccccgcgaac aacatgtcca aattttgcga tctcgcctcc atgtttgcgg  70140
ggtatggaaa ttaagcatcc cccgcatata aaatacgccc tggtagcacg ctcgttaaaa  70200
taaaacgtta cgccgttata agatacggtt gaatgatatg gaaattccat attaaagcgt  70260
ttatcggaac attaacctcg aacttgccgt cccgtgatcg tgtgatcgcc aaccttaggt  70320
ccacaccgaa tatgagaaat atataactac acgcaaacat tcaaaacacc gtggtatcat  70380
taacgtcata tgaaaagatc caatcaatcc aatcaaccac acctcctacc gtttagcacg  70440
tcagctatgt gacatgctcc aaacatacgt aaacatttag agagggtgtt ataacagtct  70500
gtcaggcggg gtatattcta cataatacaa ggatcggctt taactttgtc aacattttta  70560
ctttggacta taaactgcga ctgaacgtta tgaacccacc ccaagcccgc gtctcggaac  70620
agacaaagga cttgcttagc gttatggtta accagcaccc cgaagaggac gcaaaagtgt  70680
gtaaatccag tgataattca ccgctttata acaccatggt tatgttatcg tatgggggtg  70740
atacggactt actattaagc tctgcatgta cccgcacatc taccgtaaac aggtcggcgt  70800
ttacgcaaca ctccgtgttt tatattatat ccacggtgtt gattcaacca atatgttgta  70860
tcttcttttt tttttactat aaagcgacac gctgtatgct cttattcaca gccgggttac  70920
ttctgacgat tctacatcac tttcgactta ttattatgtt attgtgtgtc tacagaaata  70980
tacgatcaga cctgctaccc ttatctacat cccagcaact gctgcttgga attattgttg  71040
tgactcgaac aatgctattt tgtattacgg cgtattatac tctttttata gacacccggg  71100
tgttcttttt gattaccgga cacttgcaaa gtgaggttat ttttccagat agcgtttcaa  71160
aaatacttcc tgtgtcgtgg ggtccaagtc cagccgtgtt actggtaayg gcggcagtta  71220
tttacgctat ggactgtttg gtggacacgg tatcctttat tgggccaagg gtgtgggtcc  71280
gtgttatgtt aaaaacatct atttcgtttt agtccatttc aataaatgta ctataattgt  71340
tcagtctaaa aataatgttg ggtatttata attaccgccc ccgtgttact tggaaacacc  71400
catacatatg ttccactcta catcaaactt ctcgcagttt tcttgttccc gcacacgttt  71460
acacgtccgg attcaagtcg caacgctgct gacaaaatga caacggtttc atgtcccgct  71520
```

-continued

```
aacgtgatta ctacaacgga atctgatcgt attgctgggt tatttaacat cccagcgggg  71580
atcattccaa ctggaaatgt gctgtcaacc atagaggtgt gtgcacaccg ttgcattttt  71640
gatttttta aacaaatacg atcagatgat aacagccttt actcggctca attcgatatt  71700
cttttgggga catactgcaa tacattaaac tttgtgcgtt ttctagaact tggactgtct  71760
gtcgcttgca tctgtactaa atttccggag ctggcttacg tgcgagatgg cgttattcaa  71820
tttgaggtac aacaacccat gatagcacgt gatggcccac atcccgtcga tcagcctgtt  71880
cataattata tggttaagcg gatacacaag cgttcgttaa gcgctgcgtt tgcaattgca  71940
tcggaagcgt tgagtttgtt aagtaacaca tatgtcgatg ggacagagat tgactcatcg  72000
ttacgtataa gagctatcca acagatggct cgtaatttac gcaccgtttt ggactcattt  72060
gaacgaggca ctgccgatca acttcttggt gttctattgg agaaagcccc accgctatcg  72120
ctgctttcac caattaataa attccaaccc gagggacatc taaatcgtgt tgcacgcgcg  72180
gccctacttt cggacctcaa acgtagagtc tgtgcggata tgttttttat gacccgacac  72240
gccagggaac ctaggctgat ctctgcgtat ctgtcggata tggtttcgtg cacccaacca  72300
tcggtgatgg tatcacgaat aactcataca aacactcgcg gacggcaggt tgacggtgtg  72360
ttggtaacaa cagcaacctt aaaacggcaa ctattacagg gaattttaca aattgacgac  72420
accgccgctg acgtaccagt aacatatggc gaaatggttc tacaggggac aaacttggta  72480
accgcccttg tgatgggaaa ggccgtccgc ggaatggatg atgtagcccg ccatctcctt  72540
gatataaccg accctaacac gttaaacata ccgtctatac ccccacaatc caactccgat  72600
tcaacgacag ctgggcttcc ggttaacgcc cgtgttcctg cggatttagt gattgttggg  72660
gataaacttg tattcttaga agcattagaa cggcgggtct accaagctac gcgcgttgcc  72720
taccctctta ttggaaatat agatattacg tttatcatgc caatgggagt gtttcaggca  72780
aactccatgg acagatatac acgacacgcc ggcgattttt caactgtatc cgaacaggat  72840
ccacgtcaat ttccacccca agggattttt ttttataata aagatgggat attaacacag  72900
ttgactcttc gtgatgcaat gggtaccatc tgccacagtt cattgcttga tgttgaggcc  72960
acacttgttg ccctccgcca acaacattta gatcgtcagt gttattttgg tgtatacgtg  73020
gccgagggta cagaggacac attggatgtt caaatgggga ggtttatgga aacgtgggca  73080
gatatgatgc ctcatcaccc tcattgggta aacgaacatt taacaattct acagtttata  73140
gctccgagca acccgcgtct aaggtttgaa ttaaaccccg cctttgattt ttttgttgca  73200
ccgggggacg tagaccttcc cggaccgcag cgtcccccgg aagccatgcc aaccgttaac  73260
gcaacattac ggattatcaa cggaaacatt cccgtgcctc tatgtcccat ttcatttcga  73320
gactgtcgcg gaacccaact cggtttggga agacatacaa tgaccccggc aaccattaaa  73380
gccgtaaagg atacatttga agaccgcgca tacccaacta ttttctacat gctagaggct  73440
gttattcatg gaaacgaaag aaacttctgt gcgttactgc gactgttaac acagtgtatt  73500
cgcgggtatt gggagcaatc ccacagggtg gcatttgtaa ataactttca catgttaatg  73560
tacataacta catatctcgg aaacggtgag cttcccgaag tctgtattaa tatatatcgg  73620
gatttactgc agcatgtaag agcattacgc caaactataa ccgattttac aatacaagga  73680
gagggccata acggcgagac ctcggaagcg ctaaataaca tccttacgga tgacacgttt  73740
attgcaccta ttctatggga ttgtgatgcg ttaatatacc gtgatgaagc cgcccgagac  73800
cgactccccg caattcgtgt aagcgggcga aacggatacc aagcccttca ctttgtggat  73860
```

-continued

```
atggccgggc ataacttcca acgacgcgat aatgtgttaa tccacgggag acccgttcgg  73920
ggagacacgg gtcagggtat tcccattacc ccacaccatg accgtgaatg ggtattctc   73980
tccaagattt actactatat tgtcattcct gcattttccc gcggttcctg ttgtacaatg  74040
ggcgtgcgtt atgatcgcct ataccctgcg ttacaggcag ttatcgttcc ggaaattccc  74100
gctgatgaag aagccccaac taccccagaa gatccaagac accctcttca cgcacaccaa  74160
ctcgttccga actctcttaa cgtttacttc cataatgcac acctaaccgt tgatggtgat  74220
gcattgctca cactacaaga gttaatggga gatatggctg aacgaacgac ggccatttta  74280
gtatcaagcg cccccgatgc gggagccgcc acggcaacaa ccagaaatat gagaatatat  74340
gacggagcgc tttaccatgg ccttattatg atggcatatc aggcgtacga tgaaaccatt  74400
gcaacgggta ctttttttta tcccgttccg gtcaaccctc tgtttgcatg tccggaacat  74460
ttggcatcat tgcgtggaat gacaaatgct aggcgggttt tggcaaaaat ggtaccacca  74520
atccctcctt ttctgggagc caaccaccac gcaactatac gccaacccgt tgcctaccat  74580
gtaacgcata gtaagtcgga ttttaatact cttacatatt ctcttcttgg agggtatttt  74640
aagtttacac caatatctct tacacatcaa ctacgaacgg gatttcaccc cgggattgcc  74700
tttaccgtag tgcgccagga tcgctttgcc acagagcaac ttttatatgc cgagcgtgct  74760
tctgaatcgt actttgtcgg acaaatccaa gtacaccatc atgatgctat tgggggggta  74820
aactttaccc taacccaacc cagagctcac gtggacctgg gagtcgggta tacagctgta  74880
tgtgccacag cagccctgcg atgccctctc acggatatgg gcaatactgc ccaaaatctt  74940
ttttttttcac gaggaggagt gccaatgtta catgataacg ttaccgaatc gttgcgtcgt  75000
ataacagcat cgggggggtcg cttaaatccc accgaacccc tacccatctt cggcggacta  75060
cgtcctgcta catcggcagg aattgcacga gggcaagcct ctgtgtgtga gtttgtggcc  75120
atgccggtgt ccactgacct acaatatttt agaactgcat gcaatcctag aggtcgagca  75180
tctggaatgt tatatatggg tgaccgtgac gccgacatag aggctataat gtttgatcac  75240
acacaatcgg atgttgctta tacagatcga gcaactctta acccatgggc atcacaaaaa  75300
cattcatacg gtgacaggct atacaacgga acatacaacc ttacaggcgc ttctcctatc  75360
tacagcccat gctttaagtt ttttacacca gcggaggtta acactaattg taatacactg  75420
gatcggcttc taatggaggc aaaggctgtg gcgtcgcaaa gctccaccga cactgaatat  75480
caatttaaac gccctcccgg ttctaccgaa atgacacagg atccgtgtgg ccttttttcaa  75540
gaagcatatc caccactatg ctcaagcgat gcggccatgt tacgaacggc tcacgcggga  75600
gaaaccgggg cagatgaagt tcacttagcc caatatctga ttcgagacgc gtcgcccctt  75660
aggggatgtc ttcctcttcc gcgataattt caccacgccc acatacccac tcccaataaa  75720
agccctgtag agcgcattgg catcttactt gagatttgga tacgctcggc cgacttggtc  75780
tgtttcacgc ttccttaaac aacatggcta tgccatttga gatagaggta ttgttaccag  75840
gagaactatc cccggcggaa acatctgcat tacagaaatg tgagggaaaa attattacct  75900
tctcaaccct gcgtcatcga gcttcactgg tggatatagc gctgtcgtca tattacatta  75960
acggtgctcc accagacacg ctctcgctgt tagaggcata ccgaatgcga ttcgcggcag  76020
ttataacacg ggtcatcccg ggaaagttgt tggcgcatgc cattggcgtg ggtactccta  76080
cacccgggtt gtttattcaa aatacatccc ccgttgatct ttgtaatggc gattacatct  76140
gcttacttcc tccggttttc gggtccgcag actcaattcg cttggactct gtaggactgg  76200
aaattgtttt ccctttaacc atcccccaga ccttaatgcg agaaatcatc gccaaagtgg  76260
```

-continued

```
ttgcacgggc cgttgagcgc acggccgcgg gtgctcaaat tttaccccac gaagttctac  76320
gaggcgcgga tgtcatttgt tacaatggaa ggcgttatga actcgaaaca aatttacaac  76380
atcgggacgg atcggatgcg gctattcgca cattggtttt aaatctaatg ttttccataa  76440
acgagggatg tctgctttta ttggcgctga ttccaacttt gttagttcaa ggagcacacg  76500
acggttatgt aaatttattg atacaaacgg ccaattgcgt tagagaaacc ggccagttaa  76560
ttaatatacc gccaatgccg cggattcaag acggccatcg ccgatttccc atatatgaaa  76620
ctatttcatc ttggatatca acatcatcta gactgggga taccttggga actcgcgcaa  76680
ttttacgcgt ctgtgtgttt gatggaccct ctactgttca tccgggagac cgcacggccg  76740
tgattcaagt gtaaacaggt gttaataaaa acacaaccag tctagttaca tttcacgcgt  76800
cttgttttta tttaataggc ataaacacgg aatccggtat acatgaactg ccaatataca  76860
cggacataat taatgcaacc atcagatcat ctgacattgt tcccgtggta cctttacccg  76920
tgtaagtttt tgtgtctaga ttacccatac cgcctttaat tacctctgtc aggttatcca  76980
actgtttaca tagatactcc acggggtcta cacctaactt tactgttagg gatacaagct  77040
cctgtgaggc tattatattt ccggagttaa atcgtttaac aaaatagtct acggccggcg  77100
ttttttgttt ttgtaataaa aaaaaagggt acgccacgct acatccggga ggtatggaat  77160
gataaaacag taacactgga gcggaagata gcacgtttcc cttttcgagg acagcaaact  77220
gttgtgctat agccaacgat atggcaactg cagaatcctg gctgctgttt ccctctatag  77280
aaacgtgtac gtttgtaaat gtattggggt gtaaagcgag tatgtggcct aagcattgag  77340
taacgcaacg ccctatctca ctggaagacg tgccagttaa agctctaaga aaaaagtgct  77400
ccaatccaaa tataatccaa tccgacttat aacgaccaac aatcgctaca ccagtaccag  77460
acgctcgtgt atttgaggta aatgcagggt ctacgtaaac gtacaacact gacgataata  77520
tagcacaatt cgcaacggtt gacggccgat ataaaataaa cctctcacgg gcagtttttg  77580
taaataatgg ccggtcaaac cccacacccc cagaattctg tttacgccca cctacaattt  77640
cctgcacgaa ggagtcggcc ataaataaat ctgcagtgcg ccgcatggct ccatccattg  77700
tgatgaaaac cggcttattt aatacataac acgaacaagc tgtgacatcg ctatgtgcta  77760
aaacacgcgg catgtgatcg tcgcatacat atgtaacaac gtttaacaac tgatccgacg  77820
atccacgtaa gttatacaaa aaacttgtac ttgcttttcc ggtatttgtt gatgaaacaa  77880
aaataatttt acaattggtt tgatttaaaa atccgactat agtttgtaca gcatcaggtc  77940
gaataaaatt agcttcatcc acaaacagaa gattaaaatc ttgacctcgg ataccctgga  78000
acgatagaaa gatatatagt taccccacca aagtttaaat gtatccttaa ataccacgta  78060
cgtaaaaaat gtttgaatac gtacatattt cttttttttt ccagtacaac catatccggt  78120
gtataatgga agcccatttg gcaaatgaaa ccaaacatgc actttggcat aatgatcaca  78180
caaaaggatt actacacgtt gtgatacctta acgcggggct tattgcggcc ggaatagatc  78240
ccgcattact gattttaaag aaacccggac aacgcttcaa ggttgaagta caaacaagat  78300
atcatgctac aggtcaatgc gaaccgtggt gtcaagtttt cgccgcgtac attcccgata  78360
acgccttaac aaatctctta ataccaaaaa cggaaccatt tgtttcacac gtttttttcgg  78420
ccacgcataa ttcaggggga ttgattttat cattgcctgt ttatcttagc cccggtttat  78480
tctttgatgc atttaacgtt gtagcgatac gaataaatac tggaaaccgc aagcaccgtg  78540
atatttgtat tatgtatgca gaactaatcc caaacggaac gcgttatttt gctgatggac  78600
```

-continued

```
aacgggtact tttattatgc aaacagctga ttgcgtatat ccgatgcacc cctcgtcttg  78660
catcgtctat aaaaatatac gcagagcata tggtggcagc catgggtgaa tcacacacgt  78720
caaatgggga caatattgga cccgtttcat ccataatcga tcttgatcga cagttaactt  78780
ctggaggtat tgatgactcc cctgctgaaa cacgcataca ggaaaataat cgggacgtcc  78840
ttgagctaat aaaacgggcc gtaaacattg ttaactccag gcaccccgtc cgaccttcta  78900
gttcccgcgt tgcatctggg ttgcttcaaa gtgcaaaggg ccacggagcg caaacttcca  78960
acacagatcc gatcaataac ggttcctttg atggcgtcct tgagccgcct ggacaagggc  79020
gatttacggg aaagaaaaac aattcgtccg ccagcatccc acctttacaa gacgttctat  79080
tgtttacccc agcttcgaca gaaccccaaa gtcttatgga atggttcgac atctgttatg  79140
cccaattagt tagcggggac actccagcag atttctggaa acggcgtccc ctatcaattg  79200
taccgcgaca ttacgcagaa tcccccagtc cgttgattgt agtatcttac aacggatcct  79260
ctgcctgggg aggacgtatt accggaagtc caattttata tcactctgca caggctatta  79320
ttgatgctgc gtgtataaat gcccgggttg acaatcccca aagcctacat gtgacagctc  79380
gccaagagct agtcgcgcgt ttaccgtttt tggctaacgt cctaaataat caaacccccct 79440
tacccgcctt taaaccaggc gccgaaatgt ttttaaacca ggtatttaaa caagcgtgtg  79500
tgacatcgct aacccaaggt cttataacgg agttacaaac gaacccgact ctacaacaac  79560
tcatggaata tgatattgca gattcttccc aaacggttat tgatgaaatt gtagcccgca  79620
caccagacct gattcagact atagtttcgg tgttaacgga aatgtcaatg gatgcgtttt  79680
ataacagctc cttgatgtat gcggttttgg cgtatctgtc atctgtatat acacgaccac  79740
aaggtggggg gtatataccc taccttcacg cttccttccc atgctggtta ggtaatcgtt  79800
ctatatattt atttgactat tataattcag gaggggaaat acttaagctt tccaaggtcc  79860
ccgttcccgt agccttagaa aaggttggta ttggtaattc cacacaactg aggggtaaat  79920
ttatacgcag cgcggatatt gttgatattg gaatttgttc taagtattta cccggtcaat  79980
gttacgcgta catttgtcta ggatttaacc agcaattaca atccatttta gttttaccgg  80040
ggggatttgc ggcatgtttt tgtattaccg ataccctaca ggcagcacta cctgcatcgt  80100
taatcggacc tattctagac agattctgct tctctattcc caaccccccat aaataaatta 80160
gtgtcactat aaaaacataa caccagaatc tcttcatatt taattttacg tcatttctcc  80220
cgtttccacc ccctcttaaa atataaaata accgggtggg tggcattaaa cccacaagta  80280
cccgggcggc aatccgctag actgtttttc tgctcatgga attacaacgc atatttccgc  80340
tgtacaccgc tacgggtgca gcgcgcaaat taaccccccga ggcagttcag agactctgcg 80400
atgcattaac gctggatatg ggattatgga agtccatcct gaccgatccc cgggtgaaaa  80460
taatgcgatc aactgctttt ataactttaa ggatcgctcc gtttatcccc cttcaaacgg  80520
atactactaa tattgccgtt gttgtagcca caatttacat cacgcgccca cgtcagatga  80580
acttacctcc gaagactttt catgtaattg taaattttaa ttacgaggtc tcgtacgcaa  80640
tgacggcgac tttaagaatt tatccggttg aaaacataga ccatgttttt ggagcaacgt  80700
ttaagaaccc gatcgcgtac cccccttccaa catctattcc ggatcctcga gcagatccca 80760
cccccgcaga tcttacacca acgccaaact taagcgacta cttacaaccc ccgcggcttc  80820
cgaaaaaatcc atacgcatgt aaagttattt ctccgggagt gtggtggtca gacgaacgaa 80880
ggcgtttata tgtactggct atggaaccta atttaatagg gctatgtccc gccggatggc  80940
atgctcggat acttggctct gtattaaatc gactcctcag ccatgcggac ggatgtgatg  81000
```

-continued

```
aatgtaatca tagagttcac gtgggggcac tgtatgcgtt accccatgtc acaaatcatg  81060
cggaaggttg tgtgtgttgg gctccgtgta tgtggagaaa ggccggtcag cgggaattaa  81120
aagtggaggt agacattggc gctacgcagg ttctttttgt agatgtcacc acctgcattc  81180
gaattacgag tactaaaaat cctcgcatta ccgcaaatct tggcgacgtt atagcgggaa  81240
ccaacgccag tggtctctct gtaccagtaa attcatctgg gtggcagctt tatatgtttg  81300
gagaaacatt aagccgggct attattaacg gctgtggtct gcttcagcga atttgcttcc  81360
ccgagacaca aagattatcg ggtgaaccgg aacctacaac cacctagtat accttaactc  81420
aaccgccgtt gtggaaaggt atatgtcaac atttacagta atatattaaa ggttaaattt  81480
ataaaacact cacgtttgtg ttgtgacttg acgcgaacac cgctgtgctg taagacccgt  81540
cggtaaatga aaacgtaata gattcgcctt ttacatgatc cacgtaattt gccccaaacc  81600
actgttccag gcgagacttg ataccctcaa acacgggttc cgttgctttg cgtatatgag  81660
ccgtataacc cactttaatt cctctaaacg tggccattac taaagctatt aatggtacaa  81720
gaaaccatgt tttcccatgt ctacgtggta ccaaaaacac agttgatttt tgtttgaagt  81780
gttctaaaac actgtcagaa acacttggcg tgttaaacac tgtacgcaga aagcagtcaa  81840
ctctgtcggc atgatcgccc aatagcaccg atgaaataaa atgcgtggtg tgcatgagga  81900
tcattttttg aaacagttcc aacgtcccct tatatctgcc atagattgga acgtcaacct  81960
ttgcgcgttt gccatgactt ccacactctt caatactctc aaaagatgtt tccacaaggt  82020
acgaaaaccg ttgtgtaaag gtagacaact gacagaaact atccgacaga gaaaacgcgc  82080
gaaatgtgtt cataacaccg ctatacgcat ttcgatgagg tgctgcttct tccggtgaat  82140
attcataaaa ctgtacacta ctgacagcct tttttaattc rgggcttacg tttgcattta  82200
ccgaatatcg ccatggtttc aaaactacat tgggggtaca gttgtaccct gttgacgata  82260
gaaacgcgcc aaacattgcc cgtcgagcag tagccgagaa cagtggaata tattcacaac  82320
agttgtgaag cgttccaatt ccgggaataa cggcctgatg acgtcgggtt acatctatag  82380
caaaattcag aaacgggatt tgggttgcgt ttcccagaga cccttgccgc gtggaacacg  82440
gggtagggga ctccaacgtc ccaaagcgtt catccctacg acgctttaga cgttcaaaat  82500
atcttacaga ttcttcacca agcgtacgac caaacattat caatgacatt taacatcaat  82560
tcacggaatc cgcctcatct cttgtaagca gtaaaacagg aagccgcgtc atcttacgta  82620
ctcgttacgt atatatcata aacattttca gggccgcatt cattcacttt ggtcatgtca  82680
ggccacactc caacctacgc ttctcatagg cgtaaccgtg tcaaactagt tgaggcgcat  82740
aaccgcgcgg ggttatttaa agaacggacc ctcgatctaa tccgtggggg tgcgagtgta  82800
caagatccag catttgtgta tgcctttact gctgcaaaag aggcctgcgc cgatttaaat  82860
aaccagctcc gctctgcagc tcgcatagct tcagttgaac agaagattcg tgatatacaa  82920
tccaaggttg aggaacaaac aagtattcaa cagattttaa atacaaacag acgctatata  82980
gcacccgatt ttattcgcgg tttggataaa acagaagacg ataataccga taatatagac  83040
agactggaag acgcggtagg accgaacatc gaacacgaaa atcatacttg gtttggagaa  83100
gacgacgaag cgttacttac acaatggatg ctgacgacac accccccaac ctccaaatat  83160
ctccaactgc aggacctttg cgttcccacc acaataccga cggacatgaa ccaaatgcaa  83220
ccgcagccga tcagcaagaa cgagaatcca ccaaccccac acacggatgt gtaaatcatc  83280
catgggccaa tccgtcaact gcaacatgca tggaatcacc agaacgatca caacagacaa  83340
```

-continued

```
gcttattttt attaaagcac ggcttaacga gagatccaat acatcaacgc gaaagggtgg  83400
acgtttttcc acaatttaac aaacccccat gggtttttag aatttccaaa ttatcccgtt  83460
taattgtacc catcttcacg ctcaatgaac agttatgttt ttctaaatta cagattcgag  83520
atagacccag gtttgcggga cggggaacgt atgggcgtgt tcatatatac ccatcgtcaa  83580
aaatagctgt aaaaaccatg gacagtcgtg tttttaatag agagttaatt aacgcgattt  83640
tagcgagtga gggttctata cgagcagggg aaaggctagg tatttctagc atagtttgcc  83700
ttttaggttt ttcgttacaa accaaacagc tactgtttcc ggcatacgac atggatatgg  83760
atgaatacat tgttcgcctg tccagacggt tgacaatacc tgatcacata gacagaaaaa  83820
ttgcccatgt atttttagat ttggctcaag cgttgacgtt tttaaatcga acgtgcggcc  83880
tgacccacct agatgtgaaa tgtggcaata tttttcttaa cgtcgacaac tttgcctcgt  83940
tggaaataac cacagcagta atcggagact atagcctagt aacattaaat acgtattccc  84000
tttgtactcg agcgatattt gaagttggaa atccatccca cccggarcac gtactacgcg  84060
taccccggga tgcatcgcag atgtcatttc gtttggtgtt gagtcatgga acaaaccaac  84120
cccctgaaat cttgcttgat tatattaatg gaacgggcct tactaaatat actggaacct  84180
tgccccaaag agttggactt gcgattgatc tttatgcatt gggccaagca ctcttagaag  84240
ttatcctgct aggacgtctt cccggacaac tgcccatttc agtacatcgg accccgcatt  84300
atcactacta cggtcataag ttatcaccag atttggcgct tgatacgctg gcatatcgat  84360
gtgtcctggc gccatatata ctcccatctg acatccccgg ggacttaaat tataatccct  84420
ttatacacgc cggagagctg aacacccgta tttcccggaa ttctttacgc cggatattcc  84480
agtgtcacgc agtgcgttac ggcgtaacgc actcaaagct tttcgaaggc atacgcattc  84540
cggcctcatt atacccagcc actgttgtta cgtcgttgtt gtgtcacgat aattcagaaa  84600
tacgctcgga tcacccttta ttatggcacg atcgggattg gataggatcg acataagccc  84660
ccagccagcc aaaaaaattg cccgtgtggg aggtctacag caccctttttg taaaaacgga  84720
tattaacacg attaacgttg aacaccattt tatagacacg ctacagaaga catcaccgaa  84780
catggactgt cgcgggatga cagcgggtat ttttattcgt ttatcccaca tgtataaaat  84840
tctaacaact ctggagtctc caaatgatgt aacctacaca acacccggtt ctaccaacgc  84900
actgttcttt aagacgtcca cacagcctca ggagccgcat ccggaagagt tagcatccaa  84960
attaacccaa gacgacatta aacgtattct attaacaata gaatcggaga ctcgtggtca  85020
gggcgacaat gccatttgga cactactcag acgaaattta atcaccgcat caactcttaa  85080
atggagtgta tctggacccg tcattccacc tcagtggttt taccaccata acactacaga  85140
cacatacggt gatgcggcgg caatggcgtt tggaaaaacc aacgaaccgg cggcacgagc  85200
gatagttgaa gcattgttta tagatccggc tgatatccgt actcctgatc atttaacgcc  85260
agaagctaca actaagtttt ttaattttga catgctcaat accaaatctc caagtctcct  85320
tgtgggtaca ccaagaatcg gaacgtatga atgtggactt ttaatcgacg ttcgaacggg  85380
acttataggc gcgtcgttgg acgttcttgt atgtgacagg gaccctttaa ctggcaccct  85440
aaatccccac cctgcagaaa ccgacatttc attttttgaa attaaatgtc gtgctaaata  85500
cctctttgat ccagatgata aaaataaccc gctcggtcgg acgtacacca cgttaataaa  85560
tagacctaca atggcaaatc tacgggactt tttatatact ataaaaaacc catgtgtaag  85620
cttctttgga ccctcagcaa acccaagtac acgcgaggcc ttaataacgg atcacgttga  85680
atggaaacgt ttaggattta aaggtgggag ggcccttaca gaactcgacg cccatcattt  85740
```

-continued

```
gggcctcaat cggacaatct catcccgagt gtgggtattt aatgatccgg acatacaaaa  85800
ggggacaatt acaaccattg catgggccac tggagatacg gctcttcaaa ttcctgtatt  85860
tgccaatccg cggcacgcta actttaaaca aattgccgta caaacctatg tattatccgg  85920
ttactttcca gcgctaaaac tacggccctt ccttgtcacc tttataggac gtgtgcgccg  85980
accacacgag gtgggagtcc cattgcgcgt cgatacacaa gcggctgcca tttacgaata  86040
taactggccg actatcccac cccactgtgc ggttccggtt atagccgttc taacgcctat  86100
cgaagttgat gtgcctagag tgacaaaaat acttaaagac acaggaaaca acgcgattac  86160
atcagcattg cggtcattgc gatgggacaa tcttcatcca gcggtcgagg aggaatctgt  86220
ggattgtgca aacggtacaa cgagcttgtt acgtgcaacg gagaaaccgt tgctttgaac  86280
tcagagttct ttgaagactt tgactttgat gagaatgtaa cagaggacgc cgataaatcc  86340
acacaacgcc gcccacgagt gatcgatgta acaccaaaac gaaaaccttc gggaaagagc  86400
tcccattcca aatgcgcaaa atgttaaacc ctgataaacg ttctaataaa aacatcaaat  86460
catggttggt tactgtgaat gtttgtttta ttgcttgggg ggttacaagt acaacccacg  86520
ctactcccac ccactgtttg atcgctcgta taacagctca tcctcgcggt ccgtttcata  86580
tgttgagtca ttttcataga cgtagccgta gccttgtgat gggtaatttg tgcggcgaga  86640
atttctatgt gcaggtttta cttttcgtat gtatccccgt acccgctcgg gtactcttct  86700
tacggcaccg tagaaccgac tgcgtttctg tcgatgatac acatatgcac gcatcaatct  86760
gagaagcaac atgacaacgg aaaacacggc caggcaagcc aaggttcccc gagttgtggg  86820
aattaaccgt ggagattgaa ccgatatagg gtcatataat cggtccatat acgagtgcgc  86880
ggcggttccc aacgtagcac aggccacgag cgttcccagg gacggtccta ttaacacgtg  86940
tatataatgc gccaaaatta attctgatac tataagatat acaactgaca atgtactaaa  87000
tgtagacatg gccacggaca ccgatgacca cagtcccgta tgtagatgat tcgccaccac  87060
aagttccagc attaatgata caaataggat acatatcgcc atcaacgcag ccatcaaatt  87120
cacgaacact gcgcgcgtag gccccgcaag gcgatataaa aagacgctct gctgtcgtaa  87180
atttgcgacc gcttttatgt tcgtttcgtc caattttccg cgtccrcaaa aatacgttgt  87240
aaatattaca cytgtcgcaa aatgtccaag atataatgta gcagccacgc cgatttgctt  87300
gtaagctaat aataacacaa cggcgtttaa taaccacaat gacaaaagac cccaaaaaag  87360
tgttgtggga tctacaacta accatgcaac accggagctt tgccggacac gttgattttt  87420
cgtttctcgg tgtataatcg cggccgtgat cagtgtatat accgccatgg ccattgccgt  87480
taaagccgtg tagtaagtaa atgccacaac gctatgtggt tccaaaaaca aaaccggggc  87540
gctgtatcca cctctatttc cggaccatac ccccccatct agggtggcgt taaataactc  87600
ataatcaact acggcagcat aaaaacaagg gatcccggta tattcagaag aggcggcaat  87660
taacgtagcc aggagcatta ccgcacccaa agtgaacatc atcacctgaa ttatccaaat  87720
tcgccaatta agcgtatcca tttgatgatc taacgcttcc acctcgggtg tcgtggtgtc  87780
gtacggtgag actttttcag aacgcggccc cttcttttga gttcccatgt ctcccaacac  87840
cggggagagc aacgccgccg tctatgcgtc cagtacacag ctcgcgcggg cgttatatgg  87900
aggggatctg gtttcgtgga ttaaacacac ccacccggga attagcctgg aactgcaatt  87960
ggatgttcca gtaaaactaa taaaacctgg tatgtcacaa actcgcccgg taaccgtcgt  88020
acgtgcccct atgggctctg gtaaaacaac agccttgctt gagtggcttc aacacgcgtt  88080
```

-continued

```
aaaggcagat attagcgtac tggttgtctc atgtcgccgt agctttaccc agacgttgat  88140
tcaacggttt aacgatgcag gcctctccgg attcgtaaca tatttgacat ccgagacata  88200
tattatgggt tttaaacgtt tgattgtgca acttgaaagc ctacaccgcg tatccagcga  88260
agctatcgac agctacgacg tattaatact ggatgaggta atgtcagtga ttggacaatt  88320
atactccccc acaatgagac gtctttccgc ggttgatagc ctattatatc gtcttttaaa  88380
tcgctgttct caaattatcg cgatggatgc tacagtaaac tctcagttta ttgatttaat  88440
ctccggattg cgtggagatg aaaacataca cacaattgtg tgtacatacg cgggagttgg  88500
gttctccgga agaacttgca cgatcctgcg tgatatgggc atcgacacgc ttgtgcgagt  88560
cattaaacga tctcctgaac acgaggatgt acgtaccata caccaactac gtggaacatt  88620
ttttgacgaa ctagcactac gattacaatg tgggcataac atctgtatat tttcatcaac  88680
tttatcgttt tcggagctag ttgctcagtt ttgtgcaata tttacagact ctattcttat  88740
tttaaactca actcggcccc tatgtaatgt aaacgaatgg aaacattttc gcgtgttggt  88800
gtacactacc gtcgtgaccg ttggattgag ttttgacatg gctcattttc atagcatgtt  88860
tgcttacata aagccaatgt catatgggcc ggatatggta tcggtctacc agtcattagg  88920
gcgtgtacgt ttattgctac ttaatgaagt tttgatgtac gtcgatggct caaggaccag  88980
atgcggaccc ctgttctcgc caatgttact aaactttacc atcgcaaata aatttcaatg  89040
gtttcctaca cacacccaaa taactaacaa actgtgctgt gcatttaggc aacgatgtgc  89100
aaatgcattt acacgctcga acacccatct cttctcaaga tttaaataca aacacctttt  89160
cgagagatgc tctctttgga gtttagccga tagcattaat atcttacaaa ctcttttggc  89220
ctctaaccaa attttggttg tattggatgg catgggtcca ataacggacg tttccccagt  89280
tcaattttgt gcatttatac acgatctcag acatagcgct aacgccgtag cttcctgtat  89340
gcgttctctt agacaggaca atgacagctg cttgaccgat tttggccctt ccggatttat  89400
ggccgataac attaccgcgt ttatggaaaa gtatcttatg gagtcaatta ataccgaaga  89460
acaaattaaa gtatttaaag cccttgcatg tccaatagaa cagcctagac tagtcaatac  89520
ggcaatattg ggggcgtgta tacgaatacc tgaagcgttg gaagcatttg acgtatttca  89580
aaaaatatac acgcactacg cttccggttg gtttcccgtc ctggacaaaa ccggggaatt  89640
tagcatcgcg actataacta ccgccccaaa tttaaccacr cattgggagc tgtttcgccg  89700
ttgtgcctat attgcaaaaa cactcaagtg gaatccgtcc accgaaggct gtgtaacaca  89760
agttttggat acggacatta atacactttt caatcaacac ggggattcgc tggctcaact  89820
aatatttgag gttatgcgct gtaacgttac cgacgctaag attatattaa accgcccggt  89880
ttggcgaaca accggattct tagatggatg ccataatcaa tgcttccgtc caatccctac  89940
aaaacacgaa tataacattg ctctatttcg tttaatttgg gaacaattat ttggcgcccg  90000
cgtaactaaa agtacccaga cctttccggg aagtactcgt gtgaaaaacc taaaaaaaaa  90060
agatctagaa actttacttg attcaattaa cgtggatcgt tctgcatgtc gtacctaccg  90120
ccagttgtat aacctgctta tgagccatcg ccattcgttc tcccaacagc gttacaaaat  90180
tactgccccc gcttgggcac gccacgtgta ttttcaagca catcaaatgc acttggcccc  90240
gcatgccgaa gccatgctac aattagcgct atcggaactg tccccgggat cgtggccgcg  90300
gataaacggg gcggtaaatt ttgaaagttt ataacccatt aataccatat atggacatcc  90360
ataggggggg ttacataaat actaagcctc tgtacaacac aaagggcctc taacaatgca  90420
ctgaaccaca accaagctat ggacgcaacg cagattacct tggttagaga aagcggacac  90480
```

-continued rtttgtgccg caagcatata cacatcctgg acacagtccg gacaattaac acagaacggt 90540
ctttccgtgt tatactactt attatgcaaa aactcatgtg ggaaatacgt ccctaagttt 90600
gccgaaatta ccgtacaaca agaggattta tgtcgctact ccaggcatgg ggggagtgtt 90660
tctgcggcaa cgtttgcgtc tatctgcagg gcggcgtcct cggctgcgtt agacgcctgg 90720
ccccttgaac cactgggtaa cgcagacacc tggcgttgtc tccatggcac tgccctggcc 90780
actttacggc gcgtattagg gtttaaatcg ttttattcgc cagtaacatt cgagactgat 90840
acgaatacag gtcttctgtt aaaaacaatc cccgatgaac acgcgttgaa taatgacaac 90900
acgccatcta ccggagtatt gagggctaat tttcccgtgg ccattgatgt ttcagcagtc 90960
agcgcatgta acgcccacac gcaaggtacg tcgctagcct acgcccgcct gaccgcactt 91020
aaatctaacg gtgacaccca gcaacaaaca cctttagacg tggaggtaat tacaccaaag 91080
gcctacatac gtcggaaata taagtctacg ttttccccccc ctatagagcg ggaaggtcaa 91140
acctccgatt tgtttaacct tgaagaacgc cgcttggttc ttagtggcaa tcgcgcaatt 91200
gtggtaaggg tactcttacc gtgttatttt gactgtttaa caacggattc caccgttaca 91260
tcttcccttt caatattagc aacatataga ctgtggtacg cggcggcgtt tggaaaaccc 91320
ggggttgtcc gtccaatctt tgcgtattta ggcccggaac tcaatccgaa gggtgaagac 91380
agagactact tttgtactgt cggatttccc ggatggacca ctcttcggac acaaactcca 91440
gccgtcgaat ctattcgcac ggctacggag atgtacatgg aaacggatgg gttgtggcca 91500
gtaaccggta ttcaggcctt tcattatcta gccccctggg gacagcatcc cccttacct 91560
ccgcgggtgc aggatcttat tgggcaaatc cctcaagata ctggacatgc agatgcaact 91620
gtcaattggg acgcgggccg gatatctacc gtcttcaaac agcctgtaca actacaagat 91680
cgttggatgg caaagtttga tttcagcgcc tttttcccca cgatatactg cgctatgttc 91740
cccatgcatt ttagattagg caaaatcgtc ctggctagaa tgcgtcgagg aatggggtgc 91800
ctaaaacccg cgttggtgtc tttttttggg gggttacggc acatactccc gagtatatac 91860
aaagctatta tttttatagc caatgaaatt agcctttgcg tcgaacaaac ggccttggaa 91920
cagggctttg ctatatgtac ttatataaaa gatggatttt ggggaatctt cgccgattta 91980
catacgcgca atgtatgttc agatcaggca cgttgttcgg ccttaaattt agcggccgcc 92040
tgcgaaagag cagtcacggg cttattacga attcaactag gtcttaactt tacacccgcc 92100
atggaaccgg tactccgggt cgagggtgtg tacactcacg catttacctg gtgtaccacg 92160
ggaagctggc tgtggaattt acaaacaaac acgcctccgg atttagttgg cgtgccatgg 92220
cgaagtcagg cggcgcgaga tttaaaggag cgtctttcag gactcctatg taccgcaaca 92280
aaaattcgag aacggataca ggaaaattgc atatgggacc gtgtcctata cgacatatgg 92340
gccggacaag ttgtggaggc tgccagaaaa acatacgtcg atttttttga acatgttttt 92400
gatcgccgtt atactccggt atactggagt cttcaggagc aaaattcgga aacaaaagca 92460
ataccggcat cttatctgac atacggacac atgcaagata aggattataa accaagacag 92520
ataattatgg ttcgtaatcc caacccacat ggacctccta ctgttgttta ctgggaattg 92580
ctaccatcgt gtgcctgtat tccccccata gactgcgctg ctcatctcaa gcccccttata 92640
cacacgtttg tcactattat taaccatctt ctagatgctc ataatgattt ttcaagtcca 92700
tcattgaaat ttactgacga tccccttgct tcatataact tcttgttttt atgacaaaaa 92760
aacacgccgc aacaacccat ccttaaaata aaaggtttat ttactttaca acccgtggtg 92820

-continued

```
aatttttata cgtttcaaat aactgaacat ttttcggtgt taccatggtg cgatttaacc  92880
accaaaaata tacgctcttc tgatattccg aatctcgtaa aggtccattt aacaatcccg  92940
ggggcacttg caccacacca tctggacagg ggggggttcc gtggggcagg tcaaaacgct  93000
gacccacccc acatgaatat atagccttta taatattggg ggccgttcca ggctgagggt  93060
tcagtaactt aacaaacata taatgcggca atacgcgggt ttttgtaaag gggttgttat  93120
caacgacata cattagagtg tttaacaacc ataaaactcc ctcatataaa aaccgacgca  93180
ttttttccaa aggtcctatt tgacactcaa cgcgtctaag atatacagac aattgtacaa  93240
acagcgatgg agatgccccg gagggcccaa tgccttccag atacattaaa ataacacata  93300
aggtaaaatc taggacatta tccgggcgga atagagtcat ccgatagatt aacaggcgcg  93360
gaggcacccc caccgtatac accctatctt caaccgcagt taatacggaa aaaataaatc  93420
cgcggaacgc tggttgagta acacactcca tgtagtaacg atcacaggac acctcacttg  93480
aatcaccatt caacactact aaaacggtct cttggtgttc cggttttacg cgcagtgata  93540
caacagagtt tgccaaaaag cgtggcttca aaccggttac ctcccgcgcc tcgcatacga  93600
atcttggtat tgcttgtatt ctaagatctt cgatcacgtc gctcacatcc aacccctctt  93660
cggctcgtgt tagtaagttg tcgatcgtta cgctgcaacc taaaatgctg ggtatattta  93720
ttccggacat cccatcggcc atccccgcgc ctccggtttg ctcgaatttt atccagtaag  93780
gtcgaatccg ctgcatttac cttgtgtacc cgtaacctct caggggggtg tcctttcata  93840
aaatgggata ggtttttata tccaacatgc atgtattggt tatttatttt attgggttcc  93900
gggattcttt cgtcatcttc tgtagggtca ggcaaacccc aggaaggact tggtgttctc  93960
cgtgggcccc gttttattac ctctgcgcga acctgcattt catataatat tcggatttgg  94020
gataaatagg actctgttct cgccttttta aaaatagcct ggcataactc ttcctctgac  94080
ctatgtacct cgctttgagt taccaagaat cccaatcggg tggcccgtaa tatgaatgaa  94140
aaatacggcg caactagtaa tgagattgac gcatttgaat atgatacaga aatttcctgg  94200
ccttgattat tgtttacccg gtgaagctta aaacagcgaa caagttcctg tttccatagc  94260
tcagacaaac gttttatatc atctccataa ggggggatat aacgagattg aaaactattg  94320
gcaatatatg catcatcccc tattatgccg gtaagatcta taacctcgtg atttaaatcg  94380
gcaatacgtg tttcttctgc cattgtaata tgtgaccctt tagatggctt tatttttacc  94440
ctctcttccc gtaaccgttt cagctctcct tctttgaact ggagcctttc ggtcagatcg  94500
ctgttcacat ccttgagacc ctcaatggtt ttgaataaat tattcacata accctcgagc  94560
atgccgttga tactgttgac caccgatgtt ttaaacgcac tttgaacgtt tgttgttccg  94620
gacattgccc ccccgttaaa ggattggttg gccttgccaa accccggttg tgatgtgtcc  94680
accgatccac ttccttccag aatgtgattg cccgtttctt ctagatagga acgtacggtt  94740
tcggtaatat ctccaacatg tctcatgttt tttaagttaa ctattagctt tacaagtcta  94800
gacgcggccg atccagcccg tgttgtatcg ttctcgccca ttatacgatc aaccgcacgt  94860
gtgctgtgag atctatcatc ttcattccgg cgacctatta acacgcgcaa aggggctgta  94920
tttaaaactt ggcagacgcg agcatgttca cgtaatgcat aacaggccaa cacctcccca  94980
gaaagccgct gtaagggtga gtcaaatact acaccctccc cacatacaac gggcggccac  95040
acgaccaaac actctccctt catgcccgtt acatcatcct ttgccataat taatcttcgg  95100
ttataattat aataaagacg cgtcctatca taatccataa tagcaacatt ttgcatacac  95160
tcaactaggc ttgtgacaac cgccgcccct ctggccaacg ttgcatcggc aacttttaac  95220
```

-continued atctgggaca gttctgccgc ttgacccata tacgtattta atggtgcagg ggttccattc 95280
tgttctgatc gtacctttct tacaacgggc acaataccta cacaggctat ccagtccacg 95340
tatttggcaa aaccgaccct tccatttaaa ccactggtat agagacaacc ggttattcca 95400
cgcagaaact caagtaacga tgactgtaat gtttgacgcc aggtttcaaa aacctgatgt 95460
gcaagccgta cggcttctga ttctccacat aacccataac gttccgctag agccccggca 95520
tgcaggttac attgttggat gtggtggtcc caatctgctg ctaggtcctc ataccgagtt 95580
gcatccaacg cgttcatcaa aacggttgcc tgaacttggc gaattacagt ttccgtagac 95640
cgtacagcgc tatatatgcc ttgtccatcg gtatatccaa agtcaccggc taggattttt 95700
cgaaacaaca tactttgcgt ggttgggtgt attaacatcc agccatcttc ctccggaaat 95760
gtacaaaacc ctatatccgg ggcgtactca ttccagtata tatcgaacat gttcttgtat 95820
tggtcatttg ggttacttcc attcaagccc tggtcaatag aaacagaact tgctatcctt 95880
ttttcttcac taccggaact gttattaaaa agagacgtta tttcggccat tgaaaaccac 95940
gatgaaaaga tcaatttctg tagacagttc ttcacccaaa aacgttttta atccagagac 96000
gcccaatgga tttgatgaca gtgtatattt aaacttcacc tctatgcata gcattcaacc 96060
tatcctctca cggattcgag aacttgccgc aattacgatt ccaaaagaac gtgttccgcg 96120
gttgtgttgg tttaaacagt tactcgaact gcaagcgcct cctgaaatgc agaggaatga 96180
gctccccttc tccgtttatt taattagcgg aaatgccggc tccggaaaaa gcacgtgtat 96240
ccaaacgctt aacgaagcta tcgattgcat tattaccgga tccaccaggg ttgctgccca 96300
aaatgttcat gctaagttat caacggctta tgcgagtcgt ccgataaaca caatctttca 96360
tgaatttggt tttcgcggaa atcacattca ggctcagctg ggccgttacg catataactg 96420
gactacgacc ccccttctta ttgaggacct gcaaaaaaga gatattgtat actactggga 96480
agttttaatt gatataacaa aacgagtgtt tcaaatgggg gacgacggtc gcggaggaac 96540
atcgacattt aaaaccctgt gggcaattga acgtttgctt aataaaccta caggctcaat 96600
gtccggaacc gcgtttatcg catgcggttc ccttccggct tttacccgga gcaacgttat 96660
tgttattgat gaagcaggat tgctagggcg tcatattctc acggccgttg tttactgttg 96720
gtggcttttg aatgctatat atcaaagccc tcagtacata aacggtcgaa aaccggtcat 96780
agtatgcgtc ggttcgccca cccaaactga ctcgttagaa tctcattttc aacatgacat 96840
gcagcgttca cacgtaactc ctagtgaaaa tatactcacg tatataatct gcaatcaaac 96900
tctgcgtcaa tatactaaca tctcacataa ctgggcaatc tttattaata acaaacgatg 96960
tcaagaggac gattttggaa atcttttaaa aacgcttgag tacgggctac ctattaccga 97020
agcacatgcg cgtctggtcg atacatttgt tgtacctgca tcctatatta acaatcctgc 97080
taatctcccc ggatggacgc gtctgtattc gtcgcataag gaggtgagcg cgtatatgag 97140
taagttacac gcgcatttaa aactatcgaa aaatgaccat ttttctgtgt ttgccttacc 97200
gacttataca ttcatccggc taacggcatt tgatgaatac cgcaaattaa cgggacaacc 97260
cggactttct gttgaacatt ggatacgggc aaactccggt cgtttgcaca attattccca 97320
aagccgagat catgacatgg gaacagttaa atacgaaaca cattcaaatc gcgacttaat 97380
tgtagcccgt acagacatca cttacgtgct aaatagtctc gtagttgtaa ccacaagact 97440
acgtaagtta gttattggat tcagtggtac atttcaatcg tttgcaaagg ttttacgtga 97500
cgactccttt gtgaaggctc gaggagagac atccattgaa tatgcttacc ggtttctgtc 97560

-continued

```
aaacctaatc tttggaggct tgattaactt ttacaatttt ttgttaaata aaaacctaca  97620
tcccgataag gtatcgttag catacaaacg gttagctgcc ttaaccctgg agttattgtc  97680
tggaacaaac aaarcccccct tacacgaagc agcggttaat ggggcgggtg ccgggattga  97740
cygtgatggt gcagctactt ctgccgataa agccttctgc tttaccaaag cccccgagtc  97800
caaagtaacg gcctccatac ccgaagaccc ggatgatgta atttttacgg cacttaacga  97860
cgaggttatt gacttggtat actgccagta cgaattttcc tatcccaaat catccaatga  97920
ggtccatgct cagtttctgt taatgaaagc tatttacgat ggtcgatatg ccatattagc  97980
agagcttttc gaaagcagct ttacaaccgc cccctttagc gcgtatgtcg ataatgttaa  98040
tttcaacgga agcgagcttt tgatcggcaa tgtgcggggg gggctgttat ctttggcatt  98100
acaaacagat acgtataccc ttttggggta tacttttgca cccgtgccag tctttgtaga  98160
ggaactgacc cgaaaaaagc tgtaccgcga aactaccgaa atgttatatg ctctacacgt  98220
acctcttatg gtcttacagg atcaacatgg gtttgtgtcc atcgtaaacg ctaacgtatg  98280
tgaatttacc gagtctatag aggatgcaga attggcaatg gccaccacgg tggactatgg  98340
ccttagttct aaactagcca tgacaattgc acgctcacag ggcctgagtt tagagaaggt  98400
agctatctgt tttacggcgg ataaactgcg cctaaatagt gtgtatgttg ccatgtcgcg  98460
tacggtctcc tctaggttct taaaaatgaa tctaaaccct ctacgggaac gatatgaaaa  98520
atccgcagaa attagcgatc acattcttgc cgctctacgt gatcccaacg tacacgttgt  98580
gtattaaagc attgtataaa aacacgcatg cgggcttgct gttctcattt ctaggttttg  98640
tcttaaatac acccgccatg agcatctctg gacccccaac gacgtttatt ttatataggt  98700
tacatggggt caggcgggtt cttcactgga ctttaccgga tcatgaacaa accctctacg  98760
catttacggg tgggtcaaga tcaatggcgg tgaagacgga cgctcgatgt gatacaatga  98820
gcggtggtat gatcgtcctt caacacaccc atacagtgac cctgctaacc atagactgtt  98880
ctactgactt ttcatcatac gcatttacgc accgggattt ccacttacag gacaaacccc  98940
acgcaacatt tgcgatgccg tttatgtcct gggtcggttc tgacccaaca tctcagctgt  99000
acagtaatgt gggggggggta ctatccgtaa taacggaaga tgacctatcc atgtgtatct  99060
caattgttat atacggttta cgggtaaaca gacctgacga tcagaccaca ccaacaccaa  99120
ccccgcacca gtatacatcg caaaggcggc agcctgaaac caactgtcct tcaccacaac  99180
cggccttttt cacatcagac gacgacgttc tttcgttaat attacgggac gccgcaaacg  99240
cgtaaagaca gattcaagac taacatttat cccaactgat tacatttcat acgcgaataa  99300
acgacacaaa aaatttatat ttaacggctt ttaatttgaa gacacctatc ctcttaacgt  99360
tgaggagcct tgcaggttgg gtgccgcgct tcaccggtat tatacataac cgatttaccg  99420
tgtttacggc agtctgacca tttaccagtg tatgtctgta atacgacgtt gttgtgtccc  99480
gacaaaatta actcgcgtac aaatttctga tgttcccccg gcgtggcaac gctggcattt  99540
ccaaacacat tacgttctcg tacgtccatg accgctattt tcagtattaa ttggttggtc  99600
ggtcaaagta ttttccttat gtaaaaggac acgatctaaa gccgtaaact cgtacacaaa  99660
cactggtacc aacggacgcg attttccgtc cgttgagcgg gtgtaatatc ggcgaggtct  99720
tcttgcacga atactctcgt acagtaggtt tctgacacgg ggtgcatggg ttttttgaca  99780
caacacaaac atttgcaggc tcttatgact ggatggattg aatttatttt tagatagggt  99840
cacgtgtttt tgtcgtgaca cgcctcgacc agaaaaggct gcggttttcg tacacgcgac  99900
cgttatttca caggcgttca taatcaagct gcggcggatg gtgtcggtta attgtctccg  99960
```

-continued cccaagttcg tcaatagatg ataccatgaa caacgtatca aatggtacat agtcgtcttt 100020
ggttttctca atacagcccg cgtgcccaat cggaaaattt tcatttgcat caacgctatt 100080
ttctgtaaaa tcggtctgaa cactgtgttg gctggctacc tgtttaaaat ttgggatcga 100140
acacggtcca cgatgcaatc cccaacccca ttgaagcaat gccgtcggta cggaaggagg 100200
caactccgaa aacattatgg tacgcgagag ggtcgattgg agtgttatat aacactccaa 100260
tcgatctcgg gttcgccttt acgcgtaaaa tactcattgg cttgaacgaa atgtcgacaa 100320
ttccgaaatg gaacacggga caatggcgac ggatgcgcgt gtgttagcac cagatgacat 100380
cttgaattcg gttgggttgt cttctgtgca tgcgcacccc acagcataaa aactaaccct 100440
gtacggttct cgcataacct ctgtagcacg cgttgcacca gccgccccca gcctaagtat 100500
acatgcgacc ccggagtccc gcgacgaacc gtaagcgtgg tattcagcaa taacaccccc 100560
tgccttgccc aactctccag gcatccgtga gtgggcggag tcatatttgg gtatgattcc 100620
atgagggccg caaaaatatt tttaagacta gacggtggtg ttatgccacg ttttacacta 100680
aacgctagcc catgtgcatg tcccgcggta gggtatggat cttgaccaat aattacaacg 100740
cgaatgctct ggggtccgca aaatcgcgtc catgcaaaaa tatcgcctgt agatggaagt 100800
atttcttccc ctgaatttaa aagacgattg tattctaaaa aaataccttt cgcgtacggc 100860
tctttaagtt cgtccgacaa caggtcatac cactcagggg aaatgttaaa cttgctgaaa 100920
acttcaaccg aatccagttg cgaagagacg ggggtgaacg tttccgtgtc gtaatgatgt 100980
gacatgttat ttaacttgaa ggttgggggg tctagcttaa cccccaaagg crgcccgcgg 101040
ggtcgcttgc gggttttttt ggtaaccgga tgggccaaaa cataaatgtc ctttgaatcc 101100
gatagtttca tttcattggc atacgcgttg gaacaaacgg tcggctcccc agacacatcc 101160
attttccggg atatttgtgg aagatggagt agagtctacc catacaccgg aaagggcatc 101220
caacaaagca tcgcgtatgt ccccgctttt atgttcttca ccaacagatt gtgtcagccc 101280
ctttaaggtg acgtatggat ttgtccagta cgccatttgt ttgtctttaa accaaagtat 101340
aacttccggt actggacatt ttgtcttaac cacgattccc gatagcgcct cgctgaggtt 101400
tgataccggg ggtgccgcat agtcccacgc ctcatatacc gatgacacgc acggttccgt 101460
tataatcaaa ctcacatccg atagcggttt ggctccaaaa aacaacggag tgtcgtcttg 101520
gagatgaaga caatacgcga ttgtgatagt ttttaaaaaa actatcatct gcagtaacca 101580
tttatgtgat gccatgacgc ttgtgttttc ccttcactac gacgttgtcg tatcctttga 101640
aaaacttgac cactctaatg gaagcatgga caagtatgag ttttatatat acagttggcc 101700
tttagttaaa ctcttggtgt catatctcat tttcctaaaa agggcgatct taatatgtca 101760
aacgtcacgg cgtgccgaca aagcgaattt ccatgcaaga tttggatgta gtatttatac 101820
acccaatcac acgtcacgta ttaagcttta cagtccccg ttatctgata taatcacttt 101880
tcttaacacg tcatcgggaa aacagatgtt tatattatac ctctcgcggt catttatggc 101940
aaatacttag accgttttca agcggactga aaacgctcaa attgcctttt ggaggcctgc 102000
ccaacggcca ttatcccttg gatctaagat tgatttgcgg taacgtttgc caatcaagct 102060
ttaaaaacgt accccaaact taaaacgctc aaattgcctt ttggaggcct gcccaacggc 102120
cattatccct tggatctaag attgatttgc ggtaacgttt gccaatcaag ctttaaaaac 102180
gtaccccaaa cttaaaacgc tcaaattgcc ttttggaggc ctgcccaacg gccattatcc 102240
cttggatcta agattgattt gcggtaacgt ttgccaaacc cacgcatttc agtttaaata 102300

-continued tttctaagca ttcttagtgc gtacttggca gcgtgcttaa aatatcaacc aatatccatt 102360
atgctaaacg tttccttcta tccgtttcaa tccattaaaa gtccattacc aaaaatgatg 102420
catcatacct aattcaccta aaaacctgac tcattgcagc agcgtttcct ccttgcagac 102480
tatccagttg gcattttaaa cggtccggc tgcctgaacc gaaaacaccg ttgcctttac 102540
tgtaagtaca aaactaaaat ttatatttgc gtgcgtattt tgtaacatat atgcctttta 102600
tccccccgca agtttgcttt accctcgcct tcaccacccc cgccaccttc cggccattgt 102660
aataacttta attgctataa gacataccca aaccggatga tttttgccgc tggaaaaaca 102720
gcttctaatt ttcccgtctc aactcggcct tggttgcatc tccaagtata cctttagttt 102780
gctcccgtag aggtgtataa atacaaacgg tgacaagtat tgagcgtaat ctcaaatttt 102840
tgtaatttag ggcggagcgc ttacgacagc acatgcgtac tgttagactg ttatgtttat 102900
tgtatttgca gagcaggatg ccccggttac tccgagaccg gattgcgggc attccgaatc 102960
gtgtacggac ttaccagggg gcagtattta caccttgggt tccagatata ccaaccctta 103020
cgaccaatag caacactcag gtatttttaa aatgcacgtt taatgatcat aatttacata 103080
cagttggtaa taaagcagac cgtggatgtt taaggcattt ccttcccct cccaacaaac 103140 taggacttct tcatcttgtt tggaatacct ttacccgctt taccggcaga gctttttttg 103200
gtaaggtgtt tcagtgaacc tgatgttgat ccggaggtgg agggggtatt ggactccccc 103260
tgtggagagg caactttgcg ggttttactt cccttacatg ccgaatcaga ctcagatgtc 103320
aggtctattg ttaagcatcg tttaacgtct ctgccggtat gaaataaacg gcgcttagca 103380
ccccttgcgc ttcccggttt aatccccggt aacacagaaa aaagcctgac tttttggggt 103440
gtatttacca atcgggtatc cctttcatcg ccacgagagg tctccccggt tgaggtggtt 103500
tctggtctta caattggacc tgtaattagt tggatggctg tatctttcca ggtccaggtt 103560
tgcatggtta ggcgggttgg atcggtacat cgatccaaca agaataacat gtttgttaca 103620
aacggtcctg ttgaatcatg caaaagacaa cgcagggatg tttttaatcc cgcctcatca 103680
cgcccgtaaa tacctatata gtttaatatc aacattttg taggctctac aatttcgggt 103740
tgatacagtt ccgcaagttg atcatcaagc catccgagta aaggttgcat gtaacacggg 103800
aatctcgcgt ttccctctgt tcctctatcc gtggctcgaa aaggcagtct gtccatggtt 103860
cgtgggtctt gattaattcc cacagatact ggacgatcac ggtagtcctg ccccccggtc 103920
cggggttgct gtgcagattc aatcgagcca tacaccaccg gggtcgccga tcgaacagca 103980
ggttggtctt taaaaaatac cttccgtaaa aatgatgcgg tagagcatgt tttggttaca 104040
ccagggctcg agtctcgggt cggtggttgt atagaatcct gttgagagtc acttggtgac 104100
tctgctgtgg gctctctagc cgacgattga aggggcccag ggtttggtga ttgaatgggc 104160
tcccgactcg atcttgatgt tggctgttgg atggactccc gactcggtcc tgggcttggt 104220
ggcagaagat ctatgacatc tcccggtagg atgtcgatgg aatcttcaaa tgacggctca 104280
gaaaaaccat cgtcgtcgga tgggtgcact tcatattcct tgtaacttgt atcacttacg 104340
atcttatgca ggatggattg cactggacac cggcagagag gacactggac gctggtggag 104400
gtccatgccc gaatacaaac aaagcagaag tcgtgcaaac acggcatggt tttccgaga 104460 tcggaaacgg tgctcatgca tatggtgcag gtattatccg aagcgtcgga ggtgccgcta 104520
ccgcccgcta atatggtatc catggtaaca actggctgta ttctaatgtc cgggcatcca 104580
aacacgtagc agaactgcca tgcgttctaa attgtgagtt gtggcgagta catttttata 104640
attggtacca acgaagacac accctatat ccctccaccc atttctttta agtcccaccc 104700

-continued actaaaacgt gggtataaaa tgtgtattgg ggtaggcgga cagtcccaac aaacagggaa 104760
gttgattggt ataaccttgg gccgggtata cagctaagtg acattttaga ttctgtcttt 104820
atttagataa agagcgatac gaagacattt ctccaccccc ctgtaatacc cgtaaataaa 104880
ggtaagtcca caaacaaaag cactgtatat aggaagtcgg gtgtattggg acagttactc 104940
cattagaggc gtacagacaa tactgggata gggtaatgca agtccccccc gatggtcgcc 105000
ccgcaaacgc gcggggaggt ggggtcgctt tttttttct ctctcgaggg ggccgcgaga 105060
gggctgggcc cccccccccg gggtccgccg ggcgcccaga aaccgggggg ggttattttc 105120
ggggggggtc cgaccagccc gcccgtcgcc cgcccgcaca gacagacaga cactttttc 105180
ataaaaaccg ttccgctttt attaacaaac aacaaacagt ccgcgcgccr gtggcgctca 105240
cgagaaaagg aggggactcc gtcacccccg actctgcggg gggctcctcc ccccgcgccc 105300
tccccacaca tcgtcctcgt cctcggagga cgaggacgag gacaacagct ccaccttgac 105360
cgccgggcgc ragcccaccc ggcggtctcg cagcacaccc ggggccaccg acacgacgct 105420
caccccaaag gatgaccccg gtgcgtcccc gtcgtccccg ccccccctcct cgctgtccca 105480
cgcgtcttca caccccacct cccaatcgtc cggctccaaa gcgtgttctc tgtcgtctgc 105540
ggtgcgccgc tgtcgccccg cctgggtttc tgccggccgt tccgagcccc cgtggtgtcc 105600
gaacgcgaac cgtgttccgt cgctcccctc caacaccgtc tccgcggccc caaaaccggg 105660
cggccacatt actctgggaa tcggggggag ggcattccga gcctcgtccg ccgacgcata 105720
cagcgccacc gaccgaccgg ccacgggtgg aagcacgagt ggttccgcgg cagggtcggg 105780
ttccagcagg gcgtggcggc aaaacaccct cgcccaggtg ggtacgtcgc cggcctccgg 105840
cccggcggcc cccggtctcc gtccctcggg aaggaagacg ggtcgaagcg cggcacccag 105900
gccccatcgg tttgctgcgc ggtggctatg tgccgcctcg tccacaaagt cggctgcccc 105960
gagccccaga ccccgagact gtcgcgcgag gtccttgcaa ccgtcaaaac ccggcagcac 106020
gtactgccgg tattcacggg gcgacagggg gacgcgggtc ttggggcccg cgcgggtaca 106080
cacggtgtat gcgacgttcc caccgcggca caaacacagg ggttgttcgc ccgggtacag 106140
gttggcaaac gcagtctcga tacgagcaaa actcgctggc ccaaaggtgc gcgacgatgc 106200
aaacacggcc cgggcgagtc cttctgtgac cgccgagtct ggccatcgga cgacggcctg 106260
ggcgtccggt cgcgccgggg cccggacgta cacgtgatac tgagacaaag cgggtccatc 106320
cccgggccac ctctcgaggg ccaccgcgtc caacaccagc aaccggcgcc gggcagaggc 106380
caaccgcgag cctagatact cgacggcccc ggcaaaggcc aggtctcggg tcgacagtaa 106440
taaaacgccc cgggcgttca aagcggacac gtccggcggg ccggtccagt tcccggccca 106500
ggcatgagtg ctcggcaggc acaaccggtt actcagggct gccaggacca cagacagtcc 106560
ccctcgggat ggactccatg acggtcccgg atctgtcgcg agggtgctct cgagggggcc 106620
gttgatgtcc tctccgggca acggatcgta gatgatcaga agcctcacat cctccgggtc 106680
tgggatctgc cgcatccagg cgcacctccg tcgcagcgcc tccactccgc tgggtggacc 106740
aaaccgtcgg tctcctccgc ccggacgccg agcggcgatt tccgccaagg cgccgggatc 106800
aaagcttagc gcagggcgcc aggccgtggg aaacaatggg tcgtcgacca gacgggcgat 106860
ggtttcgggg gtacagtacg ccttgcgagc ctggtccgac gggaccgggg tatgcagggc 106920
cccccgggga atacgccgaa atccccgtt tggggccggt ccgtcaagtg gcatcgttat 106980
tacggcgggg ggatccacca cagggcccga ggtgatggtc acgggctcgg atacccgcct 107040

-continued cttggccttg gaaaccacat gatcgtctgc aacccgggcg tccgcgacgg gtgtctccct 107100
aatcttgtcg aggaggcttc tgctctcgac tggctgggac ttgcgcttgc gcggagttcg 107160
taaacgatca tccggtggac acacagaaag agagcgcgcg gcggccgacg gctgagggtc 107220
gggagtctgt gtggccgggg ttgttggaga agggtgaccg cgggagatcc gcgccgccgg 107280
actggagccc gttgcctcgg ggtatgccat gccggcaaag gctctgcgga gactctgtag 107340
gataaagtgt ttttgggccc ggtcgtaccg acggctcata gccacggccg cggccgcgtg 107400
ggggagagcc cagagggcct cccccgtggc catggcttcg cctacatgcg gaacgggaga 107460
cgctacgctc cccgtaacgg cggtacccgc ccgtcccggt ggcaacagct tttggtagaa 107520
ctggttcagg gccgagttga caccggtcag cttggggttc tggagccatg ctatagggtc 107580
tctgtctgga cagtagatca ggttaatcag cgcgcggtac tgtctagccg gatctcccaa 107640
ctccggcacg taaagcggcr cggggttcagt tgaggcctcg taacgagccc gcgccgctct 107700
cacagcctca tcctcccagt gaccctctct ggtctccccg gacggtccaa accgcaccct 107760
gttggatggg aggggcgccg atccgggcca agggcttccg tcgggcatca tgagcggccc 107820
cgacaccggg ggaattatcg gggttctgga tcgcggcagg gaaaatgatt tctgtctctg 107880
gcgccccggt tcccccgcaa gacgtttggt cttacgaatc ctcggatcgg gaccgctgat 107940
ggatcgatat cccggttgga tattttgttt cgtcgaccca ccatcatttg agtccgaatc 108000
atccgaattt gacggggaag gggcgtgttc gcgtccggac ctgctgcctg tagtttcact 108060
tcccaccgaa acgcgccggg gttcatcgtc ttcatcctcc gatgacgatc cccacgacga 108120
ggaagaggat gaagacgaaa caaactcacg actctttggc tttttctcca ccgggctgtc 108180
atcctcaatc gggtctggtg cgtgggatct tcccggcagg gccaaaaacg ctctaggttt 108240
gccccccgac gaacgtccag ggacgcgagg tgttataccc cgggcatcat gtttccttgg 108300
gcgggtatca tcggtctcaa acggcaggtc cgcctttgcc cccttagcgg gaacgctgtc 108360
cgaaaggacg tggtacaatt gctcaaccgg gccgggtaca ggtccaccgg gtttccgcgc 108420
cgggagtggg accttaacct tcaaagtctt tttcttcggg ctctttccct gagcgggccg 108480
ttgagttttc tggagaacta ctccgtcccc cgatgcatgc gcatgacccg cttgctcatc 108540
gcccggcttt ttacccgaga tggactgagt ttgtctgtct cgatggacca ccgacggcaa 108600
acctggtgaa tttcctctcg tcgtttgtcg gggtatagac cgctggtctt cccgttgatc 108660
gttcccggcg gcgtctccaa caggagacgc gggggataca ggggagaagg cctgcgggaa 108720
cggaggggtc gtacctctgc ccgtttcccc atcgttcatc ggtggttttg gagacctagc 108780
aagcttcgtt ccgagagaga ctgtctcgag ggagcgatcg gctcctgttg gttctcgcgc 108840
gccggcctcc gagaatcggg tgtggaagac ctcggccagc gggattacag gcgagcccrt 108900
tagatcctga ccgtcctcgc atacgtagtc gtcttgtgtt agctcttcgc caacatcttc 108960
cgttctgggt tctggttgaa gtcccgatac ggagggaatt gaaacgatct catgttcccg 109020
tcccaccatg accccgttct ctccaaatag tagatcgtca ggctgactcg aggtgaccac 109080
ccgggccctg tgttcggcgg ccgcggcggc cgcgtccaac aggtccatta actccaaagt 109140
atcaggcgac cccgcgcgtt ggggtgtaga gcgctgcatc ggcggcgtat ccatcgcrct 109200
ggggtgaatt tagacgtacc cgagttttcc aaacgctctc gcagccttca aaggattgcg 109260
rttgcggttg gtgagggagt tccaacagta cttaaaacgt gttgtgcccc cccctcgacc 109320
gcatatttcc tccccgtgtc gtcaccgtgt aaatattctt aatgataaga cgatgtagtg 109380
attggacgag actcgaggcg ggaagttcat ggaccatagt atgcgtttaa ggagagaccg 109440

-continued ctggttggcg atgtacgccc ggtgtctatt tccgcatacc ttacaacatc ataacaaggg 109500
ataccagaca tgtgaatttc atttacatat gtttaaataa caaccaatca tcgtgtgtct 109560
acagacgata tataatatac ataaacacaa ttggggttgt ctcacatgca aaacatctta 109620
tataacacgg gttgtttcca cccatccggc atctagttaa tcaaatgcac gtcgacggtg 109680
tgtttgggtc cctctccgtc gtcattacgt tcgctcaatc aacaagcgta tacaccacca 109740
cccctcccaa cgattatcat gtcaggcggc acgaagcccg cgataaccca taaaatacac 109800
acggggttgt ggtgttcacg taaccccccg ccgatgggga gggggcgcgg taccccgccg 109860
atggggaggg ggcgcggtac cccgccgatg gggagggggc gcggtacccc gccgatgggg 109920
agggggcgcg gtaccccgcc gatggggagg gggcgcggta ccccgccgat ggggaggggg 109980
cgcggtaccc cgccgatggg gagggggcgc ggtaccccgc cgatggggag ggggcgcggt 110040
accccgccga tggggagggg gcgcggtacc ccgccgatgt ttataaccat aattctctaa 110100
accgttgtag aaaatcacaa aaaaatttat tcaaaaacaa gtcgaagaac ttcatatctg 110160
aggcatgtaa acccattcgc acttcctggg gtggaatggg gtggggtggg ggggtgaaaa 110220
agggggggt taaattgggc gtccgcatgt ctgtggtgta cgccaatcgg atacactctt 110280
ttaatctgca ttcgcacttc ccgtttttttc actgtatggg ttttcatgtt ttggcatgtg 110340
tccaaccacc gttcgcactt tctttctata tatatatata tatagagaga gagagagaga 110400
gagggagaga gtttcttgtt cgcgcgtgtt cccgcgatgt cgcggtttta tggggtgtgg 110460
gcgggctttt cacagaatat atatattcca aatggagcgg caggcttttt aaaatcgatt 110520
tgacgtgata aaaaaaaaca cacgggcccc cccttttttt ggtgttataa aggcaaccca 110580
atcgaaggtc tcccgccccg gaatccccca ttgccatttt acccaagtag ccttattcat 110640
agatgtaaac gtttgggtgt gtgttttgtt gtgcagggtt cgtccgattc ataacgcgac 110700
agcgtcgagt cggttttaag ggaaaaggtt actacggccc caaggacatg ttttgcacct 110760
caccggctac gcggggcgac tcgtccgagt caaaacccgg ggcatcggtt gatgttaacg 110820
gaaagatgga atatggatct gcaccaggac ccctgaacgg ccgggatacg tcgcggggcc 110880
ccggcgcgtt ttgtactccg ggttgggaga tccacccggc caggctcgtt gaggacatca 110940
accgtgtttt tttatgtatt gcacagtcgt cgggacgcgt cacgcgagat tcacgaagat 111000
tgcggcgcat atgcctcgac ttttatctaa tgggtcgcac cagacagcgt cccacgttag 111060
cgtgctggga ggaattgtta cagcttcaac ccacccagac gcagtgctta cgcgctactt 111120
taatggaagt gtcccatcga ccccctcggg gggaagacgg gttcattgag gcgccgaatg 111180
ttcctttgca taggagcgca ctggaatgtg acgtatctga tgatggtggt gaagacgata 111240
gcgacgatga tgggtctacg ccatcggatg taattgaatt tcgggattcc gacgcggaat 111300
catcggacgg ggaagacttt atagtggaag aagaatcaga ggagagcacc gattcttgtg 111360
aaccagacgg ggtacccggc gattgttatc gagacgggga tgggtgcaac accccgtccc 111420
caaagagacc ccagcgtgcc atcgagcgat acgcgggtgc agaaaccgcg gaatatacgg 111480
ccgcgaaagc gctcaccgcg ttgggcgagg ggggtgtaga ttggaagcga cgtcgacacg 111540
aagccccgcg ccggcatgat ataccgcccc cccatggcgt gtagtcttta taaataaata 111600
caatggtttg gctcgtgtct ttttttgatg tctgtctgtg ggggagtggg gtgttgtgga 111660
tattagaggg tagagggtgc tggtttgaac gtctccatta acccacgggg tccccacacg 111720
ggccgtgtgg tatgaatctc tgcggatccc gcggtgagca cccgggcggt gaatatgccg 111780

-continued

```
gactttactg cacacgacac gatacccccg cgcaccrggc tctcatgaac gacgccgaac 111840
ggtacttcgc cgccgcgcta tgcgccatat ctaccgaggc ctacgaggct tttatacaca 111900
gcccctccga gagaccgtgc gcgagtttgt gggggagggc aaaggacgcc ttcggacgga 111960
tgtgcgggga gctcgcagcg gatagacaac gtccaccctc ggttccgccg atccgcagag 112020
cggtgttatc gttattacgc gagcaatgca tgccggatcc acaatcgcat ctggagctca 112080
gcgagcggct gatattgatg gcatattggt gctgtttggg acacgccgga cttccgacta 112140
ttggattgtc gcccgataat aaatgcatcc gcgccgaatt atatgaccgc cccgggggaa 112200
tttgtcacag gctttttgac gcgtacctgg gctgcgggtc ccttggagtc ccaagaaccc 112260
acgagagatc ctgacacccc atccctttat atagaaaaaa aaataaattt aaaacataca 112320
ccggataaaa gcgtactgtt ttttatttaa atttacacgc tcgacgttgc cccggttcgg 112380
tgatcaccgg gtcttatcta tatacaccgt gtaactcgaa cccccgtgac tccctccaat 112440
cgcgttacca aactcttctt ccgtatccgt agattccgag tcctcgaaat cgtccactta 112500
tccaacaaat tgtgacgtta tatatcccaa ggcaaaggcc gctcccgtca tagcaaatac 112560
aaagacaatt attagcgtaa tataacagaa ttttttacga tgatatattt tatgttgata 112620
ttttccaatt cgacgcaaaa attcatctgc cgtttcattt tcgctatcac tataataaca 112680
cttttcagcc gaacggctcg gttgtatggc tgttatcgtt gtattatttg gttgcgctcg 112740
cggggttacc accgcttcca tcagtaaggc cacggcctca ccctccatgg tgttttgtcc 112800
ggccatagaa atccagattg taaggccagc aggctagttt aaaagtgttt aataccacac 112860
cttttgatat ttatatacat gcaagattct agattattca tcaataggtc gtttaaagcg 112920
cgttttcata aacgttgtca gctataccga cattctcaca aagaggtaaa gttaccttac 112980
gttattatta aataaaacat gtagacatta ttaataatcc taggaacaat caaatccata 113040
tttgtaagtt atgtttaacc cctccccttt ttgtcattat ctccgccctc ttataatcgg 113100
atcactttat aagtgtgtcg gtgagtatat tttgtacagt tgttggacaa caggtttttg 113160
gttcattaac actatcaaca taagtcgggg tatacaagta taatgaacga cgttgatgca 113220
acagacacct ttgttggaca aggaaagttc cgtggcgcca tctcaacatc accgtcacat 113280
attatgcaaa catgtgggtt tatacaacag atgtttccag ttgaaatgtc gcccggcata 113340
gaatctgagg atgatcccaa ttatgacgtt aacatggata tacagtcttt taatatattt 113400
gatggtgtac acgaaactga agccgaagcc tctgtggcat tgtgcgcaga agcacgcgtt 113460
ggaattaata aagcgggatt tgtaatatta aaaacgttta caccaggggc ggaaggtttt 113520
gcgtttgcgt gtatggacag taaaacatgt gaacatgtgg tcattaaagc gggtcaacgt 113580
caaggaacgg ccaccgaggc aaccgtgtta agagcgttaa cccacccatc cgttgtacag 113640
cttaaaggaa cgtttacgta taacaaaatg acatgtctta tattaccacg ttaccgaaca 113700
gatttatact gctatctagc tgcaaagcgc aacctcccca tatgtgacat tttagcaatt 113760
cagcgatctg tattacgcgc gttacagtat cttcataata acagtattat tcaccgtgat 113820
ataaaatctg aaaatatatt tattaaccac ccaggtgatg tttgtgtggg agactttgga 113880
gcagcgtgtt tccccgtgga tattaatgcc aacaggtatt atggctgggc tggaacaatc 113940
gccacaaact ctcctgagtt attggctaga gatccatatg gacctgccgt ggacatatgg 114000
agtgccggga ttgtattatt tgaaatggct acaggacaga actcgttatt tgaacgagac 114060
ggtttagatg gcaattgtga cagtgagcgt caaattaaac ttattatacg acgatctgga 114120
actcatccca atgaatttcc cattaaccct acatcaaatc ttcgtcgaca atacattggt 114180
```

-continued ttggcaaaac ggtcttctcg aaaacccgga tccaggccat tgtggacaaa tctatatgag 114240
ttgccaattg atttggagta tttgatatgt aagatgttat cgtttgacgc acgtcatcga 114300
ccatcggcag aggtgttgct taaccactct gttttccaaa ctcttcccga tccatatcca 114360
aatccaatgg aagttggaga ttaaaattca ttaagcctgt taataaaata ttgtataaat 114420
tgtgtttata acgtataacc cgttaaggca aatagggtac aaacgcgcaa tgttttgaaa 114480
tactaatata aataacataa ccaatagaaa cttaatacag agtcacgccc cattacaaca 114540
aggataaaac acgggatcat tttcttaaca ttgtagtagc gctgaaaagc gtcccctccc 114600
ccggctcaca gagctgctct tcggtgtagt tgggtatact ggtgcgcctc atttaatcgc 114660
gatgttttta atccaatgtt tgatatcggc cgttatattt tacatacaag tgaccaacgc 114720
tttgatcttc aagggcgacc acgtgagctt gcaagttaac agcagtctca cgtctatcct 114780
tattcccatg caaaatgata attatacaga gataaaagga cagcttgtct ttattggaga 114840
gcaactacct accgggacaa actatagcgg aacactggaa ctgttatacg cggatacggt 114900
ggcgttttgt ttccggtcag tacaagtaat aagatacgac ggatgtcccc ggattagaac 114960
gagcgctttt atttcgtgta ggtacaaaca ttcgtggcat tatggtaact caacggatcg 115020
gatatcaaca gagccggatg ctggtgtaat gttgaaaatt accaaaccgg gaataaatga 115080
tgctggtgtg tatgtacttc ttgttcggtt agaccatagc agatccaccg atggtttcat 115140
tcttggtgta aatgtatata cagcgggctc gcatcacaac attcacgggg ttatctacac 115200
ttctccatct ctacagaatg gatattctac aagagccctt tttcaacaag ctcgtttgtg 115260
tgatttaccc gcgacaccca aagggtccgg tacctccctg tttcaacata tgcttgatct 115320
tcgtgccggt aaatcgttag aggataaccc ttggttacat gaggacgttg ttacgacaga 115380
aactaagtcc gttgttaagg aggggataga aaatcacgta tatccaacgg atatgtccac 115440
gttacccgaa aagtccctta atgatcctcc agaaaatcta cttataatta ttcctatagt 115500
agcgtctgtc atgatcctca ccgccatggt tattgttatt gtaataagcg ttaagcgacg 115560
tagaattaaa aaacatccaa tttatcgccc aaatacaaaa acaagaaggg gcatacaaaa 115620
tgcgacacca gaatccgatg tgatgttgga ggccgccatt gcacaactag caacgattcg 115680
cgaagaatcc cccccacatt ccgttgtaaa cccgtttgtt aaatagaact aattatcccg 115740
gattttatat taaataaact atatgcgttt tatttagcgt tttgattacg cgttgtgata 115800
tgaggggaag gattaagaat ctcctaacta taagttaaca cgcccacatt tgggcgggga 115860
tgttttatga agccttaaag gccgagctgg tatacacgag agcagtccat ggttttagac 115920
ctcgggcgaa ttgcgtggtt ttaagtgact atattccgag ggtcgcctgt aatatgggga 115980
cagttaataa acctgtggtg gggtattga tggggttcgg aattatcacg ggaacgttgc 116040
gtataacgaa tccggtcaga gcatccgtct tgcgatacga tgattttcac atcgatgaag 116100
acaaactgga tacaaactcc gtatatgagc cttactacca ttcagatcat gcggagtctt 116160
catgggtaaa tcggggagag tcttcgcgaa aagcgtacga tcataactca ccttatatat 116220
ggccacgtaa tgattatgat ggatttttag agaacgcaca cgaacaccat ggggtgtata 116280
atcagggccg tggtatcgat agcggggaac ggttaatgca acccacacaa atgtctgcac 116340
aggaggatct tggggacgat acgggcatcc acgttatccc tacgttaaac ggcgatgaca 116400
gacataaaat tgtaaatgtg gaccaacgtc aatacggtga cgtgtttaaa ggagatctta 116460
atccaaaacc ccaaggccaa agactcattg aggtgtcagt ggaagaaaat cacccgttta 116520

-continued ctttacgcgc accgattcag cggatttatg gagtccggta caccgagact tggagctttt 116580
tgccgtcatt aacctgtacg ggagacgcag cgcccgccat ccagcatata tgtttaaaac 116640
atacaacatg ctttcaagac gtggtggtgg atgtggattg cgcggaaaat actaaagagg 116700
atcagttggc cgaaatcagt taccgttttc aaggtaagaa ggaagcggac caaccgtgga 116760
ttgttgtaaa cacgagcaca ctgtttgatg aactcgaatt agaccccccc gagattgaac 116820
cgggtgtctt gaaagtactt cggacagaaa aacaatactt gggtgtgtac atttggaaca 116880
tgcgcggctc cgatggtacg tctacctacg ccacgttttt ggtcacctgg aaaggggatg 116940
aaaaaacaag aaaccctacg cccgcagtaa ctcctcaacc aagaggggct gagtttcata 117000
tgtggaatta ccactcgcat gtattttcag ttggtgatac gtttagcttg gcaatgcatc 117060
ttcagtataa gatacatgaa gcgccatttg atttgctgtt agagtggttg tatgtcccca 117120
tcgatcctac atgtcaacca atgcggttat attctacgtg tttgtatcat cccaacgcac 117180
cccaatgcct ctctcatatg aattccggtt gtacatttac ctcgccacat ttagcccagc 117240
gtgttgcaag cacagtgtat caaaattgtg aacatgcaga taactacacc gcatattgtc 117300
tgggaatatc tcatatggag cctagctttg gtctaatctt acacgacggg ggcaccacgt 117360
taaagtttgt agatacaccc gagagtttgt cgggattata cgtttttgtg gtgtatttta 117420
acgggcatgt tgaagccgta gcatacactg ttgtatccac agtagatcat tttgtaaacg 117480
caattgaaga gcgtggattt ccgccaacgg ccggtcagcc accggcgact actaaaccca 117540
aggaaattac ccccgtaaac cccggaacgt caccacttct acgatatgcc gcatggaccg 117600
gagggcttgc agcagtagta cttttatgtc tcgtaatatt tttaatctgt acggctaaac 117660
gaatgagggt taaagcctat agggtagaca agtccccgta taaccaaagc atgtattacg 117720
ctggccttcc agtggacgat ttcgaggact cggaatctac ggatacggaa gaagagtttg 117780
gtaacgcgat tggagggagt cacgggggtt cgagttacac ggtgtatata gataagaccc 117840
ggtgatcacc gaaccggggc aacgtcgagc gtgtaaattt aaataaaaaa cagtacgctt 117900
ttatccggtg tatgttttaa atttattttt ttttctatat aaagggatgg ggtgtcagga 117960
tctctcgtgg gttcttggga ctccaaggga cccgcagccc aggtacgcgt caaaaagcct 118020
gtgacaaatt cccccggggc ggtcatataa ttcggcgcgg atgcatttat tatcgggcga 118080
caatccaata gtcggaagtc cggcgtgtcc caaacagcac caatatgcca tcaatatcag 118140
ccgctcgctg agctccagat gcgattgtgg atccggcatg cattgctcgc gtaataacga 118200
taacaccgct ctgcggatcg gcggaaccga gggtggacgt tgtctatccg ctgcgagctc 118260
cccgcacatc cgtccgaagg cgtcctttgc cctcccccac aaactcgcgc acggtctctc 118320
ggaggggctg tgtataaaag cctcgtaggc ctcggtagat atggcgcata gcgcggcggc 118380
gaagtaccgt tcggcgtcgt tcatgagagc ccggtgcgcg ggggtatcgt gtcgtgtgca 118440
gtaaagtccg gcatattcac cgcccgggtg ctcaccgcgg gatccgcaga gattcatacc 118500
acacggcccg tgtggggacc ccgtgggtta atggagacgt tcaaaccagc accctctacc 118560
ctctaatatc cacaacaccc cactccccca cagacagaca tcaaaaaaag acacgagcca 118620
aaccattgta tttatttata aagactacac gccatggggg ggcggtatat catgccggcg 118680
cggggcttcg tgtcgacgtc gcttccaatc tacacccccc tcgcccaacg cggtgagcgc 118740
tttcgcggcc gtatattccg cggtttctgc acccgcgtat cgctcgatgg cacgctgggg 118800
tctctttggg gacggggtgt tgcacccatc cccgtctcga taacaatcgc cgggtacccc 118860
gtctggttca caagaatcgg tgctctcctc tgattcttct tccactataa agtcttcccc 118920

-continued gtccgatgat tccgcgtcgg aatcccgaaa ttcaattaca tccgatggcg tagacccatc 118980
atcgtcgcta tcgtcttcac caccatcatc agatacgtca cattccagtg cgctcctatg 119040
caaaggaaca ttcggcgcct caatgaaccc gtcttccccc cgaggggtc gatgggacac 119100
ttccattaaa gtagcgcgta agcactgcgt ctgggtgggt tgaagctgta acaattcctc 119160
ccagcacgct aacgtgggac gctgtctggt gcgacccatt agataaaagt cgaggcatat 119220
gcgccgcaat cttcgtgaat ctcgcgtgac gcgtcccgac gactgtgcaa tacataaaaa 119280
aacacggttg atgtcctcaa cgagcctggc cgggtggatc tcccaacccg gagtacaaaa 119340
cgcgccgggg ccccgcgacg tatcccggcc gttcaggggt cctggtgcag atccatattc 119400
catctttccg ttaacatcaa ccgatgcccc gggttttgac tcggacgagt cgccccgcgt 119460
agccggtgag gtgcaaaaca tgtccttggg gccgtagtaa ccttttccct taaaaccgac 119520
tcgacgctgt cgcgttatga atcggacgaa ccctgcacaa caaaacacac acccaaacgt 119580
ttacatctat gaataaggct acttgggtaa aatggcaatg ggggattccg gggcgggaga 119640
ccttcgattg ggttgccttt ataacaccaa aaaaaggggg ggcccgtgtg ttttttttta 119700
tcacgtcaaa tcgattttaa aaagcctgcc gctccatttg gaatatatat attctgtgaa 119760
aagcccgccc acaccccata aaaccgcgac atcgcgggaa cacgcgcgaa caagaaactc 119820
tctccctctc tctctctctc tctctatata tatatatata tagaaagaaa gtgcgaacgg 119880
tggttggaca catgccaaaa catgaaaacc catacagtga aaaaacggga agtgcgaatg 119940
cagattaaaa gagtgtatcc gattggcgta caccacagac atgcggacgc ccaatttaac 120000
cccccccttt ttcacccccc caccccaccc cattccaccc caggaagtgc gaatgggttt 120060
acatgcctca gatatgaagt tcttcgactt gtttttgaat aaattttttt gtgattttct 120120
acaacggttt agagaattat ggttataaac atcggcgggg taccgcgccc cctccccatc 120180
ggcggggtac cgcgccccct ccccatcggc ggggtaccgc gccccctccc catcggcggg 120240
gtaccgcgcc ccctccccat cggcggggta ccgcgccccc tccccatcgg cggggtaccg 120300
cgccccctcc ccatcggcgg ggtaccgcgc cccctcccca tcggcggggt accgcgcccc 120360
ctccccatcg gcggggtacc gcgccccctc cccatcggcg gggggttacg tgaacaccac 120420
aaccccgtgt gtattttatg ggttatcgcg ggcttcgtgc cgcctgacat gataatcgtt 120480
gggaggggtg gtggtgtata cgcttgttga ttgagcgaac gtaatgacga cggagaggga 120540
cccaaacaca ccgtcgacgt gcatttgatt aactagatgc cggatgggtg gaaacaaccc 120600
gtgttatata agatgttttg catgtgagac aaccccaatt gtgtttatgt atattatata 120660
tcgtctgtag acacacgatg attggttgtt atttaaacat atgtaaatga aattcacatg 120720
tctggtatcc cttgttatga tgttgtaagg tatgcggaaa tagacaccgg gcgtacatcg 120780
ccaaccagcg gtctctcctt aaacgcatac tatggtccat gaacttcccg cctcgagtct 120840
cgtccaatca ctacatcgtc ttatcattaa gaatatttac acggtgacga cacggggagg 120900
aaatatgcgg tcgagggggg ggcacaacac gttttaagta ctgttggaac tccctcacca 120960
accgcaaycg caatcctttg aaggctgcga gagcgtttgg aaaactcggg tacgtctaaa 121020
ttcaccccag ygcgatggat acgccgccga tgcagcgctc tacaccccaa cgcgcggggt 121080
cgcctgatac tttggagtta atggacctgt tggacgcggc cgccgcggcc gccgaacaca 121140
gggcccgggt ggtcacctcg agtcagcctg acgatctact atttggagag aacggggtca 121200
tggtgggacg ggaacatgag atcgtttcaa ttccctccgt atcgggactt caaccagaac 121260

-continued ccagaacgga agatgttggc gaagagctaa cacaagacga ctacgtatgc gaggacggtc 121320
aggatctaay gggctcgcct gtaatcccgc tggccgaggt cttccacacc cgattctcgg 121380
aggccggcgc gcgagaacca acaggagccg atcgctccct cgagacagtc tctctcggaa 121440
cgaagcttgc taggtctcca aaaccaccga tgaacgatgg ggaaacgggc agaggtacga 121500
cccctccgtt cccgcaggcc ttctcccctg tatccccgc gtctcctgtt ggagacgccg 121560
ccgggaacga tcaacgggaa gaccagcggt ctataccccg acaaacgacg agaggaaatt 121620
caccaggttt gccgtcggtg gtccatcgag acagacaaac tcagtccatc tcgggtaaaa 121680
agccgggcga tgagcaagcg ggtcatgcgc atgcatcggg ggacggagta gttctccaga 121740
aaactcaacg gcccgctcag ggaaagagcc cgaagaaaaa gactttgaag gttaaggtcc 121800
cactcccggc gcggaaaccc ggtggacctg tacccggccc ggttgagcaa ttgtaccacg 121860
tcctttcgga cagcgttccc gctaaggggg caaaggcgga cctgccgttt gagaccgatg 121920
atacccgccc aaggaaacat gatgcccggg gtataacacc tcgcgtccct ggacgttcgt 121980
cggggggcaa acctagagcg tttttggccc tgccgggaag atcccacgca ccagacccga 122040
ttgaggatga cagcccggtg gagaaaaagc caaagagtcg tgagtttgtt tcgtcttcat 122100
cctcttcctc gtcgtgggga tcgtcatcgg aggatgaaga cgatgaaccc cggcgcgttt 122160
cggtgggaag tgaaactaca ggcagcaggt ccggacgcga acacgcccct tccccgtcaa 122220
attcggatga ttcggactca aatgatggtg ggtcgacgaa acaaaatatc caaccgggat 122280
atcgatccat cagcggtccc gatccgagga ttcgtaagac caaacgtctt gcgggggaac 122340
cggggcgcca gagacagaaa tcattttccc tgccgcgatc cagaaccccg ataattcccc 122400
cggtgtcggg gccgctcatg atgcccgacg gaagcccttg gcccggatcg gcgcccctcc 122460
catccaacag ggtgcggttt ggaccgtccg gggagaccag agagggtcac tgggaggatg 122520
aggctgtgag agcggcgcgg gctcgttacg aggcctcaac tgaacccgyg ccgctttacg 122580
tgccggagtt gggagatccg gctagacagt accgcgcgct gattaacctg atctactgtc 122640
cagacagaga ccctatagca tggctccaga accccaagct gaccggtgtc aactcggccc 122700
tgaaccagtt ctaccaaaag ctgttgccac cgggacgggc gggtaccgcc gttacgggga 122760
gcgtagcgtc tcccgttccg catgtaggcg aagccatggc cacgggggag gccctctggg 122820
ctctccccca cgcggccgcg gccgtggcta tgagccgtcg gtacgaccgg gcccaaaaac 122880
actttatcct acagagtctc cgcagagcct ttgccggcat ggcatacccc gaggcaacgg 122940
gctccagtcc ggcggcgcgg atctcccgcg gtcacccttc tccaacaacc ccggccacac 123000
agactcccga ccctcagccg tcggccgccg cgcgctctct ttctgtgtgt ccaccggatg 123060
atcgtttacg aactccgcgc aagcgcaagt cccagccagt cgagagcaga agcctcctcg 123120
acaagattag ggagacaccc gtcgcggacg cccgggttgc agacgatcat gtggtttcca 123180
aggccaagag gcgggtatcc gagcccgtga ccatcacctc gggccctgtg gtggatcccc 123240
ccgccgtaat aacgatgcca cttgacggac cggccccaaa cgggggattt cggcgtattc 123300 cccgggggc cctgcatacc ccggtcccgt cggaccaggc tcgcaaggcg tactgtaccc 123360
ccgaaaccat cgcccgtctg gtcgacgacc cattgtttcc cacggcctgg cgccctgcgc 123420
taagctttga tcccggcgcc ttggcggaaa tcgccgctcg gcgtccgggc ggaggagacc 123480
gacggtttgg tccacccagc ggagtggagg cgctgcgacg gaggtgcgcc tggatgcggc 123540
agatcccaga cccggaggat gtgaggcttc tgatcatcta cgatccgttg cccggagagg 123600
acatcaacgg ccccctcgag agcaccctcg cgacagatcc gggaccgtca tggagtccat 123660

-continued

```
cccgaggggg actgtctgtg gtcctggcag ccctgagtaa ccggttgtgc ctgccgagca 123720

ctcatgcctg ggccgggaac tggaccggcc cgccggacgt gtccgctttg aacgcccggg 123780

gcgttttatt actgtcgacc cgagacctgg cctttgccgg ggccgtcgag tatctaggct 123840

cgcggttggc ctctgcccgg cgccggttgc tggtgttgga cgcggtggcc ctcgagaggt 123900

ggcccgggga tggacccgct ttgtctcagt atcacgtgta cgtccgggcc ccggcgcgac 123960

cggacgccca ggccgtcgtc cgatggccag actcggcggt cacagaagga ctcgcccggg 124020

ccgtgtttgc atcgtcgcgc acctttgggc cagcgagttt tgctcgtatc gagactgcgt 124080

ttgccaacct gtacccgggc gaacaacccc tgtgtttgtg ccgcggtggg aacgtcgcat 124140

acaccgtgtg tacccgcgcg ggccccaaga cccgcgtccc cctgtcgccc cgtgaatacc 124200

ggcagtacgt gctgccgggt tttgacggtt gcaaggacct cgcgcgacag tctcggggtc 124260

tggggctcgg ggcagccgac tttgtggacg aggcggcaca tagccaccgc gcagcaaacc 124320

gatggggcct gggtgccgcg cttcgacccg tcttccttcc cgagggacgg agaccggggg 124380

ccgccgggcc ggaggccggc gacgtaccca cctgggcgag ggtgttttgc cgccacgccc 124440

tgctggaacc cgaccctgcc gcggaaccac tcgtgcttcc acccgtggcc ggtcggtcgg 124500

tggcgctgta tgcgtcggcg gacgaggctc ggaatgccct ccccccgatt cccagagtaa 124560

tgtggccgcc cggttttggg gccgcggaga cggtgttgga ggggagcgac ggaacacggt 124620

tcgcgttcgg acaccacggg ggctcggaac ggccggcaga aacccaggcg gggcgacagc 124680

ggcgcaccgc agacgacaga gaacacgctt tggagccgga cgattgggag gtggggtgtg 124740

aagacgcgtg ggacagcgag gagggggcg gggacgacgg ggacgcaccg gggtcatcct 124800

ttggggtgag cgtcgtgtcg gtggccccgg gtgtgctgcg agaccgccgg gtgggctygc 124860

gcccggcggt caaggtggag ctgttgtcct cgtcctcgtc ctccgaggac gaggacgatg 124920

tgtggggagg gcgcgggggg aggagccccc cgcagagtcg ggggtgacgg agtcccctcc 124980

ttttctcgtg agcgccacyg gcgcgcggac tgtttgttgt ttgttaataa aagcggaacg 125040

gtttttatga aaaaagtgtc tgtctgtctg tgcgggcggg cgacgggcgg gctggtcgga 125100

cccccccga aaataacccc ccccggtttc tgggcgcccg gcggaccccg ggggggg    125157
```

<210> SEQ ID NO 3
<211> LENGTH: 25
<212> TYPE: DNA
<213> ORGANISM: Artificial Sequence
<220> FEATURE:
<223> OTHER INFORMATION: PCR Primer used for detecting a mutation of the 560th nucleotide of a varicella vaccine virus

<400> SEQUENCE: 3

```
tcgtttactg ctcggatggc gaccg                                        25
```

<210> SEQ ID NO 4
<211> LENGTH: 25
<212> TYPE: DNA
<213> ORGANISM: Artificial Sequence
<220> FEATURE:
<223> OTHER INFORMATION: PCR Primer used for detecting a mutation of the 560th nucleotide of a varicella vaccine virus

<400> SEQUENCE: 4

```
gtgtttatgt atcagcatac agagc                                        25
```

<210> SEQ ID NO 5

-continued

```
<211> LENGTH: 24
<212> TYPE: DNA
<213> ORGANISM: Artificial Sequence
<220> FEATURE:
<223> OTHER INFORMATION: PCR Primer used for detecting a mutation of the
      5745th nucleotide of a varicella vaccine virus

<400> SEQUENCE: 5

ttgtatgcat gcgattgcta tcgc                                          24


<210> SEQ ID NO 6
<211> LENGTH: 25
<212> TYPE: DNA
<213> ORGANISM: Artificial Sequence
<220> FEATURE:
<223> OTHER INFORMATION: PCR Primer used for detecting a mutation of the
      5745th nucleotide of a varicella vaccine virus

<400> SEQUENCE: 6

ggtcttccac tttaaagggg tttgc                                         25


<210> SEQ ID NO 7
<211> LENGTH: 25
<212> TYPE: DNA
<213> ORGANISM: Artificial Sequence
<220> FEATURE:
<223> OTHER INFORMATION: PCR Primer used for detecting a mutation of the
      26125th nucleotide of a varicella vaccine virus

<400> SEQUENCE: 7

gaatcattag tatatatttt tctgc                                         25


<210> SEQ ID NO 8
<211> LENGTH: 25
<212> TYPE: DNA
<213> ORGANISM: Artificial Sequence
<220> FEATURE:
<223> OTHER INFORMATION: PCR Primer used for detecting a mutation of the
      26125th nucleotide of a varicella vaccine virus

<400> SEQUENCE: 8

tgttcagagg ggatgaatcg ttgcg                                         25


<210> SEQ ID NO 9
<211> LENGTH: 25
<212> TYPE: DNA
<213> ORGANISM: Artificial Sequence
<220> FEATURE:
<223> OTHER INFORMATION: PCR Primer used for detecting a mutation of the
      94167th nucleotide of a varicella vaccine virus

<400> SEQUENCE: 9

cgatcacgtc gctcacatcc aaccc                                         25


<210> SEQ ID NO 10
<211> LENGTH: 25
<212> TYPE: DNA
<213> ORGANISM: Artificial Sequence
<220> FEATURE:
<223> OTHER INFORMATION: PCR Primer used for detecting a mutation of the
      94167th nucleotide of a varicella vaccine virus

<400> SEQUENCE: 10

atggcagaag aaacacgtat tgccg                                         25


<210> SEQ ID NO 11
<211> LENGTH: 25
```

-continued

<212> TYPE: DNA
<213> ORGANISM: Artificial Sequence
<220> FEATURE:
<223> OTHER INFORMATION: PCR Primer used for detecting a mutation of the 105356th, 124353rd, and 124541st nucleotide of a varicella vaccine virus

<400> SEQUENCE: 11
gaggacaaca gctccacctt gaccg 25

<210> SEQ ID NO 12
<211> LENGTH: 25
<212> TYPE: DNA
<213> ORGANISM: Artificial Sequence
<220> FEATURE:
<223> OTHER INFORMATION: PCR Primer used for detecting a mutation of the 105356th, 124353rd, and 124541st nucleotide of a varicella vaccine virus

<400> SEQUENCE: 12
gagtaatgtg gccgcccggt tttgg 25

<210> SEQ ID NO 13
<211> LENGTH: 25
<212> TYPE: DNA
<213> ORGANISM: Artificial Sequence
<220> FEATURE:
<223> OTHER INFORMATION: PCR Primer used for detecting a mutation of the 105705th, 106262nd, 123635th, and 124192nd nucleotide of a varicella vaccine virus

<400> SEQUENCE: 13
ccaaaaccgg gcggccacat tactc 25

<210> SEQ ID NO 14
<211> LENGTH: 25
<212> TYPE: DNA
<213> ORGANISM: Artificial Sequence
<220> FEATURE:
<223> OTHER INFORMATION: PCR Primer used for detecting a mutation of the 105705th, 106262nd, 123635th, and 124192nd nucleotide of a varicella vaccine virus

<400> SEQUENCE: 14
attactgtcg acccgagacc tggcc 25

<210> SEQ ID NO 15
<211> LENGTH: 18
<212> TYPE: DNA
<213> ORGANISM: Artificial Sequence
<220> FEATURE:
<223> OTHER INFORMATION: PCR Primer used for detecting a mutation of the 107136th, 107252nd, 122645th, and 122761st nucleotide of a varicella vaccine virus

<400> SEQUENCE: 15
gatcaaagct tagcgcag 18

<210> SEQ ID NO 16
<211> LENGTH: 18
<212> TYPE: DNA
<213> ORGANISM: Artificial Sequence
<220> FEATURE:
<223> OTHER INFORMATION: PCR Primer used for detecting a mutation of the 107136th, 107252nd, 122645th, and 122761st nucleotide of a varicella vaccine virus

<400> SEQUENCE: 16

-continued cctatagcat ggctccag 18

<210> SEQ ID NO 17
<211> LENGTH: 25
<212> TYPE: DNA
<213> ORGANISM: Artificial Sequence
<220> FEATURE:
<223> OTHER INFORMATION: PCR Primer used for detecting a mutation of the 108111st and 121786th nucleotide of a varicella vaccine virus

<400> SEQUENCE: 17
aagggcttcc gtcgggcatc atgag 25

<210> SEQ ID NO 18
<211> LENGTH: 25
<212> TYPE: DNA
<213> ORGANISM: Artificial Sequence
<220> FEATURE:
<223> OTHER INFORMATION: PCR Primer used for detecting a mutation of the 108111st and 121786th nucleotide of a varicella vaccine virus

<400> SEQUENCE: 18
tcgggtaaaa agccgggcga tgagc 25

<210> SEQ ID NO 19
<211> LENGTH: 18
<212> TYPE: DNA
<213> ORGANISM: Varicella virus

<400> SEQUENCE: 19
ggacgcgatc gacgacga 18

<210> SEQ ID NO 20
<211> LENGTH: 18
<212> TYPE: DNA
<213> ORGANISM: Varicella virus

<400> SEQUENCE: 20
ggacgcgatt gacgacga 18

<210> SEQ ID NO 21
<211> LENGTH: 15
<212> TYPE: DNA
<213> ORGANISM: Varicella virus

<400> SEQUENCE: 21
gggagaggcg gagga 15

<210> SEQ ID NO 22
<211> LENGTH: 15
<212> TYPE: DNA
<213> ORGANISM: Varicella virus

<400> SEQUENCE: 22
ggacgcggcg gagga 15

<210> SEQ ID NO 23
<211> LENGTH: 261
<212> TYPE: DNA
<213> ORGANISM: Varicella virus
<220> FEATURE:
<221> NAME/KEY: misc_feature
<222> LOCATION: (1)..(261)
<223> OTHER INFORMATION: Attenuated Oka strain

<400> SEQUENCE: 23

-continued

```
ggacgcgatc gacgacgagg gagaggcgga ggagggagag gcggaggagg acgcgatcga     60

cgacgaggga gaggcggagg agggagaggc ggaggaggac gcgattgacg acgagggaga    120

ggcggaggag ggagaggcgg aggaggacgc ggcggaggag gacgcgatcg acgacgaggg    180

agaggcggag gaggacgcga tcgacgacga gggagaggcg gaggaggacg cgatcgacga    240

cgagggagag gcggaggagg a                                              261


<210> SEQ ID NO 24
<211> LENGTH: 27
<212> TYPE: DNA
<213> ORGANISM: Varicella virus

<400> SEQUENCE: 24

ccccgccgat ggggaggggg cgcggta                                         27


<210> SEQ ID NO 25
<211> LENGTH: 11
<212> TYPE: DNA
<213> ORGANISM: Varicella virus

<400> SEQUENCE: 25

ccccgccgat g                                                          11


<210> SEQ ID NO 26
<211> LENGTH: 335
<212> TYPE: DNA
<213> ORGANISM: Varicella virus
<220> FEATURE:
<221> NAME/KEY: misc_feature
<222> LOCATION: (1)..(335)
<223> OTHER INFORMATION: Attenuated Oka strain

<400> SEQUENCE: 26

ccccgccgat ggggaggggg cgcggtaccc cgccgatggg gagggggcgc ggtaccccgc     60

cgatggggag ggggcgcggt accccgccga tggggagggg gcgcggtacc ccgccgatgg    120

ggagggggcg cggtaccccg ccgatgggga gggggcgcgg taccccgccg atggggaggg    180

ggcgcggtac cccgccgatg gggagggggc gcggtacccc gccgatgggg agggggcgcg    240

gtaccccgcc gatggggagg gggcgcggta ccccgccgat ggggaggggg cgcggtaccc    300

cgccgatggg gagggggcgc ggtaccccgc cgatg                               335


<210> SEQ ID NO 27
<211> LENGTH: 14
<212> TYPE: DNA
<213> ORGANISM: Varicella virus

<400> SEQUENCE: 27

tatatatata tata                                                       14


<210> SEQ ID NO 28
<211> LENGTH: 265
<212> TYPE: DNA
<213> ORGANISM: Varicella virus
<220> FEATURE:
<221> NAME/KEY: misc_feature
<222> LOCATION: (1)..(265)
<223> OTHER INFORMATION: Dumas strain

<400> SEQUENCE: 28

gtacgccaat cggatacact cttttgatct gcattcgcac ttcccgtttt ttcactgtat     60
```

-continued

```
gggtttcatt gttttggcat gtgtccaacc accgttcgca ctttctttct atatatatat    120

atatatatat atatatatat agagaaagag agagagtttc ttgttcgcgc gtgttcccgc    180

gatgtcgcgg ttttatgggg tgtgggcggg cttttcacag aatatatata ttccaaatgg    240

agcggcaggc tttttaaaat cgatt                                          265


<210> SEQ ID NO 29
<211> LENGTH: 271
<212> TYPE: DNA
<213> ORGANISM: Varicella virus
<220> FEATURE:
<221> NAME/KEY: misc_feature
<222> LOCATION: (1)..(271)
<223> OTHER INFORMATION: Parental Oka strain

<400> SEQUENCE: 29

gtacgccaat cggatacact cttttaatct gcattcgcac ttcccgtttt ttcactgtat     60

gggtttcatt gttttggcat gtgtccaacc accgttcgca ctttctttct atatatatat    120

atatatatat atagagagag agagagagag agagggagag agtttcttgt tcgcgcgtgt    180

tcccgcgatg tcgcggtttt atggggtgtg ggcgggcttt tcacagaata tatatattcc    240

aaatggagcg gcaggctttt taaaatcgat t                                   271


<210> SEQ ID NO 30
<211> LENGTH: 263
<212> TYPE: DNA
<213> ORGANISM: Varicella virus
<220> FEATURE:
<221> NAME/KEY: misc_feature
<222> LOCATION: (1)..(263)
<223> OTHER INFORMATION: Attenuated Oka strain

<400> SEQUENCE: 30

gtacgccaat cggatacact cttttaatct gcattcgcac ttcccgtttt ttcactgtat     60

gggtttcatt gttttggcat gtgtccaacc accgttcgca ctttctttct atatatatat    120

atatatagag agagagagag agagagggag agagtttctt gttcgcgcgt gttcccgcga    180

tgtcgcggtt ttatggggtg tgggcgggct tttcacagaa tatatatatt ccaaatggag    240

cggcaggctt tttaaaatcg att                                            263


<210> SEQ ID NO 31
<211> LENGTH: 228
<212> TYPE: DNA
<213> ORGANISM: Varicella virus
<220> FEATURE:
<221> NAME/KEY: misc_feature
<222> LOCATION: (1)..(228)
<223> OTHER INFORMATION: Parental Oka strain

<400> SEQUENCE: 31

ggacgcgatc gacgacgagg gagaggcgga ggagggagag gcggaggagg acgcgatcga     60

cgacgaggga gaggcggagg agggagaggc ggaggaggac gcgattgacg acgagggaga    120

ggcggaggag ggagaggcgg aggaggacgc ggcggaggag gacgcgatcg acgacgaggg    180

agaggcggag gaggacgcga tcgacgacga gggagaggcg gaggagga                 228


<210> SEQ ID NO 32
<211> LENGTH: 306
<212> TYPE: DNA
<213> ORGANISM: Varicella virus
<220> FEATURE:
<221> NAME/KEY: misc_feature
```

-continued

<222> LOCATION: (1)..(306)
<223> OTHER INFORMATION: Dumas strain

<400> SEQUENCE: 32

```
ggacgcgatc gacgacgagg gagaggcgga ggagggagag gcggaggagg acgcgatcga     60

cgacgaggga gaggcggagg agggagaggc ggaggaggac gcgattgacg acgagggaga    120

ggcggaggag ggagaggcgg aggaggacgc gattgacgac gagggagagg cggaggaggg    180

agaggcggag gagggagagg cggaggaggg agaggcggag gaggacgcga tcgacgacga    240

gggagaggcg gaggaggacg cggcggagga ggacgcgatc gacgacgagg gagaggcgga    300

ggagga                                                               306
```

<210> SEQ ID NO 33
<211> LENGTH: 138
<212> TYPE: DNA
<213> ORGANISM: Varicella virus
<220> FEATURE:
<221> NAME/KEY: misc_feature
<222> LOCATION: (1)..(138)
<223> OTHER INFORMATION: Attenuated Oka strain

<400> SEQUENCE: 33

```
gcccgtccag cccgtccagc ccgcgcagcc cgtccagccc gtccagcccg cgcagcccgt     60

ccagcccgtc cagcccgcgc agcccgtcca gcccgcgcag cccgtccagc ccgcgcagcc    120

cgtccagccc gcgcagga                                                  138
```

<210> SEQ ID NO 34
<211> LENGTH: 93
<212> TYPE: DNA
<213> ORGANISM: Varicella virus
<220> FEATURE:
<221> NAME/KEY: misc_feature
<222> LOCATION: (1)..(93)
<223> OTHER INFORMATION: Attenuated Oka strain

<400> SEQUENCE: 34

```
gcccgtccag cccgtccagc ccgcgcagcc cgtccagccc gcgcagcccg cgcagcccgt     60

ccagcccgcg cagcccgtcc agcccgcgca gga                                  93
```

<210> SEQ ID NO 35
<211> LENGTH: 93
<212> TYPE: DNA
<213> ORGANISM: Varicella virus
<220> FEATURE:
<221> NAME/KEY: misc_feature
<222> LOCATION: (1)..(93)
<223> OTHER INFORMATION: Attenuated Oka strain

<400> SEQUENCE: 35

```
gcccgtccag cccgtccagc ccgcgcagcc cgtccagccc gcgcagcccg tccagcccgt     60

ccagcccgcg cagcccgtcc agcccgcgca gga                                  93
```

<210> SEQ ID NO 36
<211> LENGTH: 75
<212> TYPE: DNA
<213> ORGANISM: Varicella virus
<220> FEATURE:
<221> NAME/KEY: misc_feature
<222> LOCATION: (1)..(75)
<223> OTHER INFORMATION: Attenuated Oka strain

<400> SEQUENCE: 36

-continued

```
gcccgtccag cccgtccagc ccgcgcagcc cgtccagccc gcgcagcccg cgcagcccgt     60

ccagcccgcg cagga                                                      75


<210> SEQ ID NO 37
<211> LENGTH: 48
<212> TYPE: DNA
<213> ORGANISM: Varicella virus
<220> FEATURE:
<221> NAME/KEY: misc_feature
<222> LOCATION: (1)..(48)
<223> OTHER INFORMATION: Attenuated Oka strain

<400> SEQUENCE: 37

gcccgtccag cccgtccagc ccgcgcagcc cgtccagccc gcgcagga                  48


<210> SEQ ID NO 38
<211> LENGTH: 30
<212> TYPE: DNA
<213> ORGANISM: Varicella virus
<220> FEATURE:
<221> NAME/KEY: misc_feature
<222> LOCATION: (1)..(30)
<223> OTHER INFORMATION: Attenuated Oka strain

<400> SEQUENCE: 38

gcccgtccag cccgtccagc ccgcgcagga                                      30


<210> SEQ ID NO 39
<211> LENGTH: 66
<212> TYPE: DNA
<213> ORGANISM: Varicella virus
<220> FEATURE:
<221> NAME/KEY: misc_feature
<222> LOCATION: (1)..(66)
<223> OTHER INFORMATION: Parental Oka strain

<400> SEQUENCE: 39

gcccgtccag cccgtccagc ccgcgcagcc cgtccagccc gcgcagcccg tccagcccgc     60

gcagga                                                                66


<210> SEQ ID NO 40
<211> LENGTH: 66
<212> TYPE: DNA
<213> ORGANISM: Varicella virus
<220> FEATURE:
<221> NAME/KEY: misc_feature
<222> LOCATION: (1)..(66)
<223> OTHER INFORMATION: Dumas strain

<400> SEQUENCE: 40

gcccgcgcag cccgcgcagc ccgcgcagcc cgcgcagccc gcgcagaccg tccagcccgc     60

gcagga                                                                66


<210> SEQ ID NO 41
<211> LENGTH: 308
<212> TYPE: DNA
<213> ORGANISM: Varicella virus
<220> FEATURE:
<221> NAME/KEY: misc_feature
<222> LOCATION: (1)..(308)
<223> OTHER INFORMATION: Parental Oka strain

<400> SEQUENCE: 41

ccccgccgat ggggaggggg cgcggtaccc cgccgatggg gagggggcgc ggtaccccgc     60

cgatggggag gggggcgcggt accccgccga tggggagggg gcgcggtacc ccgccgatgg    120
```

-continued

```
ggagggggcg cggtaccccg ccgatgggga gggggcgcgg taccccgccg atggggaggg    180

ggcgcggtac cccgccgatg gggagggggc gcggtacccc gccgatgggg agggggcgcg    240

gtaccccgcc gatggggagg gggcgcggta ccccgccgat ggggaggggg cgcggtaccc    300

cgccgatg                                                             308


<210> SEQ ID NO 42
<211> LENGTH: 146
<212> TYPE: DNA
<213> ORGANISM: Varicella virus
<220> FEATURE:
<221> NAME/KEY: misc_feature
<222> LOCATION: (1)..(146)
<223> OTHER INFORMATION: Dumas strain

<400> SEQUENCE: 42

ccccgccgat ggggaggggg cgcggtaccc cgccgatggg gagggggcgc ggtaccccgc     60

cgatggggag ggggcgcggt accccgccga tggggagggg gcgcggtacc ccgccgatgg    120

ggagggggcg cggtaccccg ccgatg                                         146
```

METHOD FOR QUALITY CONTROL OF AN ATTENUATED VERICELLA LIVE VACCINE

This application is the national phase under 35 U.S.C. §371 of PCT International Application No. PCT/JP01/00678 which has an International filing date of Jan. 31, 2001, which designated the United States of America and was not published in English.

BACKGROUND OF THE INVENTION

1. Field of the Invention

The present invention relates to a method for quality control of an attenuated varicella live vaccine. More particularly, the present invention relates to a method for quality control of an attenuated varicella live vaccine, which comprises subjecting the genomic DNA of a sample varicella vaccine virus to sequence analysis and confirming that the genomic DNA of the sample varicella vaccine virus conserves the specific nucleotides without suffering mutation. By the use of the method of the present invention, it has become possible to determine very accurately the qualification of an attenuated varicella virus as an active ingredient of an attenuated varicella live vaccine and, consequently, to conduct an exact quality control of the vaccines.

2. Prior Art

As is well known, attenuated varicella live vaccines used today are produced from a seed strain of varicella virus which is derived from the attenuated varicella virus Oka strain (see Examined Japanese Patent Application Publication No. 53-41202 and U.S. Pat. No. 3,985,615), and the attenuated live vaccines are used widely throughout the world (Requirements for Varicella Vaccine (Live) Adopted 1984; Revised 1993: WHO Technical Report Series, No. 848, pp. 22–38, 1994). To ensure the safety and effectiveness of the vaccine, the number of passages of a virus used for producing the vaccine is restricted under the control of a seed lot system, taking into consideration the potential genetic mutation which is likely to occur during the passage. That is, the manufacturers are under an obligation to produce varicella vaccines only from the virus derived from the approved seed virus for the live varicella vaccine, wherein the number of passages of the virus is not more than 10 as counted from the approved seed virus which is counted as 0 passage. In other words, the quality control and quality assurance of the attenuated varicella live vaccine rely upon the fulfillment of the seed lot system by the manufacturers, and such a method for the quality control and quality assurance is not a method which can be traced and analyzed by a person skilled in the art.

Further, from the viewpoint of epidemiology which involves a tracing of the effects of the varicella vaccine and a post-market surveillance (PMS), the virological difference between the fresh wild-type strains isolated from the naturally infected varicella patients and the vaccine virus strains derived from the above-mentioned Oka strain needs to be determined, and various analyses, such as those utilizing immunological techniques and genetic engineering techniques, have been attempted for determination of the virological difference. For example, the following analyses have been reported: the difference in DNA sequence between the various VZV strains (Journal of virology, 59, 660–668, 1986; Journal of General virology, 67, 1759–1816, 1986), the difference in the absence or presence of a restriction enzyme Pst I cleavage site (Japanese Journal of Experimental Medicine, 59, 233–237, 1989), the difference in RFLP (restriction fragment length polymorphism) of the PCR (polymerase chain reaction) product (Journal of virology, 66, 1016–1020, 1992), and the difference in the absence or presence of a restriction enzyme Pst I restriction site which is taken in combination with the difference in RFLP of the PCR product (Journal of Clinical Microbiology, 33, 658–660, 1995). However, all of these analyses only propose criteria which can be used for differentiating a fresh wild-type strain from a vaccine strain derived from the Oka strain, and such analyses lack reliability and exactness. In addition, a method for identifying the attenuated varicella virus Oka strain by using gene 14 region (U.S. Pat. No. 6,093,535) and a method for identifying the attenuated varicella live vaccine virus by using gene 62 region (International Patent Application Publication No. WO 00/50603) have been known. Both of these methods enabled a determination of the differences among the varicella virus Oka strain (virulent parental strain), a vaccine strain derived therefrom (attenuated Oka strain) and a varicella virus strain other than the Oka strain, but neither of these methods was satisfactory as a standard for the quality control and quality assurance of the attenuated varicella live vaccine.

As mentioned above, at present, the quality of the attenuated varicella virus used as an active ingredient of an attenuated varicella live vaccine is controlled by the fulfillment of the seed lot system by the manufacturers. In other words, a method which can be traced and analyzed by a third party for evaluating and confirming the effectiveness of the vaccine, such as a method utilizing a direct and quantitative genetic analysis of the genomic DNA of a seed virus or a vaccine virus, has not been used for the quality control of the vaccine and, thus, the exactness of the quality control is incomputable and vague. Therefore, an improvement in the exactness of the quality control and quality assurance is critically important for assuring the effectiveness, safety and uniformity of the attenuated varicella live vaccine. However, as mentioned above, a reliable method for the quality control has not been established, and a development of such a method has been earnestly desired in the art.

SUMMARY OF THE INVENTION

In the above situation, the present inventors have made extensive and intensive studies with a view toward developing a novel method for accurately and quantitatively conducting the quality control of an attenuated varicella live vaccine. Specifically, the present inventors determined the whole genomic nucleotide sequence of the attenuated varicella virus Oka strain containing more than 120,000 nucleotides, conducted a comparative analysis between the determined nucleotide sequence of the attenuated Oka strain and the whole genomic nucleotide sequences of the virulent strain and the parental Oka strain (virulent strain), and identified the genetic mutations of the attenuated varicella virus Oka strain. As a result, they have found that, by evaluating and determining whether or not a varicella virus strain conserves the below-mentioned specific nucleotides, a virus strain conserving the specific nucleotides can be determined accurately as a virus strain capable of functioning as an attenuated varicella vaccine virus. The present invention has been completed, based on this novel finding.

Therefore, it is an object of the present invention to provide a novel method for the quality control of an attenuated varicella live vaccine.

It is another object of the present invention to provide an attenuated varicella live vaccine which is quality-controlled by the above-mentioned method.

It is a further object of the present invention to provide a vaccine strain capable of functioning as an attenuated varicella vaccine virus, which is identified by a method used in the above-mentioned method.

The foregoing and other objects, features and advantages of the present invention will be apparent to those skilled in the art from the following detailed description and the appended claims taken in connection with the accompanying sequence listing and drawings.

SEQUENCE LISTING FREE TEXT

SEQ ID NOs: 3 and 4 are of PCR primers used for detecting a mutation of the 560th nucleotide of a varicella vaccine virus.

SEQ ID NOs: 5 and 6 are of PCR primers used for detecting a mutation of the 5,745th nucleotide of a varicella vaccine virus.

SEQ ID NOs: 7 and 8 are of PCR primers used for detecting a mutation of the 26,125th nucleotide of a varicella vaccine virus.

SEQ ID NOs: 9 and 10 are of PCR primers used for detecting a mutation of the 94,167th nucleotide of a varicella vaccine virus.

SEQ ID NOs: 11 and 12 are of PCR primers used for detecting mutations of the 105,356th, 105,544th, 124,353rd and 124,541st nucleotides of a varicella vaccine virus.

SEQ ID NOs: 13 and 14 are of PCR primers used for detecting mutations of the 105,705th, 106,262nd, 123,635th and 124,192nd nucleotides of a varicella vaccine virus.

SEQ ID NOs: 15 and 16 are of PCR primers used for detecting mutations of the 107,136th, 107,252nd, 122,645th and 122,761st nucleotides of a varicella vaccine virus.

SEQ ID NOs: 17 and 18 are of PCR primers used for detecting mutations of the 108,111st and 121,786th nucleotides of a varicella vaccine virus.

BRIEF DESCRIPTION OF THE DRAWINGS

In the drawings:

FIG. 2(*a*) was obtained using Nla III, FIG. 2(*b*) was obtained using Alu I, FIG. 2(*c*) was obtained using BstX I, FIG. 2(*d*) was obtained using SfaN I, FIG. 2(*e*) was obtained using Acc II, FIG. 2(*f*) was obtained using Sac II, FIG. 2(*g*) was obtained using Sma I, FIG. 2(*h*) was obtained using BssH II and Nae I in combination, and FIG. 2(*i*) was obtained using Bsr I; and wherein, V represents the attenuated Oka strain, P represents the parental Oka strain, and K represents the Kawaguchi strain.

Figure 1:
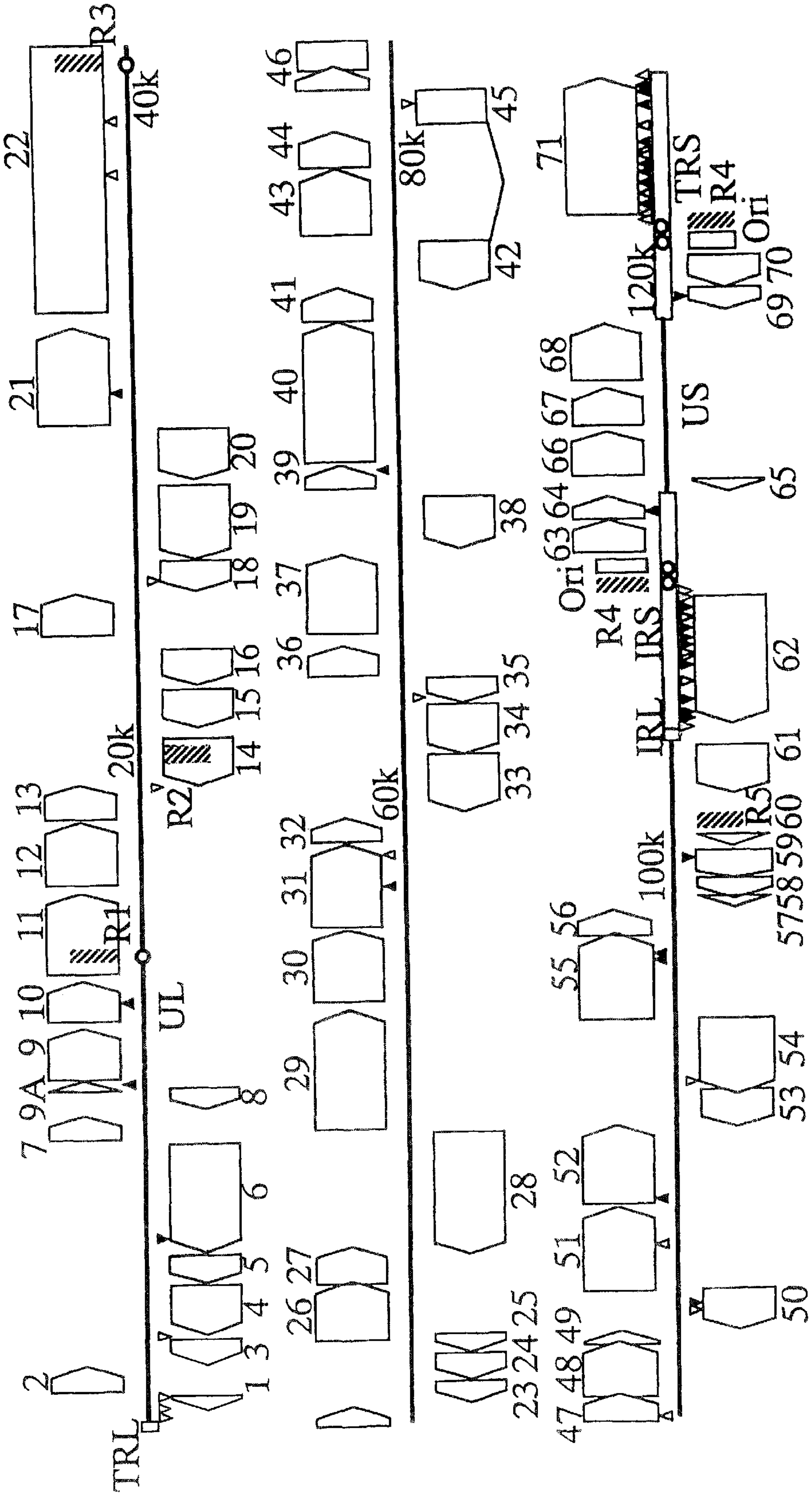
FIG. 1 is a genetic map of the varicella virus Oka strain showing the number and direction of each gene, wherein, ▽ represents a synonymous substitution, ▼ represents a non-synonymous substitution, ▽ represents a mutation in a noncoding region, ○ represents deletion or insertion, the genome length is shown every 20 kb, R1 to R4 represent repetitive sequences, Ori represents an origin of replication, TRL represents a "Terminal Repeat Long", UL represents a "Unique Long", IRL represents an "Internal Repeat Long", IRS represents an "Internal Repeat Short", US represents a "Unique Short", and TRS represents a "Terminal Repeat Short"; and wherein the nucleotide sequence of gene 62 to gene 64 and the nucleotide sequence of gene 69 to gene 71 are symmetrical to each other (i.e., the two nucleotide sequences are inverted repeats)

The terminologies used in the present specification are defined in the following items (a) to (g).

(a) VZV: A virus which causes varicella and herpes zoster. "VZV" is an abbreviation for "varicella-zoster virus" which is frequently referred to simply as "varicella virus".

(b) Varicella vaccine virus and varicella vaccine: A varicella vaccine virus is an active ingredient of a vaccine and it is an attenuated virus. A varicella vaccine is a vaccine effective for preventing the infection with a VZV or the onset of the disease after the infection.

(c) Attenuated Oka strain: Attenuated Oka strain is the attenuated varicella virus Oka strain (see Examined Japanese Patent Application Publication 53-41202 and U.S. Pat. No. 3,985,615) or an attenuated varicella virus derived therefrom. The attenuated Oka strain is deposited under the deposition number VR-795 on Mar. 14, 1975 with ATCC.

(d) Parental Oka strain: Parental Oka strain is the originally isolated, wild-type (virulent) varicella virus Oka strain.

(e) Quality control: For assuring the effectiveness, safety and uniformity of a vaccine, raw materials for a vaccine, intermediates obtained during the production of a vaccine, and final products are subjected to various tests or analyses for confirming and assuring their qualification as a vaccine. With respect to an attenuated varicella live vaccine, at present, the quality control of the vaccine is conducted in accordance with Pharmaceutical Affairs Law (the Law No. 145 established in 1960), Article 42, Item 1 and a provision entitled "Dried Attenuated Varicella Virus Live Vaccine" in the Notification No. 217 of the Japanese Ministry of Health and Welfare: Seibutsugakuteki Seizai Kijun (Minimum Requirements for Biological Products) or the above-mentioned "Requirements for Varicella Vaccine (Live)" of WHO.

(f) Nucleotide number of a DNA sequence: In the present invention, all nucleotide numbers of the varicella viruses are in accordance with the nucleotide numbering system of the nucleotide sequence of the genomic DNA of the varicella virus Dumas strain (Journal of General Virology, 67, 1759–1816, 1986 and GenBank (National Center for Biotechnology Information, National Library of Medicine, Building 38A, Room 8N805, Bethesda, Md. 20894, USA), Accession No. X04370) which is shown in SEQ ID NO: 1. Further, in the present invention, the nucleotide sequences are the sequences of a sense strand unless otherwise specified.

(g) DNA mutation: Mutations in the genomic DNA of the attenuated Oka strain were identified by conducting homology searches among the nucleotide sequences of the attenuated Oka strain, the Dumas strain and the virulent parental Oka strain. For example, the DNA mutation is described as follows: "The nucleotide A which is the 5,745th nucleotide of the Dumas strain and a nucleotide at a corresponding site of the parental Oka strain has been mutated to G in the attenuated Oka strain. This nucleotide mutation is a non-synonymous substitution in which Ser is replaced with Pro."

DETAILED DESCRIPTION OF THE INVENTION

In an aspect of the present invention, there is provided an accurate method for the quality control of an attenuated varicella live vaccine.

For easy understanding of the present invention, the essential features and various embodiments of the present invention are enumerated below.

1. A method for the quality control of an attenuated varicella live vaccine, which comprises subjecting the genomic DNA of a sample varicella vaccine virus to sequence analysis and confirming that the genomic DNA of the sample varicella vaccine virus conserves without suffering mutation the following 5 nucleotides:

the 5,745th G, the 105,356th C, the 105,544th G, the 106,262nd C and the 107,252nd C, wherein the nucleotide numbers are in accordance with the nucleotide numbering system of the nucleotide sequence of the genomic DNA of the varicella virus Dumas strain of SEQ ID NO: 1.

2. The method according to item 1 above, wherein the conservation of the 5 nucleotides combination is confirmed by an RFLP analysis using the following primers:

a pair of primers of SEQ ID NOs: 5 and 6 with respect to the confirmation of the 5,745th G;

a pair of primers of SEQ ID NOs: 11 and 12 with respect to the confirmation of the 105,356th C and the 105,544th G;

a pair of primers of SEQ ID NOs: 13 and 14 with respect to the confirmation of the 106,262nd C; and a pair of primers of SEQ ID NOs: 15 and 16 with respect to the confirmation of the 107,252nd C.

3. The method according to item 1 or 2 above, which further comprises confirming that the the genomic DNA of sample varicella vaccine virus conserves without suffering mutation the following 4 nucleotides:

the 122,645th G, the 123,635th G, the 124,353rd C and the 124,541st G, wherein the nucleotide numbers are in accordance with the nucleotide numbering system of the nucleotide sequence of the genomic DNA of the varicella virus Dumas strain of SEQ ID NO: 1.

4. The method according to item 3 above, wherein the conservation of the 4 nucleotides is confirmed by an RFLP analysis using the following primers:

a pair of primers of SEQ ID NOs: 11 and 12 with respect to the confirmation of the 124,353rd C and the 124,541st G;

a pair of primers of SEQ ID NOs: 13 and 14 with respect to the confirmation of the 123,635th G; and a pair of primers of SEQ ID NOs: 15 and 16 with respect to the confirmation of the 122,645th G.

5. The method according to any one of items 1 to 4 above, which further comprises confirming that the genomic DNA of the sample varicella vaccine virus conserves without suffering mutation the following 49 nucleotides:

the 560th C, the 703rd Y, the 763rd Y, the 2,515th Y, the 10,900th Y, the 12,779th Y, the 19,431st Y, the 26,125th G, the 31,732nd Y, the 38,036th Y, the 39,227th K, the 58,595th R, the 59,287th R, the 64,067th R, the 71,252nd Y, the 82,225th R, the 84,091st R, the 87,280th R, the 87,306th Y, the 89,734th R, the 90,535th R, the 94,167th C, the 97,748th R, the 97,796th Y, the 101,089th R, the 105,169th R, the 105,310th R, the 105,705th C, the 106,710th R, the 107,136th C, the 107,599th R, the 107,797th R, the 108,111st C, the 108,838th R, the 109,137th R, the 109,200th R, the 111,650th R, the 118,247th Y, the 120,697th Y, the 120,760th Y, the 121,059th Y, the 121,786th G, the 122,100th Y, the 122,298th Y, the 122,761st G, the 123,187th Y, the 124,192nd G, the 124,587th Y and the 124,728th Y, wherein:

the nucleotide numbers are in accordance with the nucleotide numbering system of the nucleotide sequence of the genomic DNA of the varicella virus Dumas strain of SEQ ID NO: 1, R represents A or G, Y represents C or T, and K represents G or T.

6. The method according to item 5 above, wherein the conservation of the 560th C, the 26,125th G, the 94,167th C, the 105,705th C, the 107,136th C, the 108,111st C, the 121,786th G, the 122,761st G and the 124,192nd G among the 49 nucleotides is confirmed by an RFLP analysis using the following primers:

a pair of primers of SEQ ID NOs: 3 and 4 with respect to the confirmation of the 560th C;

a pair of primers of SEQ ID NOs: 7 and 8 with respect to the confirmation of the 26,125th G;

a pair of primers of SEQ ID NOs: 9 and 10 with respect to the confirmation of the 94,167th C;

a pair of primers of SEQ ID NOs: 13 and 14 with respect to the confirmation of the 105,705th C and the 124,192nd G;

a pair of primers of SEQ ID NOs: 15 and 16 with respect to the confirmation of the 107,136th C and the 122,761st G; and a pair of primers of SEQ ID NOs: 17 and 18 with respect to the confirmation of the 108,111st C and the 121,786th G.

7. The method according to any one of items 1 to 6 above, which further comprises confirming deletion mutations in two origins of replication of the genomic DNA of the sample varicella vaccine virus, wherein the two origins of replication are a region corresponding to the 110,087th to 110,350th nucleotides of the sense strand of the genomic DNA of the varicella virus Dumas strain of SEQ ID NO: 1 and a region corresponding to the 119,547th to 119,810th nucleotides of the genomic DNA of the antisense strand of the Dumas strain, and wherein the deletion mutations occur with respect to segments each having a nucleotide sequence of ATATATATA arranged in the direction of from the 5' end to the 3' end, the segments being a segment corresponding to the 110,219th to 110,227th nucleotides of the genomic DNA of the sense strand of the Dumas strain and a segment corresponding to the 119,670th to 119,678th nucleotides of the antisense strand of the genomic DNA of the Dumas strain.

8. The method according to any one of items 1 to 7 above, which further comprises confirming that the repetitive sequence of one whole R1 region of the genomic DNA of said sample varicella vaccine virus is a nucleotide sequence of abbabba'bbb'abababx (SEQ ID NO:23) arranged in the direction of from the 5' end to the 3' end, wherein:

a represents a nucleotide sequence of GGACGCGATCGACGACGA (SEQ ID NO:19);

a' represents a nucleotide sequence of GGACGCGATTGACGACGA (SEQ ID NO:20);

b represents a nucleotide sequence of GGGAGAGGCGGAGGA (SEQ ID NO:21);

b' represents a nucleotide sequence of GGACGCGGCGGAGGA (SEQ ID NO:22); and x represents a nucleotide sequence of GGA, wherein said whole R1 region is a region corresponding to the 13,937th to 14,242nd nucleotides of the genomic DNA of the varicella virus Dumas strain of SEQ ID NO: 1.

9. The method according to any one of items 1 to 8 above, which further comprises confirming that the repetitive sequence of each of two whole R4 regions of the genomic DNA of said sample varicella vaccine virus is a nucleotide sequence of aaaaaaaaaaaax (SEQ ID NO:26) arranged in the direction of from the 5' end to the 3' end, wherein:

a represents a nucleotide sequence of CCCCGC-CGATGGGGAGGGGGCGCGGTA (SEQ ID NO:24); and x represents a nucleotide sequence of CCCCGC-CGATG (SEQ ID NO:25)

wherein said two whole R4 regions are a region corresponding to the 109,762nd to 109,907th nucleotides of the sense strand of the genomic DNA of the varicella virus Dumas strain of SEQ ID NO: 1 and a region corresponding to the 119,990th to 120,135th nucleotides of the antisense strand of the genomic DNA of said Dumas strain.

10. An attenuated varicella live vaccine which is quality-controlled by the method of any one of items 1 to 9 above.

11. A virus strain capable of functioning as an attenuated varicella vaccine virus, which is identified by a method used in the method of any one of items 1 to 9 above.

The present invention is described in detail below.

During the course of studies for completing the method of the present invention, the present inventors determined for the first time the whole nucleotide sequence of the genomic DNA of the attenuated Oka strain (deposited under the deposition number VR-795 on Mar. 14, 1975 with ATCC (American Type Culture Collection; 10801 University Boulevard, Manassas, Va. 20110-2209, USA)). This sequence is shown in SEQ ID NO:2. Further, using the determined whole genomic DNA sequence of the attenuated Oka strain, the present inventors conducted a homology search among the whole genomic DNA sequences of the Dumas strain, the parental Oka strain and the attenuated Oka strain. As a result, the present inventors disclosed the nucleotide mutations of the attenuated Oka strain (i.e., the nucleotides of the attenuated Oka strain which are different from the nucleotides of the Dumas strain and/or the parental Oka strain at the corresponding sites) shown in Table 1 below. The present inventors made further analyses of the nucleotide mutations and identified the synonymous substitutions (no amino acid replacement resulting from the nucleotide mutations) and nonsynonymous substitutions (amino acid replacements resulting from the nucleotide mutations); mutations in noncoding regions (ncr mutation); stop codon mutations (ochre/amber mutation); number of repetitions and the sequence size of the repetitive sequences and the differences in the order of the repetitions; and mutations in the origins of replication (inverted repeats; see FIG. 1). As explained in detail below, the mutations of the attenuated Oka strain which have been disclosed by the present inventors are useful for differentiating the attenuated Oka strain from other varicella virus strains, especially from the virulent strains and, therefore, theses mutations can be used for the quality control of the attenuated varicella live vaccine.

Among the nucleotide mutations of the attenuated Oka strain shown in Table 1, the important mutations show the XXY pattern or the XX(X/Y) pattern. The mutation showing the XXY pattern is a mutation wherein a nucleotide of the parental Oka strain is identical to a corresponding nucleotide of the Dumas strain (that is, both nucleotides are “X”), but the corresponding nucleotide of the attenuated Oka strain is a mutated nucleotide (that is, the nucleotide is mutated to “Y”). Such a mutation is unique to the attenuated Oka strain. The mutation showing the XX(X/Y) pattern is a mutation wherein a nucleotide of the parental Oka strain is identical to a corresponding nucleotide of the Dumas strain (that is, both nucleotides are “X”), but a corresponding nucleotide of the attenuated Oka strain is a mixture of a nucleotide which is identical to that of the Dumas strain and a mutated nucleotide (that is, the mixture of the identical nucleotide “X” and the mutated nucleotide “Y”). In the genome of the attenuated Oka strain, there are 18 nucleotide mutations showing the XXY pattern and 40 nucleotide mutations showing the XX(X/Y) pattern. Among the total of 58 nucleotide mutations, 49 nucleotide mutations are found in the coding regions, 8 nucleotide mutations are found in the noncoding regions, and 1 nucleotide mutation is found in a stop codon. Further, among the 49 nucleotide mutations in the coding regions, 29 nucleotide mutations are nonsynonymous substitutions, and 20 nucleotide mutations are synonymous substitutions. Further detailed analyses revealed that among the 18 nucleotide mutations showing the XXY pattern, 9 nucleotide mutations are nonsynonymous substitutions, 8 nucleotide mutations are synonymous substitutions, and 1 nucleotide mutation is found in a noncoding region. The following nucleotide mutations which show the XXY pattern and are nonsynonymous substitutions are unique to the attenuated Oka strain: the 5,745th G of gene 6; the 105,356th C, 105,544th G, 106,262nd C and 107,252nd C of gene 62; and the 122,645th G, 123,635th G, 124,353rd C and 124,541st G of gene 71. These unique nucleotides of the attenuated Oka strain are considered to be closely related to the attenuation and safety of a varicella virus and, thus these nucleotide are very important. Among the above-mentioned 9 nucleotides, 4 nucleotides are found in gene 62 and 4 nucleotides are found in gene 71. Since gene 62 and gene 71 are contained in the inverted repeats (see FIG. 1), in the present invention, the quality control of an attenuated varicella live vaccine is conducted by subjecting the genomic DNA of a sample varicella vaccine virus to sequence analysis and confirming that the above-mentioned 1 nucleotide of gene 6 and 4 nucleotides of gene 62 are conserved without suffering mutation. For improving the exactness of the quality control, it is preferred that the sample virus is further confirmed to conserve the above-mentioned 4 nucleotides of gene 71 without suffering mutation.

Further in the present invention, it is preferred to confirm that the sample varicella vaccine virus conserves, without suffering mutation, all 58 nucleotides which are unique to the attenuated Oka strain. Specifically, together with the above-mentioned unique nucleotides of the attenuated Oka strain which show the XXY pattern and are nonsynonymous substitutions, the conservation of the following 49 nucleotides without suffering mutation is confirmed in the present invention:

the 560th C, the 703rd Y, the 763rd Y, the 2,515th Y, the 10,900th Y, the 12,779th Y, the 19,431st Y, the 26,125th G, the 31,732nd Y, the 38,036th Y, the 39,227th K, the 58,595th R, the 59,287th R, the 64,067th R, the 71,252nd Y, the 82,225th R, the 84,091st R, the 87,280th R, the 87,306th Y, the 89,734th R, the 90,535th R, the 94,167th C, the 97,748th R, the 97,796th Y, the 101,089th R, the 105,169th R, the 105,310th R, the 105,705th C, the 106,710th R, the 107,136th C, the 107,599th R, the 107,797th R, the 108,111st C, the 108,838th R, the 109,137th R, the 109,200th R, the 111,650th R, the 118,247th Y, the 120,697th Y, the 120,760th Y, the 121,059th Y, the 121,786th G, the 122,100th Y, the 122,298th Y, the 122,761st G, the 123,187th Y, the 124,192nd G, the 124,587th Y and the 124,728th Y, wherein, R represents A or G, Y represents C or T, and K represents G or T.

In addition to the above-mentioned 58 nucleotide mutations, the following unique mutations of the attenuated Oka strain were found by the homology search conducted among the whole genomic DNA sequences of the Dumas strain, the parental Oka strain and the attenuated Oka strain: a deletion mutation in the origin of replication, a mutation in the repetitive region R1 of gene 11 and a mutation in the repetitive region R4 of the noncoding regions.

In a varicella virus genome, there are two origins of replication which are contained in the inverted repeats (see FIG. 1) The origins of replication are a region corresponding to the 110,087th to 110,350th nucleotides of the sense strand of the genomic DNA of the Dumas strain and a region corresponding to the 119,547th to 119,810th nucleotides of the antisense strain of the genomic DNA of the Dumas strain. The nucleotide sequence of the sense strand is shown in Table 4. As is apparent from Table 4, the deletion in the origins of replication of the attenuated Oka strain occur with respect to segments each having a nucleotide sequence of TATATATATATATA (SEQ ID NO:27) arranged in the direction of from the 5' end to the 3' end, and the segments are a segment corresponding to the 110,214th to 110,227th nucleotides of the sense strand and a segment corresponding to the 119,670th to 119,683rd nucleotides of the antisense strand. In the present invention, it is preferred that the presence of this deletion is further confirmed. Specifically, this deletion can be confirmed by determining the presence or absence of the segments each having a nucleotide sequence of ATATATATA which correspond to the 110,219th to 110,227th nucleotides of the sense strand and the 119,670th to 119,678th nucleotides of the antisense strand.

The repetitive region R1 of gene 11 is a region corresponding to the 13,937th to 14,242nd nucleotides of the genomic DNA of the Dumas strain, and the nucleotide sequence of the R1 region is shown in Table 5. As is apparent from Table 5, the nucleotide sequence of the R1 region of the attenuated Oka strain is different from that of not only the Dumas strain, but also the parental Oka strain. Therefore, for the quality control of the vaccine, it is preferred that the R1 region of the sample varicella vaccine virus is confirmed to be identical with the R1 region of the attenuated Oka strain. Specifically, it is confirmed that the repetitive sequence of one whole R1 region of the genomic DNA of the sample varicella vaccine virus is a nucleotide sequence of abbabba'bbb'abababx (SEQ ID NO:23) arranged in the direction of from the 5' end to the 3' end (wherein, a represents a nucleotide sequence of GGACGCGATCGACGACGA (SEQ ID NO:19); a' represents a nucleotide sequence of GGACGCGATTGACGACGA (SEQ ID NO:20); b represents a nucleotide sequence of GGGAGAGGCGGAGGA (SEQ ID NO:21); b' represents a nucleotide sequence of GGACGCGGCGGAGGA (SEQ ID NO:22); and x represents a nucleotide sequence of GGA).

In a varicella virus genome, two repetitive regions R4 which are contained in the inverted repeats are found in the noncoding regions (see FIG. 1). The R4 regions are a region corresponding to the 109,762nd to 109,907th nucleotides of the sense strand of the genomic DNA of the Dumas strain and a region corresponding to the 119,990th to 120,135th nucleotides of the antisense strand of the genomic DNA of the Dumas strain. The nucleotide sequence of the R4 region in the direction of the 5' end to the 3' end is shown in Table 7. As is apparent from Table 7, the repetitive sequence of the R4 region of the attenuated Oka strain is different from that of not only the Dumas strain, but also the parental Oka strain. Therefore, for the quality control of the vaccine, it is preferred that the R4 region of the sample varicella vaccine virus is confirmed to be identical with the R4 region of the attenuated Oka strain. Specifically, it is confirmed that the repetitive sequence of each of two whole R4 regions of the genomic DNA of the sample varicella vaccine virus is a nucleotide sequence of aaaaaaaaaaaax (SEQ ID NO:26) arranged in the direction of from the 5' end to the 3' end (wherein, a represents a nucleotide sequence of CCCCGCCGATGGGGAGGGGGCGCGGTA (SEQ ID NO:24); and x represents a nucleotide sequence of CCCCGCCGATG (SEQ ID NO:25)).

In addition, the mutations shown in Table 6 have been found in the repetitive region R3 of gene 22. However, as is apparent from Table 6, there is a large diversity among the repetitive sequences of the R3 region of the attenuated Oka strain and the parental Oka strain.

The method of the present invention has been completed based on the above-mentioned nucleotide mutations which are unique to the attenuated Oka strain. Therefore, the methods used in the methods for the quality control of the present invention can be used not only for the quality control of an attenuated varicella virus live vaccine (that is, determining whether a seed virus for a vaccine, an attenuated varicella virus as a raw material of a vaccine or a live vaccine has been mutated or not), but also for the identification of a virus strain capable of functioning as an attenuated varicella vaccine virus (a virus which can be used as an active ingredient of a varicella vaccine) and the analysis of a virulent strain (the parental Oka strain or a natural wild-type strain). In addition, the method of the present invention provides an exact and advantageous techniques to be used for tracing the effects of the vaccination and for the researches in the field of epidemiology of varicella and zoster, and also provides an exact measure for preventing varicella and zoster.

The specific methods for conducting the quality control of the present invention will be described in detail below.

Preparation of a genomic DNA of a sample varicella virus: In the method of the present invention, a virus suspension or a bulk vaccine solution for use as an active ingredient of an attenuated varicella live vaccine, a virus suspension obtained by propagating a desired VZV, and vesicle fluid and the like obtained from a naturally infected varicella patient can be used as a sample varicella virus. The genomic DNA can be extracted and purified directly from the sample viruses by a conventional method. Alternatively, cells can be infected with VZV to be used as the sample virus, and the genomic DNA of the virus can be extracted and purified from the infected cells by a conventional method (with respect to the methods for extracting and purifying a DNA, reference can be made to "Current Protocol in Molecular Biology", Volume 1, Chapter 2, 2.0.1–2.6.12, John Wiley & Sons, Inc., 1987–2000 (the loose-leaf system)). For propagating the VZV, WI-38 cells and MRC-5 cells can be used. It is preferred that the vesicle fluid used as a material for isolating, propagating and preparing a fresh wild-type strain or an epidemic strain is obtained from a naturally infected patient within 3 days after the onset of varicella.

Preparation of PCR primers: A desired nucleotide sequence of a VZV genomic DNA can be amplified by a PCR method. First, polynucleotide strands consisting of contiguous sequences of about 15 to 30 nucleotides which correspond to the 5'-terminal sequence of the sense and antisense sequences of the desired region are prepared by a DNA synthesizer. The prepared polynucleotide strands are used as a pair of primers. The whole genomic DNA sequence of the attenuated Oka strain shown in SEQ ID NO:2 and the patent documents mentioned under "Prior Art" of the specification (U.S. Pat. No. 6,093,535 and International Application Publication WO 00/50603) can be reffered when designing the PCR primers.

Determination of the nucleotide sequence of the PCR products: From the view point of saving labor for conducting the experiments, it is preferred that the PCR products are analyzed by a direct DNA sequencing method without the preparation of a genomic DNA library (this method is described in "Current Protocol in Molecular Biology", Volume 3, Chapter 15, 15.2.1–15.2.11, ditto). In this method, the sequencing of a nucleotide sequence can be determined by conventional methods, for example, dideoxy method, a method using Cycle Sequence Kit (manufactured and sold by TAKARA SHUZO Co. Ltd., Japan), and a method using DNA Sequencing Kit (manufactured and sold by Perkin Elmer Applied Biosystems, USA).

Homology search of DNA sequences: Homology search of DNA sequences can be performed using commercially available computer software for gene analysis. For example, GENETYX-WIN (ver. 3.1) (manufactured and sold by Software Development Co., Ltd., Japan), DNASIS (ver. 3.7) (manufactured and sold by Hitachi Software Engineering Co., Ltd., Japan), FASTA (http://www.ddjb.nig.ac.jp/), and BLAST (http://www.ncbi.nlm.nih.gov/) can be used. Whether or not a sample varicella vaccine virus has a specific nucleotide sequence of the attenuated varicella Oka strain disclosed in the present specification can be determined by a homology search.

Confirmation of a nucleotide mutation by an RFLP analysis: In addition to the homology search conducted after determining the (whole or partial) nucleotide sequence of the genomic DNA of a sample virus, an RFLP (Restriction Fragment Length Polymorphism) analysis can be conducted to confirm that the unique nucleotides of the attenuated Oka strain are conserved by the sample virus without suffering mutation. Specifically, polynucleotide strands consisting of contiguous sequences of about 15 to 30 nucleotides which correspond to the 5'-terminal sequence of the sense and antisense sequences of the desired region are prepared by a DNA synthesizer, and the prepared polynucleotide strands are used as a pair of PCR primers. A pair of PCR primers are simultaneously used for amplifying the desired region to be used as a sample DNA. Thus obtained sample DNA is digested with a restriction enzyme and applied to a gel electrophoresis. The presence of a mutation can be determined by the difference in the size of the detected DNA fragments. The RFLP analysis which is easier to perform than the homology search is preferably used in the method for the quality control of the present invention. With respect to the 9 specific nucleotide mutations of the attenuated Oka strain which show the XXY pattern and are nonsynonymous substitutions (the 5,745th G, the 105,356th C, the 105,544th G, the 106,262nd C, the 107,252nd C, the 122,645th G, the 123,635th G, the 124,353rd C and the 124,541st G), and the 560th C, the 26,125th G, the 94,167th C, the 105,705th C, the 107,136th C, the 108,111st C, the 121,786th G, the 122,761st G and the 124,192nd G among the remaining 49 nucleotide mutations of the attenuated Oka strain, the presence or the absence of the mutations can be determined by the RFLP analysis using the eight primer pairs shown in Table 8 (SEQ ID NOs: 3 to 18). The restriction sites of the PCR products obtained by using the PCR primers shown in Table 8 are summarized in Table 9, together with the sizes of the restriction fragments. For example, the mutation of gene 6 (the 5,745th nucleotide G found in gene 6 of the attenuated Oka strain) can be detected by the absence or presence of the restriction enzyme Alu I site. Specifically, 763 bp DNA fragment corresponding to the 5,372nd to 6,134th nucleotides of the genomic DNA of a sample varicella vaccine virus is amplified using the primers 01-N12 and 01-R13 shown in Table 8. The amplified fragment is digested with Alu I and applied to an agarose gel electrophoresis. In the case of a virulent strain, the PCR product is cleaved into three fragments (170 bp, 205 bp and 388 bp). On the other hand, the PCR product of the attenuated Oka strain is cleaved into two fragments (170 bp and 593 bp). Therefore, whether or not a sample varicella vaccine virus is a virus capable of functioning as a vaccine strain can be determined from the restriction-fragment pattern.

In the present invention, the 9 unique nucleotide mutations of the attenuated Oka strain which show the XXY pattern and are nonsynonymous substitutions are preferably confirmed by the RFLP analysis using the following primers: a pair of primers of SEQ ID NOs: 5 and 6 with respect to the confirmation of the 5,745th G; a pair of primers of SEQ ID NOs: 11 and 12 with respect to the confirmation of the 105,356th C, the 105,544th G, the 124,353rd C and the 124,541st G; a pair of primers of SEQ ID NOs: 13 and 14 with respect to the confirmation of the 106,262nd C and the 123,635th G; and a pair of primers of SEQ ID NOs: 15 and 16 with respect to the confirmation of the 107,252nd C and the 122,645th G. Since gene 62 and gene 71 are inverted repeats (see FIG. 1), the quality control of an attenuated varicella live vaccine can be conducted by confirming the conservation of at least 5 nucleotides (namely 1 nucleotide of gene 6 and 4 nucleotides of gene 62) by the RFLP analysis.

As mentioned above, the whole genomic DNA sequence of the attenuated Oka strain (SEQ ID NO:2) and the nucleotide mutations which are unique to the attenuated Oka strain have been disclosed for the first time by the present inventors. Since the unique nucleotide mutations of the attenuated Oka strain are considered to be very important for the attenuation of a varicella viruses, an attenuated strain can be constructed by introducing a nucleotide substitution to a genomic DNA of a virulent strain (for example a wild type VZV strain or an epidemic strain), or by inducing an amino acid mutation in a virulent strain. The method described in Proc. Natl. Acad. Sci., USA, 90(15), 7376–7380, 1998 can be used as a genetic engineering technique for inducing a nucleotide or amino acid mutation. Specifically, the 58 nucleotide mutations which are unique to the attenuated Oka strain can be used as an index for inducing a mutation to a virulent strain, and the 9 nucleotide substitutions which are nonsynonymous substitutions are especially useful. In addition, taking into account the fact that gene 62 and gene 71 are contained in the inverted repeats (see FIG. 1), among the above-mentioned nucleotide substitutions, at least 5 nucleotide mutations (namely a mutation found in gene 6 and the mutations found in either gene 62 or gene 71) are considered to be very important.

BEST MODE FOR CARRYING OUT THE INVENTION

Hereinbelow, the present invention will be described in more detail with reference to the following Examples, but they should not be construed as limiting the scope of the present invention.

Example 1

The attenuated Oka strain (attenuated vaccine strain) and its parental strain (parental Oka strain; a virulent strain which is not attenuated) were individually inoculated into MRC-5 cells to thereby obtain infected cells. The genomic DNAs of the attenuated Oka strain and the parental Oka strain were extracted individually from the infected cells by phenol extraction and chloroform/isoamyl alcohol extraction, and purified by ethanol precipitation, thereby obtaining DNA. PCR products covering the entire genome of each strain were prepared using the obtained DNA as a template and 88 synthetic primers (44 primer pairs). Subsequently, the nucleotide sequences of the PCR products were determined by the direct DNA sequencing method using 520 synthetic primers and the DNA Sequencing Kit (manufactured and sold by Perkin Elmer Applied Biosystems, USA). Using the whole genomic sequence of the Dumas strain (virulent strain) shown in SEQ ID NO: 1 as a standard, the homology search was conducted with respect to the obtained whole genomic DNA sequences of the attenuated Oka strain and the parental Oka strain. DNASIS (version 3.7) (manufactured and sold by Hitachi Software Engineering Co., Ltd., Japan) was used for conducting the homology search. The characteristics of the attenuated Oka strain which became apparent from the homology search are summarized in Tables 1 to 7.

The nucleotide mutations which were detected by comparing the sequences among the three varicella strains (Dumas strain, parental Oka strain and attenuated Oka strain) are listed in Table 1. Specifically, the nucleotide number, the gene number, the mutated nucleotide and the amino acid mutation caused by the nucleotide mutation are described for each nucleotide mutation. In Table 1, Y represents a pyrimidine base (i.e., C or T), R represents a purine base (i.e., A or G), K represents G or T, (ncr) represents a noncoding region, an alphabet letter in parentheses (for example "(W)") is a one-letter abbreviation of an amino acid, (och) represents ochre codon, (amb) represents amber codon, (W/R) represents tryptophan (W) or arginine (R), and (del) represents deletion.

Among the mutations listed in Table 1, the mutations which were detected by the sequence alignment between the attenuated Oka strain and the parental Oka strain are listed in Table 2. Specifically, the nucleotide number, the gene number, the mutated nucleotide and the amino acid mutation caused by the nucleotide mutation are described for each nucleotide mutation. In Table 2, X/Y represents X or Y, and a three-letter abbreviation of an amino acid encoded by a nucleotide is shown in parentheses following the nucleotide (when a nucleotide is located in a noncoding region, the nucleotide is followed by "(ncr)"). All other abbreviations used in Table 2 are the same as those used in Table 1.

The nucleotide mutations described in Tables 1 and 2 are summarized in Table 3, based on the mutation patterns. The mutation patterns and abundance thereof are listed together with the details of the mutation patterns, that is, the specific types of mutation (a stop codon (och/amb) mutation, a synonymous or nonsynonymous substitution, and deletion (or addition)) and the abundance of each type of mutation.

The findings based on Tables 1 to 3 are explained in detail below.

Among the major nucleotide and amino acid mutations which were determined by the comparison between the whole genomic DNA sequences of the attenuated Oka strain and the parental Oka strain, the mutations described in the following items (a) to (f) were found to be especially useful and important for the quality control of an attenuated varicella live vaccine.

(a) There were 58 important nucleotide mutations of the attenuated Oka strain, namely 18 nucleotide mutations showing the XXY pattern and 40 nucleotide mutations showing the XX(X/Y) pattern.

(b) Among the above-mentioned 58 mutations, 49 mutations were found in the coding regions, 8 mutations were found in the noncoding regions and 1 mutation was found in a stop codon.

(c) Among the 49 mutations found in the coding regions, 29 mutations were nonsynonymous substitutions and 20 mutations were synonymous substitutions.

(d) Among the 18 mutations showing the XXY pattern, 9 mutations were nonsynonymous substitutions, 8 mutations were synonymous substitutions, and 1 mutation was found in a noncoding region.

(e) The above-mentioned 9 mutations showing the XXY pattern which are nonsynonymous substitutions (namely the 5,745th nucleotide G of gene 6; the 105,356th nucleotide C, the 105,544th nucleotide G, the 106,262nd nucleotide C and the 107,252nd nucleotide C of gene 62; and the 122,645th nucleotide G, the 123,635th nucleotide G, the 124,353rd nucleotide C and the 124,541st nucleotide G of gene 71) can be used as markers for the attenuation or safety of a virus strain capable of functioning as an active ingredient of a live vaccine. Therefore, these nucleotide mutations are useful and important for the quality control of a vaccine. It should be noted that gene 62 and gene 71 are contained in the inverted repeats (see FIG. 1).

(f) 40 nucleotides of the vaccine strain showed the XX(X/Y) pattern (that is, a mutation pattern wherein the virus strain is a mixture of a virus having nucleotide X and a virus having nucleotide Y). When the attenuated Oka strain was subcultured experimentally (i.e., the virus was passaged 5 times, 10 times, 17 times and the like), all the nucleotides of the XX(X/Y) pattern, except for the 106,710th nucleotide, showed the following tendency. The detection frequency of nucleotide Y increased in accordance with the number of passages (that is, the nucleotide changed from X/Y to Y) and the mutation pattern of the nucleotide converged to the XXY pattern. In other words, the ratio of X to Y (x/y) decreased in accordance with the number of passages. Based on the above-mentioned phenomenon, it is considered that the number of passages of a seed virus used in a seed lot system can be estimated by measuring the x/y value. It should be noted that among the above-mentioned mutations, 20 mutations converged to nonsynonymous substitutions. With respect to the remainder of the mutations, 12 mutations were synonymous substitutions, 1 mutation was found in a stop codon (specifically, an ochre codon/amber codon mixture converged to an amber mutation), and 7 mutations were found in the noncoding regions.

TABLE 1

| Nucleotide no. | Gene no. | Dumas | strain | Parental Oka strain | Attenuated Oka strain |
|---|---|---|---|---|---|
| 1 | 5'/gene 1 | A | (ncr) | G (ncr) | G (ncr) |
| 3 | 5'/gene 1 | G | (nor) | C (ncr) | C (ncr) |
| 117 | 5'/gene 1 | C | (ncr) | del | del |

TABLE 1-continued

| Nucleotide no. | Gene no. | Dumas | strain | Parental Oka strain | Attenuated Oka strain |
|---|---|---|---|---|---|
| 236 | 5'/gene 1 | A | (ncr) | G (ncr) | G (ncr) |
| 262 | 5'/gene 1 | C | (ncr) | T (ncr) | T (ncr) |
| 560 | 5'/gene 1 | T | (ncr) | T (ncr) | C (ncr) |
| 685 | gene 1 | G | (N) | A (N) | A (N) |
| 703 | gene 1 | T | (Q) | T (Q) | Y (Q) |
| 763 | gene 1 | T | (P) | T (P) | Y (P) |
| 789 | gene 1 | T | (T) | C (A) | C (A) |
| 790–1 | gene 1 | TT | (Q) | CC (R) | CC (R) |
| 2515 | gene 3/4 | T | (ncr) | T (ncr) | Y (ncr) |
| 3764 | gene 4 | A | (T) | G (T) | G (T) |
| 4258 | gene 5 | C | (K) | T (K) | T (K) |
| 5745 | gene 6 | A | (S) | A (S) | G (P) |
| 6853 | gene 6 | G | (H) | T (Q) | T (Q) |
| 7091 | gene 6 | C | (G) | A (V) | A (V) |
| 7753 | gene 6 | C | (P) | T (P) | T (P) |
| 9460 | gene 7/8 | T | (ncr) | C (ncr) | C (ncr) |
| 10079 | gene 8 | G | (P) | A (S) | A (S) |
| 10900 | gene 9A | T | (W) | T (W) | Y (W/R) |
| 11890 | gene 9 | T | (S) | G (S) | G (S) |
| 11906 | gene 9 | A | (T) | G (A) | G (A) |
| 12188 | gene 10 | C | (P) | A (H) | A (H) |
| 12284 | gene 10 | T | (F) | C (S) | C (S) |
| 12285 | gene 10 | T | (F) | C (S) | C (S) |
| 12779 | gene 10 | C | (A) | C (A) | Y (A/V) |
| 13173 | gene 10 | T | (G) | G (G) | G (G) |
| 13407 | gene 10/11 | G | (ncr) | A (ncr) | A (ncr) |
| 14390 | gene 11 | T | (C) | C (C) | C (C) |
| 17404 | gene 12 | C | (V) | T (V) | T (V) |
| 17834 | gene 12 | C | (L) | T (L) | T (L) |
| 18082 | gene 12 | C | (T) | T (T) | T (T) |
| 18467 | gene 13 | G | (K) | A (K) | A (K) |
| 19431 | gene 14 | T | (o) | T (o) | Y (o/a) |
| 19719 | gene 14 | A | (I) | G (I) | G (I) |
| 20656 | gene 14 | T | (Y) | A (F) | A (F) |
| 20684 | gene 14 | T | (T) | C (A) | C (A) |
| 21371 | gene 15 | G | (L) | A (L) | A (L) |
| 21734 | gene 15 | G | (R) | T (R) | T (R) |
| 22311 | gene 15 | G | (S) | A (S) | A (S) |
| 22504 | gene 15/16 | A | (ncr) | G (ncr) | G (ncr) |
| 22794 | gene 16 | A | (M) | G (T) | G (T) |
| 23294 | gene 16 | A | (F) | G (F) | G (F) |
| 24515–7 | gene 17 | TCA | (S) | del | del |
| 24578 | gene 17 | A | (T) | G (A) | G (A) |
| 24654 | gene 17 | C | (T) | T (M) | T (M) |
| 25067 | gene 17 | G | (V) | A (I) | A (I) |
| 26125 | gene 18 | A | (N) | A (N) | G (N) |
| 27523 | gene 19 | A | (H) | G (H) | G (H) |
| 29201 | gene 20 | T | (G) | C (G) | G (G) |
| 31732 | gene 21 | C | (T) | C (T) | Y (T/I) |
| 32274 | gene 21 | A | (T) | G (A) | G (A) |
| 33722 | gene 21 | T | (H) | C (H) | C (H) |
| 33725 | gene 21 | T | (D) | C (D) | C (D) |
| 33728 | gene 21 | T | (N) | C (N) | C (N) |
| 35543 | gene 22 | T | (V) | C (V) | C (V) |
| 37649 | gene 22 | A | (L) | G (L) | G (L) |
| 37902 | gene 22 | A | (I) | G (V) | G (V) |
| 38036 | gene 22 | T | (T) | T (T) | Y (T) |
| 38055 | gene 22 | T | (V) | C (H) | C (H) |
| 38081 | gene 22 | A | (P) | C (P) | C (P) |
| 38177 | gene 22 | G | (E) | A (E) | A (E) |
| 38714 | gene 22 | G | (T) | T (T) | T (T) |
| 38717 | gene 22 | C | (A) | T (A) | T (A) |
| 39023 | gene 22 | A | (R) | G (R) | G (R) |
| 39227 | gene 22 | T | (P) | T (P) | K (P) |
| 39263 | gene 22 | G | (Q) | A (Q) | A (Q) |
| 39394 | gene 22 | G | (R) | A (H) | A (H) |
| 39530 | gene 22 | A | (V) | G (V) | G (V) |
| 40388 | gene 22 | A | (Q) | G (Q) | G (Q) |
| 41057 | gene 22 | T | (P) | C (P) | C (P) |
| 41452 | gene 22 | G | (R) | A (Q) | A (Q) |
| 41618 | gene 22 | C | (T) | T (T) | T (T) |
| 41764 | gene 22 | G | (S) | A (N) | A (N) |
| 42069 | gene 22 | C | (Q) | G (E) | G (E) |
| 42176 | gene 22 | C | (R) | T (R) | T (R) |
| 42242 | gene 22 | A | (A) | C (A) | C (A) |
| 42401–3 | gene 22/23 | AAA | (ncr) | del | del |
| 42476 | gene 23 | T | (S) | G (S) | G (S) |

TABLE 1-continued

| Nucleotide no. | Gene no. | Dumas | strain | Parental Oka strain | Attenuated Oka strain |
| --- | --- | --- | --- | --- | --- |
| 43262 | gene 24 | T | (I) | C (V) | C (V) |
| 44835 | gene 26 | C | (C) | T (C) | T (C) |
| 47162 | gene 28 | A | (C) | G (R) | G (R) |
| 47940 | gene 28 | C | (L) | T (L) | T (L) |
| 48050 | gene 28 | T | (S) | C (G) | C (G) |
| 48825 | gene 28 | G | (T) | A (T) | A (T) |
| 49535 | gene 28 | G | (L) | A (L) | A (L) |
| 50081 | gene 28 | C | (G) | A (C) | A (C) |
| 51168 | gene 29 | C | (S) | T (S) | T (S) |
| 52917 | gene 29 | A | (Q) | G (Q) | G (Q) |
| 53482 | gene 29 | A | (I) | C (L) | C (L) |
| 53938 | gene 29 | G | (A) | A (T) | A (T) |
| 54359–73 | gene 29 | AACATTTC AGGGTCA | (NISGS) | del | del |
| 54562 | gene 29/30 | T | (ncr) | del (ncr) | del (ncr) |
| 54564 | gene 29/30 | T | (ncr) | C (ncr) | C (ncr) |
| 55820 | gene 30 | A | (P) | G (P) | G (P) |
| 57224 | gene 31 | A | (T) | C (P) | C (P) |
| 57301 | gene 31 | A | (A) | C (A) | C (A) |
| 57397 | gene 31 | G | (A) | T (A) | T (A) |
| 58595 | gene 31 | A | (I) | A (I) | R (I/V) |
| 59287 | gene 31 | A | (P) | A (P) | R (P) |
| 59760–1 | gene 31/32 | del | (ncr) | G (ncr) | G (ncr) |
| 60276–8 | gene 32/33 | AAA | (ncr) | del | del |
| 60279 | gene 32/33 | A | (ncr) | C (ncr) | C (ncr) |
| 60405 | gene 33 | C | (A) | A (A) | A (A) |
| 60781 | gene 33 | T | (Y) | G (S) | G (S) |
| 61018–9 | gene 33 | GG | (P) | AA (F) | AA (F) |
| 61201–2 | gene 33 | TT | (N) | CC (G) | CC (G) |
| 64067 | gene 35 | A | (A) | A (A) | R (A) |
| 64136 | gene 35 | A | (C) | G (C) | G (C) |
| 64259 | gene 35 | T | (P) | C (P) | C (P) |
| 64375 | gene 35 | T | (M) | C (V) | C (V) |
| 64989 | gene 36 | C | (A) | T (A) | T (A) |
| 65669 | gene 36 | C | (S) | T (L) | T (L) |
| 66646 | gene 37 | G | (L) | T (L) | T (L) |
| 66879 | gene 37 | C | (P) | T (L) | T (L) |
| 68172 | gene 37 | G | (R) | A (K) | A (K) |
| 69349 | gene 38 | A | (T) | G (T) | G (T) |
| 69756 | gene 38 | T | (S) | C (G) | C (G) |
| 71252 | gene 39 | T | (M) | T (M) | Y (M/T) |
| 72997 | gene 40 | C | (V) | T (V) | T (V) |
| 73993 | gene 40 | T | (T) | C (T) | C (T) |
| 76530 | gene 41 | C | (V) | T (V) | T (V) |
| 78144 | gene 42/43 | T | (ncr) | del | del |
| 80244 | gene 43/44 | G | (ncr) | T (ncr) | T (ncr) |
| 80840 | gene 44 | A | (N) | G (D) | G (D) |
| 81187 | gene 44 | C | (A) | T (A) | T (A) |
| 82225 | gene 45 | A | (P) | A (P) | R (P) |
| 84091 | gene 47 | G | (E) | G (E) | R (E) |
| 84616 | gene 47 | A | (T) | G (T) | G (T) |
| 84983 | gene 48 | G | (R) | A (H) | A (H) |
| 85563 | gene 48 | C | (D) | T (D) | T (D) |
| 86170 | gene 48 | C | (Q) | A (K) | A (K) |
| 86484–93 | gene 49/50 | CCTGATAA AC | (ncr) | del (ncr) | del (ncr) |
| 86556 | gene 49/50 | T | (ncr) | G (ncr) | G (ncr) |
| 87280 | gene 50 | A | (C) | A (C) | R (C) |
| 87306 | gene 50 | T | (S) | T (S) | Y (S/G) |
| 87841 | gene 50 | C | (S) | T (S) | T (S) |
| 88477 | gene 51 | G | (S) | T (S) | T (S) |
| 89734 | gene 51 | A | (T) | A (T) | R (T) |
| 89905 | gene 51 | T | (T) | C (T) | C (T) |
| 90202 | gene 51 | G | (Q) | T (H) | T (H) |
| 90217 | gene 51 | T | (S) | C (S) | C (S) |
| 90392 | gene 51/52 | G | (ncr) | A (ncr) | A (ncr) |
| 90535 | gene 52 | A | (I) | A (I) | R (I/V) |
| 91191 | gene 52 | C | (G) | T (G) | T (G) |
| 92026 | gene 52 | A | (T) | G (A) | G (A) |
| 92092 | gene 52 | A | (T) | G (A) | G (A) |
| 92375 | gene 52 | A | (H) | G (R) | G (R) |
| 92999 | gene 53 | T | (V) | C (V) | C (V) |
| 94167 | gene 54 | T | (L) | T (L) | C (L) |
| 94632 | gene 54 | A | (V) | G (V) | G (V) |
| 94641 | gene 54 | A | (T) | T (T) | T (T) |
| 95241 | gene 54 | T | (G) | C (G) | C (G) |
| 95546 | gene 54 | G | (L) | A (L) | A (L) |

TABLE 1-continued

| Nucleotide no. | Gene no. | Dumas | strain | Parental Oka strain | Attenuated Oka strain |
|---|---|---|---|---|---|
| 95601 | gene 54 | T | (E) | G (D) | G (D) |
| 97141 | gene 55 | T | (L) | C (L) | C (L) |
| 97591 | gene 55 | C | (I) | T (I) | T (I) |
| 97748 | gene 55 | G | (A) | G (A) | R (A/T) |
| 97796 | gene 55 | T | (C) | T (C) | Y (C/R) |
| 98437 | gene 55 | T | (G) | C (G) | C (G) |
| 98765 | gene 56 | A | (V) | C (V) | C (V) |
| 98807 | gene 56 | A | (T) | C (T) | C (T) |
| 99226–8 | gene 56 | CTT | (S) | del | del |
| 99421 | gene 57 | T | (H) | G (P) | G (P) |
| 99709 | gene 57 | A | (Y) | G (Y) | G (Y) |
| 99981 | gene 58 | C | (V) | T (K) | T (K) |
| 100114 | gene 58 | T | (K) | A (N) | A (N) |
| 100151 | gene 58 | T | (N) | G (T) | G (T) |
| 100283 | gene 58/59 | A | (ncr) | G (ncr) | G (ncr) |
| 101089 | gene 59 | A | (L) | A (L) | R (L/P) |
| 101331 | gene 60 | C | (A) | T (T) | T (T) |
| 101623–4 | gene 60 | del | | ATC (H) | ATC (H) |
| 101886 | gene 60/61 | T | (ncr) | C (ncr) | C (ncr) |
| 101991 | gene 60/61 | C | (ncr) | T (ncr) | T (ncr) |
| 102192 | gene 60/61 | G | (ncr) | A (ncr) | A (ncr) |
| 102203 | gene 60/61 | A | (ncr) | G (ncr) | G (ncr) |
| 102309 | gene 6o/61 | C | (ncr) | A (ncr) | A (ncr) |
| 102351 | gene 60/61 | A | (ncr) | C (ncr) | C (ncr) |
| 102458 | gene 60/61 | A | (ncr) | G (ncr) | G (ncr) |
| 102601 | gene 60/61 | T | (ncr) | G (ncr) | G (ncr) |
| 103043 | gene 60/61 | T | (ncr) | C (ncr) | C (ncr) |
| 104898 | gene 61/62 | A | (ncr) | G (ncr) | G (ncr) |
| 105009–10 | gene 61/62 | del | | G (ncr) | G (ncr) |
| 105012 | gene 61/62 | T | (ncr) | C (ncr) | C (ncr) |
| 105015 | gene 61/62 | T | (ncr) | C (ncr) | C (ncr) |
| 105017 | gene 61/62 | T | (ncr) | C (ncr) | C (ncr) |
| 105054 | gene 61/62 | G | (ncr) | del | del |
| 105071 | gene 61/62 | G | (ncr) | del | del |
| 105151–2 | gene 61/62 | del | (ncr) | ACAA (ncr) | ACAA (ncr) |
| 105169 | gene 61/62 | A | (ncr) | A (ncr) | R (ncr) |
| 105310 | gene 62 | A | (L) | A (L) | R (L/S) |
| 105312 | gene 62 | A | (G) | G (G) | G (G) |
| 105356 | gene 62 | T | (I) | T (I) | C (V) |
| 105451 | gene 62 | A | (L) | G (P) | G (P) |
| 105512 | gene 62 | A | (S) | C (A) | C (A) |
| 105544 | gene 62 | A | (V) | A (V) | G (A) |
| 105705 | gene 62 | T | (A) | T (A) | C (A) |
| 106262 | gene 62 | T | (R) | T (R) | C (G) |
| 106710 | gene 62 | A | (A) | A (A) | R (A) |
| 107136 | gene 62 | T | (A) | T (A) | C (A) |
| 107165 | gene 62 | C | (A) | T (T) | T (T) |
| 107252 | gene 62 | T | (S) | T (S) | C (G) |
| 107307 | gene 62 | T | (R) | C (R) | C (R) |
| 107599 | gene 62 | A | (V) | A (V) | R (V/A) |
| 107607 | gene 62 | C | (T) | A (T) | A (T) |
| 107715 | gene 62 | T | (A) | C (A) | C (A) |
| 107797 | gene 62 | A | (L) | A (L) | R (L/P) |
| 108111 | gene 62 | T | (P) | T (P) | G (P) |
| 108747 | gene 62 | A | (L) | G (L) | G (L) |
| 108838 | gene 62 | A | (M) | A (M) | R (M/T) |
| 108951 | gene 62 | G | (H) | A (H) | A (H) |
| 109044 | gene 62 | C | (A) | G (A) | G (A) |
| 109137 | gene 62/63 | A | (ncr) | A (ncr) | R (ncr) |
| 109200 | gene 62/63 | A | (ncr) | A (ncr) | R (ncr) |
| 109654 | gene 62/63 | G | (ncr) | T (ncr) | T (ncr) |
| 109696–7 | gene 62/63 | del | | CAT (ncr) | CAT (ncr) |
| 110003 | gene 62/63 | G | (ncr) | A (ncr) | A (ncr) |
| 110058 | gene 62/63 | G | (ncr) | del | del |
| 110112 | gene 62/63 | G | (ncr) | A (ncr) | A (ncr) |
| 110378 | gene 62/63 | G | (ncr) | del | del |
| 110386 | gene 62/63 | C | (ncr) | del | del |
| 111312 | gene 63 | A | (T) | G (T) | G (T) |
| 111650 | gene 64 | A | (Q) | A (Q) | R (Q/R) |
| 112093 | gene 64 | T | (Y) | C (H) | C (H) |
| 112137 | gene 64/65 | A | (ncr) | del | del |
| 112198 | gene 64/65 | G | (ncr) | A (ncr) | A (ncr) |
| 114140 | gene 66 | A | (S) | G (S) | G (S) |
| 115041 | gene 67 | G | (P) | A (P) | A (P) |
| 115926 | gene 68 | C | (T) | T (I) | T (I) |
| 117699 | gene 68/69 | C | (ncr) | T (ncr) | T (ncr) |
| 117760 | gene 68/69 | T | (ncr) | del | del |

TABLE 1-continued

| Nucleotide no. | Gene no. | Dumas | strain | Parental Oka strain | Attenuated Oka strain |
|---|---|---|---|---|---|
| 117804 | gene 69 | A | (Y) | G (H) | G (H) |
| 118247 | gene 69 | T | (Q) | T (Q) | Y (Q/R) |
| 118585 | gene 70 | T | (T) | C (T) | C (T) |
| 119511 | gene 70/71 | G | (ncr) | del | del |
| 119519 | gene 70/71 | C | (ncr) | del | del |
| 119785 | gene 70/71 | C | (ncr) | T (ncr) | T (ncr) |
| 119839 | gene 70/71 | C | (ncr) | del | del |
| 119894 | gene 70/71 | C | (ncr) | T (ncr) | T (ncr) |
| 120200–1 | gene 70/71 | del | | ATG (ncr) | ATG (ncr) |
| 120243 | gene 70/71 | C | (ncr) | A (ncr) | A (ncr) |
| 120697 | gene 70/71 | T | (ncr) | T (ncr) | Y (ncr) |
| 120760 | gene 70/71 | T | (ncr) | T (ncr) | Y (ncr) |
| 120853 | gene 71 | G | (A) | C (A) | C (A) |
| 120946 | gene 71 | C | (H) | T (H) | T (H) |
| 121059 | gene 71 | T | (M) | T (M) | Y (M/T) |
| 121150 | gene 71 | T | (L) | C (L) | C (L) |
| 121786 | gene 71 | A | (P) | A (P) | G (P) |
| 122100 | gene 71 | T | (L) | T (L) | Y (L/P) |
| 122182 | gene 71 | A | (A) | G (A) | G (A) |
| 122290 | gene 71 | G | (T) | T (T) | T (T) |
| 122298 | gene 71 | T | (V) | T (V) | Y (V/A) |
| 122590 | gene 71 | A | (R) | G (R) | G (R) |
| 122645 | gene 71 | A | (S) | A (S) | G (G) |
| 122732 | gene 71 | G | (A) | A (T) | A (T) |
| 122761 | gene 71 | A | (A) | A (A) | G (A) |
| 123187 | gene 71 | T | (A) | T (A) | Y (A) |
| 123635 | gene 71 | A | (R) | A (R) | G (G) |
| 124192 | gene 71 | A | (A) | A (A) | G (A) |
| 124353 | gene 71 | T | (V) | T (V) | C (A) |
| 124385 | gene 71 | T | (S) | G (A) | G (A) |
| 124446 | gene 71 | T | (L) | C (P) | C (P) |
| 124541 | gene 71 | A | (I) | A (I) | G (V) |
| 124585 | gene 71 | T | (G) | C (G) | C (G) |
| 124587 | gene 71 | T | (L) | T (L) | Y (L/S) |
| 124728 | gene 71/3' | T | (ncr) | T (ncr) | Y (ncr) |
| 124745–6 | gene 71/3' | del | (ncr) | TTGT (ncr) | TTGT (ncr) |
| 124826 | gene 71/3' | C | (ncr) | del | del |
| 124843 | gene 71/3' | C | (ncr) | del | del |
| 124880 | gene 71/3' | A | (ncr) | G (ncr) | G (ncr) |
| 124882 | gene 71/3' | A | (ncr) | G (ncr) | G (ncr) |

TABLE 2

| Gene no. | Nucleotide no. | Attenuated Oka strain | Parental Oka strain | Dumas strain |
|---|---|---|---|---|
| 1 | 560 | C (ncr) | T (ncr) | T (ncr) |
| | 703 | T/C (Gln) | T (Gln) | T (Gln) |
| | 763 | T/C (Pro) | T (Pro) | T (Pro) |
| 3–4 | 2515 | T/C (ncr) | T (ncr) | T (ncr) |
| 6 | 5745 | G (Pro) | A (Ser) | A (Ser) |
| 9A | 10900 | T/C (Trp/Arg) | T (Trp) | T (Trp) |
| 10 | 12779 | C/T (Ala/Val) | C (Ala) | C (Ala) |
| 14 | 19431 | T/C (och/amb) | T (och) | T (och) |
| 18 | 26125 | G (Asn) | A (Asn) | A (Asn) |
| 21 | 31732 | C/T (Thr/Ile) | C (Thr) | C (Thr) |
| 22 | 38036 | T/C (Thr) | T (Thr) | T (Thr) |
| | 39227 | G/T (Pro) | T (Pro) | T (Pro) |
| 31 | 58595 | A/G (Ile/Val) | A (Ile) | A (Ile) |
| | 59287 | A/G (Pro) | A (Pro) | A (Pro) |
| 35 | 64067 | A/G (Ala) | A (Ala) | A (Ala) |
| 39 | 71252 | T/C (Met/Thr) | T (Met) | T (Met) |
| 45 | 82225 | A/G (Pro) | A (Pro) | A (Pro) |
| 47 | 84091 | A/G (Glu) | G (Glu) | G (Glu) |
| 50 | 87280 | A/G (Cys) | A (Cys) | A (Cys) |
| | 87306 | T/C (Ser/Gly) | T (Ser) | T (Ser) |
| 51 | 89734 | A/G (Thr) | A (Thr) | A (Thr) |
| 52 | 90535 | A/G (Ile/Val) | A (Ile) | A (Ile) |
| 54 | 94167 | C (Leu) | T (Leu) | T (Leu) |
| 55 | 97748 | G/A (Ala/Thr) | G (Ala) | G (Ala) |
| | 97796 | T/C (Cys/Arg) | T (Cys) | T (Cys) |
| 59 | 101089 | A/G (Leu/Pro) | A (Leu) | A (Leu) |
| 61–62 | 105169 | A/G (ncr) | A (ncr) | A (ncr) |

TABLE 2-continued

| Gene no. | Nucleotide no. | Attenuated Oka strain | Parental Oka strain | Dumas strain |
|---|---|---|---|---|
| 62 | 105310 | A/G (Leu/Ser) | A (Leu) | A (Leu) |
| | 105356 | C (Val) | T (Ile) | T (Ile) |
| | 105544 | G (Ala) | A (Val) | A (Val) |
| | 105705 | C (Ala) | T (Ala) | T (Ala) |
| | 106262 | C (Gly) | T (Arg) | T (Arg) |
| | 106710 | A/G (Ala) | A (Ala) | A (Ala) |
| | 107136 | C (Ala) | T (Ala) | T (Ala) |
| | 107252 | C (Gly) | T (Ser) | T (Ser) |
| | 107599 | A/C (Val/Ala) | A (Val) | A (Val) |
| | 107797 | A/G (Leu/Pro) | A (Leu) | A (Leu) |
| | 108111 | C (Pro) | T (Pro) | T (Pro) |
| | 108838 | A/G (Met/Thr) | A (Met) | A (Met) |
| 62–63 | 109137 | A/G (ncr) | A (ncr) | A (ncr) |
| | 109200 | A/G (ncr) | A (ncr) | A (ncr) |
| 64 | 111650 | A/G (Gln/Arg) | A (Gln) | A (Gln) |
| 69 | 118247 | T/C (Gln/Arg) | T (Gln) | T (Gln) |
| 70–71 | 120697 | T/C (ncr) | T (ncr) | T (ncr) |
| | 120760 | T/C (ncr) | T (ncr) | T (ncr) |
| 71 | 121059 | T/C (Met/Thr) | T (Met) | T (Met) |
| | 121786 | G (Pro) | A (Pro) | A (Pro) |
| | 122100 | T/C (Leu/Pro) | T (Leu) | T (Leu) |
| | 122298 | T/C (Val/Ala) | T (Val) | T (Val) |
| | 122645 | G (Gly) | A (Ser) | A (Ser) |
| | 122761 | G (Ala) | A (Ala) | A (Ala) |
| | 123187 | T/C (Ala) | T (Ala) | T (Ala) |
| | 123635 | G (Gly) | A (Arg) | A (Arg) |
| | 124192 | G (Ala) | A (Ala) | A (Ala) |

TABLE 2-continued

| Gene no. | Nucleotide no. | Attenuated Oka strain | Parental Oka strain | Dumas strain |
|---|---|---|---|---|
| | 124353 | C (Ala) | T (Val) | T (Val) |
| | 124541 | G (Val) | A (Ile) | A (Ile) |
| | 124587 | T/C (Leu/Ser) | T (Leu) | T (Leu) |
| 71-3' | 124728 | T/C (ncr) | T (ncr) | T (ncr) |

ncr: noncoding region
X/Y: X or Y
och/amb: stop codon mutation of an ochre codon or an amber codon

TABLE 3

| Pattern of nucleotide mutation | Dumas strain | Parental Oka strain | Attenuated Oka strain | Amino acid replacement | Number of nucleotides |
|---|---|---|---|---|---|
| XXX pattern | ○ | ○ | ○ | | 124,585 |
| XYY pattern | ○ | ● | ● | | 189 |
| | | | | Synonymous | 91 |
| | | | | Nonsynonymous | 62 |
| | | | | ncr | 36 |
| XXY pattern | ○ | ○ | ● | | 18 |
| | | | | Synonymous | 8 |
| | | | | Nonsynonymous | 9 |
| | | | | ncr | 1 |
| XX(X/Y) pattern | ○ | ○ | ○/● | | 40 |
| | | | | Synonymous | 12 |
| | | | | Nonsynonymous | 20 |
| | | | | ncr | 7 |
| | | | | och/amb | 1 |
| XYX pattern | ○ | ● | ○ | | 0 |
| XYZ pattern | ○ | ● | ◆ | | 0 |
| XDD pattern | ○ | del | del | | 52 |
| DXX pattern | del | ○ | ○ | | 19 |

XXX pattern: All three starins have the same nucleotide at anucleotide number which corresponds to the same nuclotide site (i.e. “corresponding nucleotide number”).
XYY pattern: Only the Dumas strain has a different nucleotide at the corresponding nucleotide number.
XXY pattern: Only the attenuated Oka strain has a different nucleotide at the corresponding nucleotide number.
XX(X/Y) pattern: Only the attenuated Oka strain has a nucleotide X/Y (X or Y) at the corresponding nucleotide number. Therefore, the attenuated Oka strain is a mixture of the XXX and XXY patterns. For example , with respect to the 8 mutations showing the XX(X/Y) pattern which are located in gene 62, the ratio of x to y (x/y) transiently decreased as the number of passages increased from 5 times, 10 times to 17 times, and the mutation pattern converged to the XXY pattern. However, only the 106,710th nucleotide A/G remained unchanged without converging from A to G.
XYX pattern: Only the parental Oka strain has a different nucleotide at the corresponding nucleotide number.
XYZ pattern: All three strains have a different nucleotide at the corresponding nucleotide number.
XDD pattern: The nucleotide at the corresponding nucleotide number is either deleted (del) in both the parental Oka strain and the attenuated Oka strain, or added in only the Dumas strain.
DXX pattern: The nucleotide at the corresponding nucleotide number is either deleted (del) in only the Dumas strain, or added in both the parental Oka strain and the attenuated Oka strain.
ncr: noncoding region
och/amb: stop codon mutation of an ochre codon or an amber codon Table 4 shows the sequence alignment of the nucleotide sequences of the sense strand of the origin of replication of the Dumas strain, the parental Oka strain and the attenuated Oka strain. In this table, “-” represents a deletion.

In the attenuated Oka strain, deletions occur with respect to segments each having a nucleotide sequence of TATATATATATATA (SEQ ID NO:27) arranged in the direction of from the 5' end to the 3' end, which correspond to the 110,214th to 110,227th nucleotides of the sense strand of the genomic DNA of the Dumas strain of SEQ ID NO:1 and a segment corresponding to the 119,670th to 119,683rd nucleotides of the antisense strand of the genomic DNA of the Dumas strain. Therefore, taking into consideration the difference between the parental Oka strain and the attenuated Oka strain, it became apparent that the deletion with respect to segments ATATATATA at the 3' end is useful for the quality control of a vaccine.

TABLE 4

```
  110087
D G T A C G C C A A T C G G A T A C A C T C T T T
P G T A C G C C A A T C G G A T A C A C T C T T T
V G T A C G C C A A T C G G A T A C A C T C T T T
                                        T G A T C T
                                        T A A T C T
```

TABLE 4-continued

```
                                        T A A T C T

  110117
D G C A T T C G C A C T T C C C G T T T T T T C A
P G C A T T C G C A C T T C C C G T T T T T T C A
V G C A T T C G C A C T T C C C G T T T T T T C A
                                        C T G T A T
                                        C T G T A T
                                        C T G T A T

  110147
```

TABLE 4-continued

```
D   G G G T T T C A T T G T T T T G G C A T G T G T
P   G G G T T T C A T T G T T T T G G C A T G T G T
V   G G G T T T C A T T G T T T T G G C A T G T G T
                                        C C A A C C
                                        C C A A C C
                                        C C A A C C

    110177
D   A C C G T T C G C A C T T T C T T T C T A T A T
P   A C C G T T C G C A C T T T C T T T C T A T A T
V   A C C G T T C G C A C T T T C T T T C T A T A T
                                        A T A T A T
                                        A T A T A T
                                        A T A T A T

    110207
D   A T A T A T A T A T A T A T A T A T A T A G A G
P   A T A T A T A T A T A T A - - - - - - - - G A G
V   A T A T A T A - - - - - - - - - - - - - - G A G
                                        A A A G A G
                                        A G A G A G
                                        A G A G A G

    110237
D   A G A G A G - - - - - - - - - - - - - - T T T C
P   A G A G A G A G A G A G G G A G A G A G T T T C
V   A G A G A G A G A - - G G G A G A G A G T T T C
                                        T T G T T C
                                        T T G T T C
                                        T T G T T C

    110267
D   G C G C G T G T T C C C G C G A T G T C G C G G
P   G C G C G T G T T C C C G C G A T G T C G C G G
V   G C G C G T G T T C C C G C G A T G T C G C G G
                                        T T T T A T
                                        T T T T A T
                                        T T T T A T

    110297
D   G G G G T G T G G G C G G G C T T T T C A C A G
P   G G G G T G T G G G C G G G C T T T T C A C A G
V   G G G G T G T G G G C G G G C T T T T C A C A G
                                        A A T A T A
                                        A A T A T A
                                        A A T A T A

    110327
D   T A T A T T C C A A A T G G A G C G G C A G G C
P   T A T A T T C C A A A T G G A G C G G C A G G C
V   T A T A T T C C A A A T G G A G C G G C A G G C
                                        T T T T T A
                                        T T T T T A
                                        T T T T T A

    110357
D   A A A T C G A T T
P   A A A T C G A T T
V   A A A T C G A T T
```

D: Dumas strain (SEQ ID NO:28)
P: Parental Oka strain (SEQ ID NO:29)
V: Attenuated Oka strain (SEQ ID NO:30)

Table 5 shows the sequence alignment of the repetitive region R1 (in the direction of from the 5' end to the 3' end) of gene 11 of the Dumas strain, the parental Oka strain and the attenuated Oka strain.

Table 6 shows the sequence alignment of the repetitive region R3 (in the direction of from the 5' end to the 3' end) of gene 22 of the Dumas strain, the parental Oka strain and the attenuated Oka strain.

Table 7 shows the sequence alignment of the repetitive region R4 (in the direction of from the 5' end to the 3' end) of the Dumas strain, the parental Oka strain and the attenuated Oka strain.

As shown in Table 5, the repetitive sequences of whole R1 region of all three strains, namely the attenuated Oka strain, the parental Oka strain and the Dumas strain, are different from each other. Similarly, the repetitive sequences of whole R4 region of all three strains, namely the attenuated Oka strain, the parental Oka strain and the Dumas strain, are different from each other. Therefore, the repetitive sequence abbabba'bbb'abababx (SEQ ID NO:23) of R1 region (wherein, a represents a nucleotide sequence of GGACGCGATCGACGACGA (SEQ ID NO:19); a' represents a nucleotide sequence of GGACGCGATTGACGACGA (SEQ ID NO:20); b represents a nucleotide sequence of GGGAGAGGCGGAGGA (SEQ ID NO:21); b' represents a nucleotide sequence of GGACGCGGCGGAGGA (SEQ ID NO:22); and x represents a nucleotide sequence of GGA) and the repetitive sequence aaaaaaaaaaaax (SEQ ID NO:26) of R4 region (wherein, a represents a nucleotide sequence of CCCCGCCGATGGGGAGGGGGCGCGGTA (SEQ ID NO:24); and x represents a nucleotide sequence of CCCCGCCGATG (SEQ ID NO:25)) are unique to the attenuated varicella virus, and these sequences are useful for the quality control of an attenuated varicella live vaccine.

With respect to the sequences of the repetitive region R3 of gene 22 which are shown in Table 6, the sequences were diverse among the clones of the attenuated Oka strain and the parental Oka strain. Therefore, no unique sequence was found in the attenuated Oka strain.

TABLE 5

| R1 region (gene 11) | |
|---|---|
| | (SEQ ID NO:23) |
| Attenuated Oka strain | abbabba'bbb'abababx |
| | (SEQ ID NO:31) |
| Parental Oka strain | abbabba'bbb'ababx |
| | (SEQ ID NO:32) |
| Dumas strain | abbabba'bba'bbbbabb'abx |

a: GGACGCGATCGACGACGA (SEQ ID NO:19)
a': GGACGCGATTGACGACGA (SEQ ID NO:20)
b: GGGAGAGGCGGAGGA (SEQ ID NO:21)
b': GGACGCGGCGGAGGA (SEQ ID NO:22)
x: GGA

TABLE 6

| R3 region (gene 22) | | |
|---|---|---|
| Attenuated Oka strain | | |
| clone 1 | b'b'ab'b'ab'b'ab'ab'ab'ax | (SEQ ID NO:33) |
| clone 2 | b'b'ab'aab'ab'ax | (SEQ ID NO:34) |
| clone 3 | b'b'ab'aab'ab'ax | (SEQ ID NO:34) |
| clone 4 | b'b'ab'aab'ab'ax | (SEQ ID NO:34) |
| clone 5 | b'b'ab'ab'b'ab'ax | (SEQ ID NO:35) |
| clone 6 | b'b'ab'aab'ax | (SEQ ID NO:36) |
| clone 7 | b'b'ab'ax | (SEQ ID NO:37) |
| clone 8 | b'b'ab'ax | (SEQ ID NO:37) |
| clone 9 | b'b'ax | (SEQ ID NO:38) |
| clone 10 | b'b'ax | (SEQ ID NO:38) |
| Parental Oka strain | | |
| clone 1 | b'b'ab'aab'ab'ax | (SEQ ID NO:34) |
| clone 2 | b'b'ab'aab'ax | (SEQ ID NO:36) |
| clone 3 | b'b'ab'ab'ax | (SEQ ID NO:39) |
| clone 4 | b'b'ab'ax | (SEQ ID NO:37) |

TABLE 6-continued

| R3 region (gene 22) | |
|---|---|
| clone 5 b'b'ab'ax | (SEQ ID NO:37) |
| clone 6 b'b'ab'ax | (SEQ ID NO:37) |
| clone 7 b'b'ab'ax | (SEQ ID NO:37) |
| clone 8 b'b'ax | (SEQ ID NO:38) |
| clone 9 b'b'ax | (SEQ ID NO:38) |
| Dumas strain (SEQ ID NO:33) aaaaabax | |

a: GCCCGCGCA
b: GACCGTCCA
b': GCCCGTCCA
x: GGA

TABLE 7

| R4 region (noncoding region) | | |
|---|---|---|
| Attenuated Oka strain | aaaaaaaaaaaax | (SEQ ID NO:26) |
| Parental Oka strain | aaaaaaaaaaax | (SEQ ID NO:41) |
| Dumas strain | aaaaax | (SEQ ID NO:42) |

a: CCCCGCCGATGGGGAGGGGGCGCGGTA (SEQ ID NO:24)
x: CCCCGCCGATG (SEQ ID NO:25)

Example 2

The genomic DNA of each of the attenuated Oka strain, the parental Oka strain and the Kawaguchi strain (wild-type strain of a varicella virus) was individually prepared in the same manner as in Example 1.

Using the PCR primers 01-N12 (SEQ ID NO:5) and 01-R13 (SEQ ID NO:6) shown in Table 8, a region corresponding to a part of gene 6 (a region corresponding to the 5,372nd to 6,134th nucleotides of the Dumas strain) was amplified by PCR, thereby obtaining a PCR product. The obtained PCR product (763 bp) was digested with the restriction enzyme Alu I to thereby cleave the DNA into fragments, and the restriction-fragment pattern was determined by an RFLP analysis. Specifically, each of the PCR products of the attenuated Oka strain, the parental Oka strain and the Kawaguchi strain was digested with the restriction enzyme Alu I, thereby obtaining a DNA fragment mixture, and the obtained DNA fragment mixture was applied to 4.0% (w/v) agarose gel electrophoresis to determine the size of each DNA fragment.

Two fragments individually having a size of 170 bp and 593 bp were detected for the attenuated Oka strain. On the other hand, three fragments individually having a size of 170 bp, 205 bp and 388 bp were detected for the parental Oka strain and the Kawaguchi strain. These results show that the parental Oka strain and the Kawaguchi strain have the Alu I site located between the 205 bp fragment and the 388 bp fragment, but the attenuated Oka strain does not have this restriction site. It was confirmed from these results that the mutation of the 5,745th nucleotide A in gene 6 can be confirmed by detecting the absence of the Alu I site.

Example 3

54 epidemic varicella strains derived from the varicella patients and the zoster patients were individually subjected to an RFLP analysis. Specifically, the difference in a restriction-fragment pattern obtained by digesting a PCR product with the restriction enzyme Alu I was determined by an RFLP analysis in the same manner as in Example 2. As a result, it was found that the PCR products of all epidemic strains were cleaved into three fragments individually having a size of 170 bp, 205 bp and 388 bp. Such a restriction-fragment pattern was the same as that of the parental Oka strain obtained in Example 2 above.

Example 4

Figure 2:
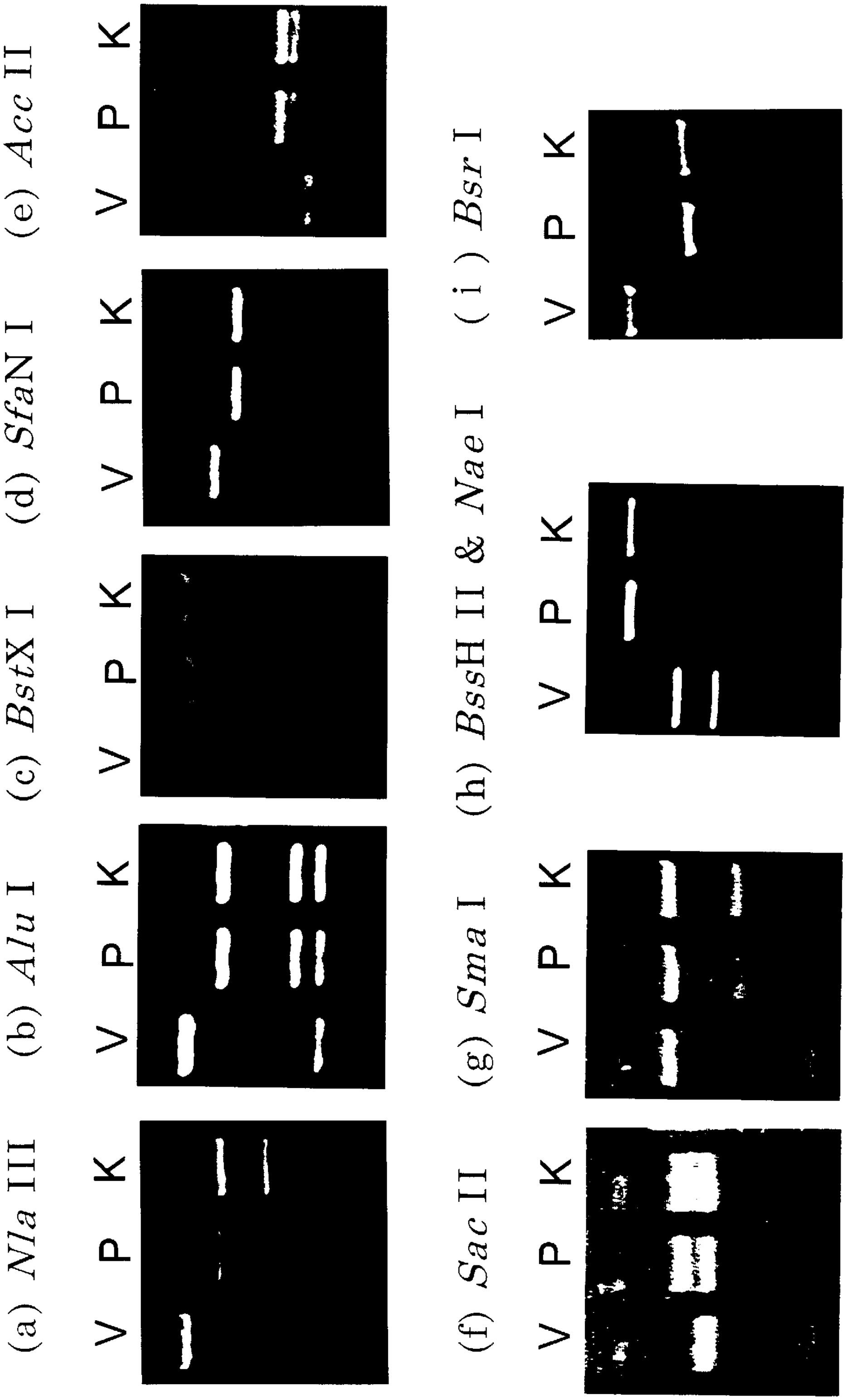
FIG. 2 shows the electropherograms which are the results of the RFLP analyses conducted in Example 4, wherein, the restriction enzymes used for treating the PCR products are as follows.

The primers shown in Table 8 (SEQ ID NOs: 3 to 6 and 9 to 18) and the restriction enzymes Nla III, Alu I, BstX I, SfaN I, Acc II, Sac II, Sma I, a combination of BssH II and Nae I, or Bsr I were used to conduct an RFLP analysis in the same manner as in Example 2. Specifically, the genomic DNAs of each of the attenuated Oka strain, the parental Oka strain and the Kawaguchi strain were individually prepared in the same manner as in Example 1. Next, a specific region of the genomic DNA was amplified using the PCR primers shown in Table 8 in a specific combination shown in Table 9. The resultant PCR product was digested with a restriction enzyme and applied to an agarose gel electrophoresis. The results are shown in FIG. 2. In addition, the restriction enzymes used for the RFLP analysis and the sizes of the restriction fragments are summarized in Table 9.

As is shown in FIG. 2 and Table 9, it became apparent that the numbers and sizes of the fragments resulting from the digestion of a PCR product of the attenuated Oka strain were different from those of the parental Oka strain and the Kawaguchi strain under all of the specific conditions employed for the RFLP analyses. Therefore, with respect to the 560th C, the 5,745th G, the 94,167th C, the 105;356th C (the 124,541st G), the 105,544th G (the 124,353rd C), the 105,705th C (the 124,192nd G), the 106,262nd C (the 123,635th G), the 107,136th C (the 122,761st G), the 107,252nd C (the 122,645th G), and the 108,111st C (the 121,786th G), the nucleotide mutations can be confirmed by an RFLP analysis without determining the nucleotide sequence of the genome.

TABLE 8

| Primer | Nucleotide sequence | Nucleotide No. | |
|---|---|---|---|
| 01-N01 | 5'-TCGTTTACTGCTC GGATGGCGACCG-3' | 158–172 | |
| 01-R02 | 5'-GTGTTTATGTATC AGCATACAGAGC-3' | 849–825 | |
| 01-N12 | 5'-ATTGTATGCATGC GATTGCTATCGC-3' | 5372–5396 | |
| 01-R13 | 5'-GGTCTTCCACTTT AAAGGGGTTTGC-3' | 6134–6110 | |
| 10-N29A | 5'-GAATCATTAGTAT ATATTTTTCTGC-3' | 26025–26049 | |
| 10-R30 | 5'-TGTTCAGAGGGGA TGAATCGTTGCG-3' | 26165–26141 | |
| 50-N15 | 5'-CGATCACGTCGCT CACATCCAACCC-3' | 93685–93709 | |
| 50-R17 | 5'-ATGGCAGAAGAAA CACGTATTGCCG-3' | 64457–64433 | |
| 60-N06 | 5'-GAGGACAACAGCT CCACCTTGACCG-3' | 105277–105301 | 124620–124596 |
| 60-R06 | 5'-GAGTAATGTGGCC GCCCGGTTTTGG-3' | 105613–105589 | 124284–124308 |
| 60-N26 | 5'-CCAAAACCGGGCG GCCACATTACTC-3' | 105589–105613 | 124308–124284 |
| 60-R28 | 5'-ATTACTGTCGACC CGAGACCTGGCC-3' | 106380–106356 | 123517–123541 |
| G62-N04 | 5'-GATCAAAGCTTAG CGCAG-3' | 106736–106753 | 123161–123144 |
| G62-R04 | 5'-CCTATAGCATGGC TCCAG-3' | 107499–107482 | 122398–122415 |

TABLE 8-continued

| Primer | Nucleotide sequence | Nucleotide No. | |
|---|---|---|---|
| 60-N11 | 5'-AAGGGCTTCCGTC GGGCATCATGAG-3' | 107729–107753 | 122168–122144 |
| 60-R12 | 5'-TCGGGTAAAAAGC CGGGCGATGAGC-3' | 108497–108473 | 121400–121424 |

TABLE 9

| PCR primer | Amplified fragmentary region (nucleotide no.) | Restriction enzyme | Restriction site (nucleotide no.) | | Detected mutation (nucleotide no.) | Size of restriction fragment (bp) |
|---|---|---|---|---|---|---|
| 01-N01 | 158–849 | Nla III | 560 | | 560 | V 692 |
| 01-R02 | | | | | | W 402 + 290 |
| 01-N12 | 5372–6134 | Alu I | 5542 | | 5745 | V 170 + 593 |
| 01-R13 | | | 5747 | | | W 170 + 205 + 388 |
| 10-N29R | 26025–26165 | Mae II | 26125 | | 26125 | V 100 + 6 + 35 |
| 10-R30 | | | 26131 | | | W 106 + 35 |
| 50-N15 | 93685–94457 | BstX I | 94172 | | 94167 | V 487 + 286 |
| 50-R17 | | | | | | W 773 |
| 60-N06 | 105277–105613 | SfaN I | 105347 | 124550 | 105356 | V 337 |
| 60-R06 | 124284–124620 | | | | 124541 | W 70 + 267 |
| | | Acc II | 105422 | 124475 | 105544 | V 145 + 123 + 39 + 30 |
| | | | 105545 | 124352 | 124353 | W 145 + 162 + 30 |
| | | | 105584 | 124313 | | |
| 60-N26 | 105589–106380 | Sac II | 105707 | 124190 | 105705 | V 118 + 338 + 336 |
| 60-R28 | 123517–124308 | | 106045 | 123852 | 124192 | W 456 + 336 |
| | | Sma I | 106072 | 123825 | 106262 | V 483 + 79 + 112 + 118 |
| | | | 106151 | 123746 | 123635 | W 483 + 79 + 230 |
| | | | 106263 | 123634 | | |
| G62-N04 | 106736–107499 | BssH II | 107136 | 122761 | 107136 | V 400 + 117 + 247 |
| G62-R04 | 122398–123161 | | | | 122761 | W 764 |
| | | Nae I | 107252 | 122645 | 107252 | |
| | | | | | 122645 | |
| 60-N11 | 107729–108497 | Bsr I | 108113 | 121784 | 108111 | V 769 |
| 60-R12 | 121400–122168 | | | | 121786 | W 384 + 385 |

V: Attenuated Oka strain
W: Wild-type strain (Virulent strain)

INDUSTRIAL APPLICABILITY

According to the method for quality control of the present invention, it has become possible to conduct an exact quality control and quality assurance of an attenuated varicella live vaccines, particularly with respect to the safety, effectiveness and uniformity of the vaccine. Further, the present invention provides exact and advantageous techniques which can be used for research in the field of epidemiology of varicella and zoster, including a tracing of the effects of vaccination, and these techniques may expedite and enhance the research. Consequently, the present invention provides an exact and very effective measure for preventing varicella and zoster, which contributes to the health of human beings.

What is claimed is:

1. A method for the quality control of an attenuated varicella live vaccine, which comprises subjecting the genomic DNA of a sample varicella vaccine virus to sequence analysis and confirming that the genomic DNA of said sample varicella vaccine virus conserves without suffering mutation the following 5 nucleotides:

the 5,745th G, the 105,356th C, the 105,544th G, the 106,262nd C and the 107,252nd C, wherein the nucleotide numbers are in accordance with the nucleotide numbering system of the nucleotide sequence of the genomic DNA of the varicella virus Dumas strain of SEQ ID NO: 1.

2. The method according to claim 1, wherein the conservation of said 5 nucleotides combination is confirmed by an RFLP analysis using the following primers:

a pair of primers of SEQ ID NOs: 5 and 6 with respect to the confirmation of the 5,745th G;

a pair of primers of SEQ ID NOs: 11 and 12 with respect to the confirmation of the 105,356th C and the 105,544th G;

a pair of primers of SEQ ID NOs: 13 and 14 with respect to the confirmation of the 106,262nd C; and a pair of primers of SEQ ID NOs: 15 and 16 with respect to the confirmation of the 107,252nd C.

3. The method according to claim 1, which further comprises confirming that the genomic DNA of said sample varicella vaccine virus conserves without suffering mutation the following 4 nucleotides:

the 122,645th G, the 123,635th G, the 124,353rd C and the 124,541st G, wherein the nucleotide numbers are in accordance with the nucleotide numbering system of the nucleotide sequence of the genomic DNA of the varicella virus Dumas strain of SEQ ID NO: 1.

4. The method according to claim 3, wherein the conservation of said 4 nucleotides is confirmed by an RFLP analysis using the following primers:

a pair of primers of SEQ ID NOs: 11 and 12 with respect to the confirmation of the 124,353rd C and the 124,541st G;

a pair of primers of SEQ ID NOs: 13 and 14 with respect to the confirmation of the 123,635th G; and a pair of primers of SEQ ID NOs: 15 and 16 with respect to the confirmation of the 122,645th G.

5. The method according to claim 1, which further comprises confirming that the genomic DNA of said sample varicella vaccine virus conserves without suffering mutation the following 49 nucleotides:

the 560th C, the 703rd Y, the 763rd Y, the 2,515th Y, the 10,900th Y, the 12,779 the Y, the 19,431st Y, the 26,125th G, the 31,732nd Y, the 38,036th Y, the 39,227th K, the 58,595th R, the 59,287th R, the 64,067th R, the 71,252nd Y, the 82,225th R, the 84,091st R, the 87,280th R, the 87,306th Y, the 89,734th R, the 90,535th R, the 94,167th C, the 97,748th R, the 97,796th Y, the 101,089th R, the 105,169th R, the 105,310th R, the 105,705th C, the 106,710th R, the 107,136th C, the 107,599th R, the 107,797th R, the 108,111st C, the 108,838th R, the 109,137th R, the 109,200th R, the 111,640th R, the 118,247th Y, the 120,697th Y, the 120,760th Y, the 121,059th Y, the 121,786th G, the 122,100th Y, the 122,298th Y, the 122,761st G, the 123,187th Y, the 124,192nd G, the 124,587th Y, and the 124,728th Y, wherein:

the nucleotide numbers are in accordance with the nucleotide numbering system of the nucleotide sequence of the genomic DNA of the varicella virus Dumas strain of SEQ ID NO: 1, R represents A or G, Y represents C or T, and K represents G or T.

6. The method according to claim 5, wherein the conservation of the 560th C, the 26,125th G, the 94,167th C, the 105,705th C, the 107,136th C, the 108,111st C, the 121,786th G, the 122,761st G and the 124,192nd G among said 49 nucleotides is confirmed by an RFLP analysis using the following primers:

a pair of primers of SEQ ID NOs: 3 and 4 with respect to the confirmation of the 560th C;

a pair of primers of SEQ ID NOs: 7 and 8 with respect to the confirmation of the 26,125th G;

a pair of primers of SEQ ID NOs: 9 and 10 with respect to the confirmation of the 94,167th C;

a pair of primers of SEQ ID NOs: 13 and 14 with respect to the confirmation of the 105,705th C and the 124,192nd G;

a pair of primers of SEQ ID NOs: 15 and 16 with respect to the confirmation of the 107,136th C and the 122,761st G; and a pair of primers of SEQ ID NOs: 17 and 18 with respect to the confirmation of the 108,111st C and the 121,786th G.

7. The method according to claim 1, which further comprises confirming deletion mutations in two origins of replication of the genomic DNA of said sample varicella vaccine virus, wherein each of said deletion mutations occurs with respect to the 133rd to 141st nucleotides of the origin of replication of the varicella virus Dumas strain of SEQ ID NO:28, and wherein said two origins of replication are contained in the inverted repeats, and said two origins of replication are a region corresponding to the 110,087th to 110,350th nucleotides of the sense strand of the genomic DNA of the varicella virus Dumas strain of SEQ ID NO:1 and a region corresponding to the 119,547th to 119,810th nucleotides of the genomic DNA of the antisense strand of said Dumas strain.

8. The method according to claim 1, which further comprises confirming that the repetitive sequence of one whole R1 region of the genomic DNA of said sample varicella vaccine virus is a nucleotide sequence of abbabba'bbb'abababx (SEQ ID NO:23) arranged in the direction of from the 5' end to the 3' end, wherein:

a represents a nucleotide sequence of GGACGCGATCGACGACGA (SEQ ID NO:19);

a' represents a nucleotide sequence of GGACGCGATTGACGACGA (SEQ ID NO:20);

b represents a nucleotide sequence of GGGAGAGGCGGAGGA (SEQ ID NO:21);

b' represents a nucleotide sequence of GGACGCGGCGGAGGA (SEQ ID NO:22); and x represents a nucleotide sequence of GGA, wherein said whole R1 region is a region corresponding to the 13,937th to 14,242nd nucleotides of the genomic DNA of the varicella virus Dumas strain of SEQ ID NO: 1.

9. The method according to claim 1, which further comprises confirming that the repetitive sequence of each of two whole R4 regions of the genomic DNA of said sample varicella vaccine virus is a nucleotide sequence of aaaaaaaaaaaax (SEQ ID NO:26) arranged in the direction of from the 5' end to the 3' end, wherein:

a represents a nucleotide sequence of CCCCGCCGATGGGGAGGGGGCGCGGTA (SEQ ID NO:24); and x represents a nucleotide sequence of CCCCGCCGATG (SEQ ID NO:25)

wherein said two whole R4 regions are a region corresponding to the 109,762nd to 109,907th nucleotides of the sense strand of the genomic DNA of the varicella virus Dumas strain of SEQ ID NO: 1 and a region corresponding to the 119,990th to 120,135th nucleotides of the antisense strand of the genomic DNA of said Dumas strain.

* * * * *

UNITED STATES PATENT AND TRADEMARK OFFICE

CERTIFICATE OF CORRECTION

PATENT NO. : 6,653,069 B2 Page 1 of 1
DATED : November 25, 2003
INVENTOR(S) : Gomi et al.

It is certified that error appears in the above-identified patent and that said Letters Patent is hereby corrected as shown below:

Title page, Item [54], and Column 1, lines 1-2,
Title page, please replace "METHOD FOR QUALITY CONTROL OF AN ATTENUATED VERICELLA LIVE VACCINE" with -- METHOD FOR QUALITY CONTROL OF AN ATTENUATED VARICELLA LIVE VACCINE --

Signed and Sealed this

Twenty-seventh Day of July, 2004

JON W. DUDAS
*Acting Director of the United States Patent and Trademark Office*